US011447515B2

(12) United States Patent
Gin et al.

(10) Patent No.: US 11,447,515 B2
(45) Date of Patent: *Sep. 20, 2022

(54) TRITERPENE SAPONINS, METHODS OF SYNTHESIS AND USES THEREOF

(71) Applicant: SLOAN KETTERING INSTITUTE FOR CANCER RESEARCH, New York, NY (US)

(72) Inventors: David Gin, New York, NY (US); Michelle Adams, Waterville, OH (US); Kai Deng, Guilderland, NY (US); Philip Livingston, New York, NY (US); Govindaswami Ragupathi, New York, NY (US); Eric Chea, Flushing, NY (US); Alberto Fernandez-Tejada, New York, NY (US); Lars Ulrik Nordstroem, New York, NY (US); William Walkowicz, Brooklyn, NY (US); Jeffrey Gardner, New York, NY (US); Derek Tan, New York, NY (US)

(73) Assignee: SLOAN KETTERING INSTITUTE FOR CANCER RESEARCH, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/626,046

(22) Filed: Jun. 16, 2017

(65) Prior Publication Data

US 2017/0283450 A1 Oct. 5, 2017

Related U.S. Application Data

(60) Continuation of application No. 14/494,720, filed on Sep. 24, 2014, now Pat. No. 9,718,850, which is a continuation of application No. 13/613,312, filed on Sep. 13, 2012, now Pat. No. 8,889,842, which is a division of application No. 12/420,803, filed on Apr. 8, 2009, now Pat. No. 8,283,456.

(60) Provisional application No. 61/043,197, filed on Apr. 8, 2008.

(51) Int. Cl.
| | |
|---|---|
| *C07H 15/256* | (2006.01) |
| *A61K 31/704* | (2006.01) |
| *C07H 13/08* | (2006.01) |
| *A61K 31/7024* | (2006.01) |
| *C07H 15/24* | (2006.01) |
| *A61K 39/385* | (2006.01) |

(52) U.S. Cl.
CPC ......... *C07H 15/256* (2013.01); *A61K 31/704* (2013.01); *A61K 31/7024* (2013.01); *A61K 39/385* (2013.01); *C07H 13/08* (2013.01); *C07H 15/24* (2013.01)

(58) Field of Classification Search
None
See application file for complete search history.

(56) References Cited

U.S. PATENT DOCUMENTS

| | | | |
|---|---|---|---|
| 5,057,540 A | 10/1991 | Kensil et al. | |
| 5,583,112 A | 12/1996 | Kensil et al. | |
| 5,977,081 A | 11/1999 | Marciani | |
| 6,080,725 A | 6/2000 | Marchiani | |
| 6,231,859 B1 | 5/2001 | Kensil | |
| 6,262,029 B1 | 7/2001 | Press et al. | |
| 6,716,428 B1 | 4/2004 | Stevens | |
| 9,718,850 B2* | 8/2017 | Gin | C07H 15/24 |
| 11,274,116 B2* | 3/2022 | Gin | A61P 31/00 |
| 2011/0300177 A1 | 12/2011 | Gin et al. | |

FOREIGN PATENT DOCUMENTS

| | | |
|---|---|---|
| CN | 1748725 | 3/2006 |
| CN | 101322734 A | 12/2008 |
| WO | 9824319 | 6/1998 |
| WO | 9856415 | 12/1998 |
| WO | 2000009075 | 2/2000 |
| WO | 2000110870 | 11/2000 |
| WO | 04092329 A2 | 10/2004 |

OTHER PUBLICATIONS

Squarica et al., "Glycal-mediated syntheses of enantiomerically pure polyhydroxylated gamma- and delta-lactams" Tetrahedron Letters vol. 43 pp. 4653-4655 (Year: 2002).*
Bliard, G et al, "Giycosyiantion of Acids under Phase Transfer Conditions, Partial Synthesis of Saponins," Tetrahedron Letters, 1994, vol. 35, No. 33, pp. 6107-6108, Cited in parent U.S. Pat. No. 9,718,850.
Yuodvirshia, A.M. et al., "Synthesis of Triterpene Glycosides," Chemistry of Natural Compounds, 1966, vol. 2, No. 6, pp. 331-334, Cited in parent U.S. Pat. No. 9,718,850.
International Search Report and Written Opinion for PCT/US2009/039954 dated Nov. 18, 2009. Cited in parent U.S. Pat. No. 9,718,850.
Bachran et al., "The Saponin-Mediated Enhanced uptake of Targeted Saporin-based drugs is strongly dependent on the saponin structure," Exp. Biol. Med. (Maywood), Apr. 2006; 231 (4): 412-20. Cited in parent U.S. Pat. No. 9,718,850.
Zou C., et al., "Diacylated Triterpenoid Saponin from Silene Szechuensis," Chinese Chemical Letters, 1999, vol. 10, No. 1, pp. 33-36. Cited in parent U.S. Pat. No. 9,718,850.

(Continued)

*Primary Examiner* — Eric Olson
(74) *Attorney, Agent, or Firm* — Hunton Andrews Kurth LLP

(57) ABSTRACT

The present invention relates to triterpene glycoside saponin-derived adjuvants, syntheses thereof, intermediates thereto, and uses thereof. QS-7 is a potent immuno-adjuvant that is significantly less toxic than QS-21, a related saponin that is currently the favored adjuvant in anticancer and antiviral vaccines. Tedious isolation and purification protocols have hindered the clinical development of QS-7. A novel semi-synthetic method is provided wherein a hydrolyzed prosapogenin mixture is used to synthesize QS-7, QS-21, and related analogs, greatly facilitating access to QS-7 and QS-21 analogs for preclinical and clinical evaluation.

1 Claim, 16 Drawing Sheets

(56) References Cited

OTHER PUBLICATIONS

Luo J-G., et al., "New Triterpenoid Saponins with Strong a-Glucosidase Inhibitory Activity from the Roots of Gypsophila Oldhamiana," Bioorganic & Medicinal Chemistry, 2008, vol. 16, pp. 2912-2920. Cited in parent U.S. Pat. No. 9,718,850.

Kim, Y-J., et al., "Synthetic Studies of Complex Immunostimulants from Quillaja saponaria: Synthesis of the Potent Clinical Immunoadjuvant QS-21Aapi," Journal of the American Chemical Society, 2006, vol. 128, Issue 36, pp. 11906-11915. Cited in parent U.S. Pat. No. 9,718,850.

Berge, et al., "Pharmaceutical salts," J. Pharm. Sci. Jan. 1977; 66(1): 1-19. Cited in parent U.S. Pat. No. 9,718,850.

Carcaboso, et al., "Potent, long lasting systematic antibody levels and mixed Th1/Th2 immune response after nasal immunization with malaria antigen loaded PLGA micropartides," Vaccine, Mar. 29, 2004; 22(11-12): 1423-32. Cited in parent U.S. Pat. No. 9,718,850.

Chandrasekhar, et al., "Facile and selective cleavage of allyl ethers, amines and esters using polymethylhydrosiloxane-ZnCl2/ Pd(PPh3)4," Tetrahedron 2001; 57: 3435-38. Cited in parent U.S. Pat. No. 9,718,850.

Deng, et al., "Synthesis and structure verification of the vaccine adjuvant QS-7-Api. Synthetic access to homogeneous Quillaja saponaria immunostimulants," J. Am. Chem. Soc. May 7, 2008; 130(18): 5860-1. Epub Apr. 15, 2008. Cited in parent U.S. Pat. No. 9,718,850.

Deng, et al., "Synthesis of QS-21-xylose; establishment of the immunopotentiating activity of synthetic QS-21 adjuvant with a melanoma vaccine," Angew. Chem.Int. Ed, Engl. 2008; 47(34): 6395-8. Cited in parent U.S. Pat. No. 9,718,850.

Evans, et al., "QS-21 promotes an adjuvant effect allowing for reduced antigen dose during HIV-1 envelope subunit immunization in humans," Vaccine, Feb. 28, 2001; 19(15-16): 2080-91. Cited in parent U.S. Pat. No. 9,718,850.

Garcia, et al., Dehydrative Glycosylation with Activated Diphenyl Sulfonium Reagents. Scope, Mode of C(1)-Hemiacetal Activation, and Detection of Reactive Glycosyl Intermediates. J. Am. Chem. Soc. 2000; 122: 4269-79. Cited in parent U.S. Pat. No. 9,718,850.

Guo, et al., "Triterpenoid saponins from Quillaja saponaria," Phytochemistry. May 1998; 48(1): 175-80. Cited in parent U.S. Pat. No. 9,718,850.

Han, et al., "Recent development of peptide coupling reagents in organic synthesis," Tetrahedon. 2004; 60: 2447-67. Cited in parent U.S. Pat. No. 9,718,850.

Higuchi, et al., "Structure of Desacylsaponins Obtained from the Bark of Quillaja Saponaria," Phytocehmistry. 1987; 26(1): 229-235. Cited in parent U.S. Pat. No. 9,718,850.

Jacobsen, et al., "Structure of the saponin adjuvant QS-21 and its base-catalyzed isomerization product by 1H and natural abundance 13C NMR spectroscopy," Carbohydr. Res., Jan. 4, 1996; 280(1): 1-14. Cited in parent U.S. Pat. No. 9,718,850.

Kashala, et al., "Safety, tolerability and immunogenicity of new formulations of the Plasmodium falciparum malaria peptide vaccine SPf66 combined with the immunological adjuvant QS-21," Vaccine. May 22, 2002; 20 (17-18): 2263-77. Cited in parent U.S. Pat. No. 9,718,850.

Kensil, et al., "QS-21 and QS-7: purified saponin adjuvants," Dev. Biol. Stand. 1998; 92: 41-7. Cited in parent U.S. Pat. No. 9,718,850.

Kensil, et al., "Separation and characterization of saponins with adjuvant activity from Quillaja saponaria Molina cortex," J. Immunol. Jan. 15, 1991; 146(2): 431-7. Cited in parent U.S. Pat. No. 9,718,850.

Kensil, Saponins as Vaccine Adjuvants, Rev. Ther. Drug Carrier Syst 1996; 13: 1-55. Cited in parent U.S. Pat. No. 9,718,850.

Kim, et al., "Comparison of the effect of different immunological adjuvants on the antibody and T-cell response to immunization with MUC1-KLH and GD3-KLH conjugate cancer vaccines," Vaccine. Nov. 12, 1999; 18(7-8): 597-603. Cited in parent U.S. Pat. No. 9,718,850.

Kim, et al., "Synthetic studies of complex immunostimulants from Quillaja saponaria: synthesis of the potent clinical immunoadjuvant QS-21 AAPI," J. Am. Chem. Soc. Sep. 13, 2006; 128(36): 11906-15. Cited in parent U.S. Pat. No. 9,718,850.

Livingston, et al., "Cancer vaccines targeting carbohydrate antigens," Hum. Vaccin. May-Jun. 2006; 2(3): 137-43, Epub May 16, 2006. Cited in parent U.S. Pat. No. 9,718,850.

Nakata, et al., "Inhibitory effects of ginsenoside Rh2 on tumor growth in nude mice bearing human ovarian cancer cells," Jpn. J. Cancer Res. Jul. 1998; 89(7): 733-40, Cited in parent U.S. Pat. No. 9,718,850.

Nguyen, et al., "Chemoselective Iterative Dehydrative Glycosylation," Angew. Chem. Int. Ed. Engl. Jan. 19, 2001; 40(2): 414-417. Cited in parent U.S. Pat. No. 9,718,850.

Nguyen, et al., "Sulfide-mediated dehydrative glycosylation," J. Am. Chem. Soc. Sep. 12, 2001; 123(36): 8766-72. Cited in parent U.S. Pat. No. 9,718,850.

Ohtani, et al., "Selective Cleavage of Ester Type Glycoside-Linkages and Its Application to Structure Determination of Natural Oligoglycosides," Tetrahedron Letters. 1984; 25(40): 4537-40. Cited in parent U.S. Pat. No. 9,718,850.

Roush, et al., "A Highly Stereoselective Synthesis of 2-Deoxy-3-glycosides Using 2-Deoxy-2-iodoglucopyranosyl Acetate Donors," J. Am. Chem. Soc.1999; 121: 3541-42. Cited in parent U.S. Pat. No. 9,718,850.

Sasaki, et al., "Induction of systemic and mucosa! immune responses to human immunodeficiency virus type 1 by a DNA vaccine formulated with QS-21 saponin adjuvant via intramuscular and intranasal routes," J. Virol, Jun. 1998; 72 (6): 4931-9. Cited in parent U.S. Pat. No. 9,718,850.

Sjolander, et al, "ISCOMS: an adjuvant with multiple functions," J. Leukoc. Biol. Dec. 1998 64(6): 713-23. Cited in parent U.S. Pat. No. 9,718,850.

Soltysik, et al., "Structure/function studies of QS-21 adjuvant: assessment of triterpene aldehyde and glucuronic acid roles in adjuvant function," Vaccine. 1995; 13(15): 1403-10. Cited in parent U.S. Pat. No. 9,718,850.

Toshima, et al., "Recent Progress in O-Gylcosylation Methods and Its Application to Natural Products Synthesis," Chem. Rev. 1993; 93: 1503-1531. Cited in parent U.S. Pat. No. 9,718,850.

Van Setten, et al., "Glycosyl compositions and structural characteristics of the potential immunoadjuvant active saponins in the Quillaja saponaria Molina extract quil A," Rapid. Commun Mass. Spectrom. 1995; 9(8): 660-6. Cited in parent U.S. Pat. No. 9,718,850.

Wang, et al., "Synthesis of the potent immunostimulatory adjuvant QS-21A," J. Am. Chem, Soc. Mar. 16, 2005; 127(10): 3256-7. Cited in parent U.S. Pat. No. 9,718,850.

De Tomassi, et al., "Triterpenoid Saponins from Spergularia ramosa," Journal of Natural Products (1998) vol. 61 pp. 323-327. Cited in parent U.S. Pat. No. 9,718,850.

Zhao, et al., "New Triterpenoid Saponins from the Roots of Sinocrassula asclepiadea," Chemical and Pharmaceutical Bulletin (2004) vol. 52, No. 2., pp. 230-237. Cited in parent U.S. Pat. No. 9,718,850.

Fu, et al., "Silenorubicosides A-D, Triterpenoid Saponins from Silene rubicunda," Journal of Natural Products (2005) vol. 68, pp. 754-758. Cited in parent U.S. Pat. No. 9,718,850.

Bankefors, et al., "Structural classification of Quillaja saponins by electrospray ionization ion trap multiple-stage mass spectrometry in combination with multivariate analysis, proof of concept," Chemometrics and Intelligent Laboratory Systems (2008) vol. 90, pp. 178-187. Cited in parent U.S. Pat. No. 9,718,850.

Van Setten, et al., "Ion Trap Multiple-Stage Tandem Mass Spectrometry as a Pre-NMR Tool in the Structure Elucidation of Saponins," Phytochemical Analysis (2000) vol. 11, pp. 190-198. Cited in parent U.S. Pat. No. 9,718,850.

Warashina, et al., "Novel Acylated Saponins from Tragopogon porrifolious L. isolation and the Structures of Tragopogonsaponins A-R," Chem. Pharm. Bull. (1991) vol. 39, No. 2, pp. 388-396. Cited in parent U.S. Pat. No. 9,718,850.

Elgamal, et al., "Isolation of Triterpene Saponins from Gysophila Capillaris," Phytochemistry (1995) vol. 38, No. 6, pp. 1481-1485. Cited in parent U.S. Pat. No. 9,718,850.

(56) References Cited

OTHER PUBLICATIONS

Giadi, et al., "Glandulosides A-D, Triterpene Saponins from Acanthophyllum glandulosum," J. Nat Prod. (2004) vol. 67, pp. 1114-1118. Cited in parent U.S. Pat. No. 9,718,850.
Han, et al., "Analysis of multiple constituents in a Chinese herbal preparation Shuang-Huang-Lian oral liquid HPLC-DAD-ESI-MS," Journal of Pharmaceutical and Biomedical Analysis (2007) vol. 44, pp. 430-438. Cited in parent U.S. Pat. No. 9,718,850.
Oki, et al., English Abstract of JP 09169648, retrieved from STN database on Apr. 22, 2013, 4 pages. Cited in parent U.S. Pat. No. 9,718,850.
Luo, et al., Chem. Pharm. Bull., 2006, 54(8), 1200-1202. Cited in parent U.S. Pat. No. 9,718,850.
Chea, et al., "Synthesis and Preclinical Evaluation of QS-21 Variants Leading to Simplified Vaccine Adjuvants and Mechanistic Probes," J. Am, Chem. Soc., Aug. 15, 2012; 134(32): 13448-57. Epub Aug. 6, 2012. Cited in parent U.S. Pat. No. 9,718,850.
Greene, et al., "Protective Groups in Organic Synthesis," Third Edition, John Wiley & Sons, Inc. 1999, 240 pages. Cited in parent U.S. Pat. No. 9,718,850.
File history of U.S. Appl. No. 61/043,197, filed Apr. 8, 2008. Cited in parent U.S. Pat. No. 9,718,850.
File history of U.S. Appl. No. 12/420,803, filed Apr. 8, 2009. Cited in parent U.S. Pat. No. 9,718,850.
File history of U.S. Appl. No. 13/613,312, filed Sep. 13, 2012. Cited in parent U.S. Pat. No. 9,718,850.
Greene et al., "Protective Groups in Organic Synthesis," Third Edition, published by John Wiley & Sons, Inc. 1999, 240 pgs.
Notice of Preliminary Rejection for Korean Patent Application No. 10-2018-7002556 dated Jul. 3, 2018.
Extended European search report issue for European Patent Application No. 18161023.9 dated Jun. 27, 2018.
Higuchi, R. et al., "Structure of Desacylsaponions Obtained from the Bark of Quillaja Saponaria," Phytochemistry, Pergamon Press, vol. 26, No. 1, pp. 229-235, Dec. 23, 1986.
Guo, S. et al., "Structural Studies of Triterpenoid Saponins with New Acyl Components from Quillaja Saponaria Molina," Phytochemi, Pergamon Press, vol. 55, No. 5, pp. 419-428, Nov. 1, 2000.
Australian Examination Report dated Jun. 15, 2018 for Australian Patent Application No. 2017258850.
Chinese Rejection Decision dated Aug. 3, 2018 for Chinese Application No. 201510047889.3.
Zhongguo, Yaoshi et at., vol. 9, No. 9, pp. 807-809, 2006.
Sang, Shengmin et al., "Chemistry and Bioactivity of the Seeds of Vaccaria Segetatis," ACS Symposium Series, vol. 859, pp. 279-291, 2003.
Hani, M. et al., "A Novel Triterpene Saponin from Gypsophila Capillaris," vol. 50, No. 4, pp. 563-567, 1995.
Hani, M. et al "Isolation of Two Triterpene Saponins from Gypsophita Capillaris (Forssk)," Natural Product Letters, vol. 4, pp. 217-222, 1994.
Li, Hong-Yu et al., "Triterpenoid Saponins from Dianthus Chinensis," Phytochemistry, vol. 35, No. 3, pp. 751-7556, 1994.
Li, Ho et al., Phytochemistry, vol. 35, No. 3, pp. 751-756, 1994.
Communication pursuant to Article 94(3) EPC dated Jun. 13, 2017 for European Patent Application No. 09731210.2
Notice of Reasons for Rejection dated Jan. 10, 2018 for Japanese patent application No. 2017-018192.
Kato, Takeshi et al., "Chemical Components of Crude Drug 'Byakuren,'" Natural Medicines, vol. 49, No. 4, pp. 478-483, 1995.
Miyase, Toshio et al., "Araliasaponins XII-XVIII, Triterpene Saponins from the Roots of Aralia Chinensis," Phyochemistry, vol. 42, No. 4, pp. 1123-1130, 1996.
Israeli Office Action dated Aug. 1, 2018 for Israeli Patent Application No. 239051.
Qiyi, Xing et al., "Basic Organic Chemistry," 3rd Edition, pp. 1147-1162, High Education Press, 1987.
"Periodic Table of the Elements," CAS version, Handbook of Chemistry and Physics, 75th Ed, pp. 1-35.
Sorrell, Thomas N. "Organic Chemistry," University Science Books, Sausalito, pp. 1-222, 1999.
Smith, Michael B. et al., "March's Advanced Organic Chemistry," 5th Edition, March, J., John Wiley & Sons, New York, pp. 1-1,054, 2001.
Greene, Theodora W. et al., "Protecting Groups in Organic Synthesis," 3rd Edition, John Wiley & Sons, 1999.
Examiner Report dated Jan. 2, 2019 issued for Canadian Patent Application No. 2,993,582.
Notice of Final Rejection dated Sep. 6, 2018 for Japanese Patent Application No. 2017-018192.
Official Action dated Sep. 6, 2019 for Japanese patent application No. 2019-000534.
Notice of Preliminary Rejection dated May 3, 2019 for Korean Patent Application No. 10-2019-7003429.
Kim, Y.J. et al., "Synthetic studies of complex immunostimuiarits from Quillaja saponeria: Synthesis of the potent clinical immunoadjuvant . . . " J. Am. Chem. Soc., vol. 128, pp. 11906-11915, 2006.
Kite et al., Metabolic analysis of saponins in crude extracts of Quillaja saponaria by liquid chromatography/mass spectrometry for product authentication Rapid Commun. Mass Spectrm, vol. 18, pp. 2859-2870, 2004.
Lemieux et al., The Effect of substituting key hydroxyl groups by amino groups on the binding of the Lewis b tetrasaccharide by a lectin and a monoclonal antibody, Carbohydrate Research, 205, (1990) C12-C17.
Seeberger et al., Synthesis of Neomycin Analogs to Investigate Aminoglycoside-RNA Interactions, Synlett, No. 9, 2003.
Penultimate Official Action dated Mar. 24, 2020 issued in Japanese patent application No. 2017-18192.
Penultimate Official Action dated Apr. 8, 2020 issued in Japanese patent application No. 2019-534.
European Search Report dated Jul. 22, 2021 for European Patent Application No. 20186996.3.
Pawar RS et al: "Effect of oleanane triterpenoids from Terminalia arjuna—a cardioprotective drug on the process of respiratory oxyburst", Phytomedicine, Elsevier, Amsterdam, NL, vol. 12, No. 5, May 16, 2005 (May 16, 2005).
Haddad Mohamed et al.: "New Saponins fromAcanthophyllum Helvetica Chimica Acta, Triterpene 1-5,17, pachystegium", 20 vol. 87, No. 1, Jan. 1, 2004 (Jan. 1, 2004).
Alberto Fernandez-Tejada et al: "Development of a minimal saponin vaccine adjuvant based on QS-21", Nature Chemistry, vol. 6, No. 7, Jun. 1, 2014 (Jun. 1, 2014).
Alberto Fernandez-Tejada et al: 11 Development of Improved Vaccine Adjuvants Based on the Saponin Natural Product QS-21 through Chemical Synthesis 11, Accounts of Chemical Research, vol. 49, No. 9, Aug. 28, 2016 (Aug. 28, 2016).
Canadian Office Action dated Jan. 24, 2022 for Canadian Patent Application No. 3,096,084.

* cited by examiner

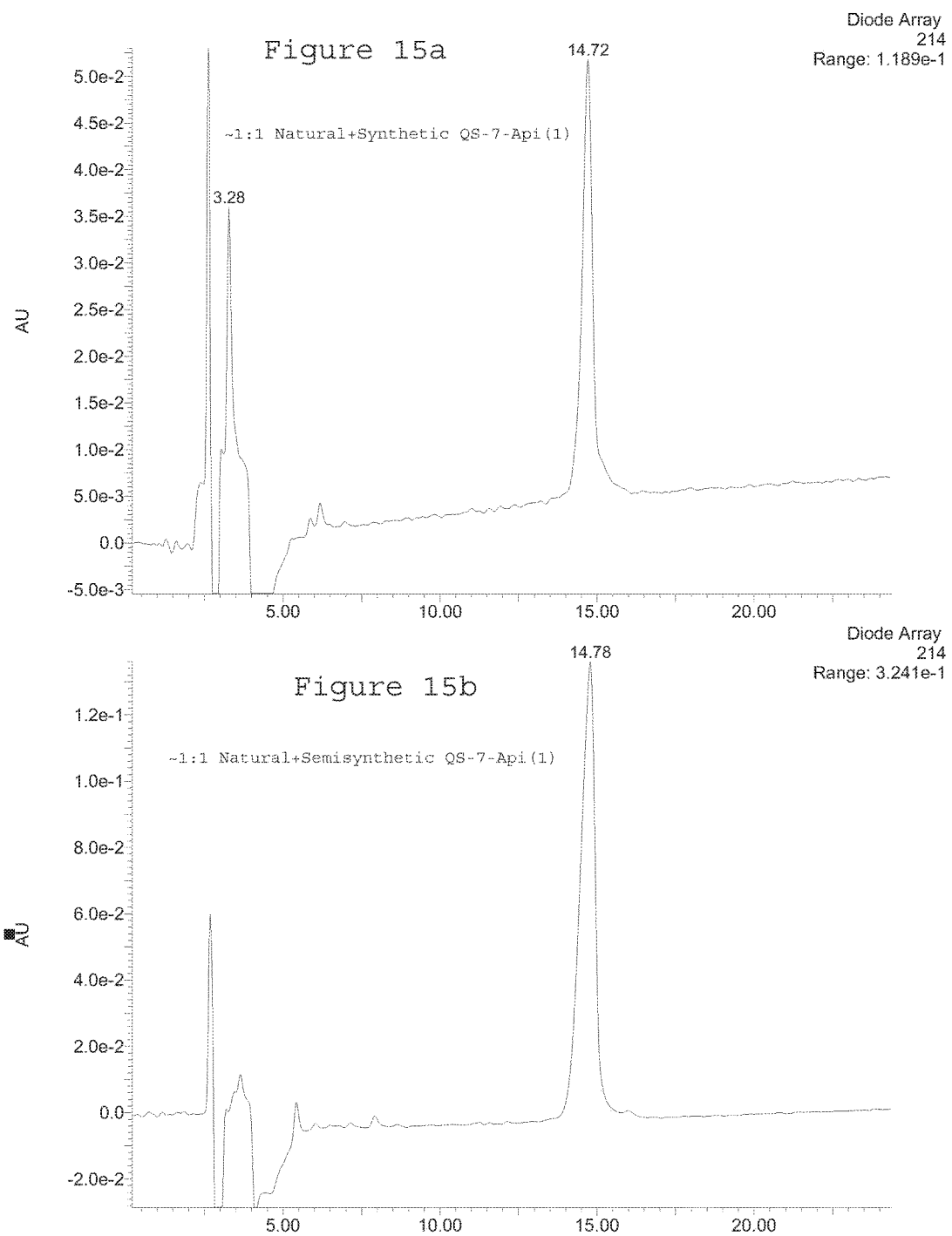

TRITERPENE SAPONINS, METHODS OF SYNTHESIS AND USES THEREOF

CROSS REFERENCE TO RELATED APPLICATIONS

The present application is a continuation of U.S. patent application Ser. No. 14/494,720, filed Sep. 24, 2014, which is a continuation of U.S. patent application Ser. No. 13/613,312, filed Sep. 13, 2012, now U.S. Pat. No. 8,889,842, which is a divisional of U.S. patent application Ser. No. 12/420,803, filed Apr. 8, 2009, now U.S. Pat. No. 8,283,456, which claims priority to U.S. Provisional Patent Application No. 61/043,197, filed Apr. 8, 2008. The entirety of the aforementioned applications are incorporated herein by reference.

GOVERNMENT SUPPORT

This invention was made with government support under grant numbers GM058833 and AI085622 awarded by the National Institutes of Health. The government has certain rights in the invention.

FIELD OF THE INVENTION

The present invention relates to triterpene glycoside saponin-derived adjuvants, syntheses thereof, and intermediates thereto. The invention also provides pharmaceutical compositions comprising compounds of the present invention and methods of using said compounds or compositions in the treatment of infectious diseases and cancer.

BACKGROUND OF THE INVENTION

Saponins are glycosidic compounds that are produced as secondary metabolites of steroids and triterpenes. They are widely distributed among plant species and in some marine invertebrates. The chemical structure of saponins imparts a wide range of pharmacological and biological activities, including some potent and efficacious immunological activity. Semi-purified saponin extracts from the bark of the South American *Quillaja saponaria* Molina tree (*Quillaja saponins*) exhibit remarkable immunoadjuvant activity. Because the *Quillaja saponins* are found as a mixture of at least one hundred structurally related saponin glycosides, their separation and isolation is often difficult if not prohibitive.

The most active fraction of these extracts, designated QS-21, has been found to include a mixture of two principal isomeric triterpene glycoside saponins, each incorporating a quillaic acid triterpene core, flanked on either side by complex oligosaccharides and a stereochemically rich glycosylated fatty acyl chain. The potency of QS-21 and its favorable toxicity profile in dozens of recent and ongoing vaccine clinical trials (melanoma, breast cancer, small cell lung cancer, prostate cancer, HIV-1, malaria) have established it as a promising new adjuvant for immune response potentiation and dose-sparing. However, the tolerated dose of QS-21 does not exceed 100 μg, above which significant local and systemic side effects arise.

Access to other potent *Quillaja saponins* has been hindered by difficulties in obtaining pure species from *Quillaja saponin* extracts. Furthermore, the structural identity of many *Quillaja saponins* remains only postulated. The discovery of new *Quillaja saponins* and related analogs with potent adjuvant activity and low toxicity presents a challenge to the fields of chemical synthesis and medicine.

SUMMARY OF THE INVENTION

The present invention encompasses the recognition that the clinical use of QS-21 as an adjuvant is limited due to toxicity at higher doses, and that QS-7, a related *Quillaja saponin*, is difficult to isolate in pure form. Moreover, synthetic access to QS-21, QS-7 and other triterpene glycoside saponins is hindered by their structural complexity. The present invention provides compounds that are analogs of QS-21 and QS-7.

In one aspect, the invention provides compounds of formula I:

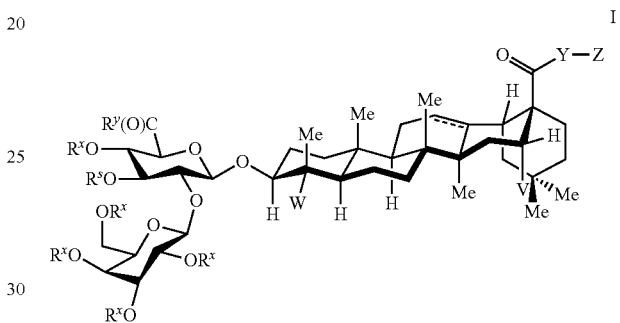

or a pharmaceutically acceptable salt thereof, wherein:

$\rightleftharpoons$ is a single or double bond;

W is Me, —CHO,

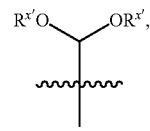

—CH$_2$OR$^x$, or —C(O)R$^y$;

V is hydrogen or —OR$^x$,

Y is CH$_2$, —O—, —NR—, or —NH—

Z is hydrogen; a cyclic or acyclic, optionally substituted moiety selected from the group consisting of acyl, aliphatic, heteroaliphatic, aryl, arylalkyl, heterocyclyl, and heteroaryl; or a carbohydrate domain having the structure:

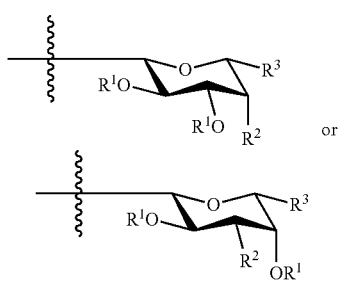

wherein:

each occurrence of $R^1$ is $R^x$ or a carbohydrate domain having the structure:

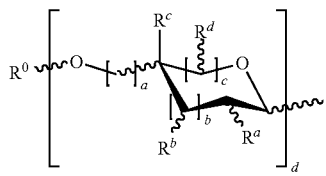

wherein:

each occurrence of a, b, and c is independently 0, 1, or 2;

d is an integer from 1-5, wherein each d bracketed structure may be the same or different; with the proviso that the d bracketed structure represents a furanose or pyranose moiety, and the sum of b and c is 1 or 2;

$R^0$ is hydrogen; an oxygen protecting group selected from the group consisting of alkyl ethers, benzyl ethers, silyl ethers, acetals, ketals, esters, carbamates, and carbonates; or an optionally substituted moiety selected from the group consisting of acyl, $C_{1-10}$ aliphatic, $C_{1-6}$ heteroaliphatic, 6-10-membered aryl, arylalkyl, 5-10-membered heteroaryl having 1-4 heteroatoms independently selected from nitrogen, oxygen, or sulfur, 4-7-membered heterocyclyl having 1-2 heteroatoms independently selected from the group consisting of nitrogen, oxygen, and sulfur;

each occurrence of $R^a$, $R^b$, $R^c$, and $R^d$ is independently hydrogen, halogen, OH, OR, $OR^x$, $NR_2$, NHCOR, or an optionally substituted group selected from acyl, $C_{1-10}$ aliphatic, $C_{1-6}$ heteroaliphatic, 6-10-membered aryl, arylalkyl, 5-10-membered heteroaryl having 1-4 heteroatoms independently selected from nitrogen, oxygen, or sulfur; 4-7-membered heterocyclyl having 1-2 heteroatoms independently selected from the group consisting of nitrogen, oxygen, and sulfur;

$R^2$ is hydrogen, halogen, OH, OR, $OC(O)R^4$, $OC(O)OR^4$, $OC(O)NHR^4$, $OC(O)NRR^4$, $OC(O)SR^4$, $NHC(O)R^4$, $NRC(O)R^4$, $NHC(O)OR^4$, $NHC(O)NHR^4$, $NHC(O)NRR^4$, $N(R^4)_2$, $NHR^4$, $NRR^4$, $N_3$, or an optionally substituted group selected from $C_{1-10}$ aliphatic, $C_{1-6}$ heteroaliphatic, 6-10-membered aryl, arylalkyl, 5-10-membered heteroaryl having 1-4 heteroatoms independently selected from the group consisting of nitrogen, oxygen, and sulfur, 4-7-membered heterocyclyl having 1-2 heteroatoms independently selected from the group consisting of nitrogen, oxygen, and sulfur;

$R^3$ is hydrogen, halogen, $CH_2OR^1$, or an optionally substituted group selected from the group consisting of acyl, $C_{1-10}$ aliphatic, $C_{1-6}$ heteroaliphatic, 6-10-membered aryl, arylalkyl, 5-10-membered heteroaryl having 1-4 heteroatoms independently selected from nitrogen, oxygen, and sulfur; 4-7-membered heterocyclyl having 1-2 heteroatoms independently selected from the group consisting of nitrogen, oxygen, and sulfur;

$R^4$ is

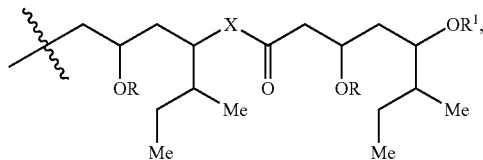

wherein X is —O— or —NR—; or

T-$R^z$, wherein:

T is a covalent bond or a bivalent $C_{1-26}$ saturated or unsaturated, straight or branched, aliphatic or heteroaliphatic chain; and $R^z$ is hydrogen, halogen, —OR, —$OR^x$, —$OR^1$, —SR, —$NR_2$, —NC(O)OR, or an optionally substituted group selected from acyl, arylalkyl, heteroarylalkyl, $C_{1-6}$ aliphatic, 6-10-membered aryl, 5-10-membered heteroaryl having 1-4 heteroatoms independently selected from nitrogen, oxygen, or sulfur, 4-7-membered heterocyclyl having 1-2 heteroatoms independently selected from the group consisting of nitrogen, oxygen and sulfur; or two $R^4$ on the same nitrogen atom are taken with the nitrogen to form a 4-7-membered heterocyclic ring having 1-2 heteroatoms independently selected from the group consisting of nitrogen, oxygen, and sulfur;

each occurrence of $R^x$ is independently hydrogen or an oxygen protecting group selected from the group consisting of alkyl ethers, benzyl ethers, silyl ethers, acetals, ketals, esters, carbamates, and carbonates;

$R^y$ is —OH, —OR, or a carboxyl protecting group selected from the group consisting of ester, amides, and hydrazides;

$R^s$ is

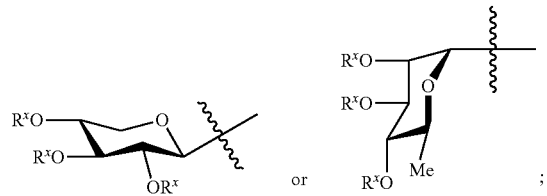

each occurrence of $R^x$ is independently an optionally substituted group selected from 6-10-membered aryl, $C_{1-6}$ aliphatic, or $C_{1-6}$ heteroaliphatic having 1-2 heteroatoms independently selected from the group consisting of nitrogen, oxygen, and sulfur; or:

two $R^{x'}$ are taken together to form a 5-7-membered heterocyclic ring having 1-2 heteroatoms independently selected from the group consisting of nitrogen, oxygen, and sulfur;

each occurrence of R is independently hydrogen, an optionally substituted group selected from acyl, arylalkyl, 6-10-membered aryl, $C_{1-6}$ aliphatic, or $C_{1-6}$ heteroaliphatic having 1-2 heteroatoms independently selected from the group consisting of nitrogen, oxygen, and sulfur; or: two R on the same nitrogen atom are taken with the nitrogen to form a 4-7-membered heterocyclic ring having 1-2 heteroatoms independently selected from the group consisting of nitrogen, oxygen, and sulfur.

According to another aspect, the invention provides compounds of formula IV:

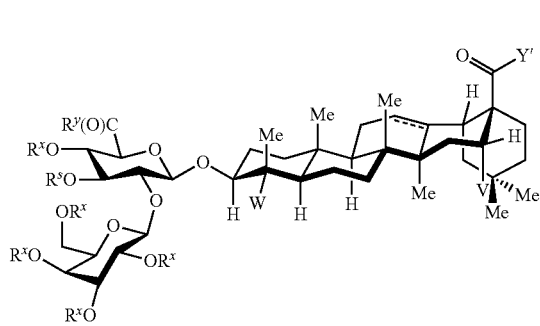

wherein:
---- is a single or double bond:
Y' is hydrogen, halogen, alkyl, aryl, OR, OR$^y$, OH, NR$_2$, NR$_3^+$, NHR, NH$_2$, SR, or NROR;
W is Me, —CHO,

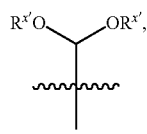

—CH$_2$OR$^x$, or —C(O)R$^y$;
V is hydrogen or —OR$^x$;
R$^y$ is —OH, or a carboxyl protecting group selected from the group consisting of ester, amides, and hydrazides;
R$^s$ is

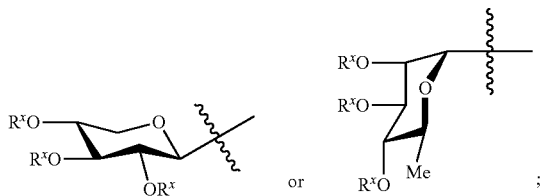

each occurrence of R$^{x'}$ is independently an optionally substituted group selected from 6-10-membered aryl, C$_{1-6}$ aliphatic, or C$_{1-6}$ heteroaliphatic having 1-2 heteroatoms independently selected from the group consisting of nitrogen, oxygen, and sulfur; or:
two R$^{x'}$ are taken together to form a 5-7-membered heterocyclic ring having 1-2 heteroatoms independently selected from the group consisting of nitrogen, oxygen, and sulfur;
each occurrence of R is independently hydrogen, an optionally substituted group selected from acyl, arylalkyl, 6-10-membered aryl, C$_{1-12}$ aliphatic, or C$_{1-12}$ heteroaliphatic having 1-2 heteroatoms independently selected from the group consisting of nitrogen, oxygen, and sulfur; and
each occurrence of R$^x$ is independently hydrogen or an oxygen protecting group.
According to another aspect, inventive compounds have been shown to be useful as adjuvants. Thus, in certain embodiments, vaccines are provided comprising one or more bacterial, viral, protozoal, or tumor-associated antigens, and one or more inventive compounds. In certain embodiments, one or more antigens are non-covalently associated with a pharmaceutically acceptable excipient. In some embodiments, one or more antigens are conjugated covalently to a pharmaceutically acceptable excipient.

In another aspect, the present invention provides a method of potentiating an immune response to an antigen, comprising administering to a subject a provided vaccine in an effective amount to potentiate the immune response of said subject to said antigen.

In another aspect, the present invention provides methods of vaccinating a subject, comprising administering a provided vaccine to said subject. In some embodiments, the subject is human. In some embodiments, the vaccine is administered orally. In other embodiments, the vaccine is administered intramuscularly. In other embodiments, the vaccine is administered subcutaneously. In certain embodiments, the amount of adjuvant compound administered is 10-1000 μg. In certain embodiments, the amount of adjuvant compound administered is 500-1000 μg. In certain embodiments, the amount of adjuvant compound administered is 100-500 μg. In certain embodiments, the amount of adjuvant compound administered is 50-250 μg. In certain embodiments, the amount of adjuvant compound administered is 50-500 μg. In certain embodiments, the amount of adjuvant compound administered is 250-500 μg. The antigen to which the subject is vaccinated may be a cancer, bacterial, viral, proatazoal, or self-antigen.

In another aspect, the invention provides pharmaceutical compositions comprising compounds of the invention and pharmaceutically acceptable excipients. In certain embodiments, the pharmaceutical composition is a vaccine comprising an antigen and an inventive adjuvant.

In another aspect, the invention provides kits comprising pharmaceutical compositions of inventive compounds. In some embodiments, the kits comprise prescribing information. In some embodiments, such kits include the combination of an inventive adjuvant compound and another immunotherapeutic agent (e.g.). The agents may be packaged separately or together. The kit optionally includes instructions for prescribing the medication. In certain embodiments, the kit includes multiple doses of each agent. The kit may include sufficient quantities of each component to treat a subject for a week, two weeks, three weeks, four weeks, or multiple months. In certain embodiments, the kit includes one cycle of immunotherapy. In certain embodiments, the kit includes a sufficient quantity of a pharmaceutical composition to immunize a subject against an antigen long term.

In another aspect, the invention provides a method of using protecting groups to isolate prosapogenins, the method comprising placing protecting groups on a mixture of prosapogenins and then separating the mixture by suitable means to isolate one or more prosapogenin compounds. In some embodiments, the method comprises the steps of:
(a) providing a mixture of prosapogenins of formula IV-a:

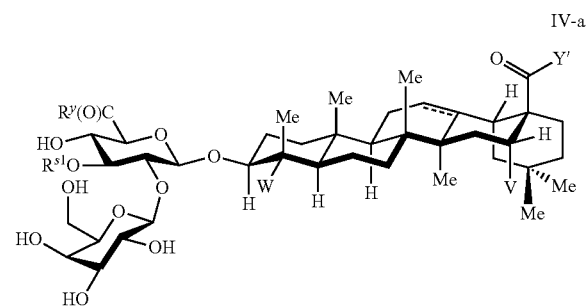

wherein:
 === is a single or double bond;
Y' is hydrogen, halogen, alkyl, aryl, OR, OR$^y$, OH, NR$_2$, NR$_3^+$, NHR, NH$_2$, SR, or NROR;
W is Me, —CHO,

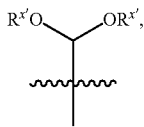

—CH$_2$OR$^x$, or —C(O)R$^y$;
V is hydrogen or —OR$^x$;
R$^y$ is —OH, or a carboxyl protecting group selected from the group consisting of esters, amides, and hydrazides;
R$^{s1}$ is

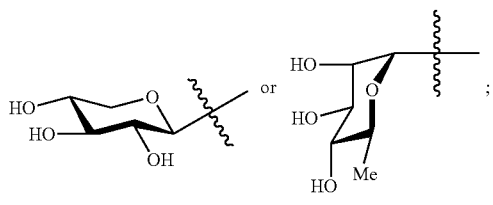

each occurrence of R$^{x'}$ is independently an optionally substituted group selected from 6-10-membered aryl, C$_{1-6}$ aliphatic, or C$_{1-6}$ heteroaliphatic having 1-2 heteroatoms independently selected from the group consisting of nitrogen, oxygen, and sulfur; or:
 two R$^{x'}$ are taken together to form a 5-7-membered heterocyclic ring having 1-2 heteroatoms independently selected from the group consisting of nitrogen, oxygen, and sulfur;
each occurrence of R is independently hydrogen, an optionally substituted group selected from acyl, arylalkyl, 6-10-membered aryl, C$_{1-12}$ aliphatic, or C$_{1-12}$ heteroaliphatic having 1-2 heteroatoms independently selected from the group consisting of nitrogen, oxygen, and sulfur;
each occurrence of R$^x$ is independently hydrogen or an oxygen protecting group selected from the group consisting of alkyl ethers, benzyl ethers, silyl ethers, acetals, ketals, esters, and carbonates;
(b) treating said compound of formula IV-a under suitable conditions to form a mixture of prosapogenins of formula IV:

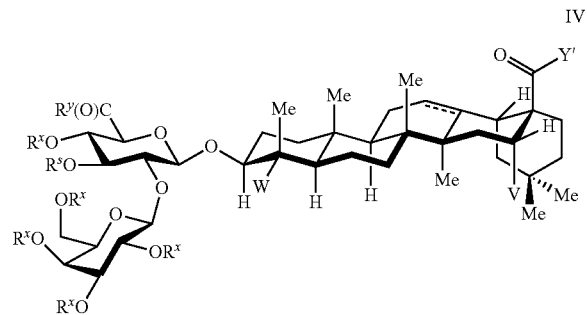

wherein each of ===, R$^y$, Y', V, and W is as defined for compounds of formula IV-a, R$^s$ is as defined for compounds of formula I, and each occurrence of R$^x$ is independently hydrogen or an oxygen protecting group selected from the group consisting of alkyl ethers, benzyl ethers, silyl ethers, acetals, ketals, esters, and carbonates;
and
(c) obtaining said compound IV by suitable physical means.

In some embodiments, the mixture of prosapogenins in step (a) is enriched one or more compounds of formula IV-a. In some embodiments, the mixture of prosapogenins in step (b) is enriched one or more compounds of formula IV.

The present invention provides novel semi-synthetic methods for synthesizing QS-7, QS-21, and related analogs, the method comprising coupling a triterpene compound with a compound comprising a saccharide to form a compound of formula I. In some embodiments, the method comprises the steps of:
(a) providing a compound of formula IV:

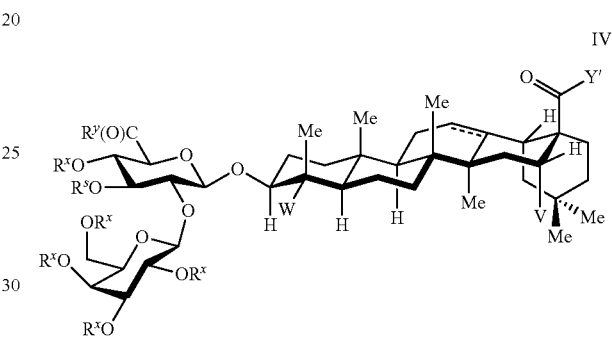

wherein:
 === is a single or double bond;
Y' is hydrogen, halogen, alkyl, aryl, OR, OR$^y$, OH, NR$_2$, NR$_3^+$, NHR, NH$_2$, SR, or NROR;
W is Me, —CHO,

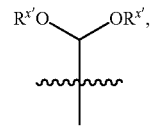

—CH$_2$OR$^x$, or —C(O)R$^y$;
V is hydrogen or —OR$^x$;
R$^y$ is —OH, or a carboxyl protecting group selected from the group consisting of ester, amides, and hydrazides;
R$^s$ is

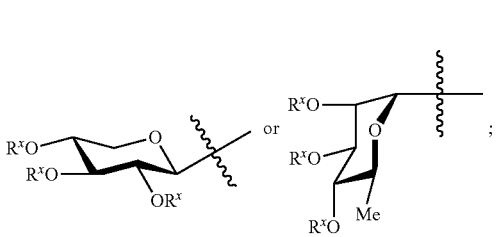

each occurrence of R$^{x'}$ is independently an optionally substituted group selected from 6-10-membered aryl, C$_{1-6}$ aliphatic, or C$_{1-6}$ heteroaliphatic having 1-2 heteroatoms independently selected from the group consisting of nitrogen, oxygen, and sulfur; or:

two $R^{x'}$ are taken together to form a 5-7-membered heterocyclic ring having 1-2 heteroatoms independently selected from the group consisting of nitrogen, oxygen, and sulfur;

each occurrence of R is independently hydrogen, an optionally substituted group selected from acyl, arylalkyl, 6-10-membered aryl, $C_{1-12}$ aliphatic, or $C_{1-12}$ heteroaliphatic having 1-2 heteroatoms independently selected from the group consisting of nitrogen, oxygen, and sulfur;

each occurrence of $R^x$ is independently hydrogen or an oxygen protecting group selected from the group consisting of alkyl ethers, benzyl ethers, silyl ethers, acetals, ketals, esters, and carbonates;

(b) treating said compound of formula IV under suitable conditions with a compound of formula V:

LG-Z    V wherein:

Z is hydrogen; a cyclic or acyclic, optionally substituted moiety selected from the group consisting of acyl, aliphatic, heteroaliphatic, aryl, arylalkyl, and heteroaryl; or a carbohydrate domain having the structure:

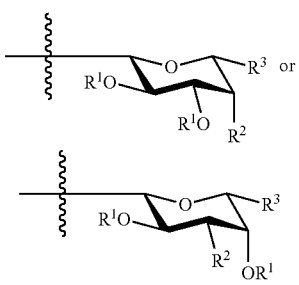

wherein:
each occurrence of $R^1$ is $R^x$ or a carbohydrate domain having the structure:

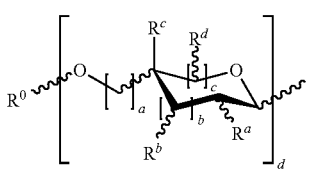

wherein:
each occurrence of a, b, and c is independently 0, 1, or 2;
d is an integer from 1-5, wherein each d bracketed structure may be the same or different; with the proviso that the d bracketed structure represents a furanose or pyranose moiety, and the sum of b and c is 1 or 2;

$R^0$ is hydrogen, an oxygen protecting group selected from the group consisting of alkyl ethers, benzyl ethers, silyl ethers, acetals, ketals, esters, carbamates, and carbonates; or an optionally substituted moiety selected from the group consisting of acyl, $C_{1-10}$ aliphatic, $C_{1-6}$ heteroaliphatic, 6-10-membered aryl, arylalkyl, 5-10-membered heteroaryl having 1-4 heteroatoms independently selected from nitrogen, oxygen, or sulfur, 4-7-membered heterocyclyl having 1-2 heteroatoms independently selected from the group consisting of nitrogen, oxygen, and sulfur;

each occurrence of $R^a$, $R^b$, $R^c$, and $R^d$ is independently hydrogen, halogen, OH, OR, $OR^x$, $NR_2$, NHCOR, or an optionally substituted group selected from acyl, $C_{1-10}$ aliphatic, $C_{1-6}$ heteroaliphatic, 6-10-membered aryl, arylalkyl, 5-10-membered heteroaryl having 1-4 heteroatoms independently selected from nitrogen, oxygen, or sulfur; 4-7-membered heterocyclyl having 1-2 heteroatoms independently selected from the group consisting of nitrogen, oxygen, and sulfur;

$R^2$ is hydrogen, halogen, OH, OR, $OC(O)R^4$, $OC(O)OR^4$, $OC(O)NHR^4$, $OC(O)NRR^4$, $OC(O)SR^4$, $NHC(O)R^4$, $NRC(O)R^4$, $NHC(O)OR^4$, $NHC(O)NHR^4$, $NHC(O)NRR^4$, $N(R^4)_2$, $NHR^4$, $NRR^4$, $N_3$, or an optionally substituted group selected from $C_{1-10}$ aliphatic, $C_{1-6}$ heteroaliphatic, 6-10-membered aryl, arylalkyl, 5-10-membered heteroaryl having 1-4 heteroatoms independently selected from the group consisting of nitrogen, oxygen, and sulfur, 4-7-membered heterocyclyl having 1-2 heteroatoms independently selected from the group consisting of nitrogen, oxygen, and sulfur;

$R^3$ is hydrogen, halogen, $CH_2OR^1$, or an optionally substituted group selected from the group consisting of acyl, $C_{1-10}$ aliphatic, $C_{1-6}$ heteroaliphatic, 6-10-membered aryl, arylalkyl, 5-10-membered heteroaryl having 1-4 heteroatoms independently selected from the group consisting of nitrogen, oxygen, and sulfur; 4-7-membered heterocyclyl having 1-2 heteroatoms independently selected from the group consisting of nitrogen, oxygen, and sulfur;

$R^4$ is

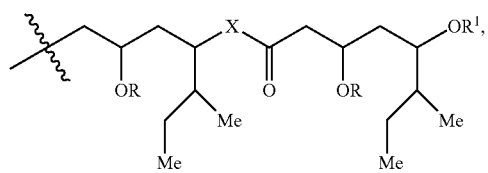

wherein X is —O— or —NR—; or

T-$R^z$, wherein:

T is a covalent bond or a bivalent $C_{1-26}$ saturated or unsaturated, straight or branched, aliphatic or heteroaliphatic chain; and $R^z$ is hydrogen, halogen, —OR, —$OR^x$, —$OR^1$, —SR, —$NR_2$, —NC(O)OR, or an optionally substituted group selected from acyl, arylalkyl, heteroarylalkyl, $C_{1-6}$ aliphatic, 6-10-membered aryl, 5-10-membered heteroaryl having 1-4 heteroatoms independently selected from nitrogen, oxygen, or sulfur, 4-7-membered heterocyclyl having 1-2 heteroatoms independently selected from the group consisting of nitrogen, oxygen and sulfur; or two $R^4$ on the same nitrogen atom are taken with the nitrogen to form a 4-7-membered heterocyclic ring having 1-2 heteroatoms independently selected from the group consisting of nitrogen, oxygen, and sulfur;

each occurrence of $R^x$ is as defined for compounds of formula IV; and

LG is a suitable leaving group selected from the group consisting of halogen, imidate, alkoxy, sulphonyloxy, optionally substituted alkylsulphonyl, optionally substituted alkenylsulfonyl, optionally substituted arylsulfonyl, and diazonium moieties;

to give a compound of formula I:

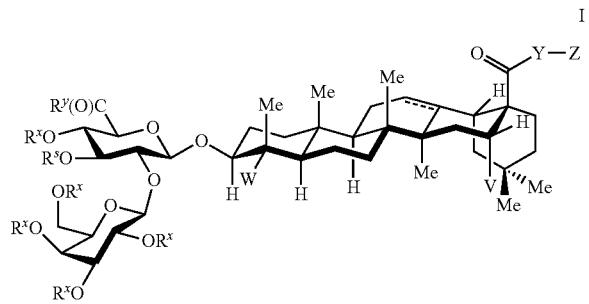

wherein each of ⚌, $R^x$, $R^y$, Z, V, and W is as defined for compounds of formula IV or V, and Y is $CH_2$, —O—, —NR—, or —NH—.

Definitions

As used herein, the following definitions shall apply unless otherwise indicated.

The term "aliphatic" or "aliphatic group," as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-12 aliphatic carbon atoms. In some embodiments, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated," as used herein, means that a moiety has one or more units of unsaturation.

As used herein, the term "bivalent $C_{1-12}$ (or $C_{1-26}$, $C_{1-16}$, $C_{1-8}$) or saturated or unsaturated, straight or branched, hydrocarbon chain," refers to bivalent alkylene, alkenylene, and alkynylene chains that are straight or branched as defined herein.

The term "alkylene" refers to a bivalent alkyl group. An "alkylene chain" is a polymethylene group, i.e., —$(CH_2)_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "alkynylene" refers to a bivalent alkynyl group. A substituted alkynylene chain is a polymethylene group containing at least one double bond in which one or more hydrogen atoms are replaced with a substituent. Suitable substituents include those described below for a substituted aliphatic group.

The term "acyl," used alone or a part of a larger moiety, refers to groups formed by removing a hydroxy group from a carboxylic acid.

The term "halogen" means F, Cl, Br, or I.

The terms "aralkyl" and "arylalkyl" are used interchangeably and refer to alkyl groups in which a hydrogen atom has been replaced with an aryl group. Such groups include, without limitation, benzyl, cinnamyl, and dihydrocinnamyl.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring."

In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The terms "heteroaralkyl" and "heteroarylalkyl" refer to an alkyl group substituted by a heteroaryl moiety, wherein the alkyl and heteroaryl portions independently are optionally substituted.

The term "heteroaliphatic," as used herein, means aliphatic groups wherein one or two carbon atoms are independently replaced by one or more of oxygen, sulfur, nitrogen, or phosphorus. Heteroaliphatic groups may be substituted or unsubstituted, branched or unbranched, cyclic or acyclic, and include "heterocycle," "heterocyclyl," "heterocycloaliphatic," or "heterocyclic" groups.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

In another aspect, the present invention provides "pharmaceutically acceptable" compositions, which comprise a therapeutically effective amount of one or more of the compounds described herein, formulated together with one or more pharmaceutically acceptable carriers (additives) and/or diluents. As described in detail, the pharmaceutical compositions of the present invention may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream or foam; sublingually; ocularly; transdermally; or nasally, pulmonary and to other mucosal surfaces.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

In other cases, the compounds of the present invention may contain one or more acidic functional groups and, thus, are capable of forming pharmaceutically-acceptable salts with pharmaceutically acceptable bases. The term "pharmaceutically acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary, tertiary, or quaternary amine. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate. Representative organic amines useful for the formation of base addition salts include ethylamine, diethylamine, ethylenediamine, ethanolamine, diethanolamine, piperazine and the like. (See, for example, Berge et al., supra).

Unless otherwise stated, structures depicted herein are also meant to include all isomeric (e.g., enantiomeric, diastereomeric, and geometric (or conformational)) forms of the structure; for example, the R and S configurations for each stereocenter, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

Provided compounds may comprise one or more saccharide moieties. Unless otherwise specified, both D- and L-configurations, and mixtures thereof, are within the scope of the invention. Unless otherwise specified, both α- and β-linked embodiments, and mixtures thereof, are contemplated by the present invention.

If, for instance, a particular enantiomer of a compound of the present invention is desired, it may be prepared by asymmetric synthesis, chiral chromatography, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention.

One of ordinary skill in the art will appreciate that the synthetic methods, as described herein, utilize a variety of protecting groups. By the term "protecting group," as used herein, it is meant that a particular functional moiety, e.g., O, S, or N, is masked or blocked, permitting, if desired, a reaction to be carried out selectively at another reactive site in a multifunctional compound. In preferred embodiments, a protecting group reacts selectively in good yield to give a protected substrate that is stable to the projected reactions; the protecting group is preferably selectively removable by readily available, preferably non-toxic reagents that do not attack the other functional groups; the protecting group forms a separable derivative (more preferably without the generation of new stereogenic centers), and the protecting group will preferably have a minimum of additional functionality to avoid further sites of reaction. As detailed herein, oxygen, sulfur, nitrogen, and carbon protecting groups may be utilized. By way of non-limiting example, hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-naphthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N, N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate. Amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10, 10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4, 4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyrrolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9- fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide. Exemplary protecting groups are detailed herein, however, it will be appreciated that the present invention is not intended to be limited to these protecting groups; rather, a variety of additional equivalent protecting groups can be readily identified using the above criteria and utilized in the method of the present invention. Additionally, a variety of protecting groups are described by Greene and Wuts (supra).

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R^\circ$; —$(CH_2)_{0-4}OR^\circ$; —$O(CH_2)_{0-4}R^\circ$, —$O$—$(CH_2)_{0-4}C(O)OR^\circ$; —$(CH_2)_{0-4}CH(OR^\circ)_2$; —$(CH_2)_{0-4}SR^\circ$; —$(CH_2)_{0-4}Ph$, which may be substituted with $R^\circ$; —$(C_2)_{0-4}O(CH_2)_{0-1}Ph$ which may be substituted with $R^\circ$; —$CH$=$CHPh$, which may be substituted with $R^\circ$; —$(CH_2)_{0-4}O(CH_2)_{0-1}$-pyridyl which may be substituted with $R^\circ$; —$NO_2$; —$CN$; —$N_3$; —$(CH_2)_{0-4}N(R^\circ)_2$; —$(CH_2)_{0-4}N(R^\circ)C(O)R^\circ$; —$N(R^\circ)C(S)R^\circ$; —$(CH_2)_{0-4}N(R^\circ)C(O)NR^\circ_2$; —$N(R^\circ)C(S)NR^\circ_2$; —$(CH_2)_{0-4}N(R^\circ)C(O)OR^\circ$; —$N(R^\circ)N(R^\circ)C(O)R^\circ$; —$N(R^\circ)N(R^\circ)C(O)NR^\circ_2$; —$N(R^\circ)N(R^\circ)C(O)OR^\circ$; —$(CH_2)_{0-4}C(O)R^\circ$; —$C(S)R^\circ$; —$(CH_2)_{0-4}C(O)OR^\circ$; —$(CH_2)_{0-4}C(O)SR^\circ$; —$(CH_2)_{0-4}C(O)OSiR^\circ_3$; —$(CH_2)_{0-4}OC(O)R^\circ$; —$OC(O)(CH_2)_{0-4}SR$—, $SC(S)SR^\circ$; —$(CH_2)_{0-4}SC(O)R^\circ$; —$(CH_2)_{0-4}C(O)NR^\circ_2$; —$C(S)NR^\circ_2$; —$C(S)SR^\circ$; —$SC(S)SR^\circ$, —$(CH_2)_{0-4}OC(O)NR^\circ_2$; —$C(O)N(OR^\circ)R^\circ$; —$C(O)C(O)R^\circ$; —$C(O)CH_2C(O)R^\circ$; —$C(NOR^\circ)R^\circ$; —$(CH_2)_{0-4}SSR^\circ$; —$(CH_2)_{0-4}S(O)_2R^\circ$; —$(CH_2)_{0-4}S(O)_2OR^\circ$; —$(CH_2)_{0-4}OS(O)_2R^\circ$; —$S(O)_2NR^\circ_2$; —$(CH_2)_{0-4}S(O)R^\circ$; —$N(R^\circ)S(O)_2NR^\circ_2$; —$N(R^\circ)S(O)_2R^\circ$; —$N(OR^\circ)R^\circ$; —$C(NH)NR^\circ_2$; —$P(O)_2R^\circ$; —$P(O)R^\circ_2$; —$OP(O)R^\circ_2$; —$OP(O)(OR^\circ)_2$; $SiR^\circ_3$; —$(C_{1-4}$ straight or branched alkylene)O—$N(R^\circ)_2$; or —$(C_{1-4}$ straight or branched alkylene)C(O)O—$N(R^\circ)_2$, wherein each $R^\circ$ may be substituted as defined below and is independently hydrogen, $C_{1-6}$ aliphatic, —$CH_2Ph$, —$O(CH_2)_{0-1}Ph$, —$CH_2$-(5-6-membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, —$(CH_2)_{0-2}R^\bullet$, -(haloR$^\bullet$), —$(CH_2)_{0-2}OH$, —$(CH_2)_{0-2}OR^\bullet$, —$(CH_2)_{0-2}CH(OR^\bullet)_2$; —$O(haloR^\bullet)$, —$CN$, —$N_3$, —$(CH_2)_{0-2}C(O)R^\bullet$, —$(CH_2)_{0-2}C(O)OH$, —$(CH_2)_{0-2}C(O)OR^\bullet$, —$(CH_2)_{0-2}SR^\bullet$, —$(CH_2)_{0-2}SH$, —$(CH_2)_{0-2}NH_2$, —$(CH_2)_{0-2}NHR^\bullet$, —$(CH_2)_{0-2}NR^\bullet_2$, —$NO_2$, —$SiR^\bullet_3$, —$OSiR^\bullet_3$, —$C(O)SR^\bullet$, —$(C_{1-4}$ straight or branched alkylene)C(O)OR$^\bullet$, or —$SSR^\bullet$ wherein each $R^\bullet$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —$O(C(R*_2))_{2-3}O$—, or —$S(C(R*_2))_{2-3}S$—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —$O(CR*_2)_{2-3}O$—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet{}_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger{}_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger{}_2$, —C(S)NR$^\dagger{}_2$, —C(NH)NR$^\dagger{}_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur. Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\circ{}_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

The term "enriched" as used herein refers to a mixture having an increased proportion of one or more species. In some embodiments, the mixture is "enriched" following a process that increases the proportion of one or more desired species in the mixture. In some embodiments, the desired species comprise(s) greater than 10% of the mixture. In some embodiments, the desired species comprise(s) greater than 25% of the mixture. In some embodiments, the desired species comprise(s) greater than 40% of the mixture. In some embodiments, the desired species comprise(s) greater than 60% of the mixture. In some embodiments, the desired species comprise(s) greater than 75% of the mixture. In some embodiments, the desired species comprise(s) greater than 85% of the mixture. In some embodiments, the desired species comprise(s) greater than 90% of the mixture. In some embodiments, the desired species comprise(s) greater than 95% of the mixture. Such proportions can be measured any number of ways, for example, as a molar ratio, volume to volume, or weight to weight.

The term "pure" refers to compounds that are substantially free of compounds of related non-target structure or chemical precursors (when chemically synthesized). This quality may be measured or expressed as "purity." In some embodiments, a target compound has less than about 30%, 20%, 10%, 5%, 2%, 1%, 0.5%, and 0.1% of non-target structures or chemical precursors. In certain embodiments, a pure compound of present invention is only one prosapogenin compound (i.e., separation of target prosapogenin from other prosapogenins).

The term "carbohydrate" refers to a sugar or polymer of sugars. The terms "saccharide", "polysaccharide", "carbohydrate", and "oligosaccharide", may be used interchangeably. Most carbohydrates are aldehydes or ketones with many hydroxyl groups, usually one on each carbon atom of the molecule. Carbohydrates generally have the molecular formula $C_nH_{2n}O_n$. A carbohydrate may be a monosaccharide, a disaccharide, trisaccharide, oligosaccharide, or polysaccharide. The most basic carbohydrate is a monosaccharide, such as glucose, sucrose, galactose, mannose, ribose, arabinose, xylose, and fructose. Disaccharides are two joined monosaccharides. Exemplary disaccharides include sucrose, maltose, cellobiose, and lactose. Typically, an oligosaccharide includes between three and six monosaccharide units (e.g., raffinose, stachyose), and polysaccharides include six or more monosaccharide units. Exemplary polysaccharides include starch, glycogen, and cellulose. Carbohydrates may contain modified saccharide units such as 2'-deoxyribose wherein a hydroxyl group is removed, 2'-fluororibose wherein a hydroxyl group is replace with a fluorine, or N-acetylglucosamine, a nitrogen-containing form of glucose. (e.g., 2'-fluororibose, deoxyribose, and hexose). Carbohydrates may exist in many different forms, for example, conformers, cyclic forms, acyclic forms, stereoisomers, tautomers, anomers, and isomers.

BRIEF DESCRIPTION OF THE DRAWINGS

FIG. 2A IgM-GD3 Ab Titers; FIG. 2B IgG-GD3 Ab Titers; and FIG. 2C IgG-KLH Ab Titers. Each value represents median value of five mice (sera tested 7 days after 3$^{rd}$ and 4$^{th}$ vaccination). NQS-21=naturally derived QS-21; SQS-21-Mix=synthetic QS-21.

FIGS. 15a-b are high-performance liquid chromatography traces of a 1:1 mixture of natural and semisynthetic QS-7-Api.

DETAILED DESCRIPTION OF CERTAIN EMBODIMENTS

Figure 1A:
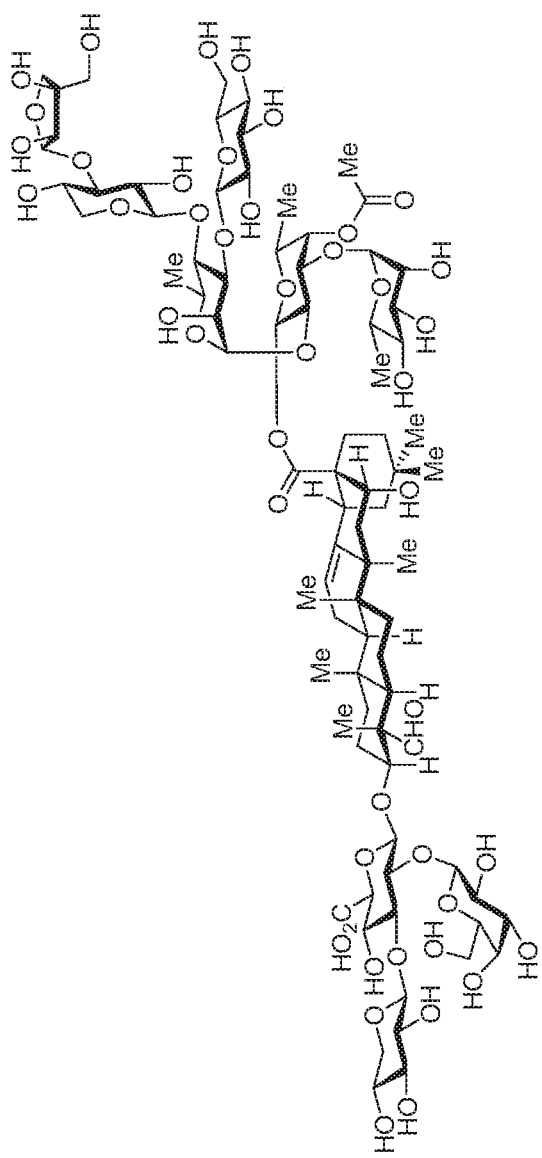
FIG. 1a depicts the chemical structure of QS-7-Api.

The clinical success of anticancer and antimicrobial vaccines critically depends on the identification of, and access to, novel potent adjuvants with attenuated toxicity. In this context, specific fractions from extracts of the bark of *Quillaja saponaria* (QS) have proven to be exceedingly powerful adjuvants in immunotherapy. The QS-21 fraction (Kensil, C. R.; Patel, U.; Lennick, M.; Marciani, D. *J. Immunol.* 1991, 146, 431-437), comprising isomeric forms of a complex triterpene glycoside saponin (Soltysik, S.; Wu, J. Y.; Recchia, J.; Wheeler, D. A.; Newman, M. J.; Coughlin, R. T.; Kensil, C. R. *Vaccine* 1995, 13, 1403-1410; Kensil, C. R. *Crit. Rev. Ther. Drug Carrier Syst.* 1996, 13, 1-55), is currently the most promising immuno-potentiator (Kim, S. K.; Ragupathi, G.; Musselli, C.; Choi, S. J.; Park, Y. S.; Livingston, P. O. *Vaccine* 2000, 18, 597-603) in several antitumor (melanoma, breast, small cell lung cancer, prostate) (Livingston, P. O.; Ragupathi, G. *Hum. Vaccines* 2006, 2, 137-143) and infectious-disease (HIV, malaria) vaccine therapies (Sasaki, S.; Sumino, K.; Hamajima, K.; Fukushima, J.; Ishii, N.; Kawamoto, S.; Mohri, H.; Kensil, C. R.; Okuda, K. *J. Virol.* 1998, 72, 4931-4939; Evans, T. G., et al. *Vaccine* 2001, 19, 2080-2091; Kashala, O., et al. *Vaccine* 2002, 20, 2263-2277; Carcaboso, A. M.; Hernandez, R. M.; Igartua, M.; Rosas, J. E.; Patarroyo, M. E.; Pedraz, J. L. *Vaccine* 2004, 22, 1423-1432). However, the tolerated dose of QS-21 in cancer patients typically does not exceed 100 µg, above which significant local erythema and systemic flu-like symptoms arise. On the other hand, QS-7, another QS extract fraction, was found not only to possess significant stand-alone adjuvant activity (Kensil, 1991; Kensil, 1998, supra), but also to induce remarkable synergistic immune response augmentation (Kensil, C. A., U.S. Pat. No. 6,231,859) when co-administered with QS-21, allowing for the administration of less QS-21. Importantly, QS-7, unlike QS-21, exhibited negligible toxicity in mice. The present invention provides an efficient semi-synthetic method of synthesizing analogs of QS-7 and QS-21, thereby significantly reducing the number of synthetic steps required to access this potent class of adjuvants.

Compounds

Compounds of this invention include those described generally above, and are further illustrated by the classes, subclasses, and species disclosed herein. In some embodiments, provided compounds are analogs of naturally occurring triterpene glycoside saponins and intermediates thereto. For purposes of this invention, the chemical elements are identified in accordance with the Periodic Table of the Elements, CAS version, *Handbook of Chemistry and Physics*, 75th Ed. Additionally, general principles of organic chemistry are described in *Organic Chemistry*, Thomas Sorrell, University Science Books, Sausalito: 1999, and *March's Advanced Organic Chemistry*, 5th Ed., Ed.: Smith, M. B. and March, J., John Wiley & Sons, New York: 2001, the entire contents of which are hereby incorporated by reference.

Description of Exemplary Compounds

In some embodiments, provided compounds are analogs of *Quillaja saponins*. In some embodiments, provided compounds are prosapogenins. In certain embodiments, provided compounds are analogs of QS-7 and QS-21 and possess potent adjuvant activity.

In certain embodiments, the present invention provides a compound of formula I:

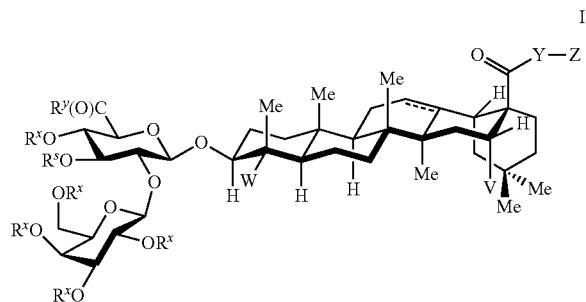

I or a pharmaceutically acceptable salt thereof, wherein:
═══ is a single or double bond,
W is Me, —CHO,

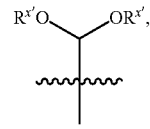

—CH$_2$OR$^x$, or —C(O)R$^y$;
V is hydrogen or —OR$^x$,
Y is CH$_2$, —O—, —NR—, or —NH—
Z is hydrogen; a cyclic or acyclic, optionally substituted moiety selected from the group consisting of acyl, aliphatic, heteroaliphatic, aryl, arylalkyl, and heteroaryl; or a carbohydrate domain having the structure:

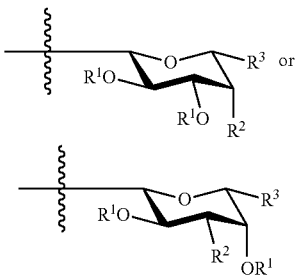

wherein:
each occurrence of R$^1$ is R$^x$ or a carbohydrate domain having the structure:

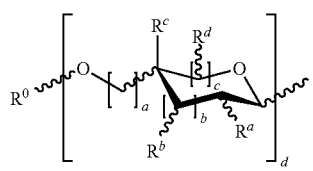

wherein:
each occurrence of a, b, and c is independently 0, 1, or 2;
d is an integer from 1-5, wherein each d bracketed structure may be the same or different; with the proviso that the d bracketed structure represents a furanose or pyranose moiety, and the sum of b and c is 1 or 2;

$R^0$ is hydrogen, an oxygen protecting group selected from the group consisting of alkyl ethers, benzyl ethers, silyl ethers, acetals, ketals, esters, carbamates, and carbonates; or an optionally substituted moiety selected from the group consisting of acyl, $C_{1-10}$ aliphatic, $C_{1-6}$ heteroaliphatic, 6-10-membered aryl, arylalkyl, 5-10-membered heteroaryl having 1-4 heteroatoms independently selected from nitrogen, oxygen, or sulfur, 4-7-membered heterocyclyl having 1-2 heteroatoms independently selected from the group consisting of nitrogen, oxygen, and sulfur;

each occurrence of $R^a$, $R^b$, $R^c$, and $R^d$ is independently hydrogen, halogen, OH, OR, $OR^x$, $NR_2$, NHCOR, or an optionally substituted group selected from acyl, $C_{1-10}$ aliphatic, $C_{1-6}$ heteroaliphatic, 6-10-membered aryl, arylalkyl, 5-10-membered heteroaryl having 1-4 heteroatoms independently selected from nitrogen, oxygen, or sulfur; 4-7-membered heterocyclyl having 1-2 heteroatoms independently selected from the group consisting of nitrogen, oxygen, and sulfur;

$R^2$ is hydrogen, halogen, OH, OR, $OR^1$, $OC(O)R^4$, $OC(O)OR^4$, $OC(O)NHR^4$, $OC(O)NRR^4$, $OC(O)SR^4$, $NHC(O)R^4$, $NRC(O)R^4$, $NHC(O)OR^4$, $NHC(O)NHR^4$, $NHC(O)NRR^4$, $N(R^4)_2$, $NHR^4$, $NRR^4$, $N_3$, or an optionally substituted group selected from $C_{1-10}$ aliphatic, $C_{1-6}$ heteroaliphatic, 6-10-membered aryl, arylalkyl, 5-10-membered heteroaryl having 1-4 heteroatoms independently selected from the group consisting of nitrogen, oxygen, and sulfur, 4-7-membered heterocyclyl having 1-2 heteroatoms independently selected from the group consisting of nitrogen, oxygen, and sulfur;

$R^3$ is hydrogen, halogen, $CH_2OR^1$, or an optionally substituted group selected from the group consisting of acyl, $C_{1-10}$ aliphatic, $C_{1-6}$ heteroaliphatic, 6-10-membered aryl, arylalkyl, 5-10-membered heteroaryl having 1-4 heteroatoms independently selected from the group consisting of nitrogen, oxygen, and sulfur; 4-7-membered heterocyclyl having 1-2 heteroatoms independently selected from the group consisting of nitrogen, oxygen, and sulfur;

$R^4$ is

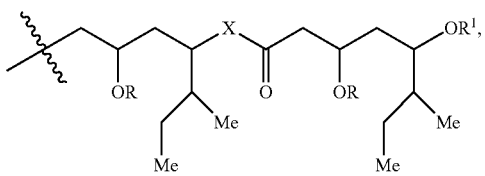

wherein X is —O— or —NR—; or

T-$R^7$, wherein:

T is a covalent bond or a bivalent $C_{1-26}$ saturated or unsaturated, straight or branched, aliphatic or heteroaliphatic chain; and $R^z$ is hydrogen, halogen, —OR, —$OR^x$, —$OR^1$, —SR, —$NR_2$, —NC(O)OR, or an optionally substituted group selected from acyl, arylalkyl, heteroarylalkyl, $C_{1-6}$ aliphatic, 6-10-membered aryl, 5-10-membered heteroaryl having 1-4 heteroatoms independently selected from nitrogen, oxygen, or sulfur, 4-7-membered heterocyclyl having 1-2 heteroatoms independently selected from the group consisting of nitrogen, oxygen and sulfur; or two $R^4$ on the same nitrogen atom are taken with the nitrogen to form a 4-7-membered heterocyclic ring having 1-2 heteroatoms independently selected from the group consisting of nitrogen, oxygen, and sulfur each occurrence of $R^x$ is independently hydrogen or an oxygen protecting group selected from the group consisting of alkyl ethers, benzyl ethers, silyl ethers, acetals, ketals, esters, carbamates, and carbonates.

$R^y$ is —OH, or a carboxyl protecting group selected from the group consisting of esters, amides, and hydrazides;

$R^s$ is

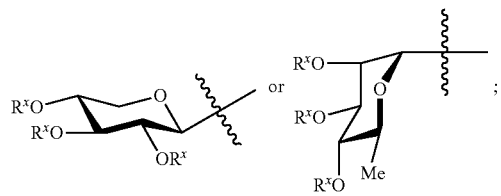

each occurrence of $R^{x'}$ is independently an optionally substituted group selected from 6-10-membered aryl, $C_{1-6}$ aliphatic, or $C_{1-6}$ heteroaliphatic having 1-2 heteroatoms independently selected from the group consisting of nitrogen, oxygen, and sulfur; or:

two $R^{x'}$ are taken together to form a 5-7-membered heterocyclic ring having 1-2 heteroatoms independently selected from the group consisting of nitrogen, oxygen, and sulfur;

each occurrence of R is independently hydrogen, an optionally substituted group selected from acyl, arylalkyl, 6-10-membered aryl, $C_{1-12}$ aliphatic, or $C_{1-12}$ heteroaliphatic having 1-2 heteroatoms independently selected from the group consisting of nitrogen, oxygen, and sulfur; or: two R on the same nitrogen atom are taken with the nitrogen to form a 4-7-membered heterocyclic ring having 1-2 heteroatoms independently selected from the group consisting of nitrogen, oxygen, and sulfur.

As defined above, W is Me, —CHO,

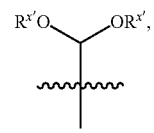

—$CH_2OR^x$, or —$C(O)OR^y$. In certain embodiments, W is methyl. In other embodiments, W is —CHO. In certain embodiments, W is —$CH_2OR^x$. In other embodiments, W is —$C(O)OR^y$. In some embodiments, W is —$CH_2OH$. In other embodiments, W is —$CH_2OBn$. In other embodiments, W is —$CH_2OSiEt_3$. In certain embodiments, W is —C(O)OH. In other embodiments, W is —C(O)OBn.

In certain embodiments, V is —$OR^x$. In some embodiments, V is —OH. In some embodiments, V is hydrogen.

As defined above, ⁓ represents a single or double bond. It will be appreciated that compounds of formula I can be subjected to hydrogenation conditions (infra) that reduce the double bond to a single bond.

As defined above, Y is $CH_2$, —O—, —NR—, or —NH—. In certain embodiments, Y is $CH_2$. In certain embodiments, Y is —O—. In other embodiments, Y is —NR—. In some embodiments, Y is —NH—.

In certain embodiments, Z is hydrogen; a cyclic or acyclic, optionally substituted moiety selected from the group consisting of acyl, aliphatic, heteroaliphatic, aryl, arylalkyl, heterocyclyl, and heteroaryl.

In some embodiments, Z comprises a carbohydrate. In some embodiments, Z is not hydrogen. In other embodiments, Z is acyl.

In some embodiments, a Z comprises a linker group that separates a carbohydrate from Y. In some embodiments, the linker group is an optionally substituted, straight or branched $C_{1-12}$ aliphatic or heteroaliphatic group. In some embodiments, the linker group is —$(CH_2)_k$—, wherein k is an integer between 1 and 10, inclusive.

In some embodiments, Z is an optionally substituted aliphatic group. In some embodiments, Z is an optionally substituted $C_{1-30}$ aliphatic group. In some embodiments, Z is an optionally substituted $C_{1-20}$ aliphatic group. In some embodiments, Z is an optionally substituted $C_{1-16}$ aliphatic group. In some embodiments, Z is an optionally substituted $C_{1-12}$ aliphatic group. In some embodiments, Z is an optionally substituted $C_{1-10}$ aliphatic group. In some embodiments, Z is an optionally substituted $C_{1-6}$ aliphatic group. In some embodiments, Z is an optionally substituted $C_{2-12}$ aliphatic group.

In some embodiments, Z is an optionally substituted heteroaliphatic group. In some embodiments, Z is an optionally substituted $C_{1-30}$ heteroaliphatic group. In some embodiments, Z is an optionally substituted $C_{1-20}$ heteroaliphatic group. In some embodiments, Z is an optionally substituted $C_{1-16}$ heteroaliphatic group. In some embodiments, Z is an optionally substituted $C_{1-12}$ heteroaliphatic group. In some embodiments, Z is an optionally substituted $C_{1-10}$ heteroaliphatic group. In some embodiments, Z is an optionally substituted $C_{1-6}$ heteroaliphatic group. In some embodiments, Z is an optionally substituted $C_{2-12}$ heteroaliphatic group.

In certain embodiments, Z is an optionally substituted heteroaryl group having 1-4 heteroatoms independently selected from nitrogen, oxygen, or sulfur. In certain embodiments, Z is an optionally substituted 5-12-membered heteroaryl group. In certain embodiments, Z is an optionally substituted 5-10-membered heteroaryl group. In certain embodiments, Z is an optionally substituted 6-8-membered heteroaryl group.

In certain embodiments, Z is an optionally substituted aryl group. In certain embodiments, Z is an optionally substituted 6-12-membered aryl group. In certain embodiments, Z is an optionally substituted 6-10-membered aryl group. In certain embodiments, Z is an optionally substituted 6-8-membered aryl group.

In some embodiments, Z is an optionally substituted heterocyclyl group. In certain embodiments, Z is an optionally substituted 4-7-membered heterocyclyl group having 1-2 heteroatoms independently selected from the group consisting of nitrogen, oxygen, and sulfur.

In some embodiments, Z is an optionally substituted arylalkyl group. In some embodiments, Z is an optionally substituted $C_{7-12}$ arylalkyl group. In some embodiments, Z is an optionally substituted $C_{7-10}$ arylalkyl group. In some embodiments, Z is an optionally substituted $C_{7-8}$ arylalkyl group.

In some embodiments, Z is a monosaccharide. In some embodiments, Z is an oligosaccharide. In certain embodiments, Z is a carbohydrate domain having the structure:

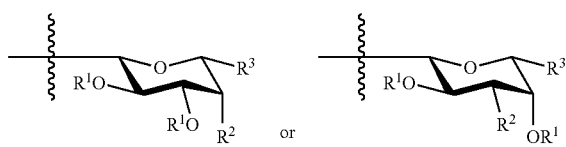

wherein each of $R^1$, $R^2$, and $R^3$ is defined as described in classes and subclasses above and herein.

In certain embodiments, Z has the structure:

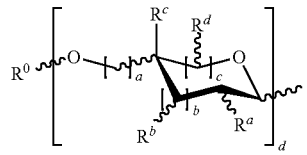

wherein each of $R^0$, $R^a$, $R^b$, $R^c$, $R^d$, a, b, c, and d is defined as described in classes and subclasses above and herein.

As described above, the Z moiety is linked to the triterpene core via Y. In some embodiments, Z is a monosaccharide and is D-fucosyl. In some embodiments, Z is a monosaccharide and is L-fucosyl. In some embodiments, Z is a monosaccharide and is not fucosyl. In some embodiments, Z is a monosaccharide and is not β-D-fucosyl.

In some embodiments, Z is an oligosaccharide, and the carbohydrate domain directly attached to Y is fucosyl. In some embodiments, Z is an oligosaccharide, and the carbohydrate domain directly attached to Y is not D-fucosyl. In some embodiments, Z is an oligosaccharide, and the carbohydrate domain directly attached to Y is not β-D-fucosyl. In some embodiments, Z is an oligosaccharide, and the carbohydrate domain directly attached to Y is not α-D-fucosyl. In some embodiments, Z is an oligosaccharide, and the carbohydrate domain directly attached to Y is not fucosyl.

In some embodiments, Z is an optionally substituted monosaccharide and is D-fucosyl. In some embodiments, Z is an optionally substituted monosaccharide and is L-fucosyl. In some embodiments, Z is an optionally substituted monosaccharide and is not β-D-fucosyl. In some embodiments, when a carbohydrate domain of Z is directly attached to Y, the carbohydrate domain directly attached to Y is not fucosyl. In certain embodiments, when Y—Z is —OH, —OMe, or —Oallyl, at least seven $R^x$ groups are silyl ethers. In some embodiments, Z and $R^x$ are not all simulataneously hydrogen or methyl. In some embodiments, Y—Z is not —OMe. In some embodiments, Y—Z is not —OH. In some embodiments, Y—Z is not —Oallyl. In some embodiments, Y—Z is not —OH or —OMe if all $R^x$ groups are simultaneously hydrogen or if at least four $R^x$ groups are simultaneously methyl.

In some embodiments, $R^y$ is not a lipophilic group. In some embodiments, when a carbohydrate moiety of Z is non-acylated and all $R^x$ are simulataneously hydrogen, the 3-O-glucuronic acid residue of the triterpene is not covalently attached, directly or indirectly, to a compound having a lipophilic domain, wherein the lipophilic domain is attached via the carboxylic acid carbon atom present on the 3-O-glucuronic acid residue.

In certain embodiments, each occurrence of $R^y$ is independently —OH. In certain embodiments, each occurrence of $R^y$ is independently —OR. In certain embodiments, each occurrence of $R^y$ is independently a carboxyl protecting group. Suitable carboxyl protecting groups are well known in the art and include those described in detail in *Protecting Groups in Organic Synthesis*, T. W. Greene and P. G. M. Wuts, 3rd edition, John Wiley & Sons, 1999, the entirety of which is incorporated herein by reference.

In some embodiments, each occurrence of $R^y$, when taken with its attached carbonyl group, independently comprises an ester. In some embodiments, each occurrence of $R^y$, when taken with its attached carbonyl group, independently comprises an amide. In some embodiments, each occurrence of $R^y$, when taken with its attached carbonyl group, independently comprises a hydrazide.

In some embodiments, each occurrence of $R^y$ is independently —OBn. In other embodiments, each occurrence of $R^y$ is independently —OEt.

In certain embodiments, each occurrence of $R^x$ is independently hydrogen. In certain embodiments, each occurrence of $R^x$ is independently a suitable hydroxyl protecting group. Suitable hydroxyl protecting groups are well known in the art and include those described herein and by Greene (supra). In some embodiments, no more than four $R^x$ groups are simultaneously methyl.

In some embodiments, $R^s$ is

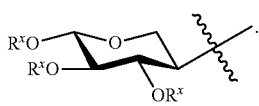

In some embodiments, $R^s$ is

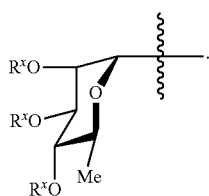

In some embodiments, $R^{s1}$ is

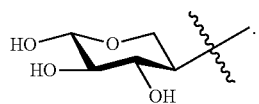

In some embodiments, $R^{s1}$ is

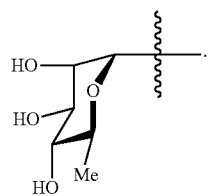

In some embodiments, each occurrence of $R^x$, when taken with its attached oxygen atom, independently comprises a methyl ether, ethyl ether, benzyl ether, silyl ether, ester, acetal, ketal, or carbonate. In some embodiments, $R^x$ comprises a methyl ether. In some embodiments, $R^x$ comprises a ethyl ether. In some embodiments, $R^x$ comprises a benzyl ether. In some embodiments, $R^x$ comprises a silyl ether. In some embodiments, $R^x$ comprises an ester. In some embodiments, $R^x$ comprises an acetal. In some embodiments, $R^x$ comprises a ketal. In some embodiments, $R^x$ comprises a carbonate.

In certain embodiments, $R^x$ is methyl. In certain embodiments, $R^x$ is ethyl. In certain embodiments, $R^x$ is benzyl. In certain embodiments, $R^x$ is $SiR_3$. In certain embodiments, $R^x$ is $SiMe_3$. In certain embodiments, $R^x$ is TBS.

In certain embodiments, $R^x$ is

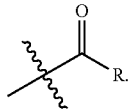

In certain embodiments, $R^x$ is

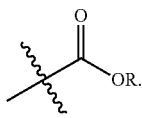

In certain embodiments, $R^x$ is

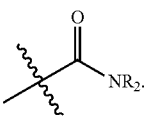

In some embodiments, two —$OR^x$ attached to adjacent carbon atoms on a saccharide ring are taken together to form a 5-7-membered heterocyclic ring having 1-2 heteroatoms independently selected from the group consisting of nitrogen, oxygen, and sulfur. In some embodiments, two —$OR^x$ attached to adjacent carbon atoms on a saccharide ring are taken together to form a cyclic acetal protecting group. In some embodiments, two —$OR^x$ attached to adjacent carbon atoms on a saccharide ring are taken together to form a cyclic ketal protecting group.

In certain embodiments, each $R^{x'}$ is independently hydrogen. In certain embodiments, each $R^{x'}$ is independently an optionally substituted 6-10-membered aryl group. In certain embodiments, each $R^{x'}$ is independently an optionally substituted $C_{1-6}$ aliphatic group. In certain embodiments, each $R^{x'}$ is independently an optionally substituted $C_{1-6}$ heteroaliphatic group having 1-2 heteroatoms independently selected from the group consisting of nitrogen, oxygen, and sulfur. In some embodiments, two $R^{x'}$ are taken together to form a 5-7-membered heterocyclic ring having 1-2 heteroatoms independently selected from the group consisting of nitrogen, oxygen, and sulfur.

In some embodiments, all $R^x$ are hydrogen.

In certain embodiments, $R^1$ is a carbohydrate domain having the structure:

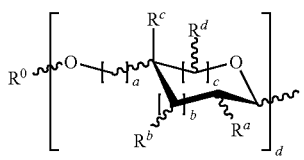

wherein each of $R^0$, $R^a$, $R^b$, $R^c$, $R^d$, a, b, c, and d is defined as described in classes and subclasses above and herein.

In some embodiments, a is 0. In some embodiments, a is 1.

In some embodiments, b is 0. In some embodiments, b is 1. In some embodiments, b is 2.

In some embodiments, c is 0. In some embodiments, c is 1. In some embodiments, c is 2.

In certain embodiments, the sum of b and c is 1. In certain embodiments, the sum of b and c is 2.

In certain embodiments, d is an integer from 1-7. In some embodiments, d is an integer from 1-5. In some embodiments, d is an integer from 1-4. In some embodiments, d is an integer from 1-2.

In certain embodiments, each d-bracketed structure is the same. In certain embodiments, each d-bracketed structure is different. In certain embodiments, two or more d-bracketed structures are the same.

In some embodiments, one or more d-bracketed structures is a furanose moiety. In some embodiments, one or more d-bracketed structure is a pyranose moiety.

In some embodiments, $R^0$ is hydrogen. In some embodiments, $R^0$ is an oxygen protecting group selected from the group consisting of alkyl ethers, benzyl ethers, silyl ethers, acetals, ketals, esters, carbamates, and carbonates. In other embodiments, $R^0$ is an optionally substituted moiety selected from the group consisting of acyl and $C_{1-10}$ aliphatic.

In some embodiments, each occurrence of $R^a$, $R^b$, $R^c$, and $R^d$ is hydrogen. In some embodiments, each occurrence of $R^a$, $R^b$, $R^c$, and $R^d$ is —OH. In some embodiments, each occurrence of $R^a$, $R^b$, $R^c$, and $R^d$ is independently —OR. In some embodiments, each occurrence of $R^a$, $R^b$, $R^c$, and $R^d$ is independently —$OR^x$. In some embodiments, each occurrence of $R^a$, $R^b$, $R^c$, and $R^d$ is independently an optionally substituted $C_{1-10}$ aliphatic group. In some embodiments, each occurrence of $R^a$, $R^b$, $R^c$, and $R^d$ is independently an optionally substituted $C_{1-6}$ heteroaliphatic group.

In some embodiments, each occurrence of $R^a$, $R^b$, $R^c$, and $R^d$ is —$CH_2OH$. In some embodiments, each occurrence of $R^a$, $R^b$, $R^c$, and $R^d$ is methyl.

As generally described above, in certain embodiments, $R^1$ is a carbohydrate domain. In some embodiments, $R^1$ is a monosaccharide. In some embodiments, $R^1$ is an oligosaccharide. In certain embodiments, each occurrence of $R^1$ is independently selected from the group consisting of:

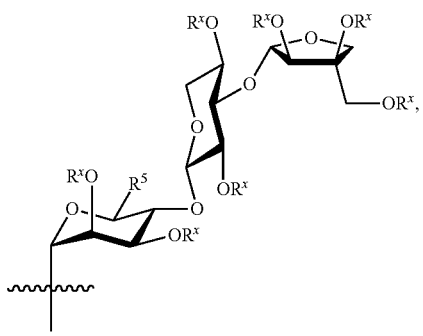

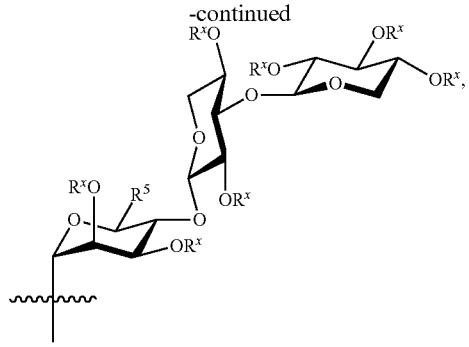

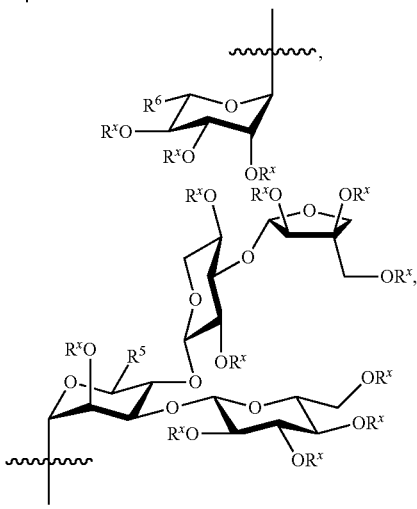

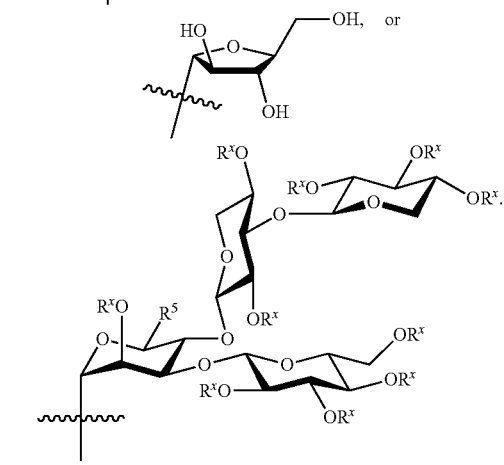

In certain embodiments, $R^2$ is hydrogen. In certain embodiments, $R^2$ is halogen. In certain embodiments, $R^2$ is —OH. In certain embodiments, $R^2$ is OR. In certain embodiments, $R^2$ is —$OC(O)R^4$. In certain embodiments, $R^2$ is —$OC(O)OR^4$. In certain embodiments, $R^2$ is —$OC(O)NHR^4$. In certain embodiments, $R^2$ is —$OC(O)NRR^4$. In certain embodiments, $R^2$ is —$OC(O)SR^4$. In certain embodiments, $R^2$ is —$NHC(O)R^4$. In certain embodiments, $R^2$ is —$NRC(O)R^4$. In certain embodiments, $R^2$ is —$NHC(O)OR^4$. In certain embodiments, $R^2$ is —$NHC(O)NHR^4$. In certain embodiments, $R^2$ is —$NHC(O)NRR^4$. In certain embodiments, $R^2$ is —$N(R^4)_2$. In certain embodiments, $R^2$ is —$NHR^4$. In certain embodiments, $R^2$ is —$NRR^4$. In some embodiments, $R^2$ is $N_3$.

In some embodiments, $R^2$ is an optionally substituted group selected from $C_{1-30}$ aliphatic. In some embodiments, $R^2$ is an optionally substituted group selected from $C_{1-20}$ aliphatic. In some embodiments, $R^2$ is an optionally substituted group selected from $C_{1-10}$ aliphatic.

In some embodiments, $R^2$ is an optionally substituted group selected from $C_{1-30}$ heteroaliphatic. In some embodiments, $R^2$ is an optionally substituted group selected from $C_{1-20}$ heteroaliphatic. In some embodiments, $R^2$ is an optionally substituted group selected from $C_{1-10}$ heteroaliphatic. In some embodiments, $R^2$ is an optionally substituted group selected from $C_{1-6}$ heteroaliphatic.

In some embodiments, $R^3$ is hydrogen. In some embodiments, $R^3$ is halogen. In some embodiments, $R^3$ is —OH. In some embodiments, $R^3$ is —OR. In some embodiments, $R^3$ is —OR$^x$. In some embodiments, $R^3$ is an optionally substituted $C_{1-10}$ aliphatic group. In some embodiments, $R^3$ is an optionally substituted $C_{1-6}$ heteroaliphatic group. In some embodiments, $R^3$ is not hydrogen. In some embodiments, $R^3$ is not —OH.

In some embodiments, $R^3$ is —CH$_2$OR. In some embodiments, $R^3$ is —CH$_2$OH. In some embodiments, $R^3$ is methyl. In some embodiments, $R^3$ is not methyl. In some embodiments, $R^3$ is CH$_2$OR$^1$.

In some embodiments, $R^4$ is

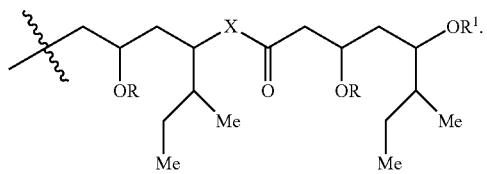

In some embodiments, X is —O—. In some embodiments, X is —NR—. In some embodiments, $R^4$ is

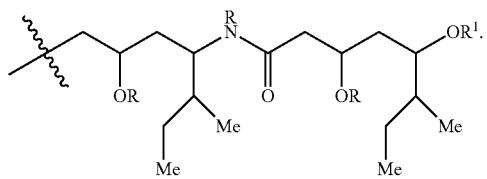

In some embodiments, $R^4$ is

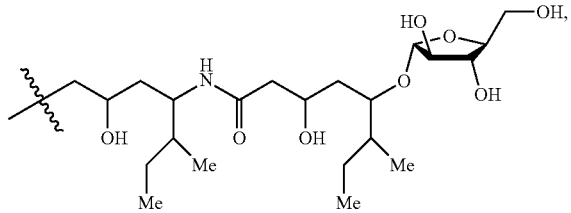

In some embodiments, $R^4$ is

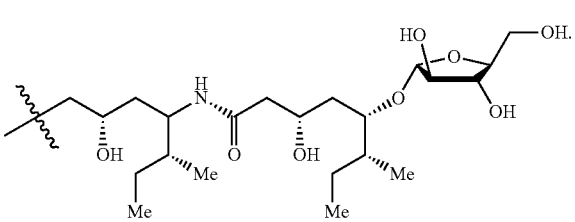

In certain embodiments, $R^2$ is —NHC(O)R$^4$; and $R^4$ is

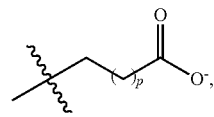

wherein p is an integer from 0 to 12, inclusive. In certain embodiments, $R^2$ is —NHC(O)R$^4$; and $R^4$ is

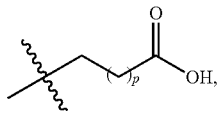

wherein p is an integer from 0 to 12, inclusive. In certain embodiments, $R^2$ is —NHC(O)R$^4$; and $R^4$ is

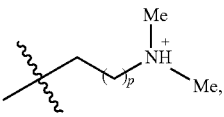

wherein p is an integer from 0 to 12, inclusive. In certain embodiments, $R^2$ is —NHC(O)R$^4$; and $R^4$ is

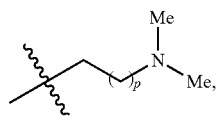

wherein p is an integer from 0 to 12, inclusive. In certain embodiments, $R^2$ is —NHC(O)R$^4$; and $R^4$ is

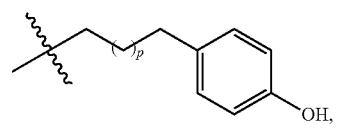

wherein p is an integer from 0 to 12, inclusive. In certain embodiments, $R^2$ is —NHC(O)R$^4$; and $R^4$ is

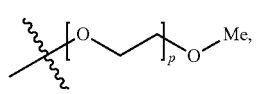

wherein p is an integer from 1 to 12, inclusive. In certain embodiments, $R^2$ is —NHC(O)R$^4$; and $R^4$ is

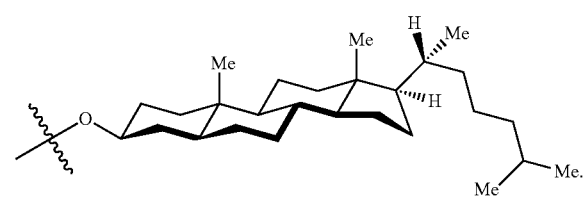

In certain embodiments, two $R^4$ on the same nitrogen atom are taken with the nitrogen to form a 4-7-membered heterocyclic ring having 1-2 heteroatoms independently selected from the group consisting of nitrogen, oxygen, and sulfur.

As described above, in certain embodiments, $R^4$ is $T-R^z$. In some embodiments, T is a covalent bond or a bivalent $C_{1-26}$ saturated or unsaturated, straight or branched, hydrocarbon chain, wherein one or two methylene units of T are optionally and independently replaced by —O—, —S—, —N(R)—, —C(O)—, —C(O)O—, —OC(O)—, —N(R)C(O)—, —C(O)N(R)—, —S(O), —S(O)$_2$—, —N(R)SO$_2$—, or —SO$_2$N(R)—. In certain embodiments, T is a covalent bond or a bivalent $C_{1-16}$ saturated or unsaturated, straight or branched, aliphatic or heteroaliphatic chain. In certain embodiments, T is a covalent bond or a bivalent $C_{1-12}$ saturated or unsaturated, straight or branched, aliphatic or heteroaliphatic chain. In certain embodiments, T is a covalent bond or a bivalent $C_{1-8}$ saturated or unsaturated, straight or branched, aliphatic or heteroaliphatic chain.

In certain embodiments, -T- is selected from the group consisting of

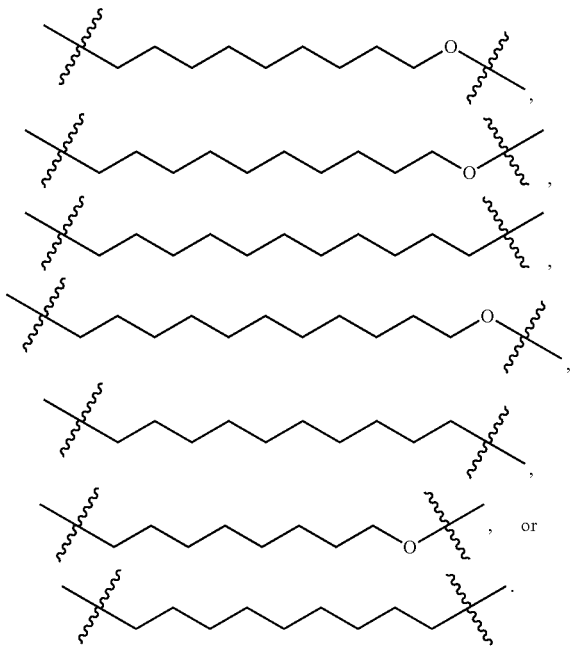

In some embodiments, $R^z$ is hydrogen. In some embodiments, $R^z$ is halogen. In certain embodiments, $R^z$ is —NC(O)OR. In some embodiments, $R^z$ is —OR. In some embodiments, $R^z$ is —OR$^x$. In some embodiments, $R^z$ is —OR$^1$. In some embodiments, $R^z$ is —NR$_2$. In certain embodiments, R is an optionally substituted acyl group. In certain embodiments, $R^z$ is an optionally substituted arylalkyl group. In certain embodiments, $R^z$ is an optionally substituted heteroarylalkyl group. In certain embodiments, $R^z$ is an optionally substituted $C_{1-6}$ aliphatic group. In certain embodiments, $R^z$ is an optionally substituted 6-10-membered aryl group. In certain embodiments, $R^z$ is an optionally substituted 5-10-membered heteroaryl having 1-4 heteroatoms independently selected from nitrogen, oxygen, or sulfur group. In certain embodiments, $R^z$ is an optionally substituted 4-7-membered heterocyclyl having 1-2 heteroatoms independently selected from the group consisting of nitrogen, oxygen and sulfur.

In certain embodiments, $R^z$ is a monosaccharide. In certain embodiments, $R^z$ is an oligosaccharide.

In certain embodiments, $R^z$ is methyl. In certain embodiments, $R^z$ is

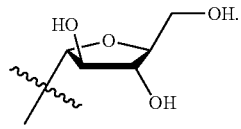

In certain embodiments, $R^z$ is

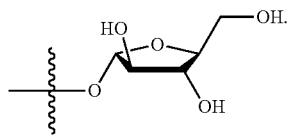

In some embodiments, each occurrence of R is independently hydrogen. In some embodiments, each occurrence of R is independently an optionally substituted acyl group. In some embodiments, each occurrence of R is independently an optionally substituted arylalkyl group. In some embodiments, each occurrence of R is independently an optionally substituted $C_{7-12}$ arylalkyl group. In some embodiments, each occurrence of R is independently an optionally substituted 6-10-membered aryl group. In some embodiments, each occurrence of R is independently an optionally substituted $C_{1-12}$ aliphatic group. In some embodiments, each occurrence of R is independently an optionally substituted $C_{1-6}$ aliphatic group. In some embodiments, each occurrence of R is independently an optionally substituted $C_{1-6}$ heteroaliphatic group having 1-2 heteroatoms independently selected from the group consisting of nitrogen, oxygen, and sulfur. In some embodiments, two R on the same nitrogen atom are taken with the nitrogen to form a 4-7-membered heterocyclic ring having 1-2 heteroatoms independently selected from the group consisting of nitrogen, oxygen, and sulfur.

In certain embodiments, $R^5$ and $R^6$ are independently hydrogen, an optionally substituted group selected from the group consisting of acyl, $C_{1-10}$ aliphatic, $C_{1-6}$ heteroaliphatic, 6-10-membered aryl, arylalkyl, 5-10-membered heteroaryl having 1-4 heteroatoms independently selected from the group consisting of nitrogen, oxygen, and sulfur; 4-7-membered heterocyclyl having 1-2 heteroatoms independently selected from the group consisting of nitrogen, oxygen, and sulfur. In certain embodiments, $R^5$ and $R^6$ are independently hydrogen. In certain embodiments, $R^5$ and $R^6$ are independently —OH. In certain embodiments, $R^1$ and $R^6$ are independently —OR. In certain embodiments, $R^5$ and $R^6$ are independently —OR$^x$. In certain embodiments, $R^5$ and $R^6$ are independently an optionally substituted $C_{1-10}$ aliphatic group. In certain embodiments, $R^5$ and $R^6$ are independently an optionally substituted $C_{1-6}$ heteroaliphatic group.

In some embodiments, $R^5$ and $R^6$ are independently —CH$_2$OR. In some embodiments, $R^5$ and $R^6$ are independently CH$_2$OH. In some embodiments, $R^5$ and $R^6$ are independently methyl.

In some embodiments, each of $R^3$, $R^5$, and $R^6$ is independently an optionally substituted $C_{1-10}$ aliphatic group. In some embodiments, each of $R^3$, $R^5$, and $R^6$ is independently methyl. In some embodiments, each of $R^3$, $R^5$, and $R^6$ is independently —CH$_2$OR. In some embodiments, one or more of R$^3$, R$^5$, and R$^6$ is —CH$_2$OH. In some embodiments, each of R$^3$, R$^5$, and R$^6$ is —CH$_2$OH.

As described in further detail below, some materials used in the synthesis of compounds of formula I may be commerically available extracts derived from natural sources as mixtures of saponins. Such extracts may contain saccharide moieties attached to the C3-position of the triterpene that differ from those depicted in formula I. Examples of saponins and prosapogenins that may be used according to the present invention include those derived from Glycyrrhizic acid, Hederasaponin C, β-Aescin, Helianthoside 2, Ginsenoside Rd, and Saponinum album, to name but a few. All naturally-derived glycosylation variants of the C3 position of the triterpene core are contemplated by the present invention.

In some embodiments, R$^s$ of formula I is a xylose moiety, thereby providing a compound of formula VII-a:

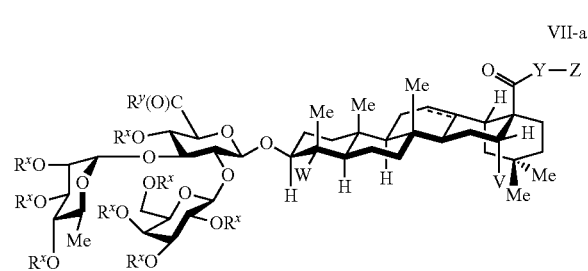

VII-a wherein each of R$^x$, R$^y$, W, V, Y and Z is defined as described in classes and subclasses above and herein.

In some embodiments, R$^s$ of formula I is a rhamnose moiety, thereby providing a compound of formula VII-b:

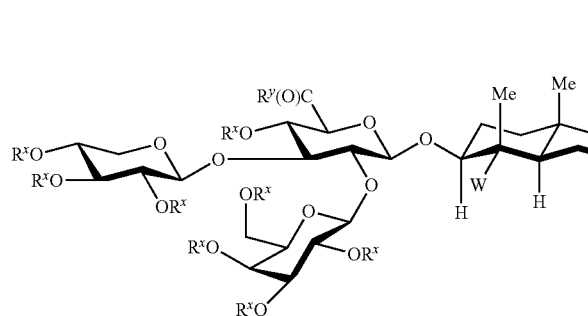

VII-b wherein each of R$^x$, R$^y$, W, V, Y and Z is defined as described in classes and subclasses above and herein.

In some embodiments, the triterpene core of formula I bears a monosaccharide at position C3. In some embodiments, a monosaccharide-substituted compound is of formula VIII:

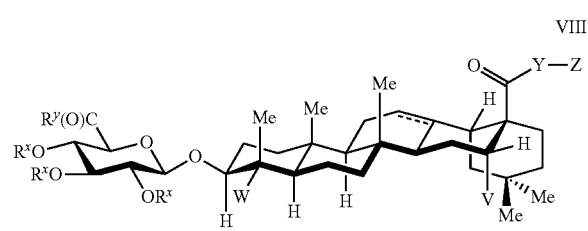

VIII wherein each of R$^x$, R$^y$, W, V, Y and Z is defined as described in classes and subclasses above and herein.

In some embodiments, the triterpene core of formula I bears an oligosaccharide at position C3. In some embodiments, oligosaccharide will contain rhamnose residues.

In certain embodiments, the triterpene core of formula I will bear disaccharides at position C3. In some embodiments, the disaccharide is galactose-glucuronic acid. In some embodiments, a disaccharide-substituted compound is of formula IX:

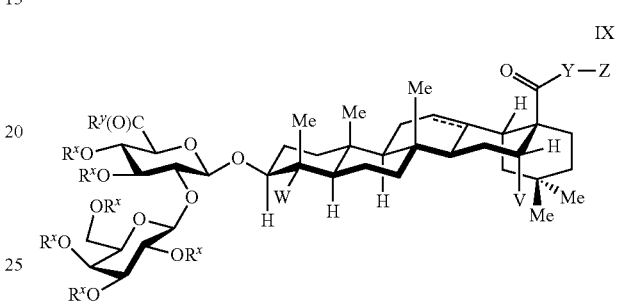

IX wherein each of R$^x$, R$^y$, W, V, Y and Z is defined as described in classes and subclasses above and herein.

In some embodiments, the triterpene core of formula I bears no saccharide group at position C3, providing a compound of formula X:

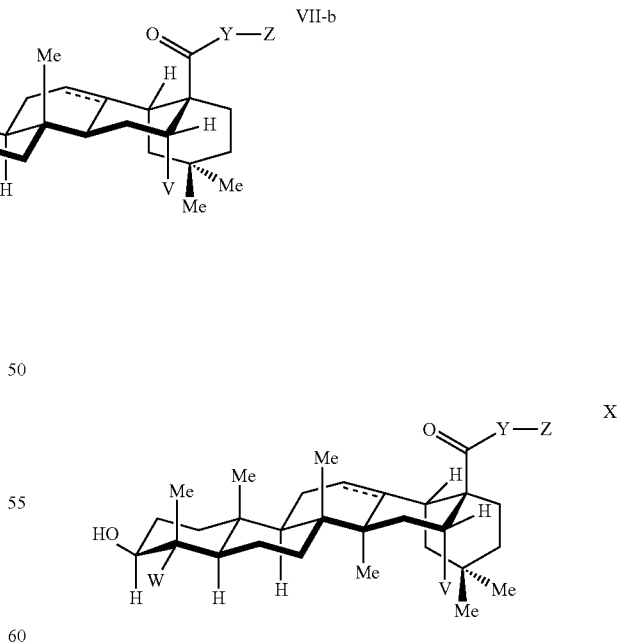

X wherein each of W, V, Y and Z is defined as described in classes and subclasses above and herein.

Exemplary compounds of formula I are set forth in Table 1 below.

TABLE 1
Exemplary compounds of formula I
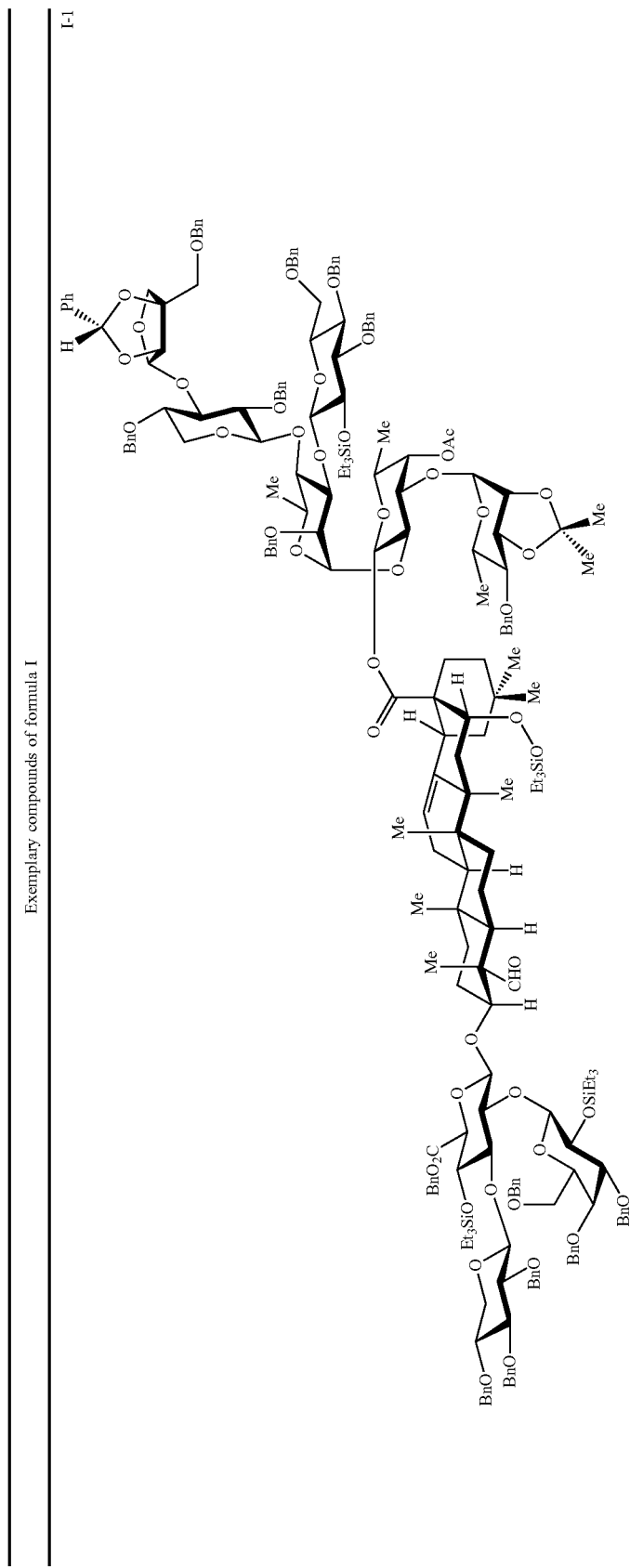
I-1

TABLE 1-continued
Exemplary compounds of formula I
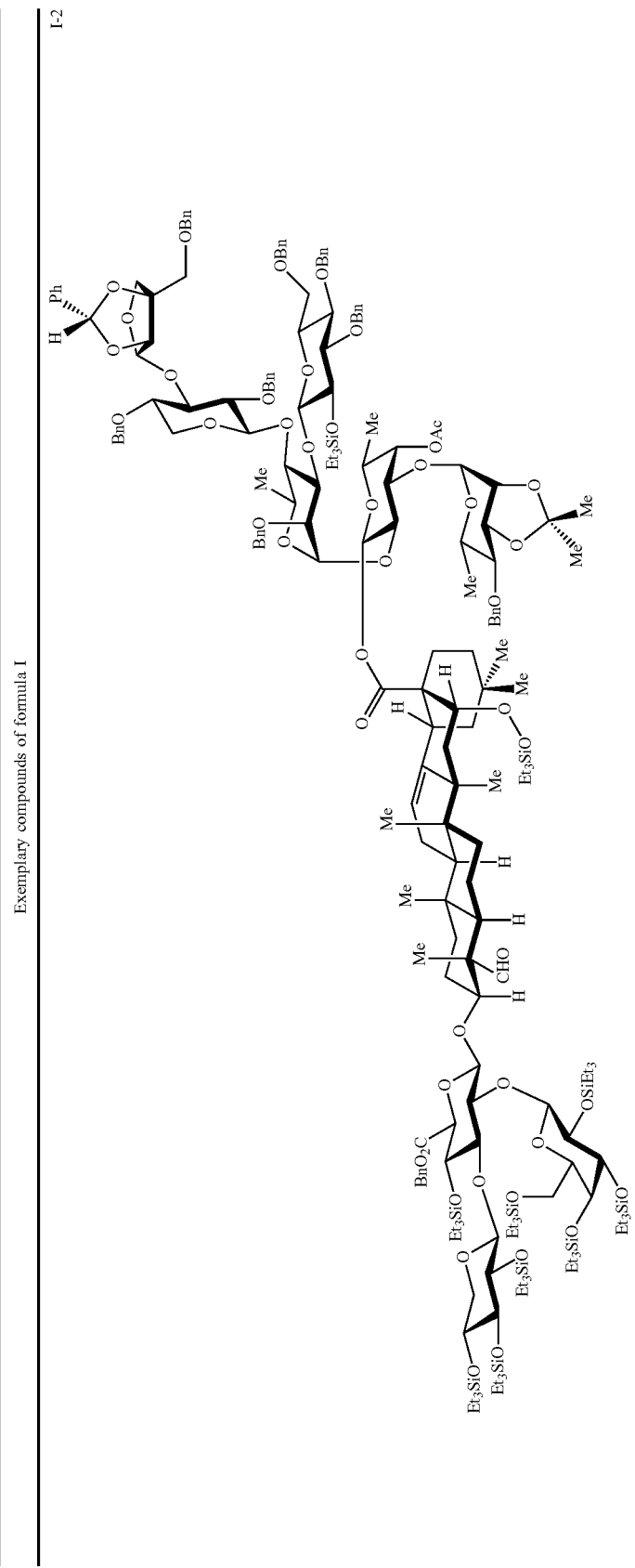
I-2

TABLE 1-continued
Exemplary compounds of formula I
I-3
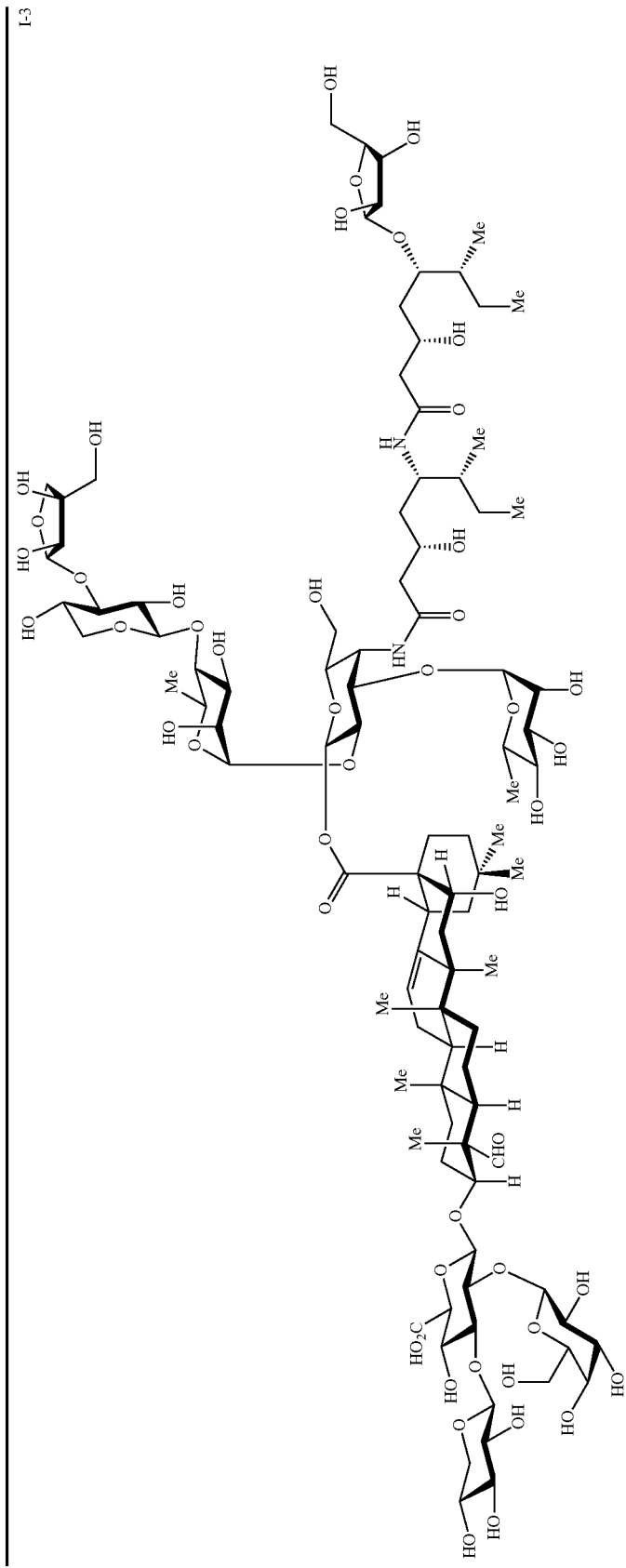

TABLE 1-continued
Exemplary compounds of formula I
I-4
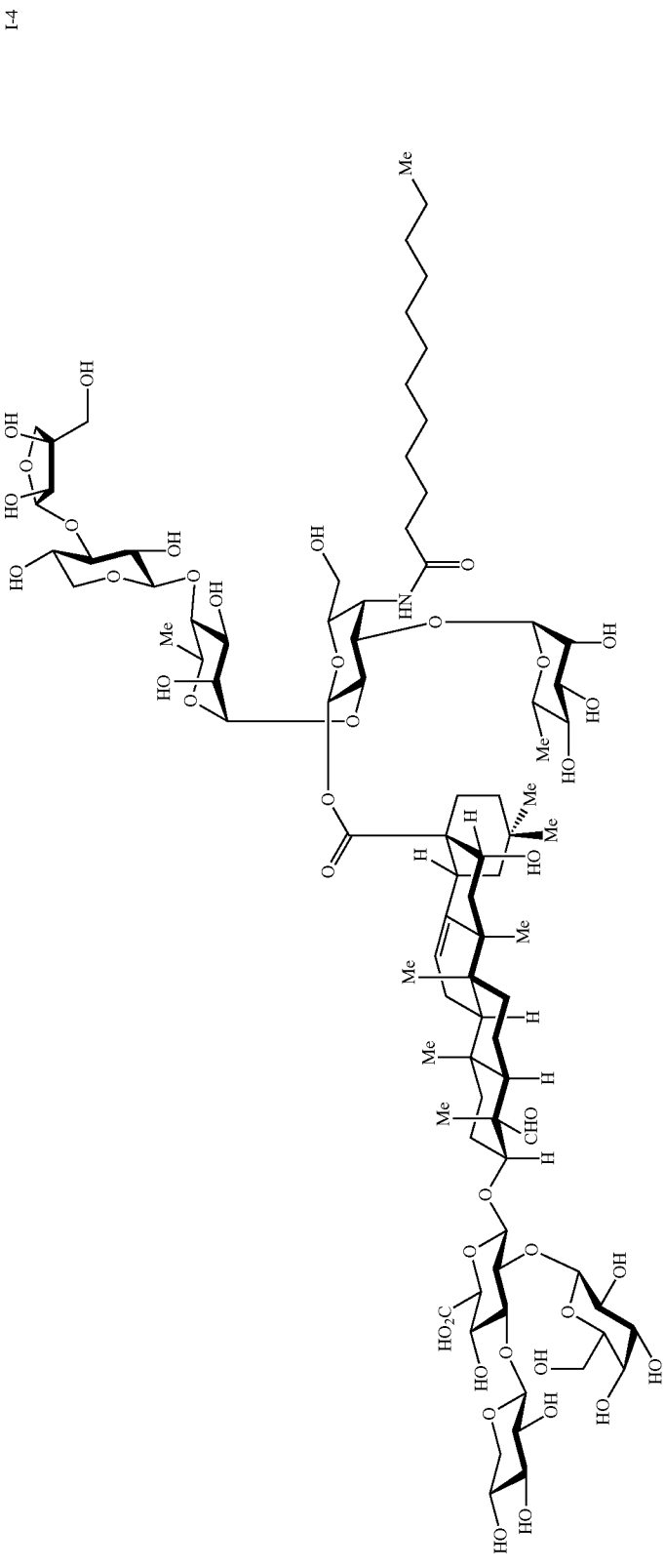

TABLE 1-continued
Exemplary compounds of formula I
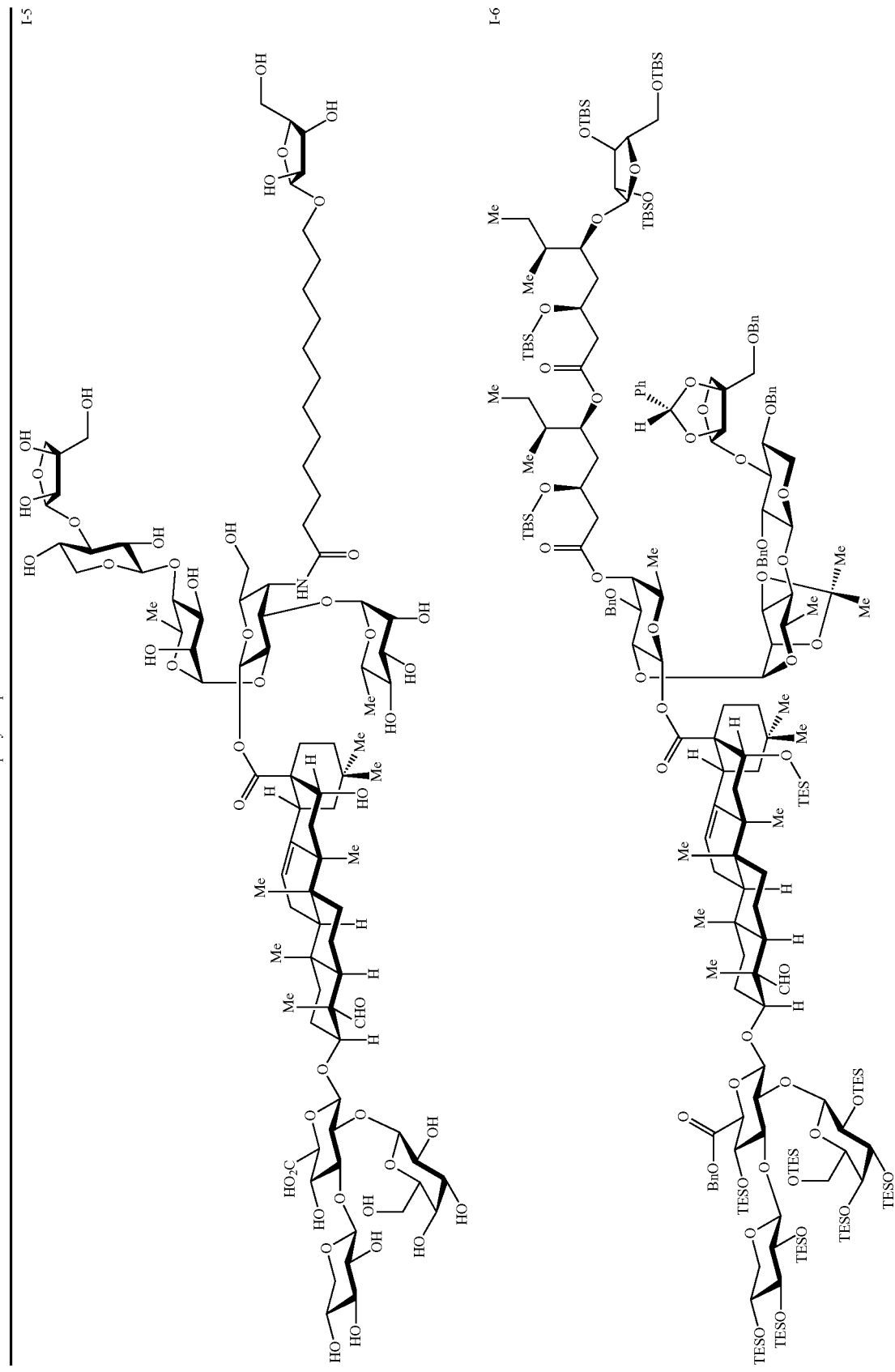

TABLE 1-continued
Exemplary compounds of formula I
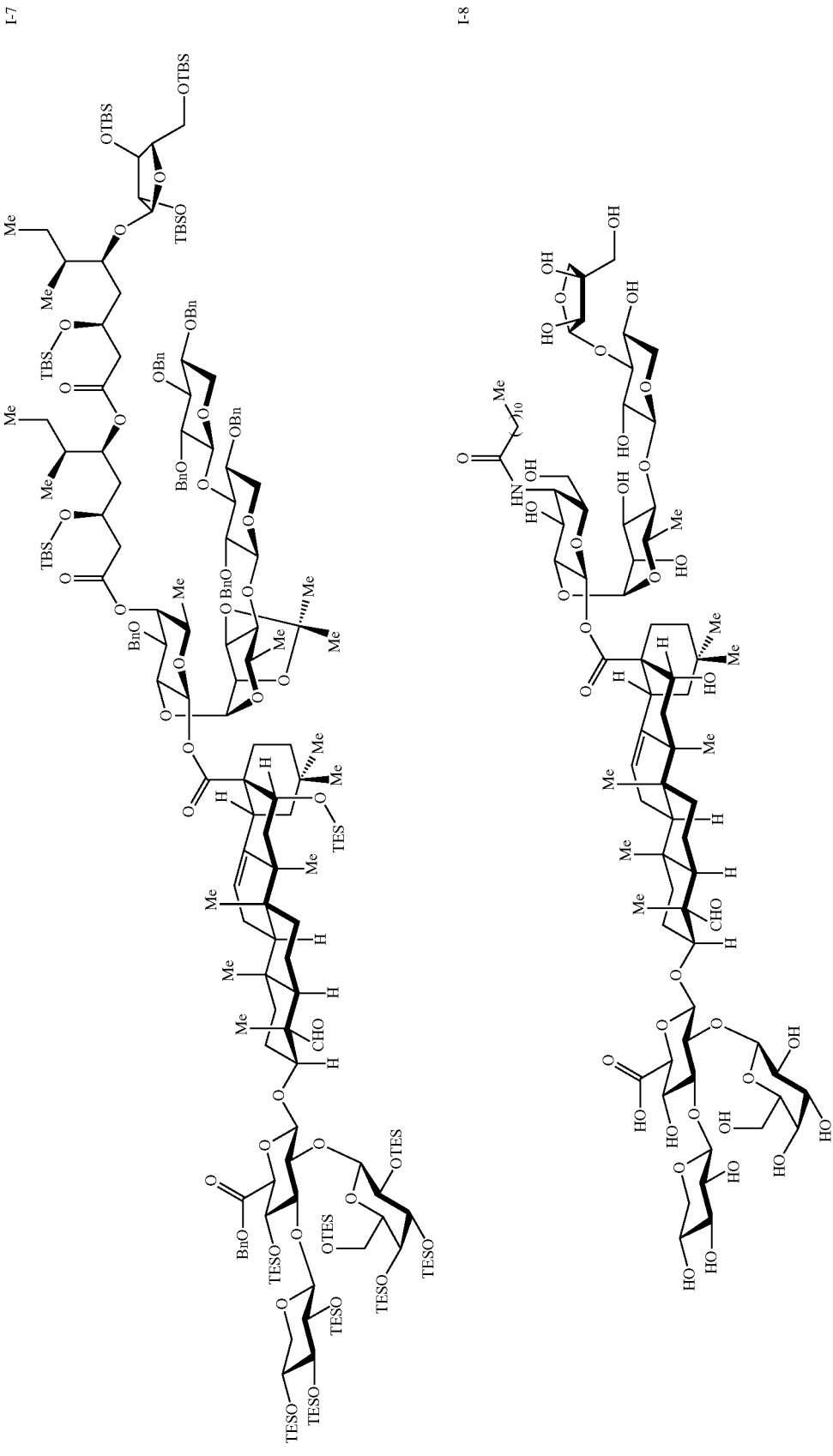

TABLE 1-continued
Exemplary compounds of formula I
I-9
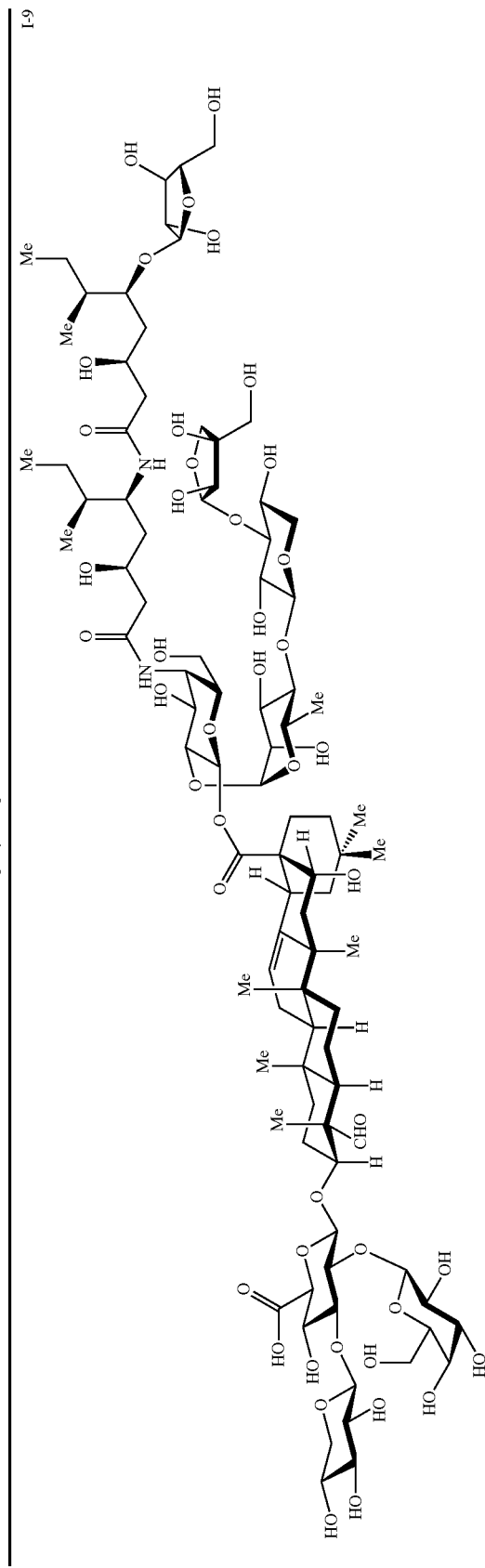
I-10
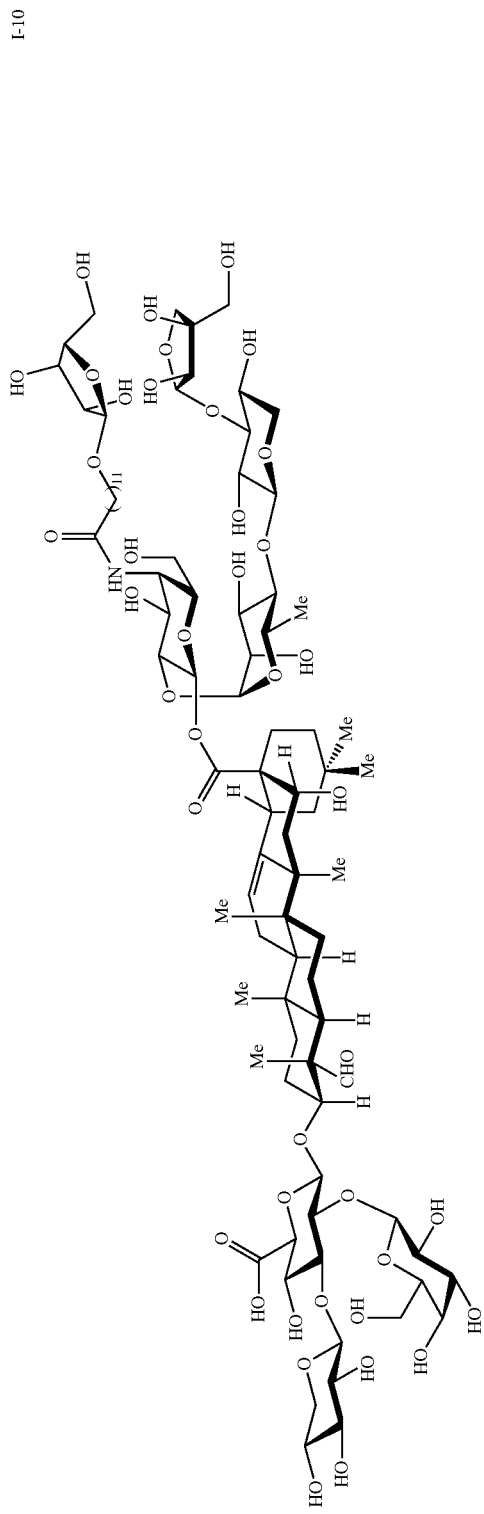

TABLE 1-continued
Exemplary compounds of formula I
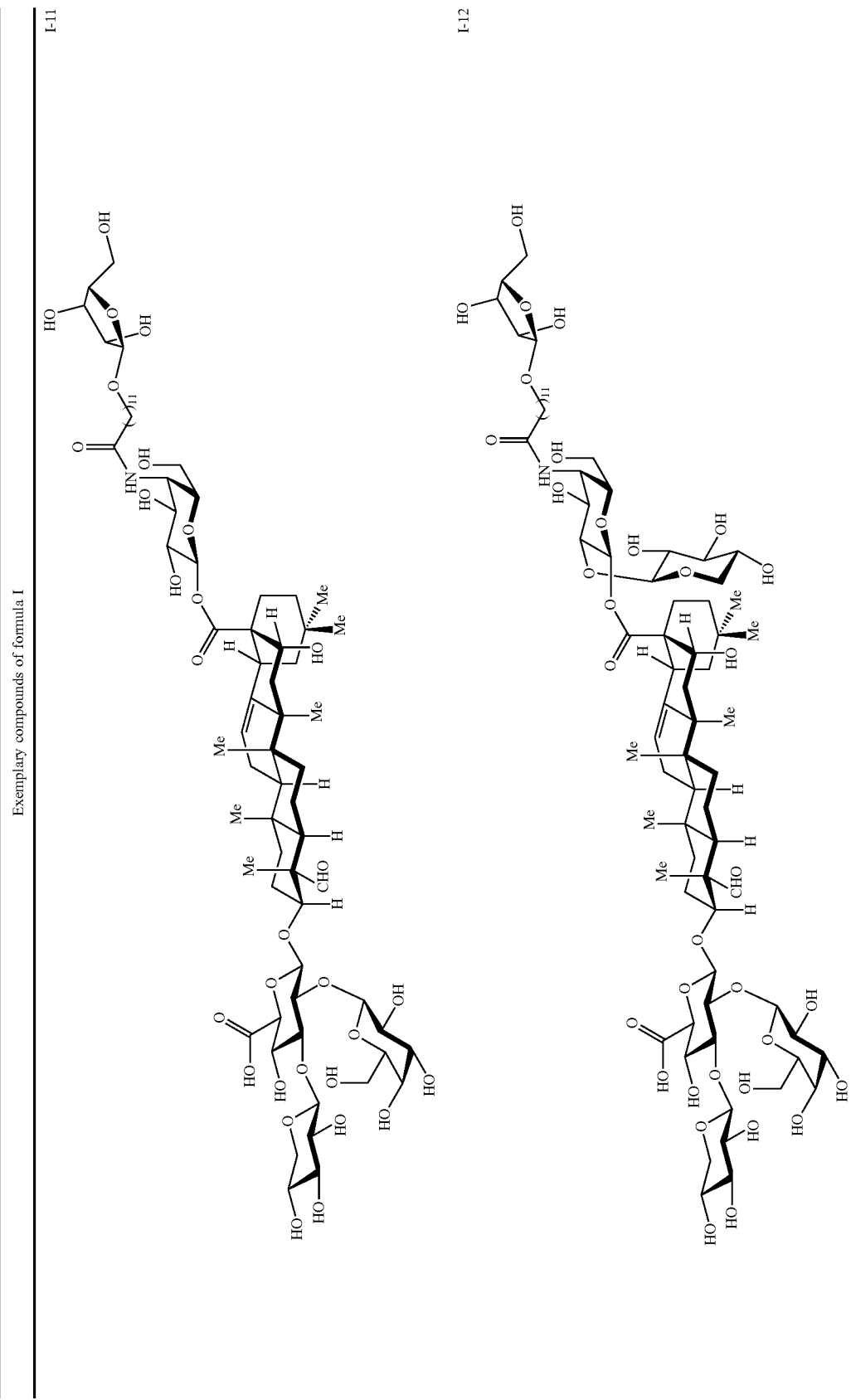

TABLE 1-continued
Exemplary compounds of formula I
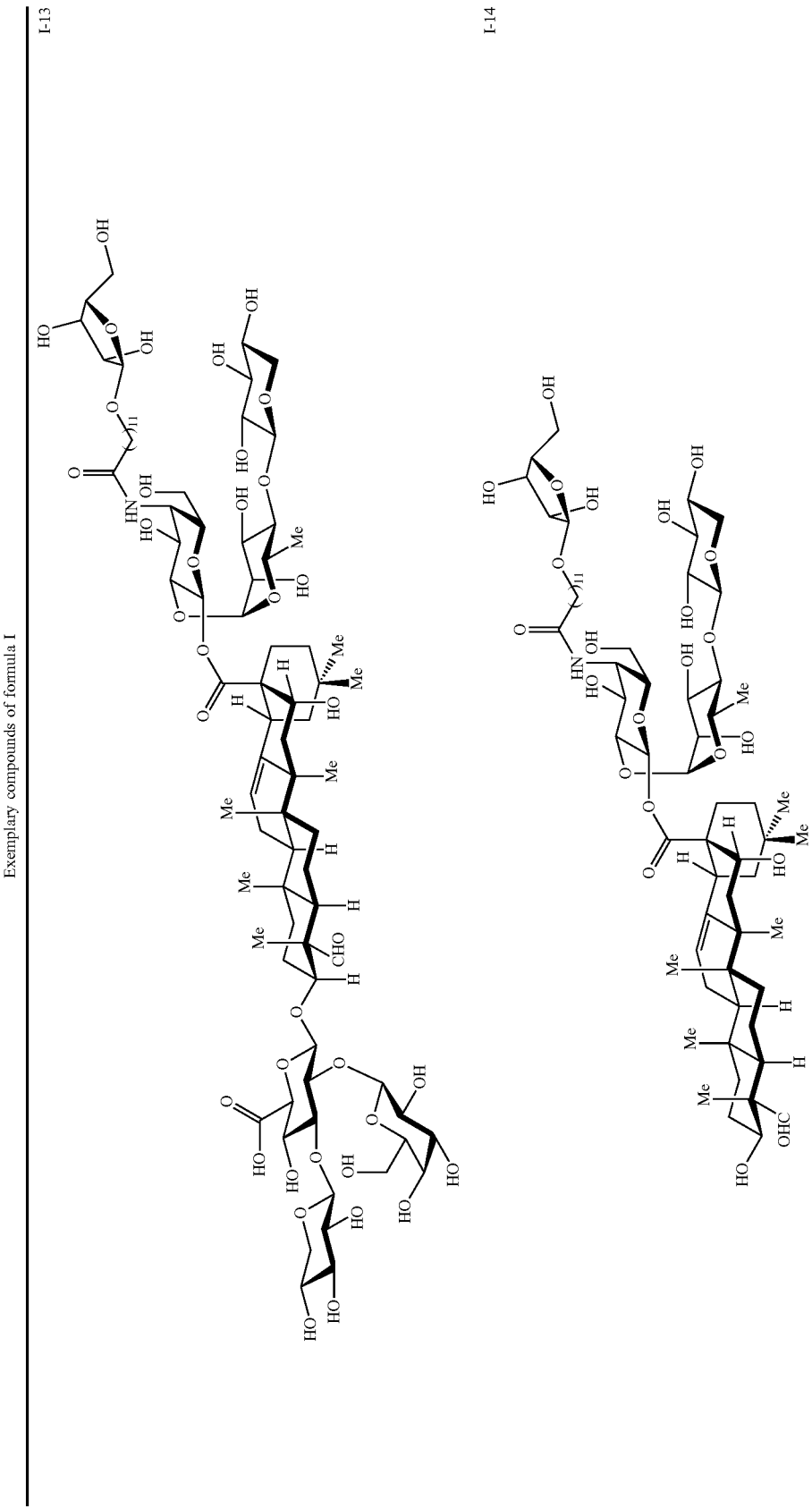

TABLE 1-continued
Exemplary compounds of formula I
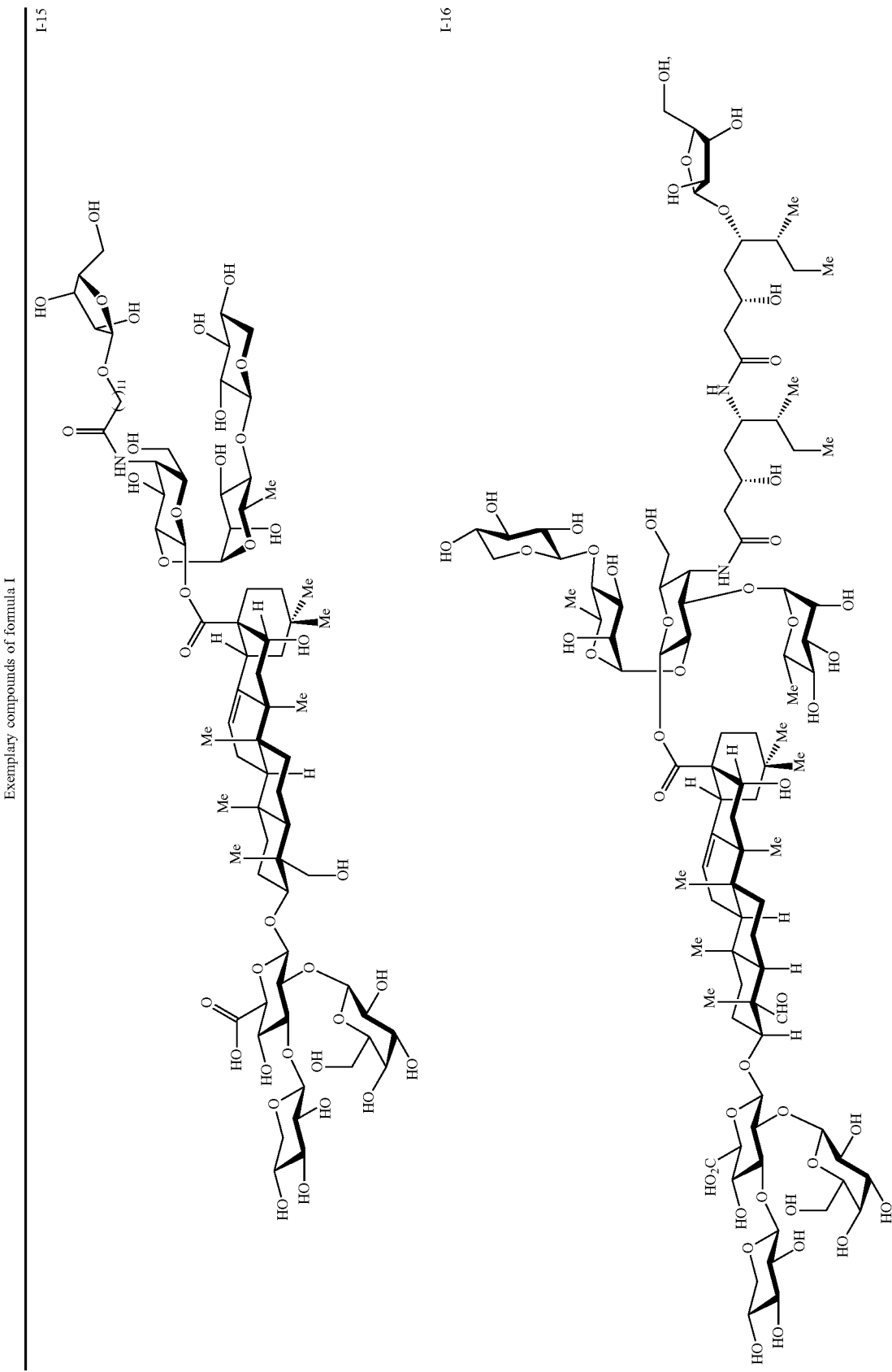

TABLE 1-continued
Exemplary compounds of formula I
I-17
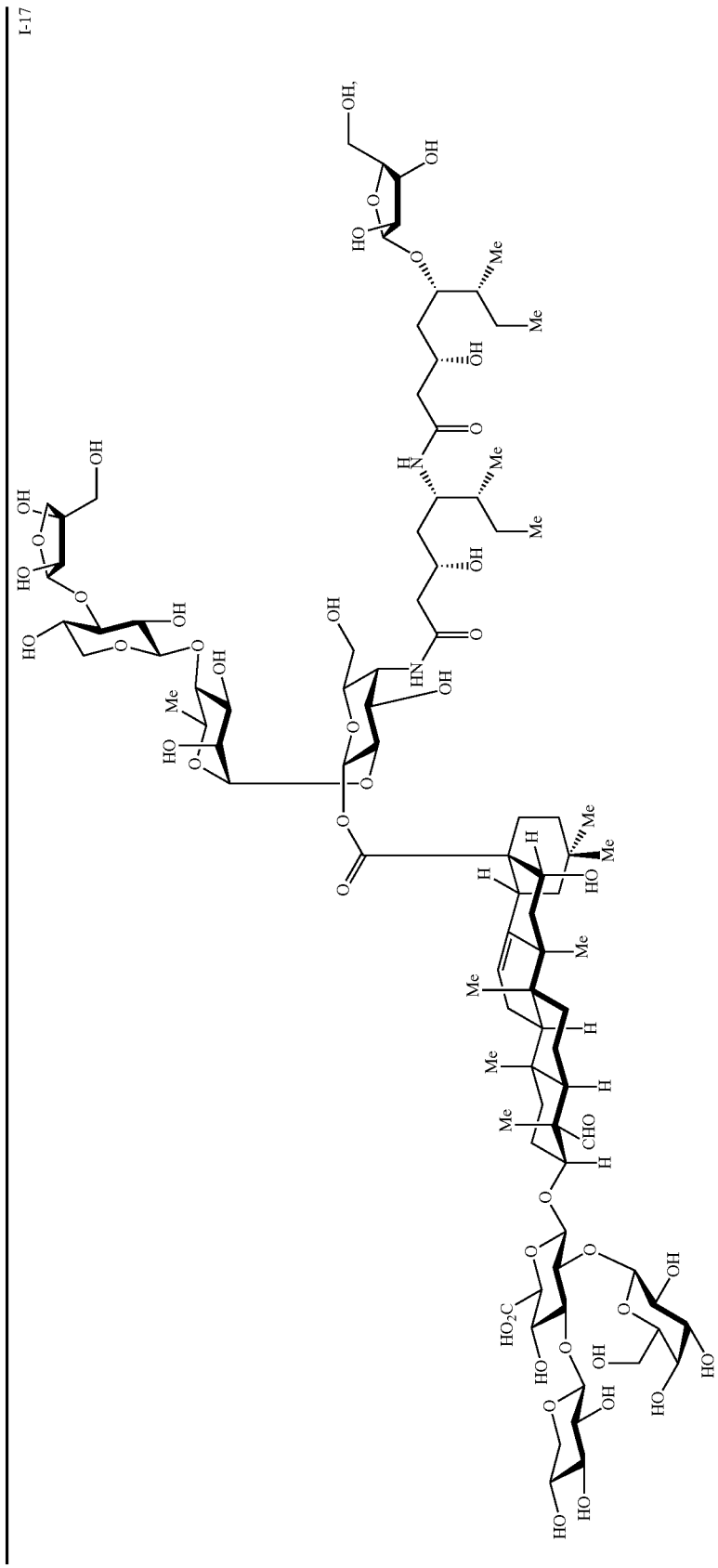

TABLE 1-continued
Exemplary compounds of formula I
I-18
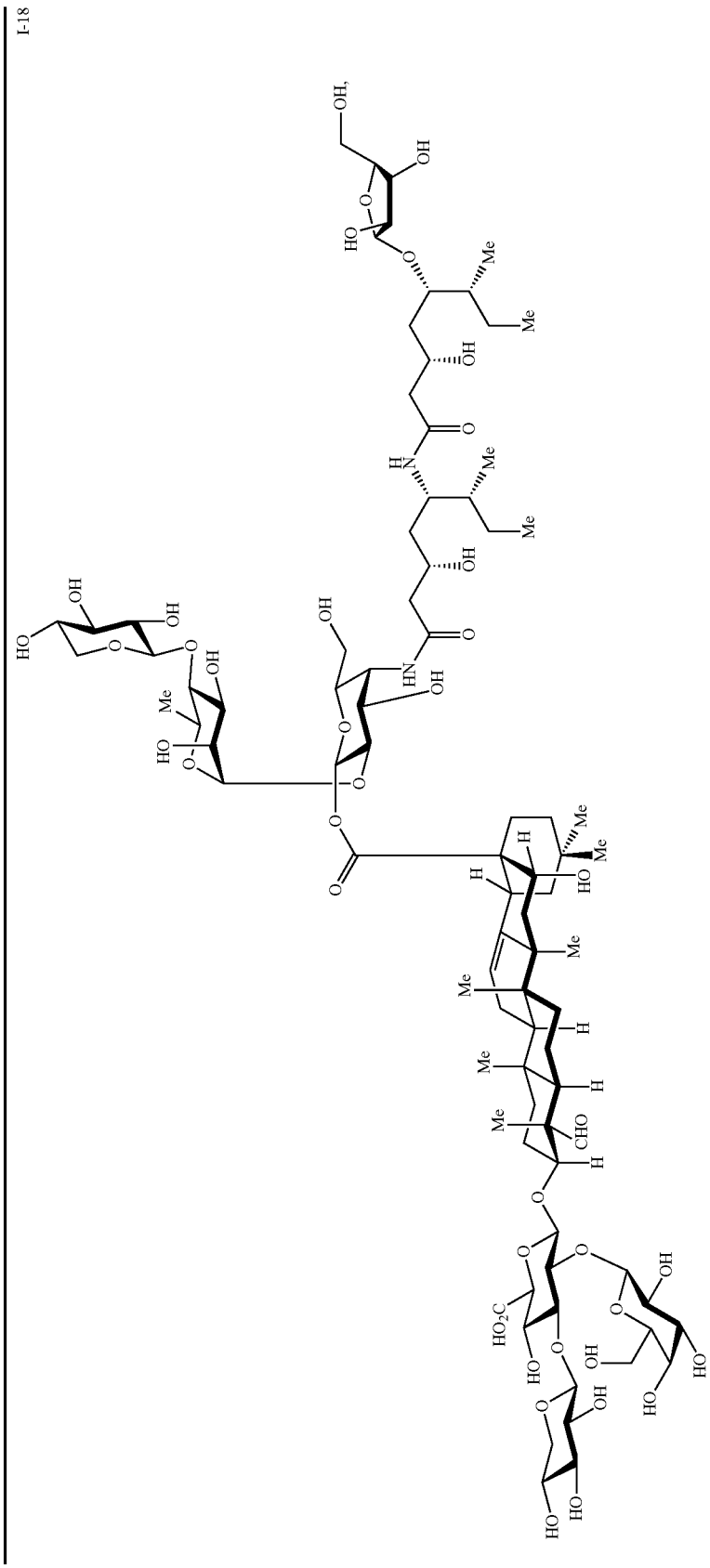

TABLE 1-continued
Exemplary compounds of formula I
I-19
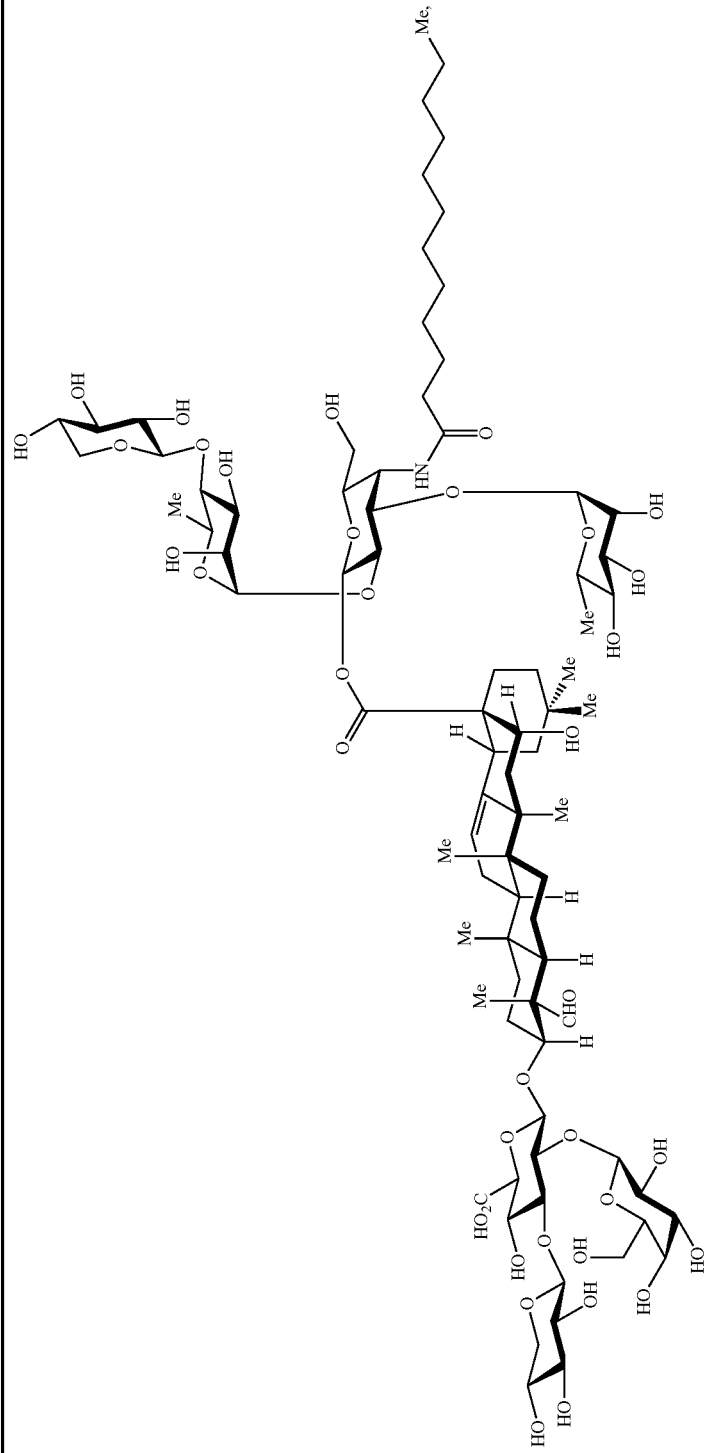

TABLE 1-continued
Exemplary compounds of formula I
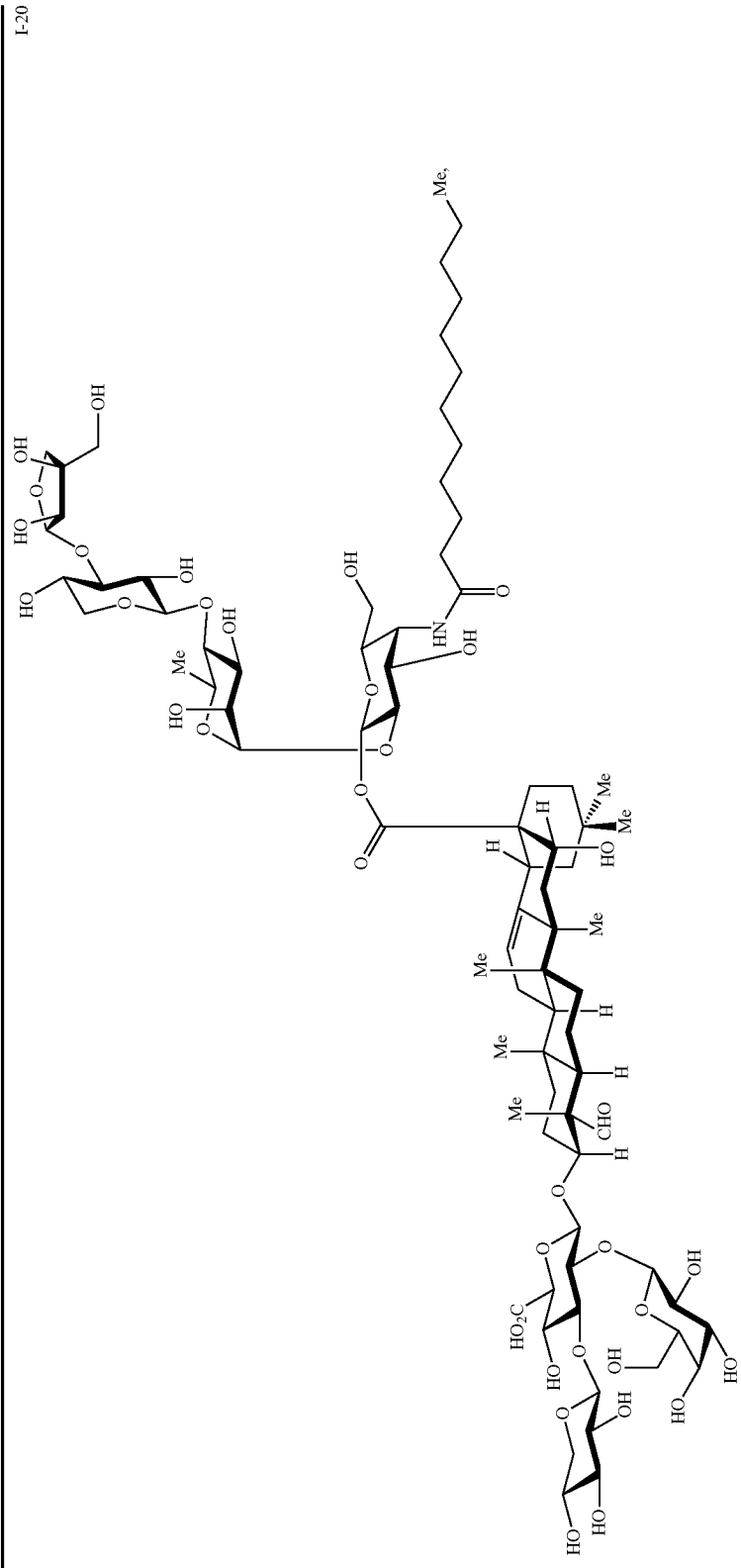
I-20

TABLE 1-continued
Exemplary compounds of formula I
I-21
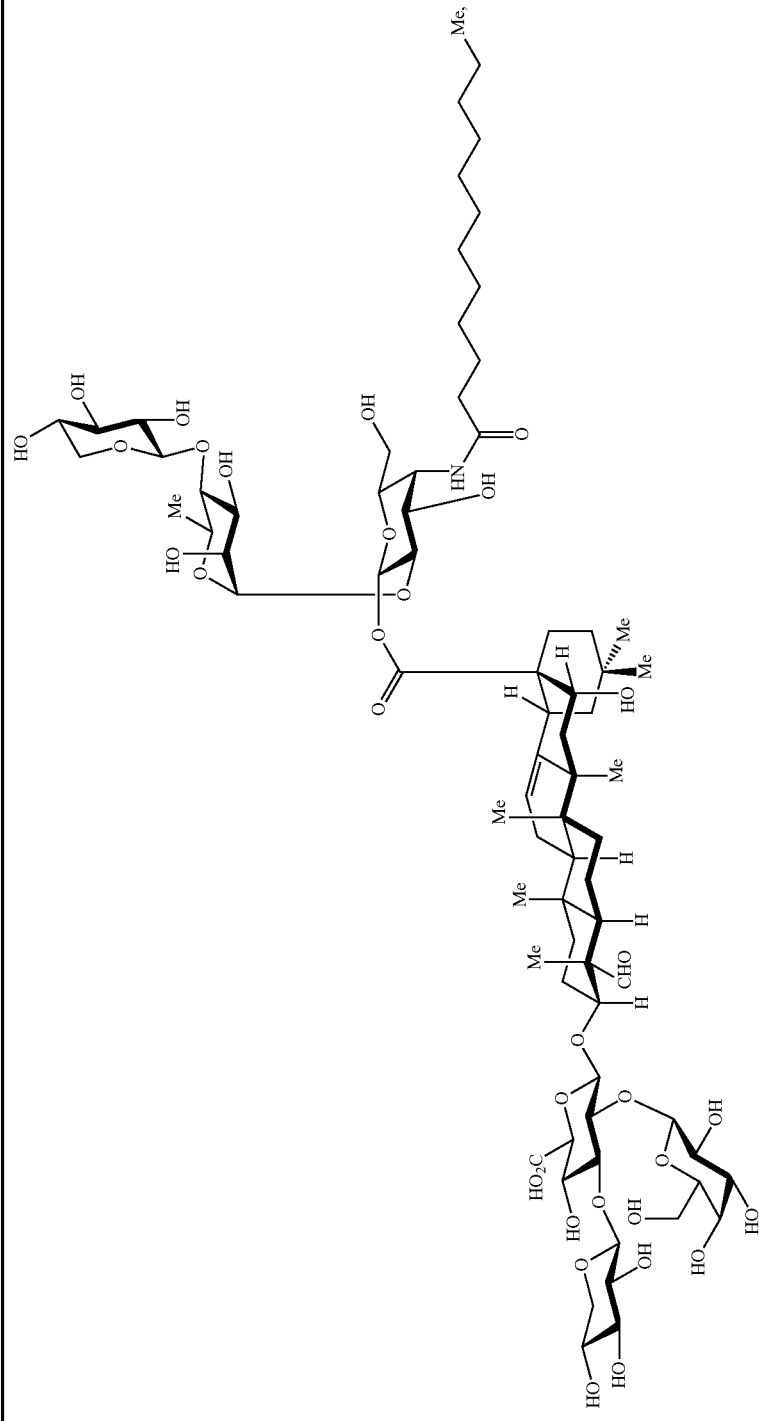

TABLE 1-continued
Exemplary compounds of formula I
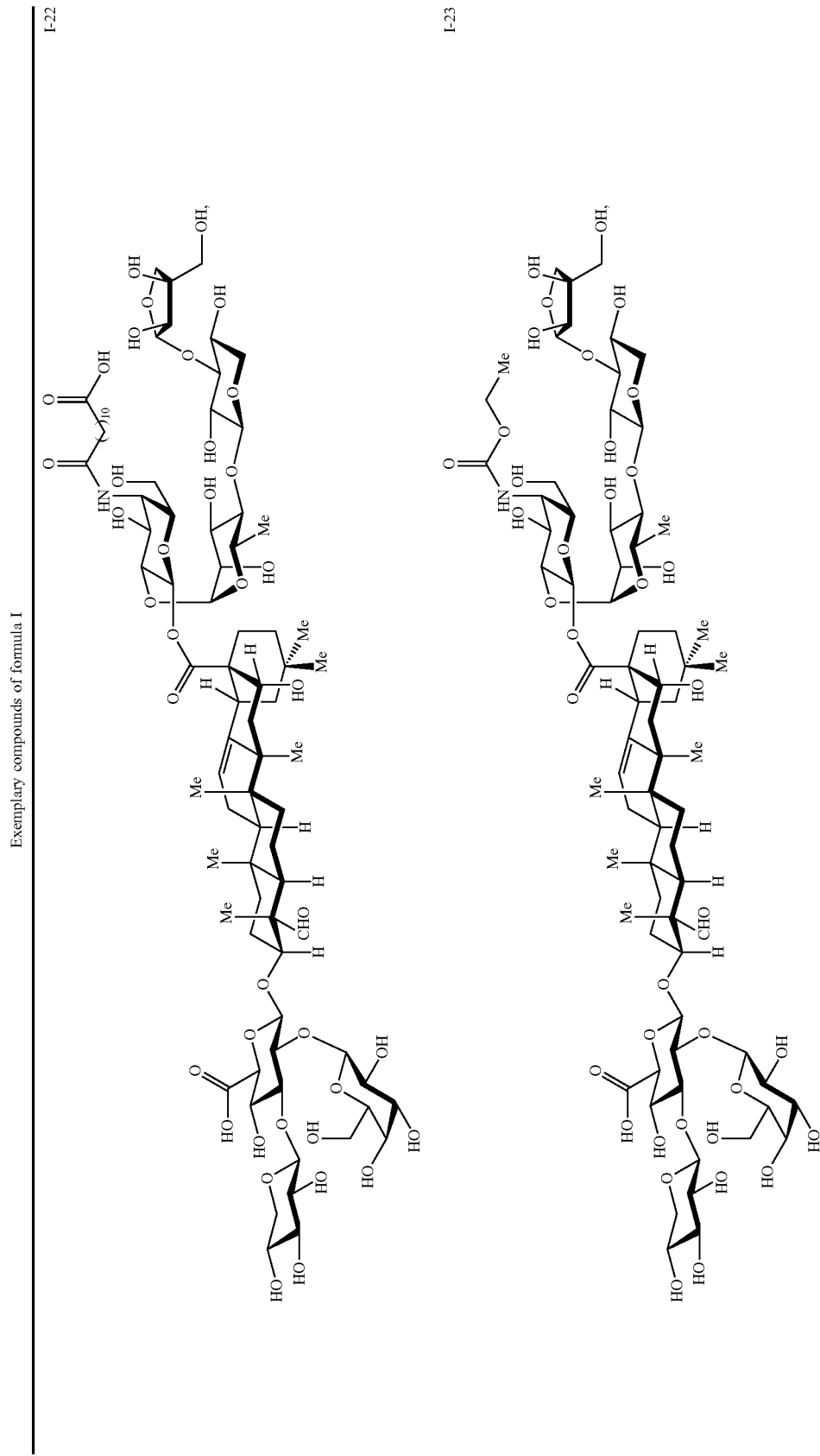

TABLE 1-continued
Exemplary compounds of formula I
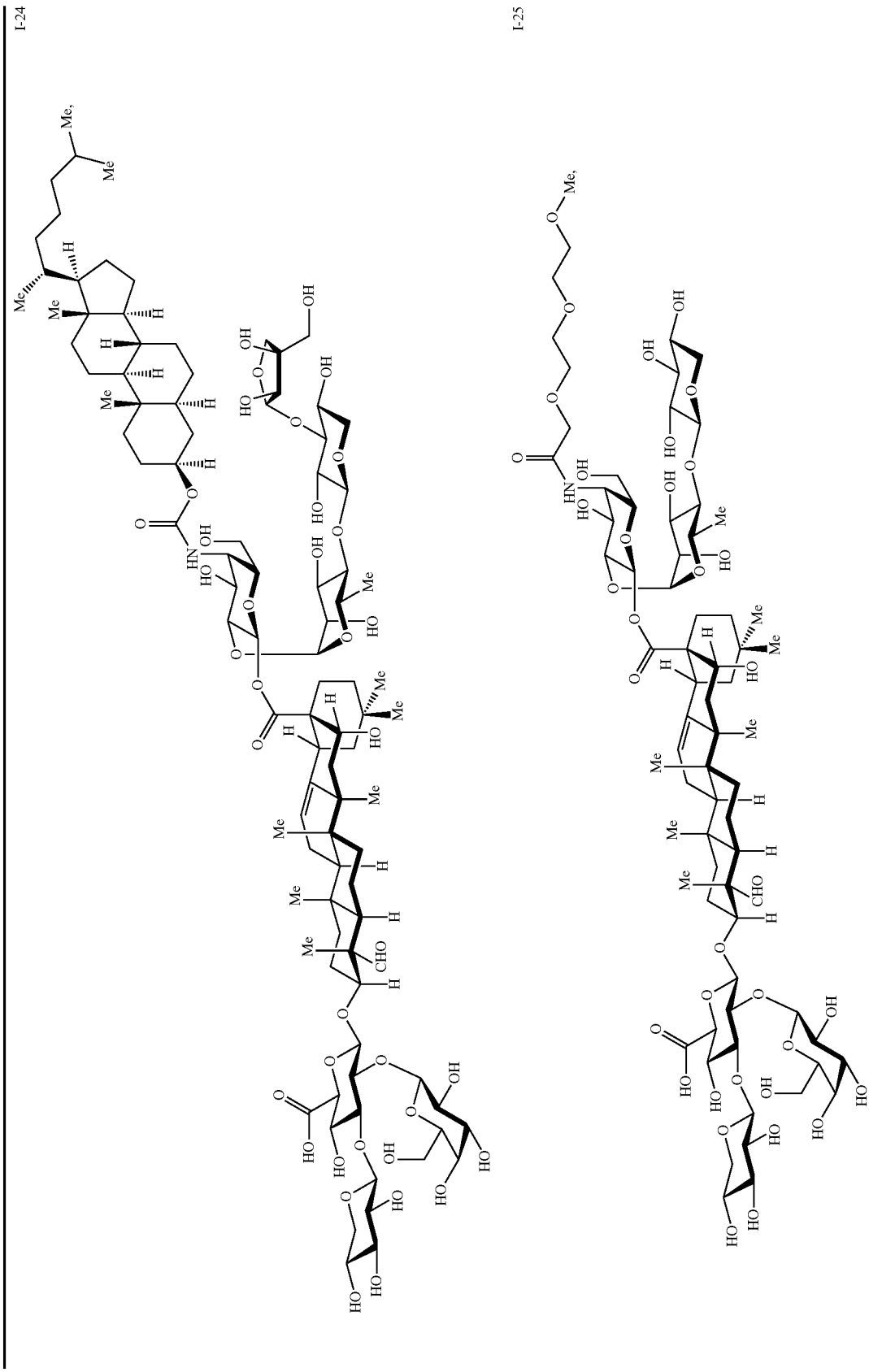

TABLE 1-continued
Exemplary compounds of formula I
I-26
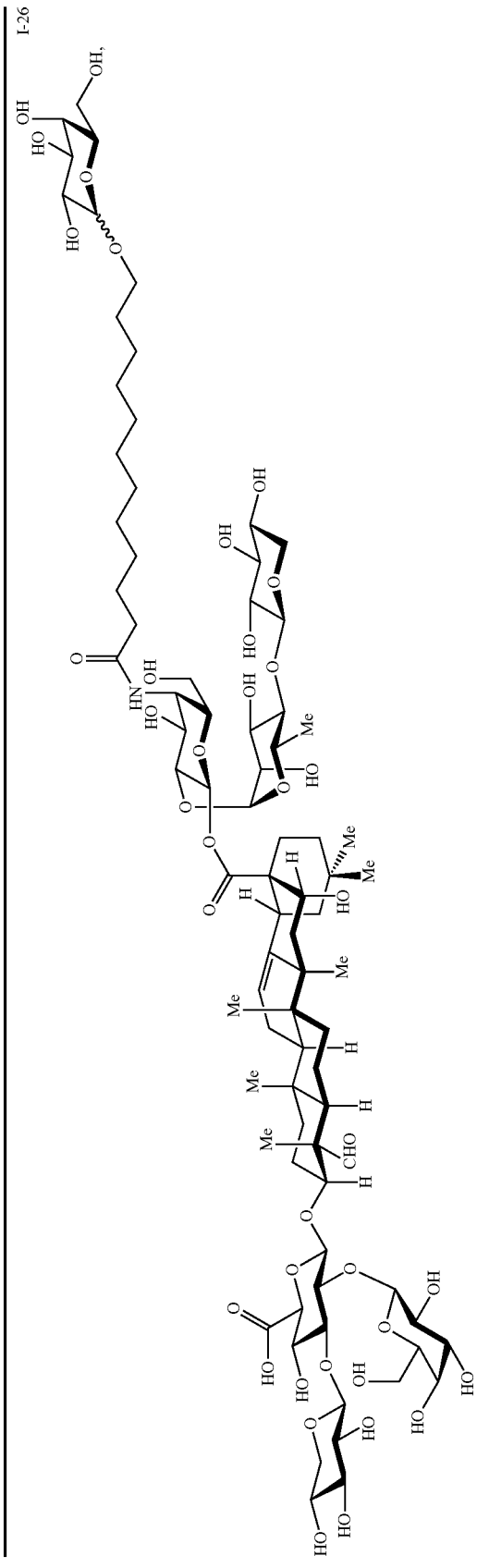
I-27
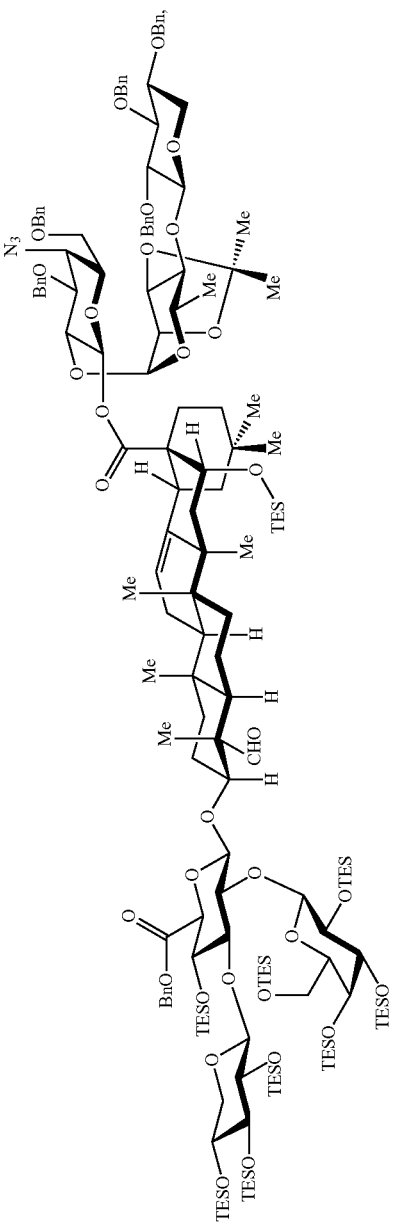

TABLE 1-continued
Exemplary compounds of formula I
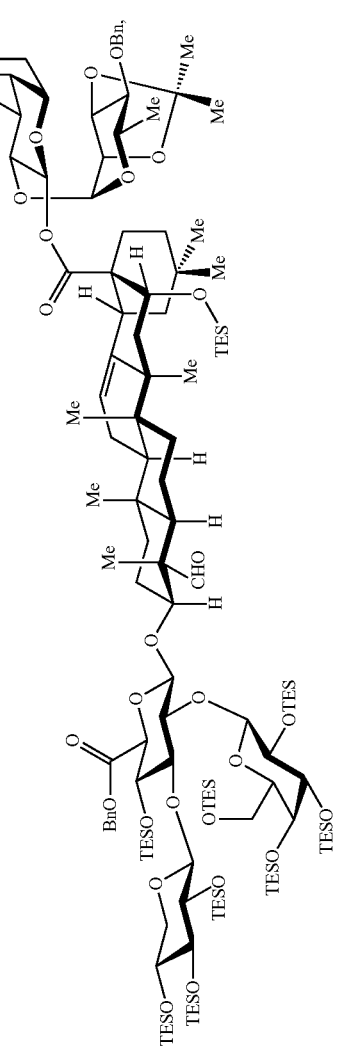
I-28
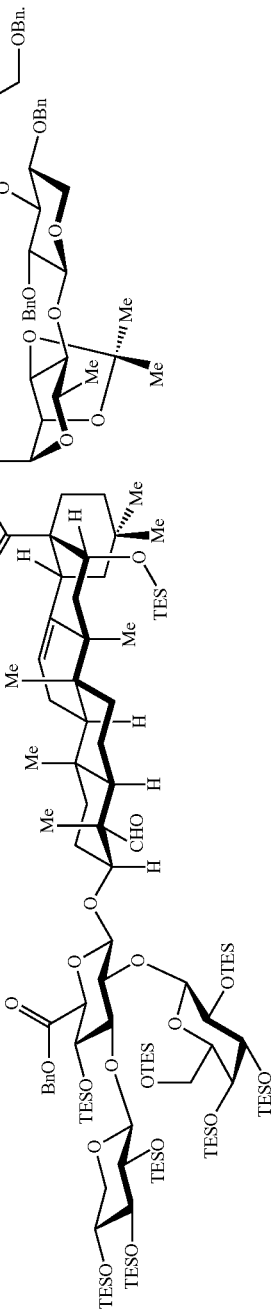
I-29

In certain embodiments, a compound of formula I is not selected from:
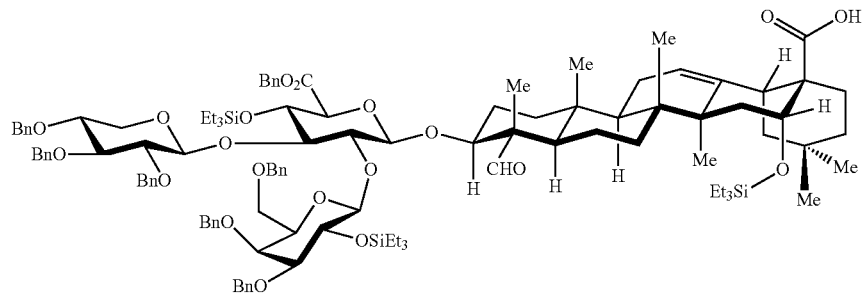
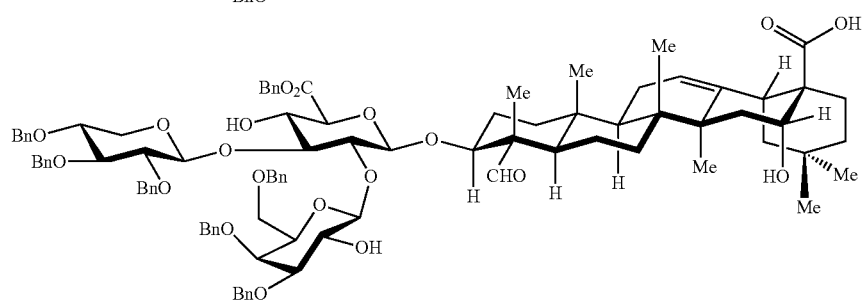
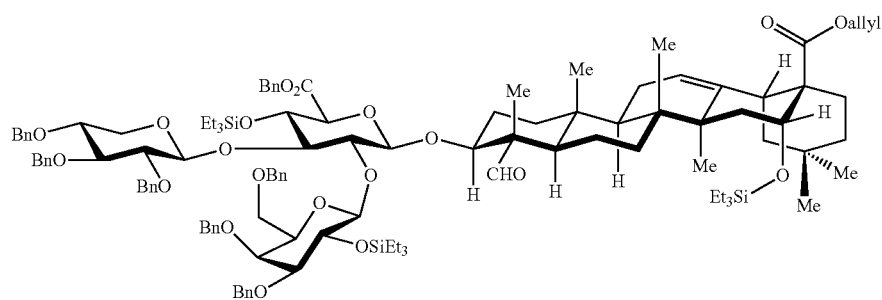
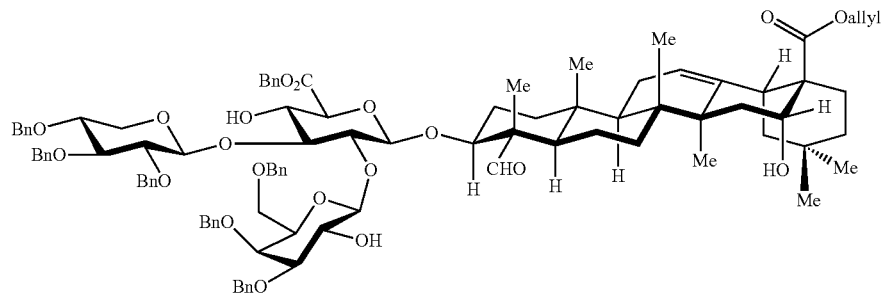
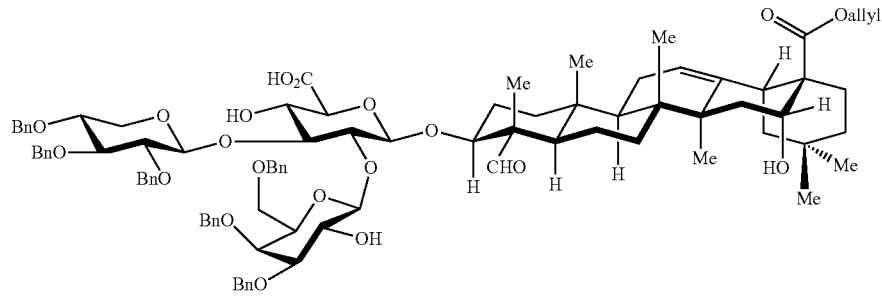

-continued

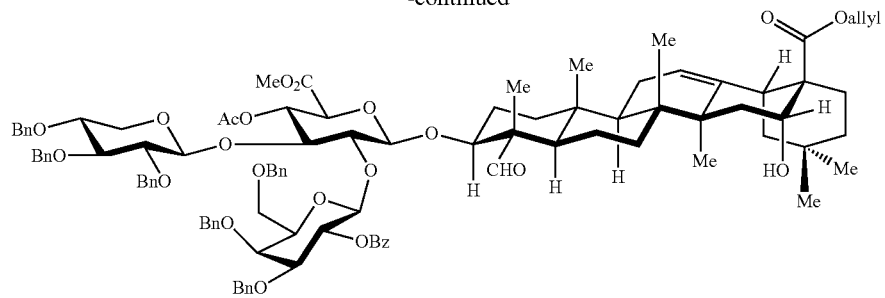

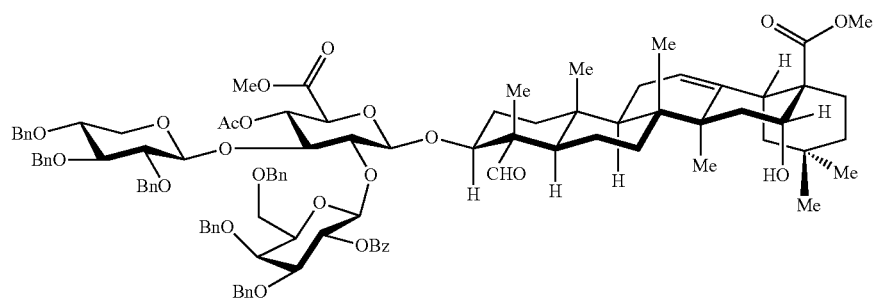

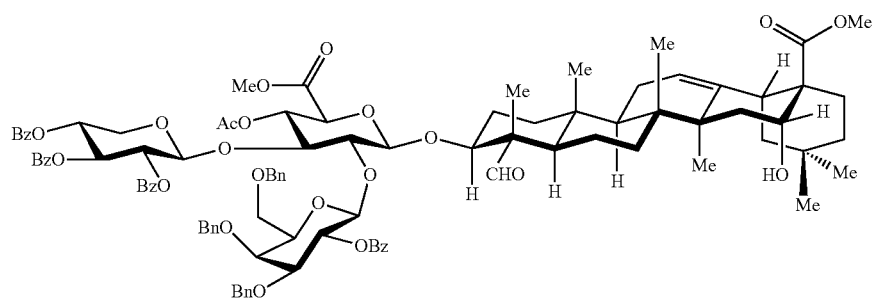

It will be appreciated that it is not an object of the present invention to claim compounds disclosed in the prior art that are the result of isolation or degradation studies on naturally-occurring prosapongenins or saponins.

As described above for compounds of formula I, in some embodiments, Y is —O—; Z is a carbohydrate domain having the structure:

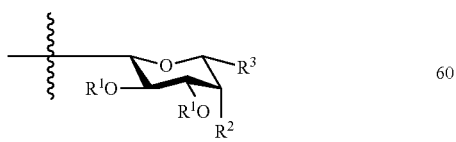

wherein each occurrence of $R^1$ is $R^x$ or a carbohydrate domain comprising furanose or pyranose moieties; and $R^2$ is —NHC(O)$R^4$.

Thus, according to one aspect, provided compounds are of formula II:

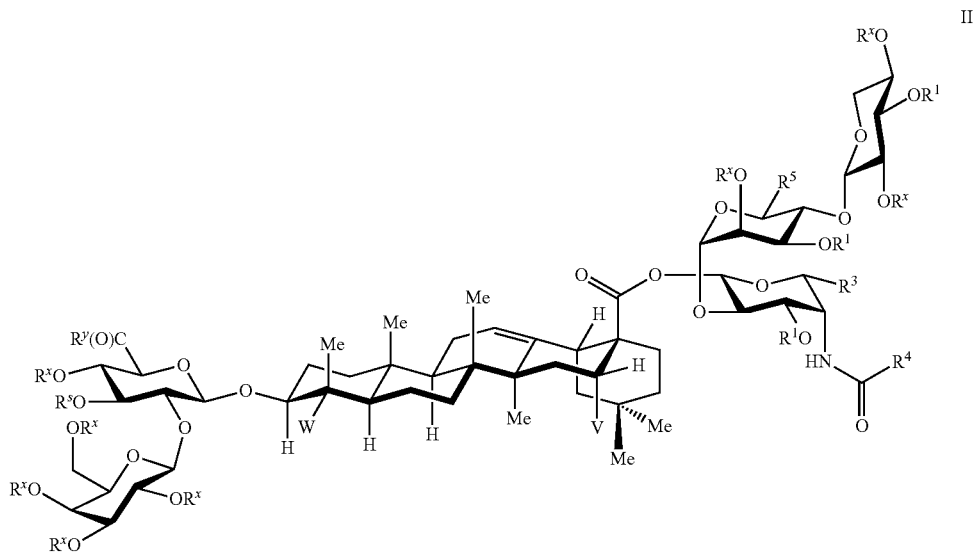

II wherein each of $R^1$, $R^3$, $R^4$, $R^5$, $R^x$, $R^s$, $R^y$, V, and W is defined as described in classes and subclasses above and herein.

In some embodiments, provided compounds are of formula II-a:

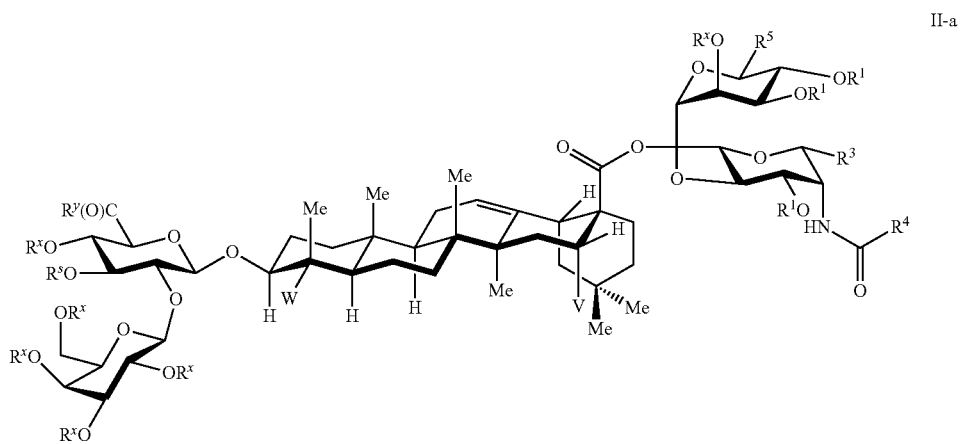

II-a wherein each of $R^1$, $R^3$, $R^4$, $R^5$, $R^x$, $R^s$, $R^y$, V, and W is defined as described in classes and subclasses above and herein.

In some embodiments, provided compounds are of formula II-b:

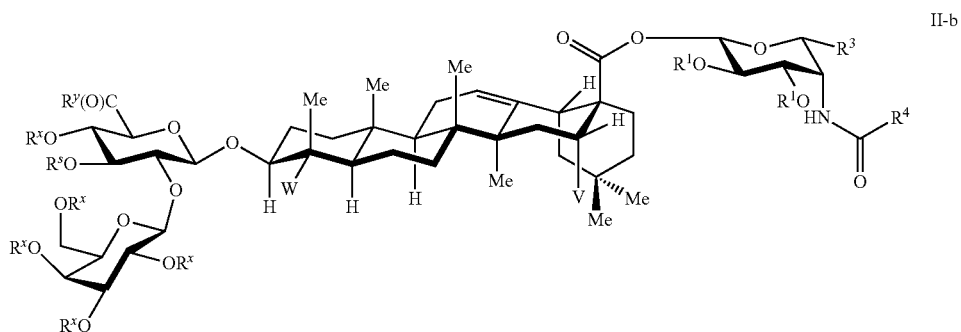

II-b wherein each of $R^1$, $R^3$, $R^4$, $R^5$, $R^x$, $R^s$, $R^y$, V, and W is defined as described in classes and subclasses above and herein.

As described above for compounds of formula I, in some embodiments, Y is —O—; and Z is a carbohydrate domain having the structure:

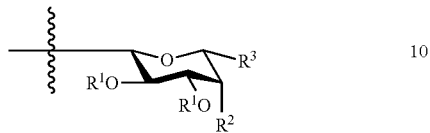

wherein each occurrence of $R^1$ is $R^x$ or a carbohydrate domain comprising furanose or pyranose moieties.

Thus, according to one aspect, provided compounds are of formula III, III-a, III-b, III-c, III-d, III-e, III-f, or III-g:

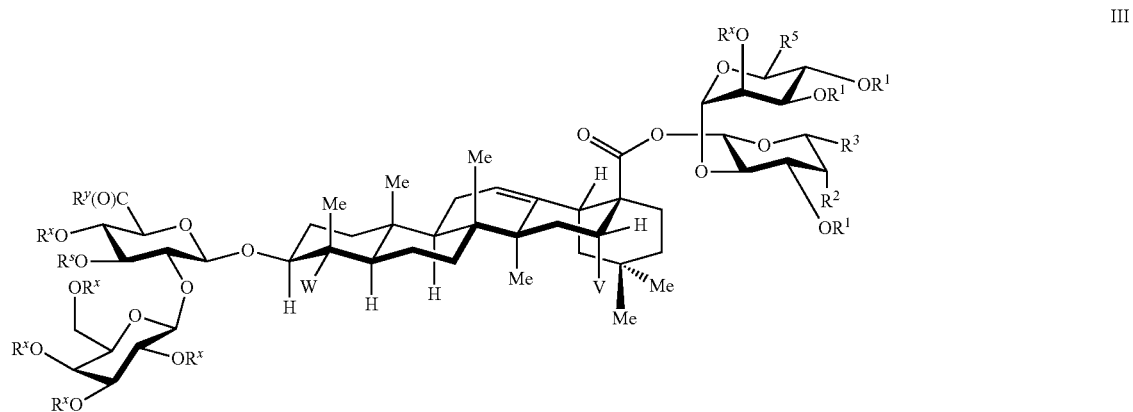

III

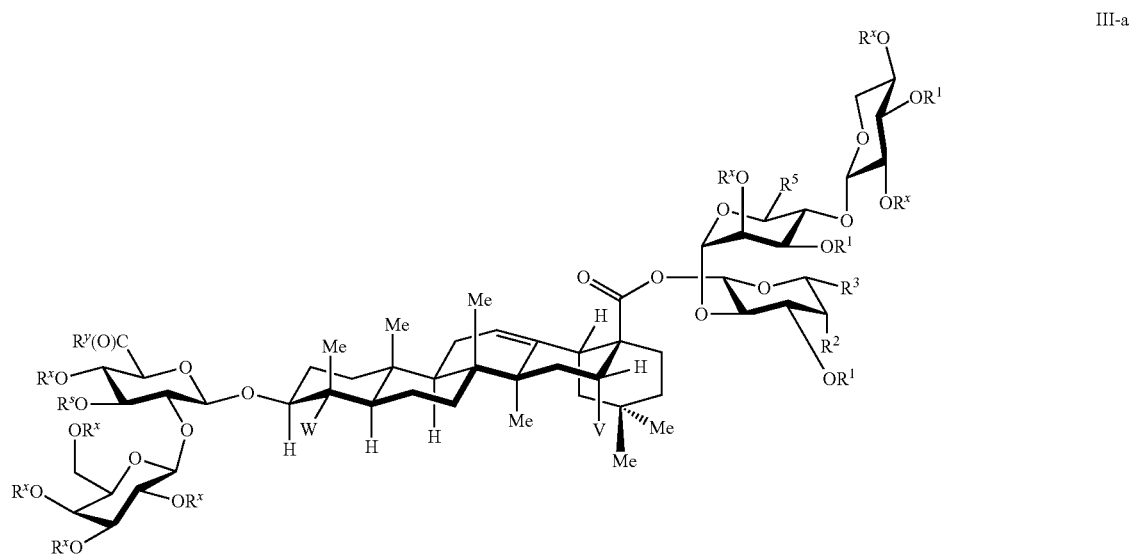

III-a

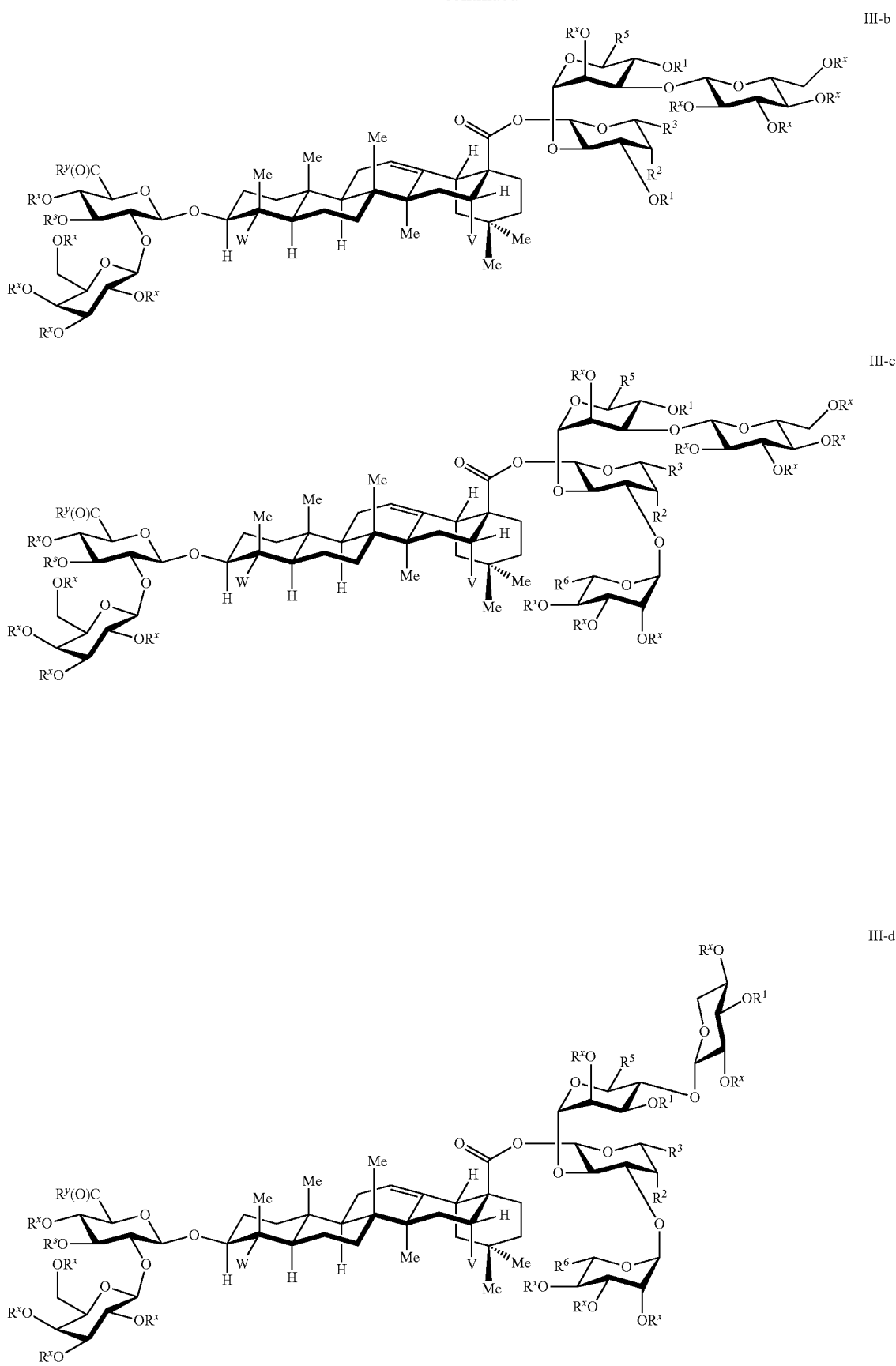

-continued
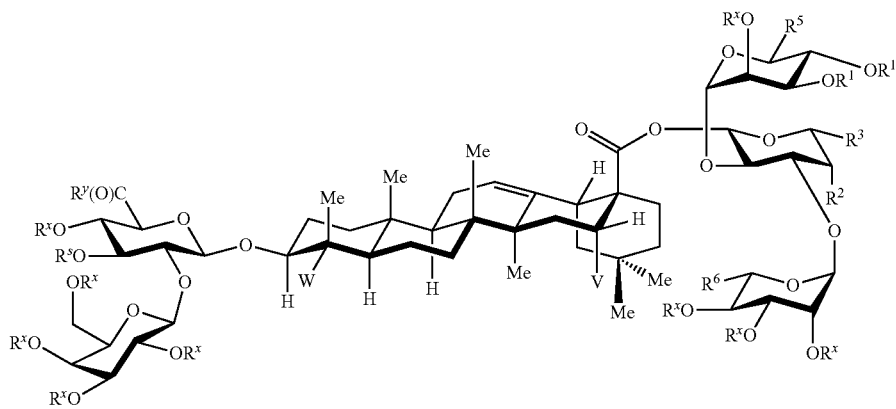
III-e
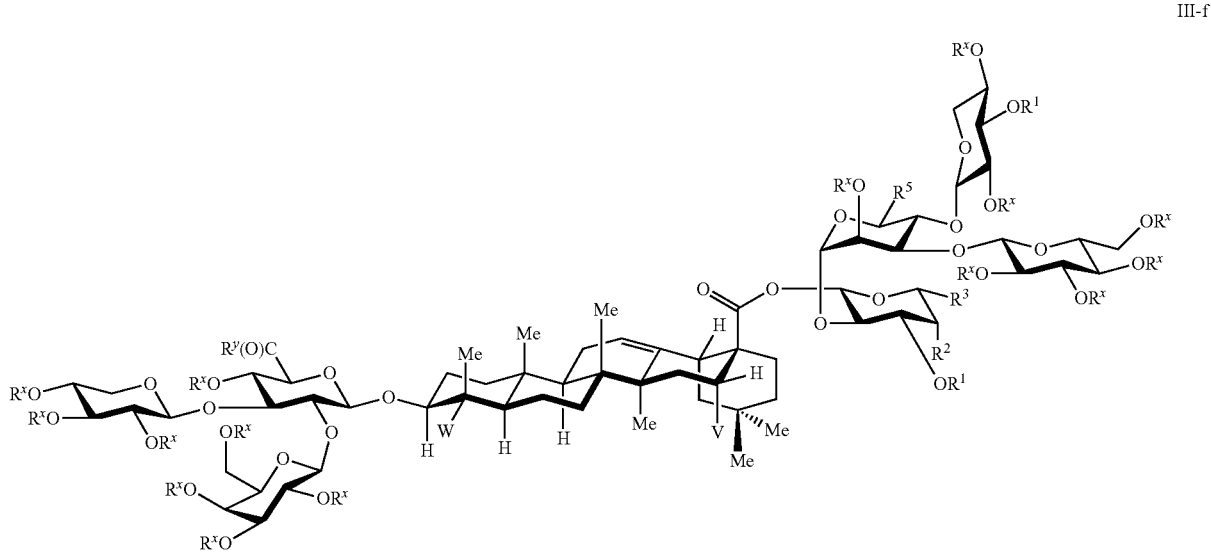
III-f
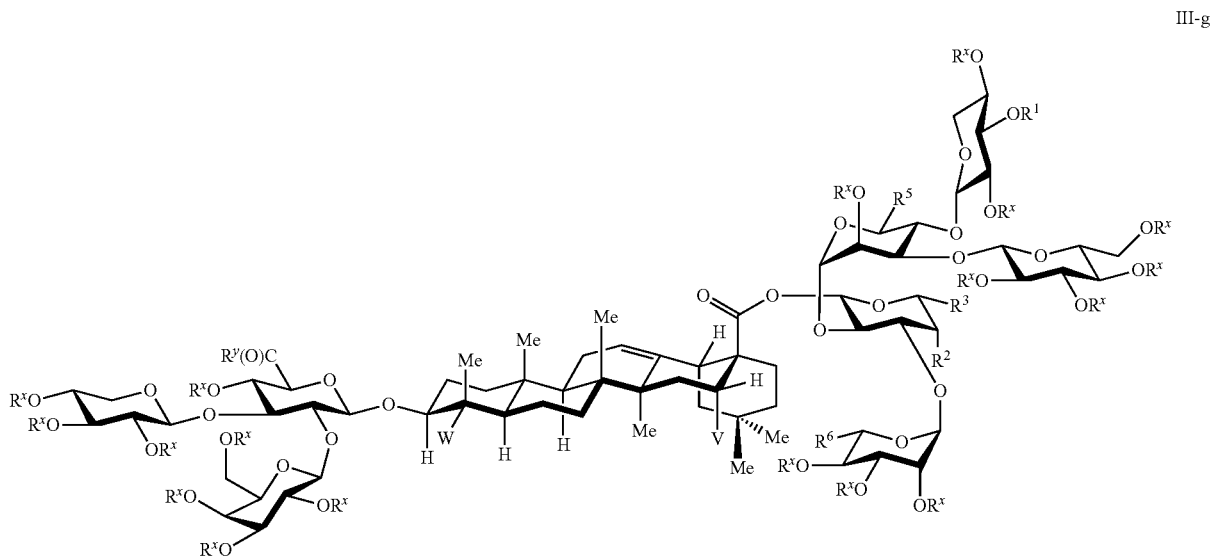
III-g wherein each of $R^1$, $R^2$, $R^3$, $R^5$, $R^6$, $R^x$, $R^s$, $R^y$, V, and W is defined as described in classes and subclasses above and herein.

As described above for compounds of formula I, in certain embodiments, each occurrence of $R^x$ is independently a suitable hydroxyl protecting group; Y is $CH_2$, —O—, —NR—, or —NH—; Z is hydrogen; a cyclic or acyclic, optionally substituted moiety selected from the group consisting of acyl, aliphatic, heteroaliphatic, aryl, arylalkyl, and heteroaryl. Thus, according to another aspect, provided compounds are of formula IV:

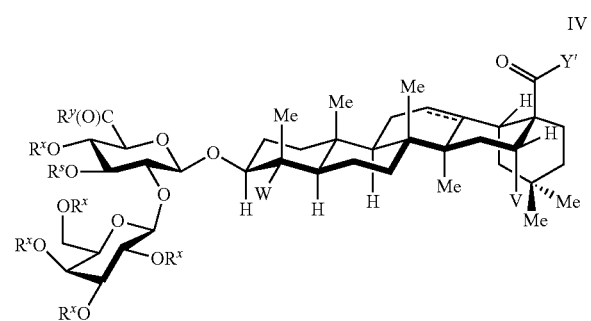

IV wherein:
 is a single or double bond;
Y' is hydrogen, halogen, alkyl, aryl, OR, OR', OH, $NR_2$, $NR_3^+$, NHR, $NH_2$, SR, or NROR;
W is Me, —CHO,

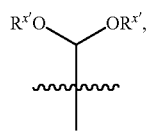

—$CH_2OR^x$, or —$C(O)R^y$;
V is hydrogen or —$OR^x$;
$R^y$ is —OH, or a carboxyl protecting group selected from the group consisting of ester, amides, and hydrazides;
$R^s$ is

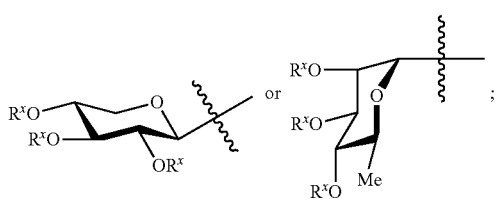

each occurrence of $R^{x'}$ is independently an optionally substituted group selected from 6-10-membered aryl, $C_{1-6}$ aliphatic, or $C_{1-6}$ heteroaliphatic having 1-2 heteroatoms independently selected from the group consisting of nitrogen, oxygen, and sulfur; or: two $R^{x'}$ are taken together to form a 5-7-membered heterocyclic ring having 1-2 heteroatoms independently selected from the group consisting of nitrogen, oxygen, and sulfur;

each occurrence of R is independently hydrogen, an optionally substituted group selected from acyl, arylalkyl, 6-10-membered aryl, $C_{1-12}$ aliphatic, or $C_{1-12}$ heteroaliphatic having 1-2 heteroatoms independently selected from the group consisting of nitrogen, oxygen, and sulfur;

each occurrence of $R^x$ is independently hydrogen or an oxygen protecting group.

In some embodiments, at least one occurrence of $R^x$ is an oxygen protecting group. In some embodiments, at least two occurrences of $R^x$ is an oxygen protecting group. In some embodiments, at least three occurrences of $R^x$ is an oxygen protecting group. In some embodiments, at least four occurrences of $R^x$ is an oxygen protecting group. In some embodiments, all $R^x$ are an oxygen protecting group. In some embodiments, each occurrence of $R^x$ is independently an oxygen protecting group. In certain embodiments, all $R^x$ oxygen protecting groups are the same. In some embodiments, at least one $R^x$ oxygen protecting group is different from the other $R^x$ oxygen protecting groups.

In some embodiments, Y' is not —OMe. In some embodiments, Y' is not —OH. In some embodiments, Y' is not —Oallyl. In some embodiments, Y' is not —OH or —OMe if all $R^x$ groups are simultaneously hydrogen or if at least four $R^x$ groups are simultaneously methyl.

In certain embodiments, at least one $R^x$ group is not hydrogen. In certain embodiments, at least one $R^x$ group is not methyl. In certain embodiments, at least one $R^x$ group is not hydrogen or methyl. In certain embodiments, no $R^x$ groups are hydrogen. In certain embodiments, no $R^x$ groups are methyl. In certain embodiments, no $R^x$ groups are hydrogen or methyl.

In certain embodiments, provided compounds are of formula IV-b:

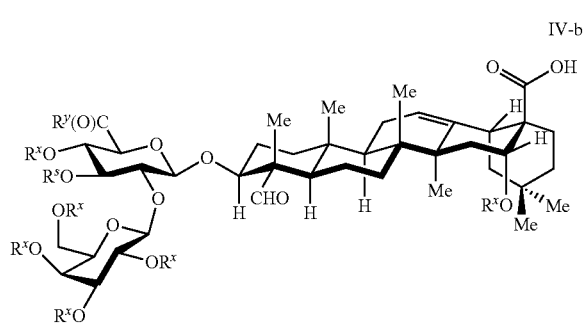

IV-b

Exemplary compounds of formula IV are set forth in Table 1a below.
TABLE 1a
Exemplary compounds of formula IV
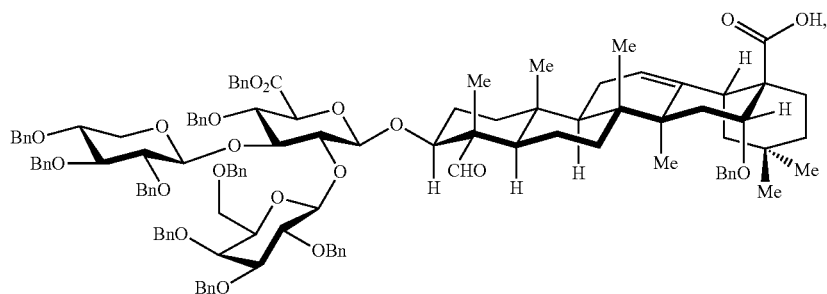
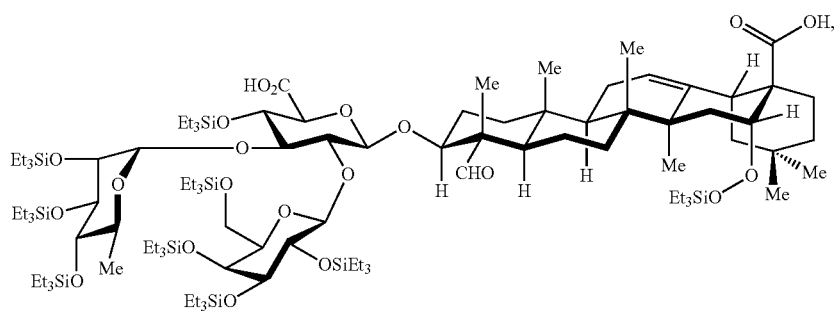
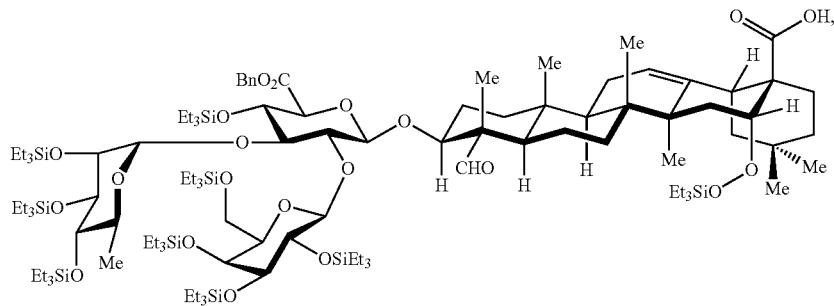
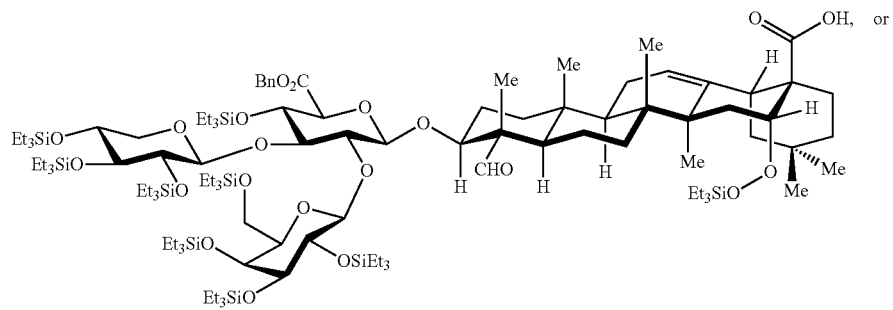

TABLE 1a-continued

Exemplary compounds of formula IV

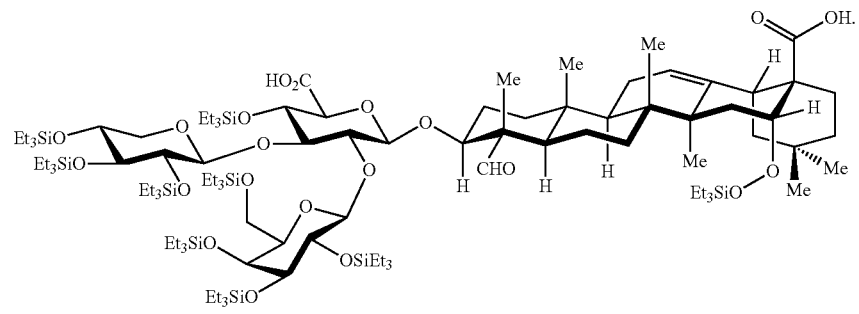

Synthesis of Compounds

Quil-A (Accurate Chemical and Scientific Corporation, Westbury, N.Y.) is a commerically available semi-purified extract from *Quillaja saponaria* which comprises a mixture of at least 50 distinct saponin species (van Setten, D. C.; Vandewerken, G.; Zomer, G.; Kersten, G. F. A. *Rapid Commun. Mass Spectrom.* 1995, 9, 660-666). Many of said saponin species include a triterpene-trisaccharide substructure as found in immunologically-active *Quillaja saponins* such as QS-21 and QS-7:

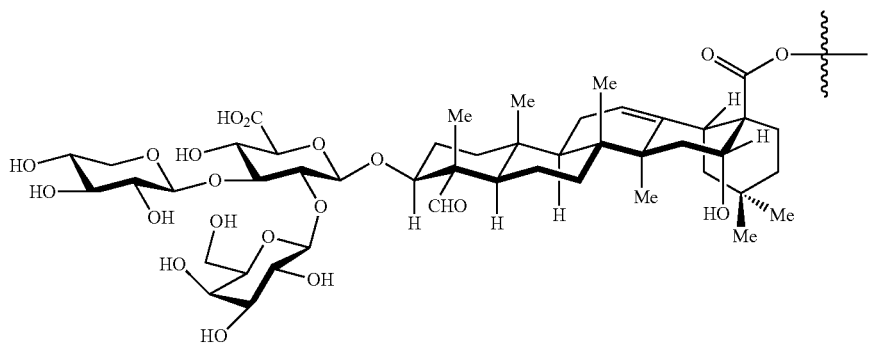

It has been demonstrated (Guo, S.; Kenne, L.; Lundgren, L. N.; Rönnberg, B.; Sundquist, B. G. *Phytochemistry,* 1998, 48, 175-180) that exposure of saponin mixtures to base hydrolysis affords a mixture enriched with three prosapongenins A, B, and C:

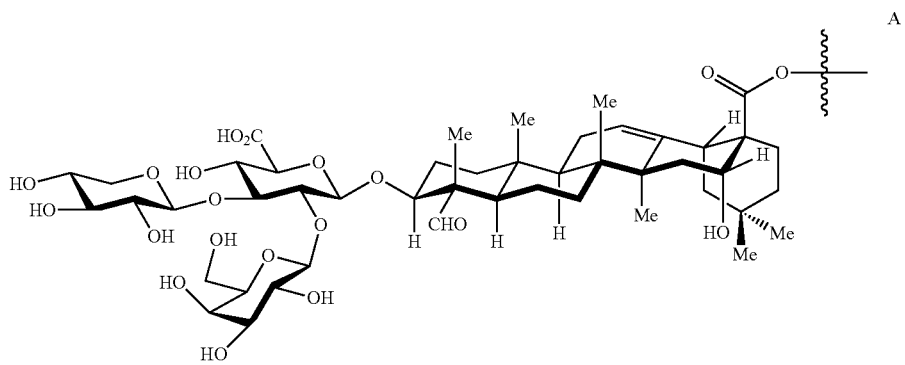

A

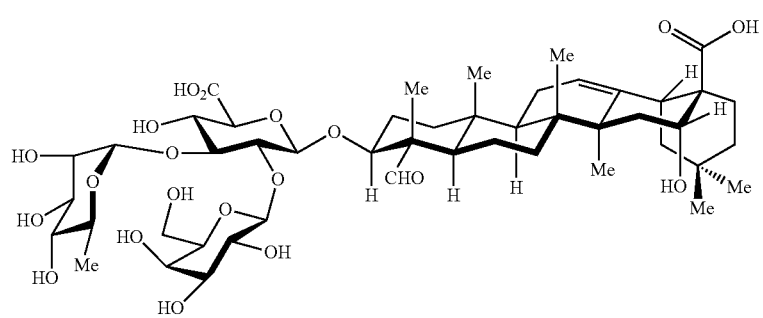

B

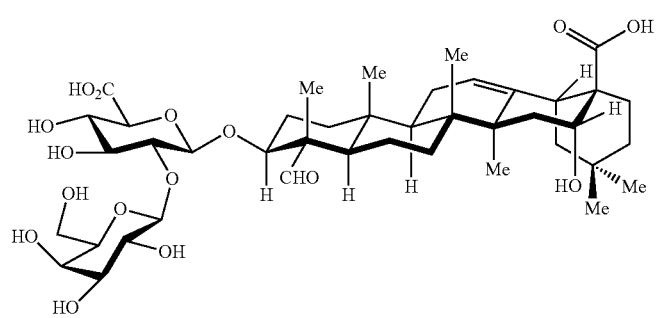

C

However, further use of this semi-pure hydrolyzed mixture of prosapongenins is hindered by the fact that prosapongenins A and B, which differ only by an α-L-Rha vs. β-D-Xyl residue, are inseperable by silica gel chromatography.

Other work has described isolation of highly pure or semi-pure prosapogenins and saponins (WO00/09075, U.S. Pat. Nos. 6,231,859, 5,977,081, 6,080,725, 6,262,029; Higuchi, et al., *Phytochemistry* 1987, 26, 229-235; Brown, F., Haahein, L R (eds), *Dev Biol Stand.*, vol. 92: Brown, F. and Haahein, L R., Karger, Basel: 1998, pp 41-47; Kensil, 1991, supra; van Setten, supra). However, these procedures are not efficient in terms of cost and labor, often requiring several rounds of silica gel and/or HPLC purification in order to isolate the desired products. Furthermore, there is batch variability between commercially available QS samples such that some batches contain no saponins with rhamnose-containing branched trisaccharides. None of the previously described isolation or degradation studies provides efficient access to pure prosapogenins or sapogenins. For example, U.S. Pat. No. 6,231,859 describes the isolation of 98% pure QS-21 following one silica gel chromatography and three or four additional rounds of HPLC run in sequence. The final yield of QS-21 was 59 mg from 20 g of *Quillaja saponaria* extract (see Examples 1 and 2). A similar procedure for the isolation of QS-7 yielded 7 mg of purified QS-7 (final purity not reported) from a 20 g *Quillaja saponaria* extract (see Examples 1 and 4). Such yields and purity are not sufficient for large scale production of pharmaceutical grade adjuvants.

In one aspect of the present invention, Applicant has unexpectedly found a strategy that allows for the facile separation of derivatized prosapogenins A and B via silica gel chromatography. In one aspect, the hydroxyl groups on prosapogenins A and B are derivatized with a suitable protecting group, as described herein, to afford derivatives that are separable by silica gel chromatography. In some embodiments, all hydroxyl groups are derivatized with the same protecting group. In other embodiments, different hydroxyl groups bear different protecting groups. In certain embodiments, the hydroxyl-protected prosapogenin A and B derivatives also have a protecting group on one or both of their carboxylic acid groups.

In certain embodiments, poly(silylation) of prosapogenins A and B, wherein all hydroxyl groups are converted to silyl ethers, gives a mixture of poly(silylated) diacid prosapogenins A and B that are easily separable via silica gel chromatography. In some embodiments, poly(silylation) is used to afford nonakis(trialkylsilyl) ethers of prosapogenins A and B. In some embodiments, poly(silylation) is used to afford nonakis(triethylsilyl) ethers of prosapogenins A and B. In some embodiments, poly(silylation) is used to afford nonakis(trimethylsilyl) ethers of prosapogenins A and B.

In other embodiments, the hydroxyl groups on prosapogenins A and B are derivatized as poly(benzyl) ethers to give a mixture of poly(benzyl) diacids of prosapogenins A and B that are easily seperable via silica gel chromatography. In some embodiments, poly(benzyl) etherification is used to afford nonakis(benzyl) ethers of prosapogenins A and B.

One of ordinary skill will appreciate that a number of suitable protecting groups may be used, and that one or both carboxylic acid groups may optionally be protected as well. In certain embodiments, the glucoronic acid group is selectively protected prior to derivitizing the hydroxyl groups of prosapogenins A and B. In some embodiments, the glucoronic acid group is selectively protected subsequent to derivitizing the hydroxyl groups of prosapogenins A and B.

Batch variability of commerically available *Quillaja saponaria* extracts may result in hydrolyzed saponin mixtures containing prosapogenins other than A, B, and C. In certain embodiments, the hydrolyzed saponin mixture subjected to the described protecting group strategy will be an enriched mixture of prosapogenins A and B. In some embodiments, the saponin mixture will contain one or more other prosapogenins such as prosapogenin C. In certain embodiments, a preliminary round of chromatography is used to render the saponin mixture enriched in prosapogenins A and B.

Other prosapongenins may be subjected to base hydrolysis and the protecting group strategies described above and herein. Examples of saponins that may be derivatized with protecting groups according to the present invention include Glycyrrhizic acid, Hederasaponin C, β-Aescin, Heliantho-side 2, Ginsenoside Rd, and Saponinum album, to name but a few.

In some embodiments, the mixture of prosapogenins will contain rhamnose residues. In some embodiments, the mixture of prosapogenins will not contain rhamnose residues. In some embodiments, the mixture of prosapogenins will be derived from Gypsoside A.

In certain embodiments, the mixture of prosapogenins will contain disaccharides. In some embodiments, the disaccharide is galactose-glucuronic acid.

As described herein, prosapogenins bearing protecting groups in accordance with the present invention may be separated and isolated from one another by suitable physical means. The term "separated by suitable physical means" refers to methods of separating mixtures of prosapogenins or saponins. Such methods are well known in the art and include preferential crystallization, chromatography, and trituration, among others. One of ordinary skill in the art will recognize that such methods may allow for the separation and isolation of both major and minor constituents.

In some embodiments, suitable protecting groups will render provided compounds crystalline. In certain embodiments, preferential crystallization is used to separate provided compounds.

It will be appreciated that chromatography steps aimed at separating derivatives of prosapogenins A and B may be carried out according to methods known in the art. In certain embodiments, chromatography is carried out on derivatives of prosapogenins A and B wherein all hydroxyl groups bear a suitable protecting group. In some embodiments, chromatography is carried out on poly(benzyl) diacids of prosapogenins A and B. In some embodiments, chromatography is carried out on poly(silyl) ether diacids of prosapogenins A and B. In some embodiments, chromatography is carried out on poly(benzyl) ethers of prosapogenins A and B wherein one or both carboxylic acid groups bears a protecting group. In some embodiments, chromatography is carried out on poly(silyl) ethers of prosapogenins A and B wherein one or both carboxylic acid groups bears a protecting group.

In certain embodiments, the chromatography is gravity silica gel chromatography. In certain embodiments, the chromatography is flash silica gel chromatography. In certain embodiments, the chromatography is gravity alumina gel chromatography. In certain embodiments, the chromatography is flash alumina gel chromatography. In certain embodiments, the chromatography is high pressure liquid chromatography (HPLC).

In some embodiments, separation by suitable physical means yields provides prosapogenin compounds of >70% purity. In some embodiments, separation by suitable physical means yields provides prosapogenin compounds of >80% purity. In some embodiments, separation by suitable physical means yields provides prosapogenin compounds of >90% purity. In some embodiments, separation by suitable physical means yields provides prosapogenin compounds of >95% purity. In some embodiments, separation by suitable physical means yields provides prosapogenin compounds of >98% purity. In some embodiments, separation by suitable physical means yields provides prosapogenin compounds of >99% purity. In some embodiments, separation by suitable physical means yields provides prosapogenin compounds of >99.5% purity. In some embodiments, separation by suitable physical means yields provides prosapogenin compounds of >99.9% purity.

In certain embodiments, provided compounds of formula I have >80% purity. In some embodiments, provided compounds of formula I have >90%, purity. In some embodiments, provided compounds of formula I have >95% purity. In some embodiments, provided compounds of formula I have >98% purity. In some embodiments, provided compounds of formula I have >99% purity. In some embodiments, provided compounds of formula I have >99.5% purity. In some embodiments, provided compounds of formula I have >99.9% purity.

Thus, according to another aspect, the invention provides a method of using protecting groups to isolate prosapogenins, the method comprising the steps of:

(a) providing a mixture of prosapogenins of formula IV-a:

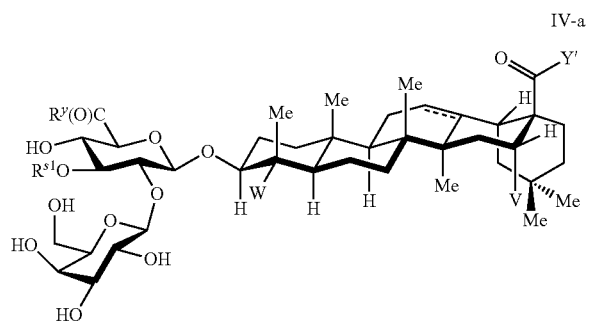

wherein:

⁝⁝⁝ is a single or double bond;

$Y^1$ is hydrogen, halogen, alkyl, aryl, OR, $OR^1$, OH, $NR_2$, $NR_3$, NHR, $NH_2$, SR, or NROR;

W is Me, —CHO,

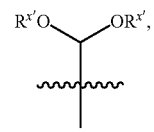

—$CH_2OR^x$, or —$C(O)R^y$;

V is hydrogen or —$OR^x$;

$R^y$ is —OH, or a carboxyl protecting group selected from the group consisting of ester, amides, and hydrazides;

$R^{s1}$ is

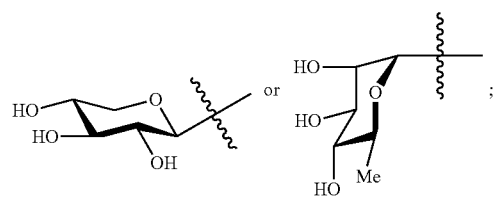

each occurrence of $R^{x'}$ is independently an optionally substituted group selected from 6-10-membered aryl, $C_{1-6}$ aliphatic, or $C_{1-6}$ heteroaliphatic having 1-2 heteroatoms independently selected from the group consisting of nitrogen, oxygen, and sulfur; or: two $R^{x'}$ are taken together to form a 5-7-membered heterocyclic ring having 1-2 heteroatoms independently selected from the group consisting of nitrogen, oxygen, and sulfur;

each occurrence of R is independently hydrogen, an optionally substituted group selected from acyl, arylalkyl, 6-10-membered aryl, $C_{1-6}$ aliphatic, or $C_{1-6}$ heteroaliphatic having 1-2 heteroatoms independently selected from the group consisting of nitrogen, oxygen, and sulfur;

each occurrence of $R^x$ is independently hydrogen or an oxygen protecting group selected from the group consisting of alkyl ethers, benzyl ethers, silyl ethers, acetals, ketals, esters, and carbonates;

(b) treating said compound of formula IV-a under suitable conditions to form a mixture of prosapogenins of formula IV:

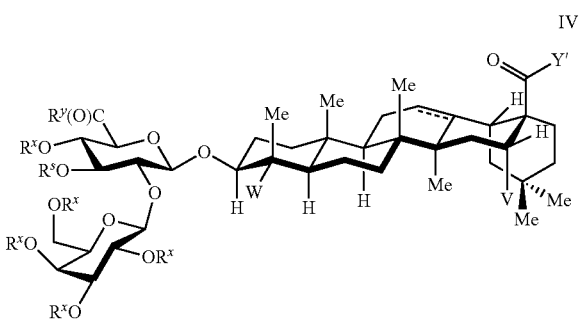

IV wherein each of ≈, $R^y$, Y', V, and W is as defined for compounds of formula IV-a, $R^s$ is as defined for compounds of formula I, and each occurrence of $R^x$ is independently hydrogen or an oxygen protecting group selected from the group consisting of alkyl ethers, benzyl ethers, silyl ethers, acetals, ketals, esters, and carbonates;

and (c) obtaining said compound IV by suitable physical means.

As described above, the present invention provides methods of preparing compounds of formula I. In some embodiments, the $R^x$ and $R^y$ groups of provided compounds are suitable protecting groups. Without wishing to be bound by any particular theory, it is believed that the presence of said protecting groups on provided compounds of formula IV is useful in the reaction of compounds of formula IV with a compound of formula V to form a compound of formula I. As depicted below in Scheme 1, a compound of formula IV may be reacted under suitable conditions with a compound of formula V to provide a compound of formula I.

Scheme 1

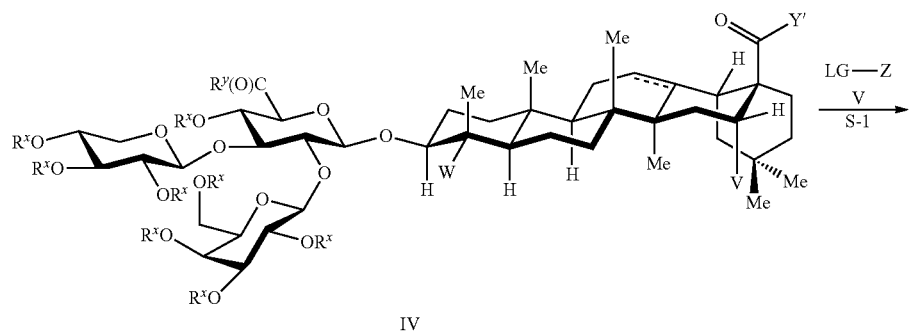

IV

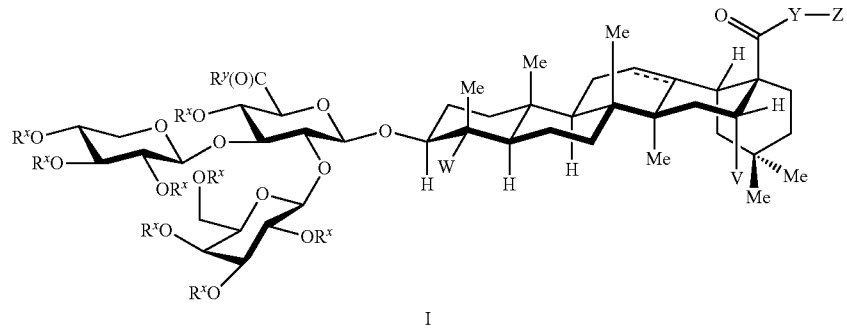

I wherein each of ═, $R^x$, $R^y$, V, and W is defined as described in classes and subclasses above and herein; ═
Y' is hydrogen, halogen, alkyl, aryl, OR, $OR^y$, OH, $NR_2$, $NR_3^+$, NHR, $NH_2$, SR, or NROR;
Z is hydrogen; a cyclic or acyclic, optionally substituted moiety selected from the group consisting of acyl, aliphatic, heteroaliphatic, aryl, arylalkyl, and heteroaryl; or a carbohydrate domain having the structure:

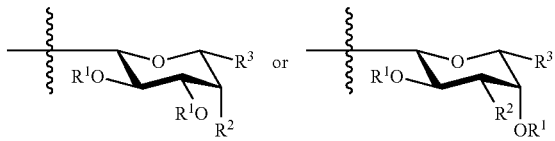

wherein:
each occurrence of $R^1$ is $R^x$ or a carbohydrate domain having the structure:

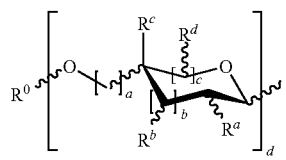

wherein:
each occurrence of a, b, and c is independently 0, 1, or 2;
d is an integer from 1-5, wherein each d bracketed structure may be the same or different; with the proviso that the d bracketed structure represents a furanose or pyranose moiety, and the sum of b and c is 1 or 2;
$R^0$ is hydrogen, an oxygen protecting group selected from the group consisting of alkyl ethers, benzyl ethers, silyl ethers, acetals, ketals, esters, carbamates, and carbonates; or an optionally substituted moiety selected from the group consisting of acyl, $C_{1-10}$ aliphatic, $C_{1-6}$ heteroaliphatic, 6-10-membered aryl, arylalkyl, 5-10-membered heteroaryl having 1-4 heteroatoms independently selected from nitrogen, oxygen, or sulfur, 4-7-membered heterocyclyl having 1-2 heteroatoms independently selected from the group consisting of nitrogen, oxygen, and sulfur;
each occurrence of $R^a$, $R^b$, $R^c$, and $R^d$ is independently hydrogen, halogen, OH, OR, $OR^x$, $NR_2$, NHCOR, or an optionally substituted group selected from acyl, $C_{1-10}$ aliphatic, $C_{1-6}$ heteroaliphatic, 6-10-membered aryl, arylalkyl, 5-10-membered heteroaryl having 1-4 heteroatoms independently selected from nitrogen, oxygen, or sulfur; 4-7-membered heterocyclyl having 1-2 heteroatoms independently selected from the group consisting of nitrogen, oxygen, and sulfur.

One of ordinary skill in the art will appreciate that provided compounds can be subjected to reductive conditions (i.e., $LiAlH_4$, $NaBH_4$, $AlH_3$, $NaBH_3(OAc)$, $Zn(BH_4)_2$, $Et_3SiH$, and others described in March, supra) to transform the aldehyde moiety into an alcohol or methyl group. Provided compounds can also be subjected to oxidative conditions (i.e., $MnO_4^-$, chromic acid, bromine, Oxone®, silver oxide, and others described in March, supra) to transform the aldehyde moiety into a carboxyl group. Such hydroxyl or carboxyl groups can be protected with suitable protecting groups as defined above and herein.

Thus, in certain embodiments, W is Me, —CHO,

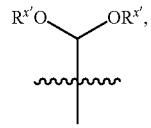

—$CH_2OR^x$, or —$C(O)OR^y$. In certain embodiments, W is methyl. In other embodiments, W is —CHO. In certain embodiments, W is —$CH_2OR^x$. In other embodiments, W is —$C(O)OR^y$. In some embodiments, W is —$CH_2OH$. In other embodiments, W is —$CH_2OBn$. In other embodiments, W is —$CH_2OSiEt_3$. In certain embodiments, W is —C(O)OH. In other embodiments, W is —C(O)OBn.

In certain embodiments, V is —$OR^x$. In some embodiments, V is —OH. In some embodiments, V is hydrogen.

As defined above, ═ represents a single or double bond. It will be appreciated that compounds of formula IV can be subjected to hydrogenation conditions (i.e., Raney-Ni, Pd/C, $NaBH_4$, reduced nickel, Adams' catalyst, zinc oxide, Wilkinson's catalyst, and others described in March, supra) that reduce the double bond to a single bond.

It will be appreciated that the C28 carboxyl group may be transformed into other carbonyl functional groups. In some embodiments, the carboxyl group is reduced to an aldehyde. In other embodiments, the carboxyl group is converted into a Weinreb amide. In other embodiments, the carboxyl group is converted into an amide. In other embodiments, the carboxyl group is converted into an ester.

As defined above, Y is $CH_2$, —O—, —NR—, or —NH—. In certain embodiments, Y is $CH_2$. In certain embodiments, Y is —O—. In other embodiments, Y is —NR—. In some embodiments, Y is —NH—.

The present invention encompasses the recognition that judicious selection of protecting groups on provided compounds of formula IV allows for the derivation of the —C(O)Y' group attached to C28. In certain embodiments, —C(O)Y' is a ketone. In other embodiments, —C(O)Y' is an amide. In some embodiments, —C(O)Y' is an ester.

The LG group of formula V is a suitable leaving group. One of ordinary skill in the art will appreciate that a variety of suitable leaving groups LG can be used to facilitate the reaction described in step S-1, and all such suitable leaving groups are contemplated by the present invention. A suitable leaving group is a chemical group that is readily displaced by a desired incoming chemical moiety. Suitable leaving groups are well known in the art, e.g., see, March, supra. Such leaving groups include, but are not limited to, halogen, alkoxy, sulphonyloxy, optionally substituted alkylsulphonyl, optionally substituted alkenylsulfonyl, optionally substituted arylsulfonyl, and diazonium moieties. Examples of some suitable leaving groups include chloro, iodo, bromo, fluoro, methanesulfonyl (mesyl), tosyl, triflate, nitro-phenylsulfonyl (nosyl), and bromo-phenylsulfonyl (brosyl). Additional leaving groups are described herein.

In certain embodiments, a compound of formula V is a monosacchide or oligosaccharide that may act as a glycosylation donor. Thus, according to another aspect of the invention, provided compounds are of formulae VI or VI':

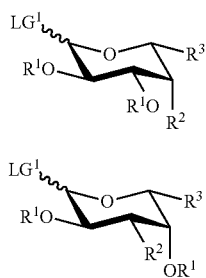

wherein each of $R^1$, $R^2$, and $R^3$ is defined as described in classes and subclasses above and herein; and $LG^1$ is a suitable leaving group.

As depicted in Scheme 2, a compound of formula IV may be reacted under suitable conditions with a compound of formula VI to give a compound of formula I-A:

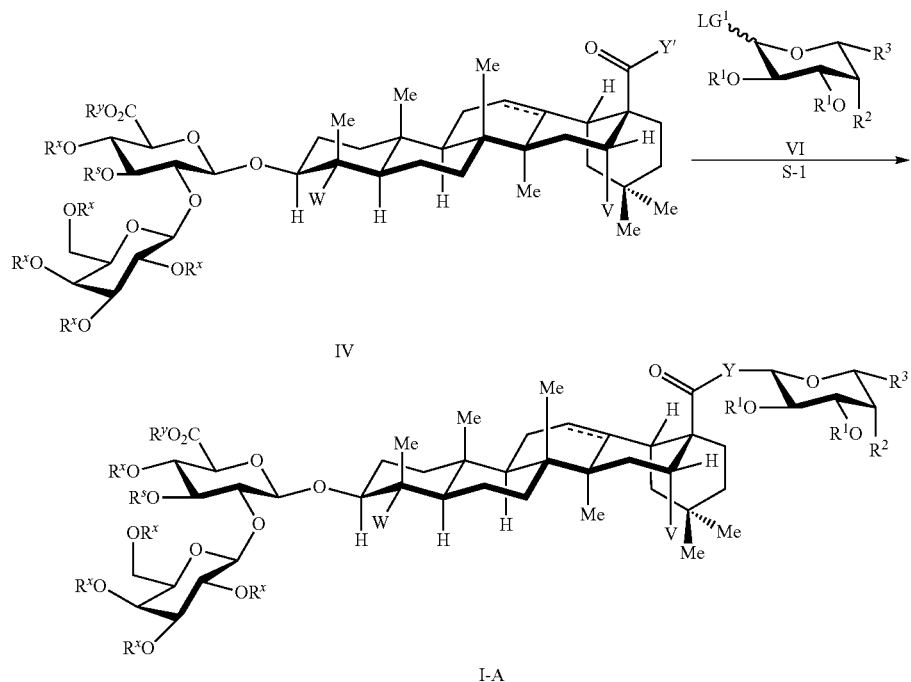

wherein each of ⸺, $R^x$, $R^y$, $R^s$, V, W, Y', Y, $R^1$, $R^2$, $R^3$, and $LG^1$ is defined as described in classes and subclasses above and herein.

The $LG^1$ group of compounds of formulae VI and VI' is a glycoside donor leaving group, as defined and described herein. One of ordinary skill in the art will appreciate that a variety of suitable leaving groups $LG^1$ can be used to facilitate the reaction described, and all such suitable leaving groups are contemplated by the present invention.

In some embodiments, $LG^1$ is monovalent. In other embodiments, $LG^1$ is divalent. In certain embodiments, the LG group of formula V is halogen, thioalkyl, thioaryl, thioheteroaryl, thiocyano, O-acyl, orthoester, O-carbonate, S-carbonate, trichloroimidate, 4-pentenyl, phosphate, O-sulfonyl, O-silyl, hydroxyl, diazirine, or arylseleno.

As described above, in certain embodiments the $LG^1$ group is halogen. In some embodiments, $LG^1$ is Br. In some embodiments, $LG^1$ is Cl. In some embodiments, $LG^1$ is F.

In some embodiments, $LG^1$ is thioalkyl. In some embodiments, $LG^1$ is —SEt. In some embodiments, $LG^1$ is —SMe.

In some embodiments, $LG^1$ is thioaryl. In some embodiments, $LG^1$ is —SPh.

In some embodiments, $LG^1$ is thioheteroaryl. In some embodiments, $LG^1$ is thiopyridinyl (—SPy). In some embodiments, $LG^1$ is

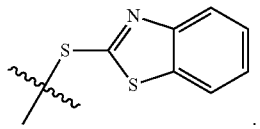 [SMILES: *Sc1nc2ccccc2s1]

In some embodiments, $LG^1$ is

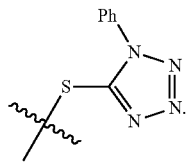 [SMILES: *Sc1nnnn1-c1ccccc1]

In some embodiments, $LG^1$ is O-acyl. In some embodiments, $LG^1$ is —OAc. In some embodiments, $LG^1$ is —OC(O)CH$_2$Br. In some embodiments, $LG^1$ is —OBz. In some embodiments, $LG^1$ is —OC(O)C$_6$H$_4$-p-NO$_2$. In some embodiments, $LG^1$ is —OC(O)Py.

In some embodiments, the $LG^1$ group maybe taken together with another part of Z to form a cyclic moiety. In certain embodiments, the taking together of $LG^1$ with another part of Z forms an ortho ester or derivative thereof. In certain embodiments, the $LG^1$ group comprises a tert-butyl ortho ester. In some embodiments, the $LG^1$ group comprises a 1-cyanoethylidene. In some embodiments, the $LG^1$ group comprises a (p-methylphenyl)thioethylidene. In some embodiments, the $LG^1$ group comprises an ethylthioethylidene. In some embodiments, the $LG^1$ group comprises an [N-(1-phenylethylidene)amino]oxyl-2,2-dimethylpropylidene. In some embodiments, the $LG^1$ group comprises a cyclic thiocarbonate. In some embodiments, the $LG^1$ group comprises a diazirine.

In some embodiments, $LG^1$ is O-carbonate. In some embodiments, $LG^1$ is O-xanthate. In some embodiments, $LG^1$ is —OC(S)SMe. In some embodiments, $LG^1$ is

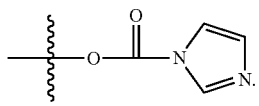 [SMILES: *OC(=O)n1ccnc1]

In some embodiments, $LG^1$ is

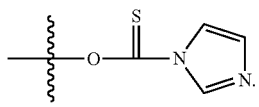

In some embodiments, $LG^1$ is —SC(S)—OEt. In some embodiments, $LG^1$ is

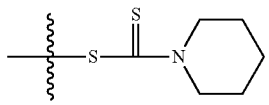

In certain embodiments, $LG^1$ is trichloroimidate. In some embodiments, $LG^1$ is —OC(NH)CCl$_3$.

In certain embodiments, $LG^1$ is 4-pentenyl. In some embodiments, $LG^1$ is —O(CH$_2$)$_3$CHCH$_2$.

In certain embodiments, $LG^1$ comprises a phosphate. In some embodiments, $LG^1$ comprises a diphenyl phosphate. In some embodiments, $LG^1$ comprises a diphenylphosphineimidate. In some embodiments, $LG^1$ comprises a phosphoroamidate. In some embodiments, $LG^1$ comprises a phosphorodiamidimidothioate. In some embodiments, $LG^1$ comprises a dimethylphosphinothioate.

In certain embodiments, $LG^1$ is O-sulfonyl. In some embodiments, $LG^1$ is —OTs. In some embodiments, $LG^1$ is —OMs. In some embodiments, $LG^1$ is —OTf.

In certain embodiments, $LG^1$ is O-silyl. In some embodiments, $LG^1$ is —OTMS. In some embodiments, $LG^1$ is —OSiEt$_3$. In some embodiments, $LG^1$ is —OTBS.

In certain embodiments, $LG^1$ is hydroxyl.

In certain embodiments, $LG^1$ is α-linked compound of formula VI. In certain embodiments, $LG^1$ is β-linked compound of formula VI.

In certain embodiments, $LG^1$ is n-alkenyl.

General methods and reagents for carrying out glycosylation reactions are described by Toshima, K. and Tatsuta, K., Chem. Rev. 1993, 93, 1503-1531, the entire contents of which is hereby incorporated by reference.

In certain embodiments, compounds of formula I are provided by conjugating an oligosaccharide of formulae VI or VI' with a compound of formula IV as described for step S-1. In some embodiments, the entire oligosaccharide is prepared as a compound of formula VI prior to step S-1. In other embodiments, a monosaccharide of formula VI is conjugated in step S-1 to a compound of formula IV, and the resulting triterpene-saccharide conjugate is subjected to further glycosylation reactions to provide a compound of formula I. In some embodiments, protecting group strategies are employed that allow for selective glycosylation reactions to occur in the assembly of the final triterpene oligosaccharide compound of formula I.

Thus, in another aspect, the present invention provides compounds of formulae VI-1, VI-2, VI-3, VI-4, VI-5, VI-6, VI-7, VI-8, VI-9, VI-10, and VI-11:

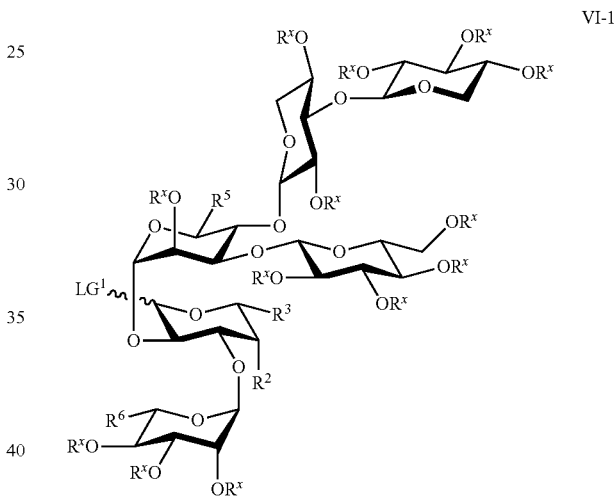

VI-1

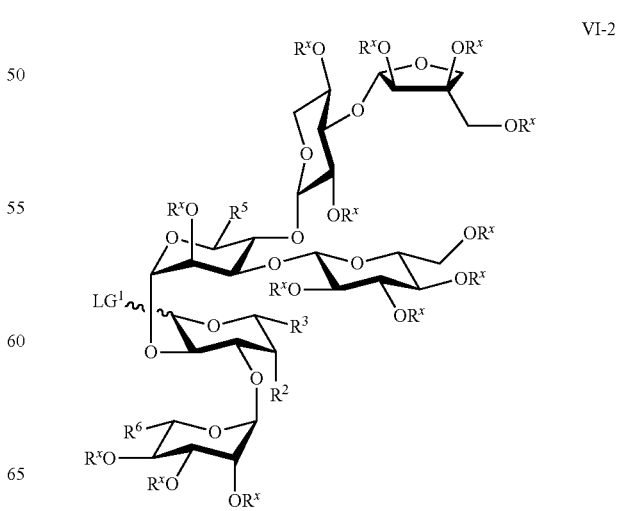

VI-2

VI-3
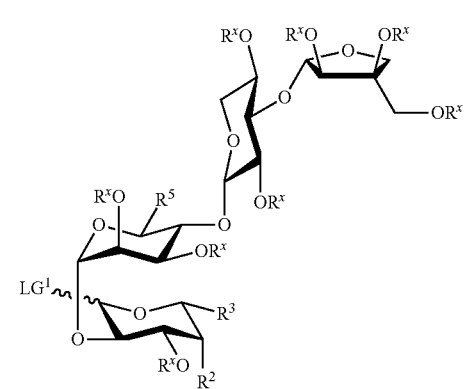
VI-4
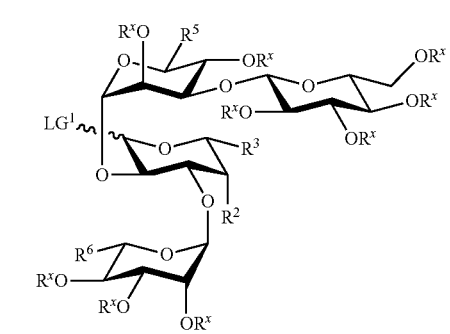
VI-5
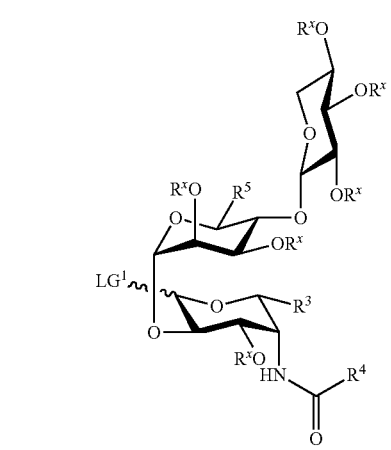
VI-6
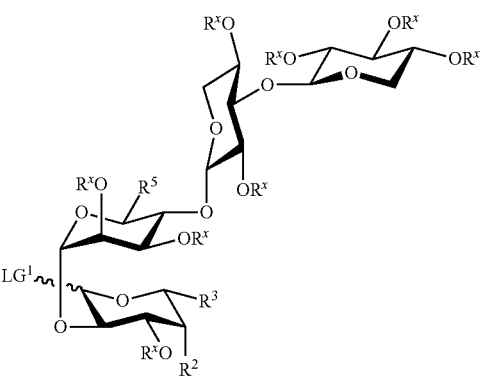
VI-7
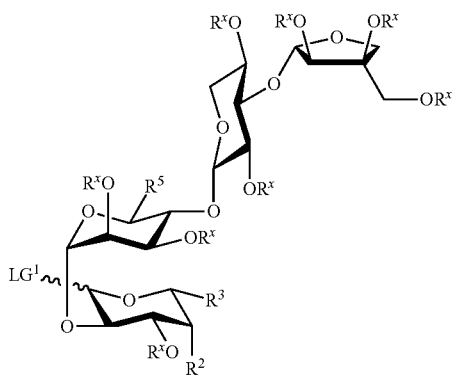
VI-8
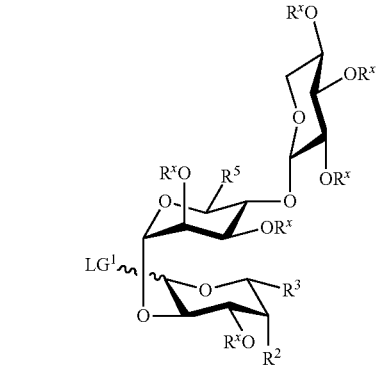
VI-9
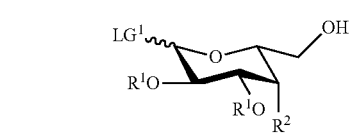
VI-10
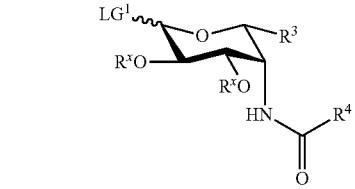
VI-11
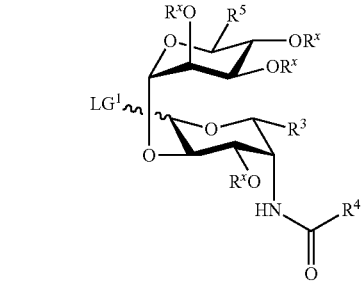
VI-12
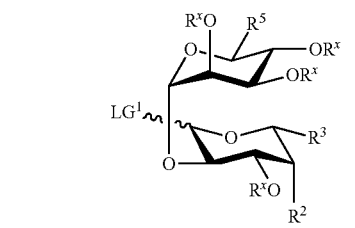

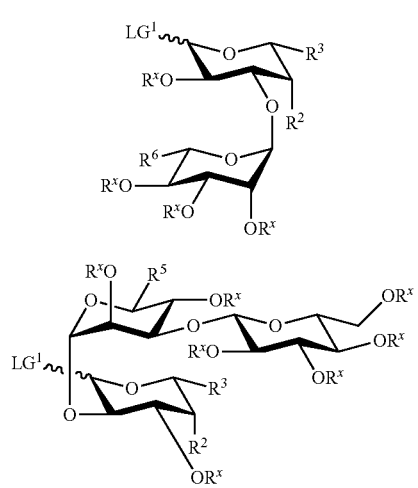

wherein each of $R^2$, $R^3$, $R^4$, $R^5$, $R^6$, $R^x$, and $LG^1$ is defined as described in classes and subclasses above and herein.

In certain embodiments, compounds of formula VI are monosaccharide and D-fucosyl. In some embodiments, compounds of formula VI are monosaccharide and L-fucosyl. In some embodiments, compounds of formula VI are monosaccharide and are not fucosyl. In some embodiments, compounds of formula VI are monosaccharide and are not D-fucosyl. In some embodiments, compounds of formula VI are monosaccharide and are not β-D-fucosyl.

In some embodiments, compounds of formula VI are oligosaccharide, and the carbohydrate domain directly attached to Y is fucosyl. In some embodiments, compounds of formula VI are oligosaccharide, and the carbohydrate domain directly attached to Y is not D-fucosyl. In some embodiments, compounds of formula VI are oligosaccharide, and the carbohydrate domain directly attached to Y is not β-D-fucosyl. In some embodiments, compounds of formula VI are oligosaccharide, and the carbohydrate domain directly attached to Y is not α-D-fucosyl. In some embodiments, compounds of formula VI are oligosaccharide, and the carbohydrate domain directly attached to Y is not fucosyl.

In some embodiments, compounds of formula VI are optionally substituted monosaccharide and D-fucosyl. In some embodiments, compounds of formula VI are optionally substituted monosaccharide and L-fucosyl. In some embodiments, compounds of formula VI are optionally substituted monosaccharide and not fucosyl. In some embodiments, compounds of formula VI are optionally substituted monosaccharide and not β-D-fucosyl.

Exemplary compounds of formula VI are set forth in Table 2.

TABLE 2

Exemplary compounds of formula VI

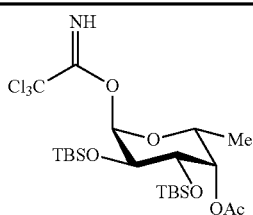

TABLE 2-continued

Exemplary compounds of formula VI

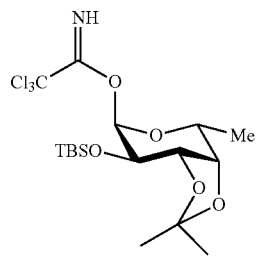

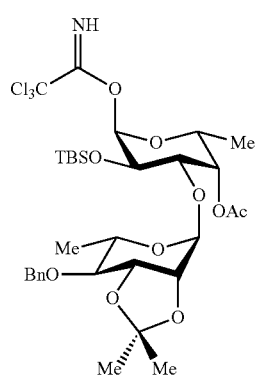

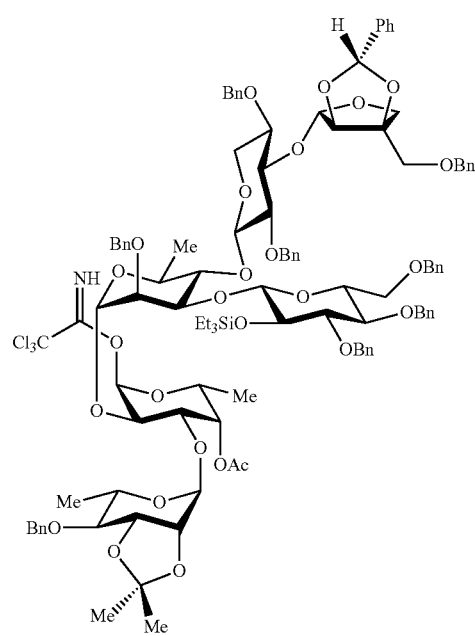

TABLE 2-continued

Exemplary compounds of formula VI

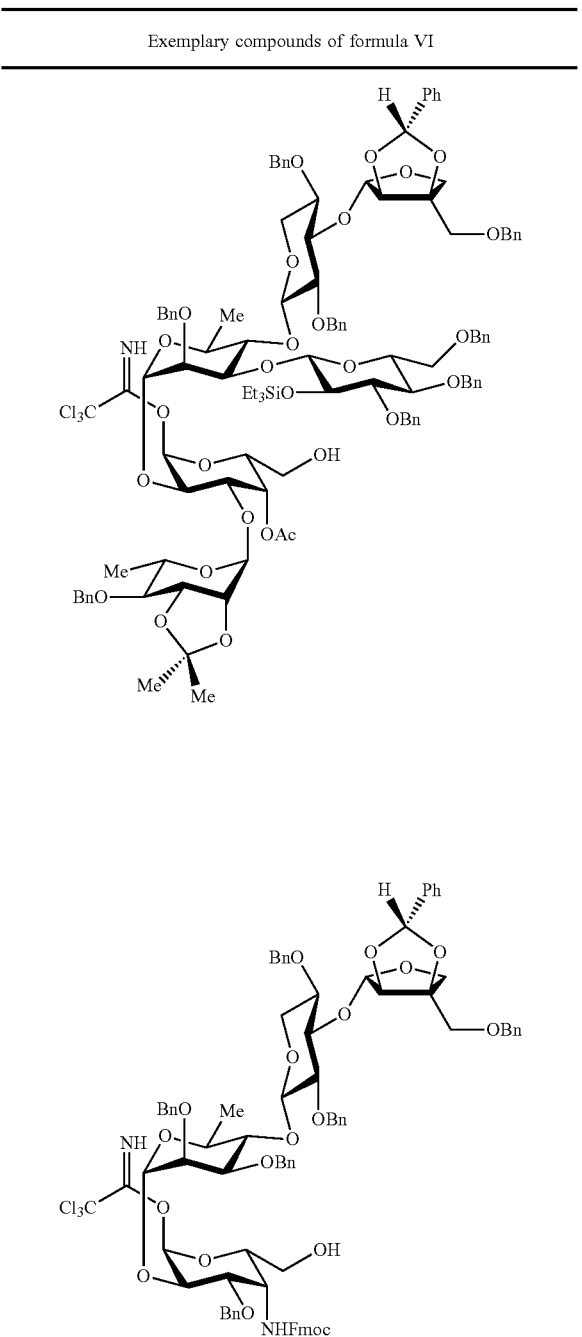

TABLE 2-continued

Exemplary compounds of formula VI

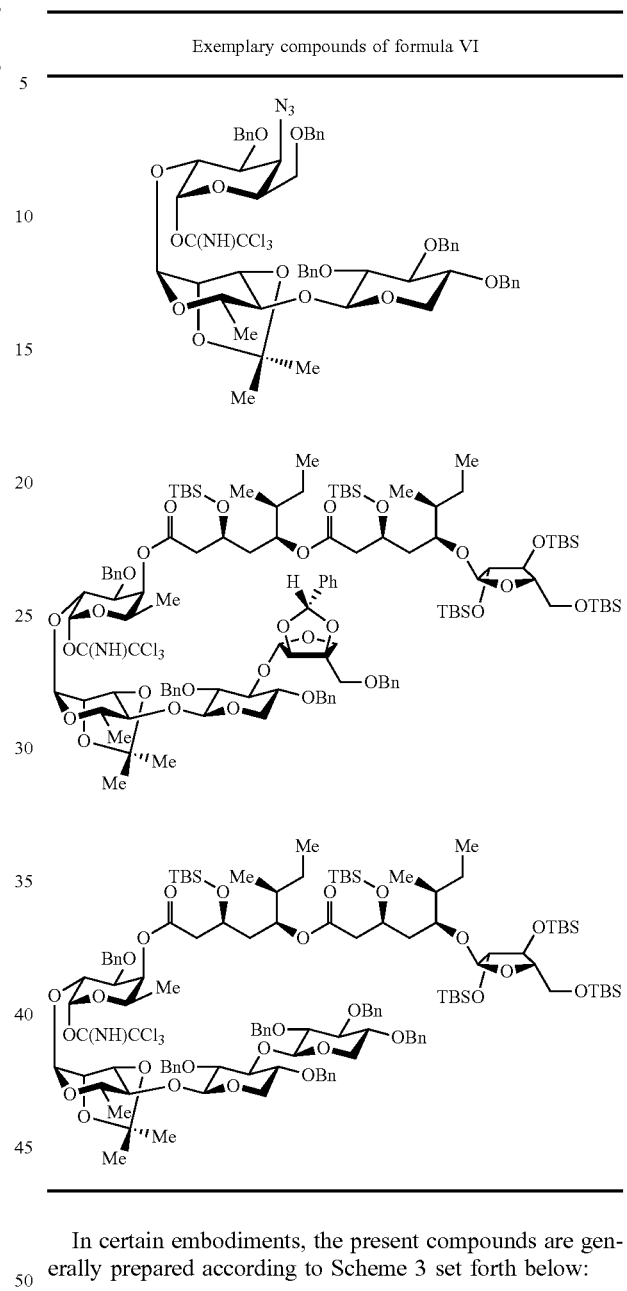

In certain embodiments, the present compounds are generally prepared according to Scheme 3 set forth below:

Scheme 3

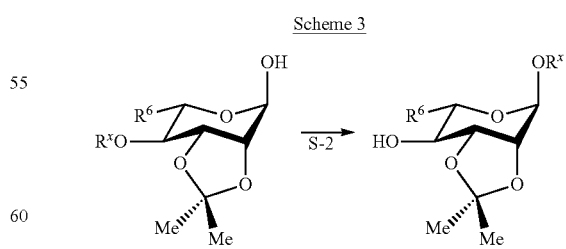

wherein each of $R^6$ and $R^x$ is defined as described in classes and subclasses above and herein.

In some embodiments, the present compounds are generally prepared according to Scheme 4 set forth below:

Scheme 4

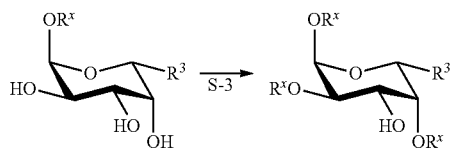

wherein each of $R^3$ and $R^x$ is defined as described in classes and subclasses above and herein.

In some embodiments, the present compounds are generally prepared according to Scheme 5 set forth below:

Scheme 5

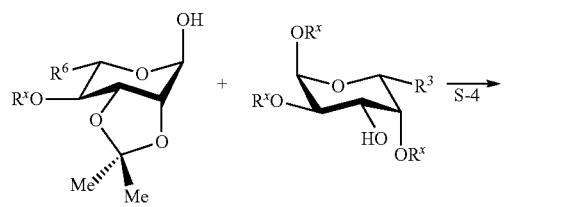

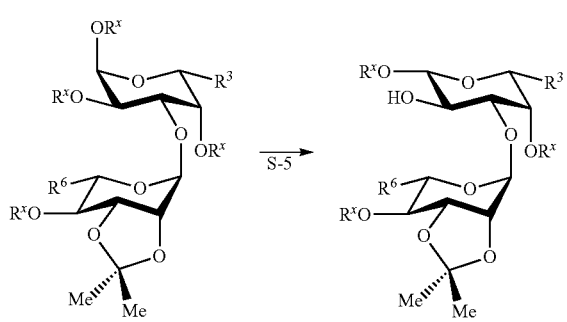

wherein each of $R^3$, $R^6$, and $R^x$ is defined as described in classes and subclasses above and herein.

In some embodiments, the present compounds are generally prepared according to Scheme 6 set forth below:

Scheme 6

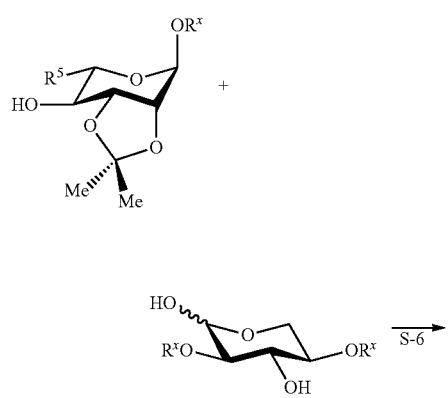

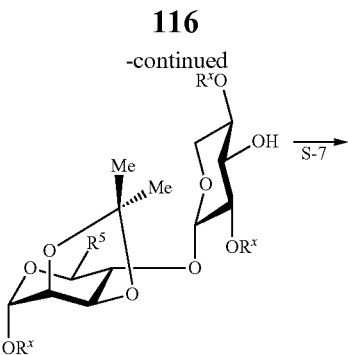

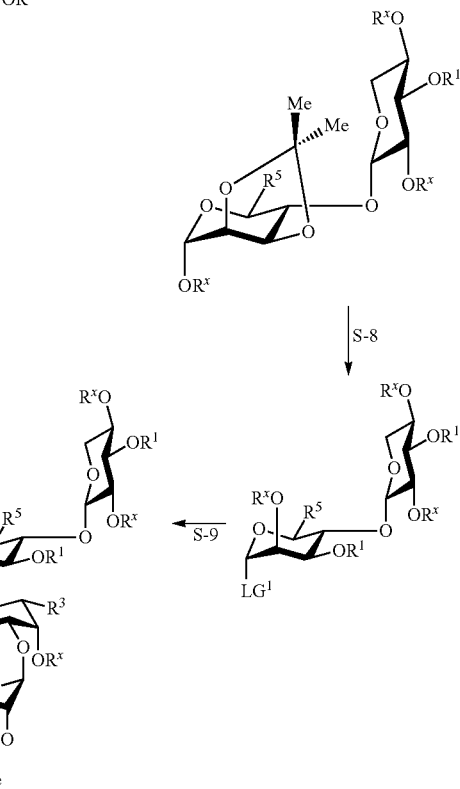

wherein each of $R^1$, $R^3$, $R^5$, $R^6$, $LG^1$, and $R^x$ is defined as described in classes and subclasses above and herein.

In each of the synthetic steps depicted in Schemes 3-6, one of ordinary skill will recognize that a variety of suitable protecting groups may be used. Orthogonal protecting group strategies are well known in the art and may be used to selectively protect and deprotect saccharide hydroxyl groups. It will be appreciated that a variety of suitable leaving groups $LG^1$ may also be employed, as described above, to carry out glycosylation step S-9.

In certain embodiments, step S-1 involves the addition of a nucleophile to a compound of formula IV. In some embodiments, the reaction between a compound of formula IV and a nucleophile is carried out using suitable esterification conditions. The term "suitable esterification conditions," as used herein, refers to the catalyzed or uncatalyzed esterification or transesterification between an oxygen nucleophile and an ester or carboxylic acid. In some embodiments, the conditions comprise the addition or one or more bases. In some embodiments, the base is an amine. In some embodiments, an additional promoter of esterification may be used such as DMAP or EDC.

In some embodiments, the reaction between a compound of formula IV and a nucleophile is carried out using suitable peptide bond forming conditions. Suitable peptide coupling conditions are well known in the art and include those described in detail in Han et al., *Tetrahedron,* 60, 2447-67 (2004), the entirety of which is hereby incorporated by reference. In certain embodiments, the peptide coupling conditions include the addition of HOBt, DMAP, BOP, HBTU, HATU, BOMI, DCC, EDC, IBCF, or a combination thereof.

In some embodiments, the nucleophile is carbon-based, such as an alkyl metal species. In some embodiments, the nucleophile is a Grignard reagent. In some embodiments, the nucleophile is an organolithium. In some embodiments, the nucleophile is an organoborane. In some embodiments, the nucleophile is an organotin. In some embodiments, the nucleophile is an enol.

Uses

Compounds of formulae I, II, III, or IV may be used as adjuvants or to enhance the cellular uptake of toxins. The inventive compounds may be particularly useful in the treatment or prevention of neoplasms or other proliferative diseases in vivo. However, inventive compounds described above may also be used in vitro for research or clinical purposes.

Adjuvants

Most protein and glycoprotein antigens are poorly immunogenic or non-immunogenic when administered alone. Strong adaptive immune responses to such antigens often requires the use of adjuvants. Immune adjuvants are substances that, when administered to a subject, increase the immune response to an antigen or enhance certain activities of cells from the immune system. An adjuvant may also allow the use of a lower dose of antigen to achieve a useful immune response in a subject.

Common adjuvants include alum, Freund's adjuvant (an oil-in-water emulsion with dead mycobacteria), Freund's adjuvant with MDP (an oil-in-water emulsion with muramyldipeptide, MDP, a constituent of mycobacteria), alum plus *Bordetella pertussis* (aluminum hydroxide gel with killed *B. pertussis*). Such adjuvants are thought to act by delaying the release of antigens and enhancing uptake by macrophages. Immune stimulatory complexes (ISCOMs) such as Quil-A (a *Quillaja saponin* extract) are open cage-like complexes typically with a diameter of about 40 nm that are built up by cholesterol, lipid, immunogen, and saponin. ISCOMs deliver antigen to the cytosol, and have been demonstrated to promote antibody response and induction of T helper cell as well as cytotoxic T lymphocyte responses in a variety of experimental animal models.

Various studies have raised the concern of potential toxicity associated with saponin-based adjuvants. Fractionation experiments testing the major components of Quil-A showed that QS-21 had low toxicity and QS-7 showed no lethality at the doses tested in CD-1 mice intradermally. QS-7 showed no hemolytic activity at levels up to 200 μg/mL of saponin (Kensil et al., 1991, supra).

In humans, QS-21 has displayed both local and systemic toxicity. Maximum doses for healthy patients are typically ≤50 μg, and ≤100 μg for cancer patients. As mentioned above, QS-7 has been found not only to possess significant stand-alone adjuvant activity, but also to induce remarkable synergistic immune response augmentation. Unfortunately, QS-7 has proven difficult to isolate in clinically useful quantities.

The present invention encompasses the recognition that synthetic access to and structural modification of QS-7 and related *Quillaja saponins* may afford compounds with high adjuvant potency and low toxicity.

Enhanced Uptake of Toxins

Saponins have been shown to exhibit cell membrane-permeabilizing properties, and have been investigated for their therapeutic potential. In some cases, saponins have virtually no effect alone, but when used in combination with another drug will significantly amplify the effects of the other drug. One example of such a combination effect is with ginsenoside and cis-diaminedichloroplatinum(II) (Nakata, H., et al., *Jpn J Cancer Res.* 1998, 89, 733-40). Therefore, saponins have potential utility in combination therapies with antitumor drugs for cancer treatment. Saponinum album from *Gypsophila paniculata* L. has been described to enhance the cytotoxicity of a chimeric toxin in cell culture, even at nonpermeabilizing concentrations.

In certain embodiments, provided compounds may be used to enhance the uptake of other cytotoxic agents.

Vaccines

Compositions of the invention are useful as vaccines to induce active immunity towards antigens in subjects. Any animal that may experience the beneficial effects of the compositions of the present invention within the scope of subjects that may be treated. In some embodiments, the subjects are mammals. In some embodiments, the subjects are humans.

The vaccines of the present invention may be used to confer resistance to infection or cancer by either passive or active immunization. When the vaccines of the present invention are used to confer resistance through active immunization, a vaccine of the present invention is administered to an animal to elicit a protective immune response which either prevents or attenuates a proliferative or infectious disease. When the vaccines of the present invention are used to confer resistance to infection through passive immunization, the vaccine is provided to a host animal (e.g., human, dog, or mouse), and the antisera elicited by this vaccine is recovered and directly provided to a recipient suspected of having an infection or disease or exposed to a causative organism.

The present invention thus concerns and provides a means for preventing or attenuating a proliferative disease resulting from organisms or tumor cells which have antigens that are recognized and bound by antisera produced in response to the immunogenic polypeptides included in vaccines of the present invention. As used herein, a vaccine is said to prevent or attenuate a disease if its administration to an animal results either in the total or partial attenuation (i.e., suppression) of a symptom or condition of the disease, or in the total or partial immunity of the animal to the disease.

The administration of the vaccine (or the antisera which it elicits) may be for either a "prophylactic" or "therapeutic" purpose. When provided prophylactically, the vaccine(s) are provided in advance of any symptoms of proliferative disease. The prophylactic administration of the vaccine(s) serves to prevent or attenuate any subsequent presentation of the disease. When provided therapeutically, the vaccine(s) is provided upon or after the detection of symptoms which indicate that an animal may be infected with a pathogen or have a certain cancer. The therapeutic administration of the vaccine(s) serves to attenuate any actual disease presentation. Thus, the vaccines may be provided either prior to the onset of disease proliferation (so as to prevent or attenuate an anticipated infection or cancer) or after the initiation of an actual proliferation.

Thus, in one aspect the present invention provides vaccines comprising one or more bacterial, viral, protozoal, or tumor-related antigens in combination with one or more inventive compounds. In some embodiments, the vaccine comprises a single bacterial, viral, protozoal, or tumor-related antigen in combination with one inventive compound. In some embodiments, the vaccine comprises two or more bacterial, viral, protozoal, or tumor-related antigens in combination with a single inventive compound. In some embodiments, the vaccine comprises a two or more bacterial, viral, protozoal, or tumor-related antigens in combination with two or more inventive compounds. In some embodiments, the vaccine comprises a single bacterial, viral, protozoal, or tumor-related antigens in combination with two or more inventive compounds.

In some embodiments, one or more antigens of provided vaccines are bacterial antigens. In certain embodiments, the bacterial antigens are antigens associated with a bacterium selected from the group consisting of *Helicobacter pylori, Chlamydia pneumoniae, Chlamydia trachomatis, Ureaplasma urealyticum, Mycoplasma pneumoniae, Staphylococcus* spp., *Staphylococcus aureus, Streptococcus* spp., *Streptococcus pyogenes, Streptococcus pneumoniae, Streptococcus viridans, Enterococcus faecalis, Neisseria meningitidis, Neisseria gonorrhoeae, Bacillus anthracis, Salmonella* spp., *Salmonella typhi, Vibrio cholera, Pasteurella pestis, Pseudomonas aeruginosa, Campylobacter* spp., *Campylobacter jejuni, Clostridium* spp., *Clostridium difficile, Mycobacterium* spp., *Mycobacterium tuberculosis, Treponema* spp., *Borrelia* spp., *Borrelia burgdorferi, Leptospria* spp., *Hemophilus ducreyi, Corynebacterium diphtheria, Bordetella pertussis, Bordetella parapertussis, Bordetella bronchiseptica, hemophilus influenza, Escherichia coli, Shigella* spp., *Erlichia* spp., *Rickettsia* spp. and combinations thereof.

In certain embodiments, one or more antigens of provided vaccines are viral-associated antigens. In certain embodiments, the viral-associated antigens are antigens associated with a virus selected from the group consisting of influenza viruses, parainfluenza viruses, mumps virus, adenoviruses, respiratory syncytial virus, Epstein-Barr virus, rhinoviruses, polioviruses, coxsackieviruses, echo viruses, rubeola virus, rubella virus, varicell-zoster virus, herpes viruses, herpes simplex virus, parvoviruses, cytomegalovirus, hepatitis viruses, human papillomavirus, alphaviruses, flaviviruses, bunyaviruses, rabies virus, arenaviruses, filoviruses, HIV 1, HIV 2, HTLV-1, HTLV-II, FeLV, bovine LV, FeIV, canine distemper virus, canine contagious hepatitis virus, feline calicivirus, feline rhinotracheitis virus, TGE virus, foot and mouth disease virus, and combinations thereof.

In certain embodiments, one or more antigens of provided vaccines are tumor-associated antigens. In some embodiments, the tumor-associated antigens are antigens selected from the group consisting of killed tumor cells and lysates thereof, MAGE-1, MAGE-3 and peptide fragments thereof; human chorionic gonadotropin and peptide fragments thereof; carcinoembryonic antigen and peptide fragments thereof, alpha fetoprotein and peptide fragments thereof; pancreatic oncofetal antigen and peptide fragments thereof; MUC-1 and peptide fragments thereof, CA 125, CA 15-3, CA 19-9, CA 549, CA 195 and peptide fragments thereof; prostate-specific antigens and peptide fragments thereof; prostate-specific membrane antigen and peptide fragments thereof; squamous cell carcinoma antigen and peptide fragments thereof; ovarian cancer antigen and peptide fragments thereof; pancreas cancer associated antigen and peptide fragments thereof; Her1/neu and peptide fragments thereof; gp-100 and peptide fragments thereof; mutant K-ras proteins and peptide fragments thereof; mutant p53 and peptide fragments thereof; truncated epidermal growth factor receptor, chimeric protein $p210^{BCR-ABL}$, KH-1, N3, GM1, GM2, GD2, GD3, Gb3, Globo-H, STn, Tn, Lewis$^x$, Lewis$^y$, TF; and mixtures thereof.

In certain embodiments, an antigen is covalently bound to a compound of formula I, II, III, or IV. In some embodiments, an antigen is not covalently bound to a compound of formula I, II, III, or IV.

One of ordinary skill in the art will appreciate that vaccines may optionally include a pharmaceutically acceptable excipient or carrier. Thus, according to another aspect, provided vaccines comprise one or more antigens that are optionally conjugated to a pharmaceutically acceptable excipient or carrier. In some embodiments, said one or more antigens are conjugated covalently to a pharmaceutically acceptable excipient. In other embodiments, said one or more antigens are non-covalently associated with a pharmaceutically acceptable excipient.

As described above, adjuvants may be used to increase the immune response to an antigen. According to the invention, provided vaccines may be used invoke an immune response when administered to a subject. In certain embodiments, an immune response to an antigen may be potentiated by administering to a subject a provided vaccine in an effect amount to potentiate the immune response of said subject to said antigen.

As described above, provided compounds may be used in cancer vaccines as adjuvants in combination with tumor-associated antigens. In certain embodiments, said vaccines may be used in the treatment or prevention of neoplasms. In certain embodiments, the neoplasm is a benign neoplasm. In other embodiments, the neoplasm is a malignant neoplasm. Any cancer may be treated using compounds of the invention with an antigen.

In certain embodiments, the malignancy is a hematological malignancy. Hematological malignancies are types of cancers that affect the blood, bone marrow, and/or lymph nodes. Examples of hematological malignancies that may be treated using compounds of formulae I, II, III, or IV include, but are not limited to, acute lymphoblastic leukemia (ALL), acute myelogenous leukemia (AML), chronic myelogenous leukemia (CML), chronic lymphocytic leukemia (CLL), hairy cell leukemia, Hodgkin's lymphoma, non-Hodgkin's lymphoma, cutaneous T-cell lymphoma (CTCL), peripheral T-cell lymphoma (PTCL), Mantle cell lymphoma, B-cell lymphoma, acute lymphoblastic T cell leukemia (T-ALL), acute promyelocytic leukemia, and multiple myeloma.

Other cancers besides hematological malignancies may also be treated using compounds of formulae I, II, III, or IV. In certain embodiments, the cancer is a solid tumor. Exemplary cancers that may be treated using compounds of formulae I, II, III, or IV include colon cancer, lung cancer, bone cancer, pancreatic cancer, stomach cancer, esophageal cancer, skin cancer, brain cancer, liver cancer, ovarian cancer, cervical cancer, uterine cancer, testicular cancer, prostate cancer, bladder cancer, kidney cancer, neuroendocrine cancer, breast cancer, gastric cancer, eye cancer, gallbladder cancer, laryngeal cancer, oral cancer, penile cancer, glandular tumors, rectal cancer, small intestine cancer, sarcoma, carcinoma, melanoma, urethral cancer, vaginal cancer, to name but a few.

In certain embodiments, compounds and pharmaceutical compositions of the present invention can be employed in combination therapies, that is, the compounds and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another antiproliferative agent), or they may achieve different effects (e.g., control of any adverse effects).

For example, other therapies or anticancer agents that may be used in combination with the inventive anticancer agents of the present invention include surgery, radiotherapy (γ-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), to name a few. Additionally, the present invention also encompasses the use of certain cytotoxic or anticancer agents currently in clinical trials and which may ultimately be approved by the FDA (including, but not limited to, epothilones and analogues thereof and geldanamycins and analogues thereof). For a more comprehensive discussion of updated cancer therapies see, www.nci.nih.gov, a list of the FDA approved oncology drugs at www.fda.gov/cder/cancer/druglistframe.htm, and The Merck Manual, Seventeenth Ed. 1999, the entire contents of which are hereby incorporated by reference.

In another aspect, the invention provides a method of treating infectious disease in a subject comprising administering to the subject a therapeutically effective amount of a compound of formulae I, II, III, or IV. In some embodiments, the infection is bacterial. In some embodiments, the infection is viral. In some embodiments, the infection is protozoal. In some embodiments, the subject is human.

Formulations

Inventive compounds may be combined with a pharmaceutically acceptable excipient to form a pharmaceutical composition. In certain embodiments, the pharmaceutical composition includes a pharmaceutically acceptable amount of an inventive compound. The amount of active ingredient which can be combined with a carrier material to produce a single dosage form will vary depending upon the host being treated, and the particular mode of administration. The amount of active ingredient that can be combined with a carrier material to produce a single dosage form will generally be that amount of the compound which produces a therapeutic effect. Generally, this amount will range from about 1% to about 99% of active ingredient, preferably from about 5% to about 70%, most preferably from about 10% to about 30%.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. In certain embodiments, a formulation of the present invention comprises an excipient selected from the group consisting of cyclodextrins, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid: binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol, glycerol monostearate, and nonionic surfactants; absorbents, such as kaolin and bentonite clay; lubricants, such as talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made in a suitable machine in which a mixture of the powdered compound is moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Dissolving or dispersing the compound in the proper medium can make such dosage forms. Absorption enhancers can also be used to increase the flux of the compound across the skin. Either providing a rate controlling membrane or dispersing the compound in a polymer matrix or gel can control the rate of such flux.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

In certain embodiments, a compound or pharmaceutical preparation is administered orally. In other embodiments, the compound or pharmaceutical preparation is administered intravenously. Alternative routs of administration include sublingual, intramuscular, and transdermal administrations.

When the compounds of the present invention are administered as pharmaceuticals, to humans and animals, they can be given per se or as a pharmaceutical composition containing, for example, 0.1% to 99.5% (more preferably, 0.5% to 90%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required to achieve the desired therapeutic effect and then gradually increasing the dosage until the desired effect is achieved.

In some embodiments, a compound or pharmaceutical composition of the invention is provided to a subject chronically. Chronic treatments include any form of repeated administration for an extended period of time, such as repeated administrations for one or more months, between a month and a year, one or more years, or longer. In many embodiments, a chronic treatment involves administering a compound or pharmaceutical composition of the invention repeatedly over the life of the subject. Preferred chronic treatments involve regular administrations, for example one or more times a day, one or more times a week, or one or more times a month. In general, a suitable dose such as a daily dose of a compound of the invention will be that amount of the compound that is the lowest dose effective to produce a therapeutic effect. Such an effective dose will generally depend upon the factors described above. Generally doses of the compounds of this invention for a patient, when used for the indicated effects, will range from about 0.0001 to about 100 mg per kg of body weight per day. Preferably the daily dosage will range from 0.001 to 50 mg of compound per kg of body weight, and even more preferably from 0.01 to 10 mg of compound per kg of body weight. However, lower or higher doses can be used. In some embodiments, the dose administered to a subject may be modified as the physiology of the subject changes due to age, disease progression, weight, or other factors.

In some embodiments, provided adjuvant compounds are administered as pharmaceutical compositions or vaccines. In certain embodiments, the amount of adjuvant compound administered is 1-2000 µg. In certain embodiments, the amount of adjuvant compound administered is 1-1000 µg. In certain embodiments, the amount of adjuvant compound administered is 1-500 µg. In certain embodiments, the amount of adjuvant compound administered is 1-250 µg. In certain embodiments, the amount of adjuvant compound administered is 100-1000 µg. In certain embodiments, the amount of adjuvant compound administered is 100-500 µg. In certain embodiments, the amount of adjuvant compound administered is 100-200 µg. In certain embodiments, the amount of adjuvant compound administered is 250-500 µg. In certain embodiments, the amount of adjuvant compound administered is 10-1000 µg. In certain embodiments, the amount of adjuvant compound administered is 500-1000 µg. In certain embodiments, the amount of adjuvant compound administered is 50-250 µg. In certain embodiments, the amount of adjuvant compound administered is 50-500 µg.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, in certain embodiments the compound is administered as a pharmaceutical formulation (composition) as described above.

The compounds according to the invention may be formulated for administration in any convenient way for use in human or veterinary medicine, by analogy with other pharmaceuticals.

The invention provides kits comprising pharmaceutical compositions of an inventive compound. In certain embodiments, such kits including the combination of a compound of formulae I, II, III, or IV and an antigen. The agents may be packaged separately or together. The kit optionally includes instructions for prescribing the medication. In certain embodiments, the kit includes multiple doses of each agent. The kit may include sufficient quantities of each component to treat a subject for a week, two weeks, three weeks, four weeks, or multiple months. The kit may include a full cycle of immunotherapy. In some embodiments, the kit includes a vaccine comprising one or more bacterial, viral, protozoal, or tumor-associated antigens, and one or more provided compounds.

The entire contents of all references cited above and herein are hereby incorporated by reference.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

tively protected monosaccharides 2-4, 6, and 8 (Scheme 7). While the xylo-, gluco- and apio-derived monosaccharides 2-4 (Scheme 7A) were obtained in multi-step sequences by previously reported procedures and modifications thereof (Kim, Y. J.; Wang, P.; Navarro-Villalobos, M.; Rohde, B. D.; Derryberry, J.; Gin, D. Y. *J. Am. Chem. Soc.* 2006, 128, 11906-11915; Nguyen, H. M.; Chen, Y. N.; Duron, S. G.; Gin, D. Y. *J. Am. Chem. Soc.* 2001, 123, 8766-8772) the novel sugars 6 and 8 were prepared from rhamnopyranose 5 and fucopyranoside 7, respectively. Silylation of the selectively-protected rhamnopyranose 5 (Scheme 7B) with TIPSOTf provided the α-TIPS glycoside (96%), which subsequently underwent C4-O-debenzylation to furnish the rhamnopyranoside 6 (98%). Synthesis of the fucosyl residue within QS-7 commenced with selective C3-O-alkylation of the allyl fucopyranoside 7 (Scheme 7C) with PMBCl (56%) via its transient stannylene acetal. This allowed for sequential selective silylation of the equatorial C2-OH (97%) and acetylation of the axial C4-OH (>99%). Finally, oxidative removal of the PMB ether with DDQ provided the selectively-protected fucopyranoside 8 (86%).

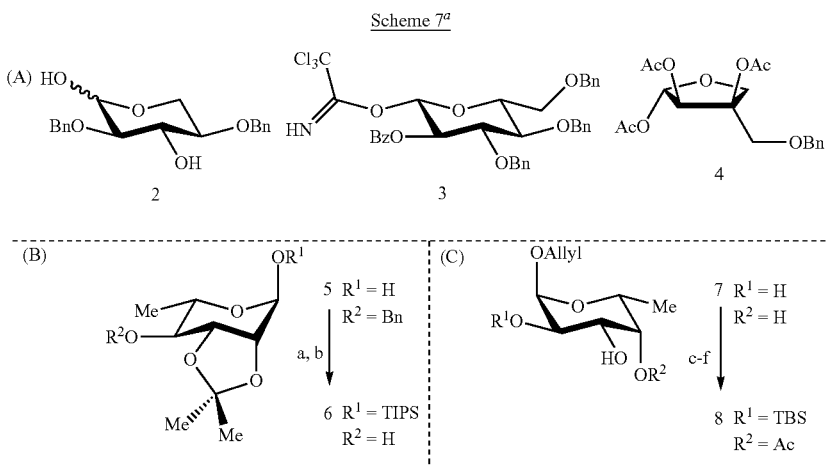

Scheme 7*a*

*a*Reagents and conditions:
a TIPSOTf, 2,6-lutidine, CH₂Cl₂, 0→23° C., 96%;
b H₂, Pd-C, MeOH, 23° C., 98%;
c n-Bu₂SnO, PhMe, reflux; CsF; PMBCl, DMF, 23° C., 56%;
d TBSCl,imidazole, DMAP, CH₂Cl₂, 23° C., 97%;
e Ac₂O, Et₃N, DMAP, CH₂Cl₂, 23° C., >99%;
f DDQ, MeOH, H₂O, 0→23° C., 86%.

EXAMPLES

Example 1

Figure 1B:
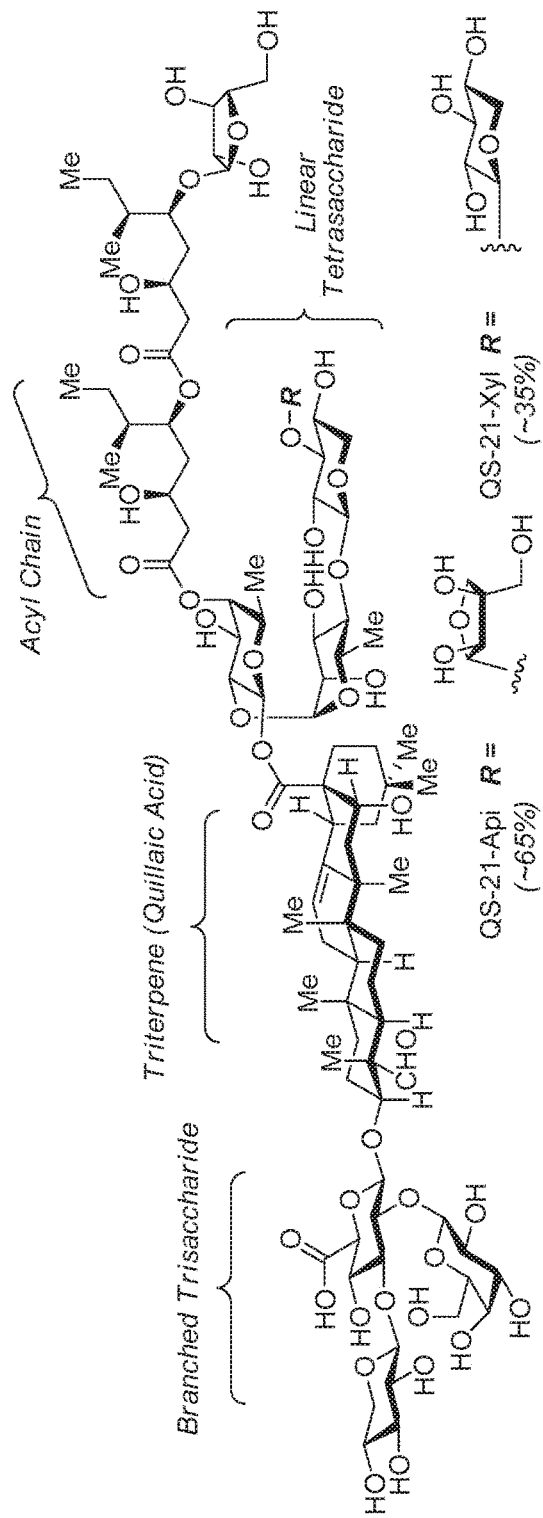
FIG. 1b depicts the chemical structures of QS-21-Api and QS-21-Xyl. Percentages correspond to the natural abundance of each isomer in isolated extracts of QS-21.

The synthesis of the hexasaccharide fragment within QS-7-Api (FIG. 1) required initial preparation of the selec- Convergent assembly of the branched hexasaccharide (Scheme 8) involved dehydrative glycosylation (Ph₂SO.Tf₂O) (Garcia, B. A.; Gin, D. Y. *J. Am. Chem. Soc.* 2000, 122, 4269-4279) of fucopyranoside 8 with rhamnopyranose 5 (84%). The resulting α-disaccharide 9 then underwent a series of protective group exchanges, including TBS removal (95%), a novel Et₂Zn/Pd(PPh₃)₄-mediated anomeric de-allylation (68%), (Chandrasekhar, S.; Reddy, C. R.; Rao, R. J. *Tetrahedron* 2001, 57, 3435-3438) and selective anomeric silylation (75%) to afford the disaccharide 10 as a suitable glycosyl acceptor. Its glycosyl donor coupling partner was prepared by chemo- and stereoselective dehydrative glycosylation of rhamnopyranoside 6 with xylopyranose 2 to afford the β-disaccharide 11 (75%), which directly underwent modified Helferich glycosylation (Roush, W. R.; Bennett, C. E. *J. Am. Chem. Soc.* 1999, 121, 3541-3542) with the apiose-derived donor 4 to afford trisaccharide 12 (86%). The acetate esters in 12 were then exchanged for a benzylidene acetal protective group (94%), followed by selective acid hydrolysis of the rhamno-derived isopropylidene ketal to afford the corresponding vicinal diol (71%). Selective alkylation of the resulting axial rhamno-C2-OH with BnBr could then be accomplished (84%), allowing for Schmidt glycosylation (Schmidt, R. R.; Kinzy, W. *Adv. Carbohydr. Chem. Biochem.* 1994, 50, 21-123) of the C3-OH with the glucosyl imidate 3 to afford the tetrasaccharide 13 (86%). Exchange of the benzoate ester for a TES ether (91%, 2 steps) and conversion of the anomeric TIPS group to its α-trichloroacetimidate counterpart 14 (92%, 2 steps) secured a suitable donor for glycosylation of disaccharide 10. This was accomplished by treating the two components with TMSOTf to afford hexasaccharide 15 (62%), whose fucosyl-TIPS-acetal was then transformed to the α-trichloroacetimidate 16 (84%, 2 steps).

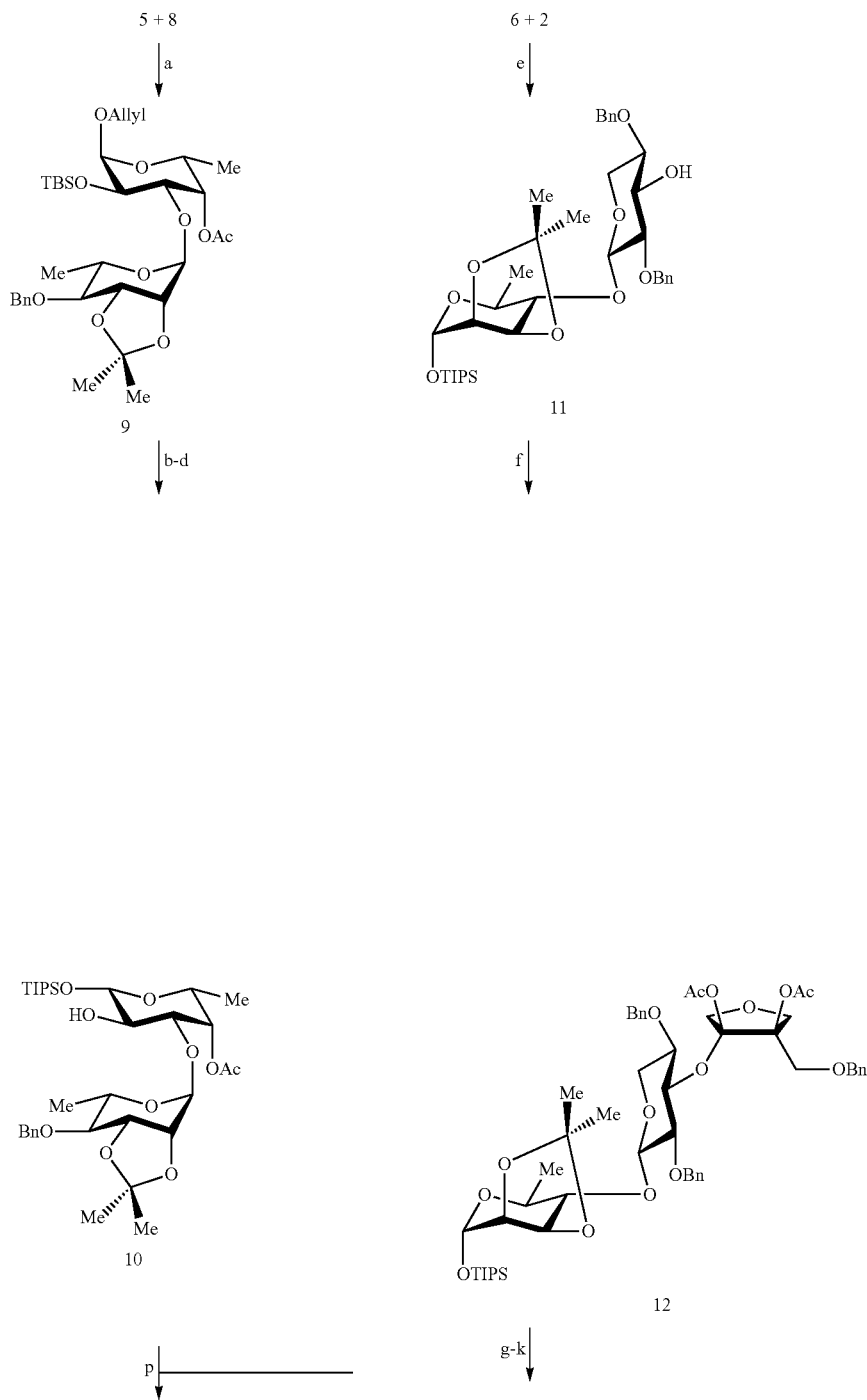

Scheme 8[a]

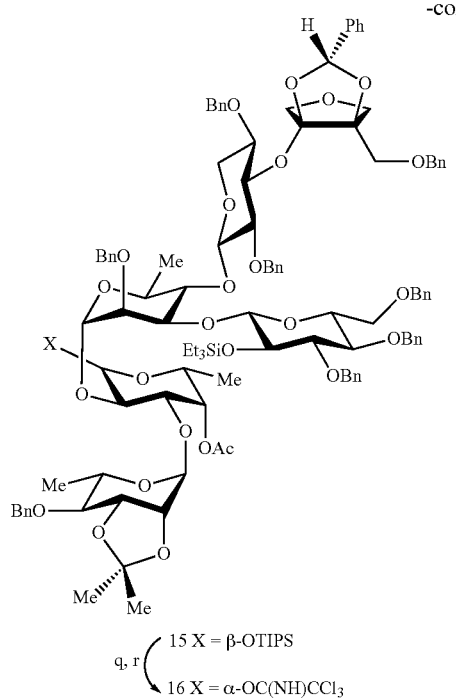
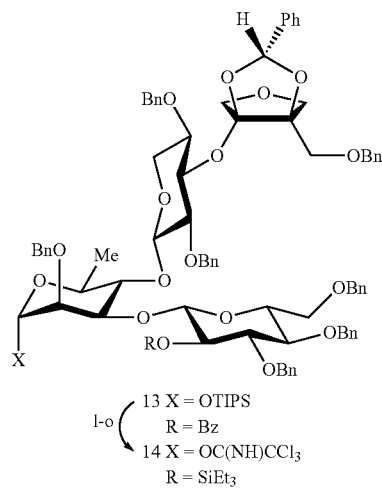

```
         ⎧ 15 X = β-OTIPS
    q, r ⎨
         ⎩ 16 X = α-OC(NH)CCl₃
```

```
         ⎧ 13 X = OTIPS
         ⎪    R = Bz
    l-o  ⎨
         ⎪ 14 X = OC(NH)CCl₃
         ⎩    R = SiEt₃
```

*Reagents and conditions:
a Ph₂SO, Tf₂O, TBP, CH₂Cl₂, -78→23° C., 84%;
b TBAF, THF, 0→23° C., 95%;
c Et₂Zn, Pd(PPh₃)₄, Et₂O, 23° C.; 68%;
d TIPSCl, imidazole, DMAP, DMF, 23° C., 75%;
e Ph₂SO, Tf₂O, TBP, CH₂Cl₂, -78→23° C., 75%
f 4, TBSOTf, CH₂Cl₂, 0° C., 86%; (g) K₂CO₃, H₂O, MeOH, 23° C.;
h PhCH(OMe)₂, p-TsOH, 23° C., 94% (2 steps);
i p-TsOH, H₂O, MeOH, 23° C., 71%;
j BnBr, Bu₄NBr, NaOH, H₂O, CH₂Cl₂, 23° C., 84%;
k 3, TMSOTf, Et₂O, -45° C., 86%;
l DIBAL-H, CH₂Cl₂, -78° C., 92%;
m TESOTf, 2,6-lutidine, CH₂Cl₂, 0→23° C., 99%;
n TBAF, THF, 0° C., >99%;
o CCl₃CN, DBU, CH₂Cl₂, 0° C., 92%;
p TMSOTf, 4Å ms, CH₂Cl₂, -15° C., 62%;
q TBAF, THF, 0° C.;
r CCl₃CN, DBU, CH₂Cl₂, 0→23° C., 84% (2 steps).

Late stage construction of the full QS-7-Api skeleton involved the elaborately-protected triterpene-trisaccharide conjugate 18 (Scheme 9A), previously prepared from glucuronolactone 17 during the course of the synthesis of QS-21 (Kim, et al., supra). This C28-carboxylic acid glycosyl acceptor 18 responded well to glycosylation with trichloroacetimidate glycosyl donor 16 (BF₃.OEt₂) to afford fully protected QS-7-Api (71%), which underwent global deprotection under carefully managed conditions (TFA; H₂, Pd—C). The resulting product (71%) was found to be identical to naturally derived QS-7-Api (1) (trace quantities of natural QS-7-Api (~70% purity, NMR) were obtained from exhaustive RP-HPLC purification of commercial Quil-A ($90/g).

This synthesis of 1 (Scheme 9A) from de novo construction of all oligosaccharide fragments confirms the structure of QS-7-Api and provides significantly more dependable access to homogeneous samples of 1 than isolation from natural sources. This notwithstanding, the synthesis of 1 can be further augmented. Quil-A (19, Scheme 9B) is a commercially available semi-purified extract from *Quillaja saponaria* and contains variable quantities of >50 distinct saponins (Vansetten, supra), many of which incorporate the triterpene-trisaccharide substructure within QS-7 (and QS-21). This monodesmoside saponin 20 (Scheme 9B) can be isolated in semi-pure form via direct base hydrolysis of the Quil-A mixture (Higuchi et al., supra). Subsequent poly(silylation) of 20 with excess TESOTf afforded the corresponding nonakis(triethylsilyl) ether (257 mg from 1.15 g of 19), whose glucuronic acid functionality could be selectively derivatized to the benzyl ester 21 (CbzCl, 68%). This triterpene-trisaccharide conjugate, obtained in only a 3-step protocol from Quil-A (19), was an effective donor in a C28-carboxylate glycosylation (80%) with hexasaccharide 16 to provide, after global deprotection, QS-7-Api (1) (77%). The evolution of the first synthesis of 1 to this semi-synthetic variant furnishes complex QS-saponin adjuvants (and likely non-natural analogues) with markedly enhanced facility, enabling heretofore untapped opportunities for novel adjuvant discovery in antitumor and antiviral vaccine development.

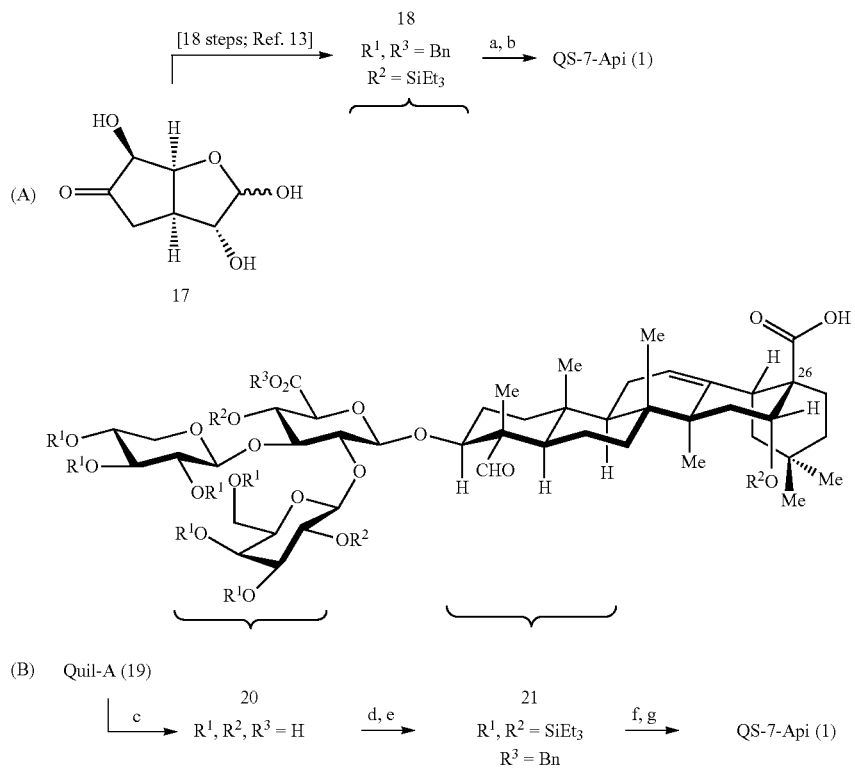

Scheme 9[a]

[a]Reagents and condtions:
a 16, BF$_3$·OEt$_2$, 4Å ms, CH$_2$Cl$_2$, -78→23° C., 71%;
b TFA, H$_2$O,CH$_2$Cl$_2$, 0° C.; H$_2$, Pd-C, EtOH, THF, 23° C., 71%;
c KOH, EtOH, H$_2$O, 80° C.;
d TESOTf, Py, 40° C.;
e CbzCl, Py, TBP, CH$_2$Cl$_2$, 23° C., 68%;
f 16, BF$_3$·OEt$_2$, 4Å ms, CH$_2$Cl$_2$, -78→23° C., 80%;
g H$_2$, Pc-C, EtOH, THF, 23° C.; TFA, H$_2$O, 0° C., 77%.

Experimental Procedures

General Procedures.

Reactions were performed in flame-dried sealed-tubes or modified Schlenk (Kjeldahl shape) flasks fitted with a glass stopper under a positive pressure of argon, unless otherwise noted. Air- and moisture-sensitive liquids and solutions were transferred via syringe. The appropriate carbohydrate and sulfoxide reagents were dried via azeotropic removal of water with toluene. Molecular sieves were activated at 350° C. and were crushed immediately prior to use, then flame-dried under vacuum. Organic solutions were concentrated by rotary evaporation below 30° C. Flash column chromatography was performed employing 230-400 mesh silica gel. Thin-layer chromatography was performed using glass plates pre-coated to a depth of 0.25 mm with 230-400 mesh silica gel impregnated with a fluorescent indicator (254 nm).

Materials.

Lyophilized QS saponin Quil-A (batch L77-244) was obtained from Brenntag Biosector (Frederikssund, Denmark) via distribution by Accurate Chemical and Scientific Corporation (Westbury, N.Y.). Dichloromethane, tetrahydrofuran, diethyl ether, hexane, toluene, and benzene were purified by passage through two packed columns of neutral alumina under an argon atmosphere. Methanol was distilled from magnesium at 760 Torr. Trifluoromethanesulfonic anhydride was distilled from phosphorus pentoxide at 760 Torr. Boron trifluoride diethyl etherate and pyridine were distilled from calcium hydride at 760 Torr. Dimethylformamide was dried over 4 Å molecular sieves. All other chemicals were obtained from commercial vendors and were used without further purification unless noted otherwise.

Instrumentation.

Infrared (IR) spectra were obtained using a Perkin Elmer Spectrum BX spectrophotometer or a Bruker Tensor 27. Data are presented as the frequency of absorption (cm$^{-1}$). Proton and carbon-13 nuclear magnetic resonance ($^1$H NMR and $^{13}$C NMR) spectra were recorded on a Varian 400, a Varian 500, a Varian Inova 500, or a Bruker Avance III instrument; chemical shifts are expressed in parts per million (δ scale) downfield from tetramethylsilane and are referenced to the residual protium in the NMR solvent (CHCl$_3$: δ 7.26 for $^1$H NMR, δ 77.16 for $^{13}$C NMR). Data are presented as follows: chemical shift, multiplicity (s=singlet, bs=broad singlet, d=doublet, bd=broad doublet, t=triplet, q=quartet, m=multiplet and/or multiple resonances), coupling constant in Hertz (Hz), integration, assignment. RP-HPLC purification and analyses were carried out on a Waters 2545 binary gradient HPLC system equipped with a Waters 2996 photodiode array detector, and absorbances were monitored at a wavelength of 214 nm.

Preparation of the Hexasaccharide

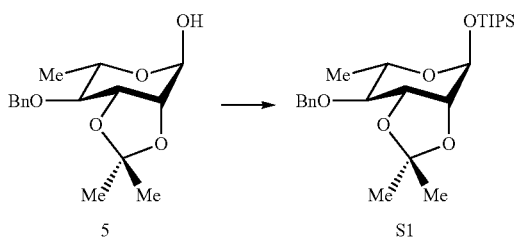

O-Triisopropyl 4-O-benzyl-2,3-di-O-isopropylidene-α-L-rhamnopyranoside (S1)

To a solution of rhamnopyranoside 5 (Nguyen, H. M.; Poole, J. L.; Gin, D. Y. *Angew. Chem. Int. Ed.* 2001, 40, 414-417) (6.00 g, 20.4 mmol, 1.00 equiv) in dichloromethane (100 mL) at 0° C. was added 2,6-lutidine (8.30 mL, 71.4 mmol, 3.50 equiv) and triisopropylsilyl trifluoromethanesulfonate (9.30 mL, 34.7 mmol, 1.70 equiv). The reaction was stirred at this temperature for 1 h and then at 23° C. for 3 h. Saturated aqueous NaHCO$_3$ (150 mL) was added, and the aqueous layer was extracted with dichloromethane (3×150 mL). The combined organic phase was washed with saturated aqueous NaCl (150 mL), dried (Na$_2$SO$_4$), filtered and concentrated. Silica gel chromatography (hexane/ethyl acetate 20:1) afforded α-anomer S1 (8.8 g, 20 mmol, 96% yield) as a colorless liquid. $^1$H NMR (CDCl$_3$, 500 MHz) δ 7.39-7.33 (m, 4H, aromatic), 7.30-7.26 (m, 1H, aromatic), 5.38 (s, 1H, H-1), 4.93 (d, J=10.2 Hz, 1H, PhC$\underline{H}_2$—), 4.65 (d, J=10.2 Hz, 1H, PhC$\underline{H}_2$—), 4.32 (dd, J=7.0, 5.6 Hz, 1H, H-3), 4.13 (d, J=5.6 Hz, 1H, H-2), 3.95 (qd, J=9.9, 6.2 Hz, 1H, H-5), 3.25 (dd, J=9.9, 7.0 Hz, 1H, H-4), 1.53 (s, 3H, Me), 1.40 (s, 3H, Me), 1.29 (d, J=6.3 Hz, 3H, Me), 1.18-1.08 (m, 21H, Si-i-Pr$_3$); $^{13}$C NMR (125 MHz, CDCl$_3$) δ 138.51, 128.41, 128.17, 127.76, 109.31, 91.80, 81.56, 78.80, 78.15, 73.25, 64.54, 28.23, 26.66, 17.89, 17.81, 12.04; FTIR (neat film) 3032, 2941, 2896, 2868, 1463, 1382, 1370, 1243, 1220, 1081, 1058, 1020, 995, 883 cm$^{-1}$.

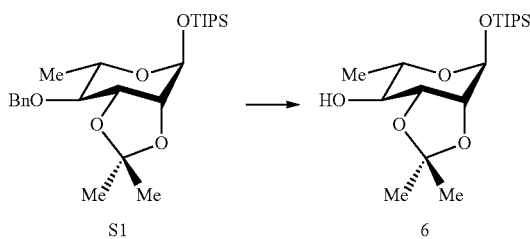

O-Triisopropyl 2,3-di-O-isopropylidene-α-L-rhamnopyranoside (6)

To a solution of S1 (5.90 g, 13.1 mmol, 1.00 equiv) in methanol (100 mL) was added 10% (dry basis) palladium on carbon, wet, Degussa type E101 NE/W (1.4 g, 0.65 mmol, 0.050 equiv). The reaction mixture was vigorously stirred under hydrogen pressure (110 psi) for 7.5 h and was then filtered through a Celite 545 plug, which was rinsed with dichloromethane. The filtrate and rinsings were concentrated, and the residue was subjected to silica gel chromatography (hexane/ethyl acetate 3:1) to afford 6 (4.6 g, 1.3 mmol, 98% yield) as a colorless oil. $^1$H NMR (CDCl$_3$, 500 MHz) δ 5.34 (s, 1H, H-1), 4.16-4.10 (m, 2H, H-2 and H-3), 3.91 (qd, J=8.8, 6.3 Hz, 1H, H-5), 3.42 (ddd, J=11.6, 6.8, 4.8 Hz, 1H, H-4), 2.33 (d, J=4.8 Hz, 1H, —OH), 1.53 (s, 3H, Me), 1.37 (s, 3H, Me), 1.28 (d, J=6.3 Hz, 3H, Me), 1.18-1.05 (m, 21H, Si-i-Pr$_3$); $^{13}$C NMR (125 MHz, CDCl$_3$) δ 109.5, 91.9, 78.2, 77.6, 74.4, 66.0, 28.0, 26.2, 17.8, 17.68, 17.66, 11.9; FTIR (neat film) 3463 (br), 2942, 2868, 1464, 1383, 1244, 1220, 1051, 1015, 883, 852, 807 cm$^{-1}$.

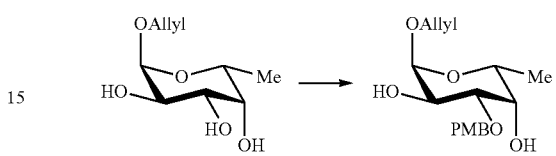

Allyl 3-O-methoxybenzyl-α-D-fucopyranoside (S2)

Allyl fucoside 7 (111 mg, 0.543 mmol, 1.00 equiv) and dibutyltin oxide (125 mg, 0.502 mmol equiv) in toluene (10 mL) were refluxed for 5 h in a Dean-Stark apparatus. After the reaction mixture cooled to 23° C., CsF (152 mg, 1.0 mmol) was added, and the solvent was evaporated. Dimethylformamide (3.0 mL) and p-methoxybenzyl chloride (0.136 mL, 1.0 mmol, 2.0 equiv) were added, and the reaction mixture was stirred at 23° C. for 48 h. The solvent was evaporated, and residue taken up in dichloromethane and filtered. The filtrate and rinsings were concentrated, and silica gel chromatography (hexane/ethyl acetate 1:1) afforded S2 (98 mg, 0.30 mmol, 56%) as a colorless oil. $^1$H NMR (500 MHz, CDCl$_3$) δ 7.32-7.29 (m, 2H), 6.90-6.88 (m, 2H), 5.92 (m, 1H), 5.30 (dq, J=17.2, 1.6 Hz, 1H), 5.21 (dq, J=10.4, 1.2 Hz, 1H), 4.93 (d, J=4.0 Hz, 1H), 4.68 (d, J=11.6 Hz, 1H, PhC$\underline{H}_2$—), 4.64 (d, J=11.6 Hz, 1H, PhC$\underline{H}_2$—), 4.20 (ddt, J=12.8, 5.4, 1.4 Hz, 1H), 4.05 (ddt, J=12.8, 6.2, 1.3 Hz, 1H), 4.00-3.89 (m, 2H), 3.81 (s, 3H, OMe), 3.80 (m, 1H), 3.64 (dd, J=9.7, 3.2 Hz, 1H), 2.40 (s, 1H), 2.11 (d, J=8.4 Hz, 1H), 1.30 (d, J=6.6 Hz, 3H); $^{13}$C NMR (125 MHz, CDCl$_3$) δ 159.5, 133.8, 130.0, 129.5, 117.7, 114.0, 97.7, 78.5, 71.8, 69.5, 68.5, 68.3, 65.7, 55.3, 16.2. FTIR (neat film) 3462 (br), 3077, 2979, 2907, 2838, 1612, 1514, 1249, 1088, 1037, 821 cm$^{-1}$.

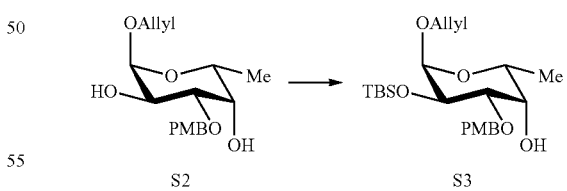

O-Allyl 2-O-t-butyldimethylsilyl-3-O-methoxybenzyl-α-D-fucopyranoside (S3)

Fucopyranoside S2 (205 mg, 0.632 mmol, 1.00 equiv), t-butyldimethylsilyl chloride (190 mg, 1.26 mmol, 1.99 equiv), imidazole (129 mg, 1.89 mmol, 3.00 equiv) and 4-(dimethylamino)-pyridine (6.2 mg, 0.051 mmol, 0.080 equiv) were dissolved in dichloromethane (8.0 mL) and stirred at 23° C. for 27 h. The reaction mixture was directly purified by silica gel chromatography (hexane/ethyl acetate 7:3) to afford S3 (270 mg, 0.62 mmol, 97% yield). $^1$H NMR (400 MHz, CDCl$_3$) δ 7.32-7.26 (m, 2H), 6.92-6.85 (m, 2H), 5.94 (m, 1H), 5.34 (dq, J=17.4, 1.4 Hz, 1H), 5.22 (dq, J=10.3, 1.3 Hz, 1H), 4.79 (d, J=3.8 Hz, 1H), 4.69 (d, J=11.3 Hz, 1H, PhCH$_2$—), 4.56 (d, J=11.3 Hz, 1H, PhCH$_2$—), 4.19 (ddt, J=13.0, 5.4, 1.3 Hz, 1H), 4.05 (ddt, J=13.2, 6.5, 1.2 Hz, 1H), 3.99 (m, 1H), 3.95 (q, J=6.5 Hz, 1H), 3.82 (s, 3H, OMe), 3.76-3.70 (m, 2H), 2.50 (s, 1H), 1.28 (d, J=6.6 Hz, 3H), 0.93 (s, 9H), 0.10 (s, 3H), 0.09 (s, 3H); $^{13}$C NMR (125 MHz, CDCl$_3$) δ 159.31, 134.16, 130.43, 129.42, 117.73, 113.83, 98.34, 78.27, 72.28, 70.11, 69.29, 68.48, 65.31, 55.21, 25.86, 18.19, 16.17, −4.43, −4.69; FTIR (neat film) 3507 (br), 2953, 2930, 2899, 2857, 1613, 1514, 1250, 1106, 1040, 875, 837, 778 cm$^{-1}$.

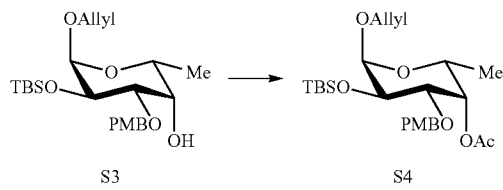

O-Allyl 4-O-acetyl-2-O-t-butyldimethylsilyl-3-O-methoxybenzyl-α-D-fucopyranoside (S4)

To fucopyranoside S3 (264 mg, 0.602 mmol, 1.00 equiv) and 4-(dimethylamino)-pyridine (7.3 mg, 0.060 mmol, 0.10 equiv) in dichloromethane (10 mL) was added triethylamine (0.25 mL, 1.8 mmol, 3.0 equiv) and acetic anhydride (0.17 mL, 0.80 mmol, 3.0 equiv). The reaction mixture was stirred at 23° C. for 22.5 h and then was concentrated and purified by silica gel chromatography (hexanes/ethyl acetate 17:3) to afford S4 (288 mg, 0.599 mmol, >99% yield) as a colorless oil. $^1$H NMR (500 MHz, CDCl$_3$) δ 7.24-7.21 (m, 2H), 6.85-6.82 (m, 2H), 5.92 (m, 1H), 5.36 (dd, J=3.2, 1.0 Hz, 1H), 5.32 (dq, J=17.2, 1.6 Hz, 1H), 5.21 (dq, J=10.4, 1.2 Hz, 1H), 4.81 (d, J=3.8 Hz, 1H), 4.60 (d, J=10.6 Hz, 1H, PhCH$_2$—), 4.40 (d, J=10.6 Hz, 1H, PhCH$_2$—), 4.18 (ddt, J=13.1, 5.2, 1.2 Hz, 1H), 4.12-4.02 (m, 2H), 3.97 (dd, J=9.9, 3.8 Hz, 1H), 3.78 (s, 3H), 3.77 (m, 1H), 2.14 (s, 3H), 1.14 (d, J=6.5 Hz, 3H), 0.89 (s, 9H), 0.04 (s, 3H), 0.03 (s, 3H); $^{13}$C NMR (125 MHz, CDCl$_3$) δ 170.84, 159.06, 134.07, 130.50, 129.58, 118.00, 113.56, 98.48, 76.12, 71.61, 71.08, 69.56, 68.74, 64.85, 55.24, 25.91, 20.96, 18.30, 16.25, −4.35, −4.90; FTIR (neat film) 2983, 2954, 2930, 2902, 2857, 1742, 1614, 1515, 1249, 1104, 1055, 1040, 1019, 837, 779, 735 cm$^{-1}$; HRMS (ESI) m/z: Calcd for C$_{25}$H$_{40}$O$_7$Si (M+Na$^+$) 503.2441. found 503.2437.

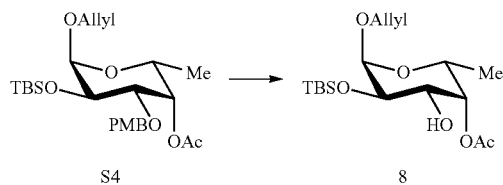

O-Allyl 4-O-acetyl-2-O-t-butyldimethylsilyl-α-D-fucopyranoside (8)

To fucopyranoside S4 (100 mg, 0.208 mmol, 1.00 equiv) in dichloromethane (4 mL) and H$_2$O (0.4 mL) at 0° C. was added 2,3-dichloro-5,6-dicyano-1,4-quinone (71 mg, 0.31 mmol, 1.5 equiv). After stirring at 0° C. for 10 min and at 23° C. for 2.5 h, reaction mixture was filtered through Celite 435, concentrated, and purified by silica gel chromatography (hexane/ethyl acetate 4:1) to afford 8 (65 mg, 0.18 mmol, 86% yield) as a colorless oil. $^1$H NMR (500 MHz, CDCl$_3$) δ 5.90 (m, 1H), 5.32 (dq, J=17.1, 1.6 Hz, 1H), 5.25 (dd, J=3.5, 1.1 Hz, 1H), 5.20 (dq, J=10.4, 1.3 Hz, 1H), 4.81 (d, J=3.7 Hz, 1H), 4.18 (ddt, J=13.1, 5.3, 1.5 Hz, 1H), 4.09 (qd, J=6.7, 1.0 Hz, 1H), 4.06 (dt, J=10.0, 3.2 Hz, 1H), 4.00 (qt, J=6.3, 1.2 Hz, 1H), 3.89 (dd, J=10.0, 3.7 Hz, 1H), 2.16 (s, 3H), 2.05 (d, J=3.0 Hz, 1H), 1.13 (d, J=6.6 Hz, 3H), 0.90 (s, 9H), 0.11 (s, 3H), 0.10 (s, 3H); $^{13}$C NMR (100.6 MHz, CDCl$_3$) δ 171.12, 133.87, 117.79, 98.26, 73.27, 70.66, 68.80, 68.77, 65.03, 25.80, 20.86, 18.22, 16.11, −4.51, −4.59; FTIR (neat film) 3503, 2927, 1737, 1372, 1242, 1170, 1136, 1087, 1038, 939, 878, 839, 778 cm$^{-1}$; HRMS (ESI) m/z: Calcd for C$_{17}$H$_{32}$O$_6$Si (M+Na$^-$) 383.1866. found 383.1864.

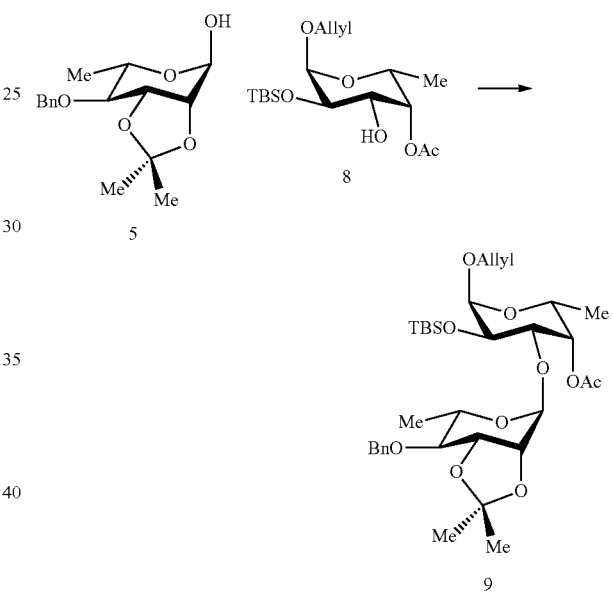

O-Allyl 4-O-acetyl-[4-O-benzyl-2,3-di-O-isopropylidene-α-L-rhamnopyranose-(1→3)]-2-O-t-butyldimethylsilyl-α-D-fucopyranoside (9)

Trifluoromethanesulfonic anhydride (0.39 mL, 2.3 mmol, 2.8 equiv) was added to a solution of rhamnopyranose 5 (245 mg, 0.832 mmol, 1.00 equiv), phenyl sulfoxide (982 mg, 4.85 mmol, 5.83 equiv) and 2,4,6-tri-t-butylpyridine (1.21 g, 4.89 mmol, 5.88 equiv) in dichloromethane (25 mL) at −78° C. After the reaction was stirred at −78° C. for 30 min and at −45° C. for 1.5 h, a solution of fucopyranoside 8 (150 mg, 0.416 mmol, 0.500 equiv) in dichloromethane (5.0 mL) was added via cannula. The reaction mixture was stirred at −45° C. for 1 h, at 0° C. for 1 h and at 23° C. for 14 h. Triethylamine (0.1 mL) was added to the reaction mixture, which was concentrated and purified by silica gel chromatography (hexanes/ethyl acetate 17:3) to afford 9 (222 mg, 0.349 mmol, 84% yield) as a colorless oil. $^1$H NMR (CDCl$_3$, 400 MHz) δ 7.38-7.22 (m, 5H), 5.90 (m, 1H), 5.23-5.16 (m, 3H), 4.88 (d, 0.1=12.0 Hz, 1H, PhCH$_2$—), 4.70 (d, J=3.6 Hz, 1H), 4.63 (d, J=12.0 Hz, 1H, PhCH$_2$—), 4.21-4.05 (m, 5H), 4.02-3.94 (m, 2H), 3.72 (dd, J=10.0, 6.5 Hz, 1H), 3.15 (dd, J=9.6, 6.0 Hz, 1H), 2.20 (s, 3H, Me), 1.46 (s, 3H, Me), 1.32 (s, 3H, Me), 1.26 (d, J=6.0 Hz, 3H), 1.09 (d, J=6.8 Hz, 3H), 0.90 (s, 9H), 0.09 (s, 3H), 0.08 (s, 3H); $^{13}$C NMR (100 MHz, CDCl$_3$) δ 170.6, 138.8, 134.1, 128.6, 128.4, 128.3, 128.2, 117.9, 108.9, 99.7, 98.7, 81.0, 78.7, 76.3, 75.1, 73.9, 73.1, 70.2, 68.9, 65.38, 65.35, 28.2, 26.4, 26.0, 21.1, 18.2, 17.8, 16.3, −4.2, −4.6; FTIR (neat film) 3066, 3033, 2985, 2934, 2857, 2905, 1747, 1455, 1382, 1373, 1236, 1138, 1096, 1057, 1012, 937, 864, 777, 736, 698 cm$^{-1}$; HRMS (ESI) m/z: Calcd for C$_{33}$H$_{52}$O$_{10}$Si (M+NH$_4^+$) 654.3674. found 654.3672.

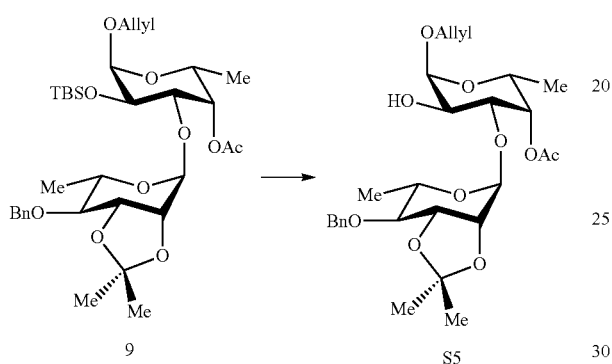

O-Allyl 4-O-acetyl-[4-O-benzyl-2,3-di-O-isopropylidene-α-L-rhamnopyranose-(1→3)]-α-D-fucopyranoside (S5)

To a solution of disaccharide 9 (190 mg, 0.298 mmol, 1.00 equiv) in tetrahydrofuran (10 mL) at 0° C. was added tetrabutylammonium fluoride solution (1.0 M in tetrahydrofuran, 0.33 mL, 0.33 mmol, 1.1 equiv). After 15 min, the reaction mixture was warmed to 23° C. and was stirred at this temperature for 4 h. Silica gel (1 g) was added, the solvent was removed, and the reaction material was purified by silica gel chromatography (hexane/ethyl acetate 3:2) to afford S5 (148 mg, 0.283 mmol, 95% yield). $^1$H NMR (CDCl$_3$, 500 MHz) δ 7.37-7.24 (m, 5H), 5.91 (m, 1H), 5.30 (m, 1H), 5.28 (s, 1H), 5.23 (m, 1H), 5.17 (dd, J=3.5, 1.0 Hz, 1H), 4.94 (d, J=3.5 Hz, 1H), 4.86 (d, J=11.5 Hz, 1H, PhCH$_2$—), 4.64 (d, J=11.5 Hz, 1H, PhCH$_2$—), 4.24-4.16 (m, 3H), 4.08-4.01 (m, 2H), 3.99-3.88 (m, 2H), 3.72 (m, 1H), 3.18 (dd, J=9.5, 6.5 Hz, 1H), 2.13 (s, 3H), 2.01 (d, J=10.0 Hz, 1H), 1.47 (s, 3H), 1.35 (s, 3H), 1.26 (d, J=6.5 Hz, 3H), 1.11 (d, J=6.5 Hz, 3H); $^{13}$C NMR (125 MHz, CDCl$_3$) δ 170.6, 138.7, 133.7, 128.4, 128.2, 127.8, 118.4, 109.2, 99.5, 98.1, 80.9, 76.3, 75.5, 73.3, 73.1, 69.4, 69.0, 65.8, 65.5, 28.2, 26.6, 21.0, 17.9, 16.4; FTIR (neat film) 3470 (br), 3032, 2985, 2936, 1744, 1454, 1381, 1237, 1168, 1092, 933, 863, 816, 737, 698 cm$^{-1}$; HRMS (ESI) m/z: Calcd for C$_{27}$H$_{38}$O$_{10}$ (M+Na$^+$) 545.2363. found 545.2355.

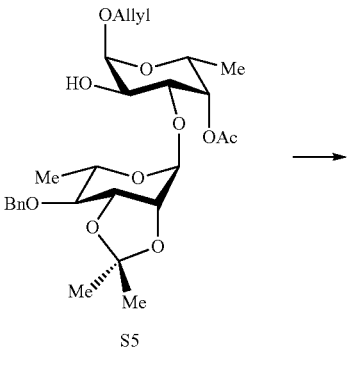

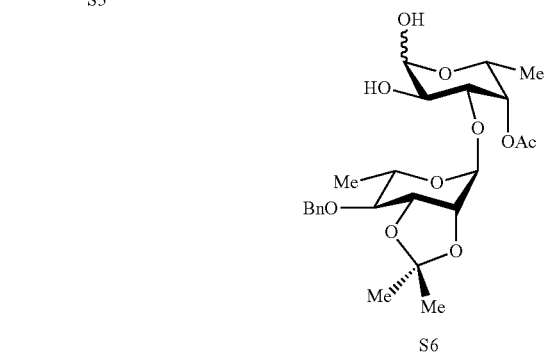

4-O-acetyl-[4-O-benzyl-2,3-di-O-isopropylidene-α-L-rhamnopyranose-(1→3)]-D-fucopyranose (S6)

To disaccharide S5 (80 mg, 0.15 mmol, 1.0 equiv) and Pd(PPh$_3$)$_4$ (18 mg, 0.015 mmol, 0.10 equiv) in diethyl ether (9.0 mL) was added Et$_2$Zn solution (1.0 M in hexane, 1.53 mL, 1.53 mmol, 10.0 equiv). The reaction mixture was stirred at 23° C. for 10 h and then another portion of Pd(PPh$_3$)$_4$ (18 mg, 0.015 mmol, 0.10 equiv) was added. After 11 h, the reaction was diluted with ethyl acetate, followed by the addition of saturated aqueous NaCl. The aqueous phase was extracted by ethyl acetate (2×50 mL). The combined organic phase was dried (MgSO$_4$), filtered, concentrated, and the residue was purified by silica gel chromatography (hexanes/ethyl acetate 1:4) to afford the hemiacetal S6 as a mixture of anomers (50 mg, 0.10 mmol, 68% yield). Characteristic peaks: $^1$H NMR (500 MHz, CDCl$_3$) δ 7.37-7.25 (m, 5H), 4.87 (d, J=11.3 Hz, 1H, PhCH$_2$—), 4.64 (d, J=11.3 Hz, 1H, PhCH$_2$—), 1.47 (s, 3H), 1.36 (s, 3H). The hemiacetal mixture was used immediately in the next silylation reaction.

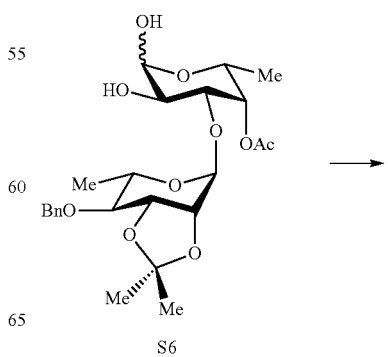

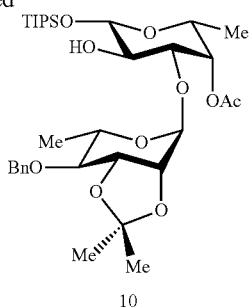

O-Triisopropylsilyl 4-O-acetyl-[4-O-benzyl-2,3-di-O-isopropylidene-α-L-rhamnopyranose-(1→3)]-β-D-fucopyranoside (10)

To a solution of hemiacetal S6 (57 mg, 0.12 mmol, 1.0 equiv), imidazole (64 mg, 0.94 mmol, 8.0 equiv) and 4-(dimethylamino)-pyridine (3 mg, 0.02 mmol, 0.2 equiv) in dimethylformamide (0.5 mL) was treated with triisopropylsilylchloride (150 µL, 0.70 mmol, 5.9 equiv). The reaction was stirred at 23° C. for 4 h, then directly purified by silica gel chromatography (hexanes/ethyl acetate 4:1) to afford 10 (56 mg, 0.088 mmol, 75%) as a white powder. $^1$H NMR (CDCl$_3$, 500 MHz) δ 7.38-7.25 (m, 5H), 5.32 (s, 1H), 5.12 (dd, J=3.0, 1.3 Hz, 1H), 4.85 (d, J=12.0 Hz, 1H, PhCH$_2$—), 4.64 (d, J=12.0 Hz, 1H, PhCH$_2$—), 4.55 (d, J=7.5 Hz, 1H), 4.18 (m, 2H), 3.82-3.64 (m, 4H), 3.18 (m, 1H), 2.18 (d, J=2.0 Hz, 1H), 2.12 (s, 3H), 1.48 (s, 3H), 1.36 (s, 3H), 1.26 (d, J=6.5 Hz, 3H), 1.14 (d, J=6.5 Hz, 3H), 1.10-1.02 (m, 21H, Si-i-Pr$_3$); $^{13}$C NMR (125 MHz, CDCl$_3$) δ 170.8, 138.7, 128.4, 128.2, 127.8, 109.2, 99.2, 97.9, 80.9, 78.6, 76.7, 76.4, 74.2, 73.1, 72.7, 70.0, 65.5, 28.2, 26.6, 21.0, 18.05, 18.00, 17.9, 16.5, 12.5; FTIR (neat film) 3496 (br), 3089, 3064, 3032, 2938, 2866, 1744, 1455, 1381, 1237, 1076, 737 cm$^{-1}$; HRMS (ESI) m/z: Calcd for C$_{33}$H$_{54}$O$_9$Si (M+Na$^+$) 645.3435. found 645.3421.

O-Triisopropylsilyl [2,4-di-O-benzyl-β-D-xylopyranosyl-(1→4)]-2,3-di-O-isopropylidene-α-L-rhamnopyranoside (11)

To a solution of xylopyranose 2 (140 mg, 0.424 mmol, 1.00 equiv), phenylsulfoxide (500 mg, 2.47 mmol, 5.83 equiv) and 2,4,6-tri-t-butylpyridine (604 mg, 2.44 mmol, 5.78 equiv) in dichloromethane (16 mL) at −78° C. was added trifluoromethanesulfonic anhydride (0.20 mL, 1.19 mmol, 2.80 equiv). After 15 min, a solution of rhamnopyranoside 6 (305 mg, 0.846 mmol, 2.00 equiv) in dichloromethane (5 mL) was added via cannula. The reaction mixture was stirred at −78° C. for 15 min, at −45° C. for 30 min, at 0° C. for 30 min, at 23° C. for 10 h, at 35° C. for 5 h, and finally at 23° C. for another 9 h. The reaction mixture was diluted with dichloromethane (100 mL) and washed with saturated aqueous NaHCO$_3$ (2×100 mL) and saturated aqueous NaCl (2×100 mL). The aqueous washings were extracted with dichloromethane (150 mL), and the combined organic phase was dried (MgSO$_4$), filtered, and concentrated to furnish a cream-colored amorphous solid. Silica gel chromatography (hexanes/ethyl acetate 7:3) afforded 11 (215 mg, 75% yield) as a white amorphous solid. $^1$H NMR (CDCl$_3$, 500 MHz) δ 7.40-7.27 (m, 10H), 5.37 (s, 1H), 4.94 (d, J=11.5 Hz, 1H, PhCH$_2$—), 4.92 (d, J=7.2 Hz, 1H), 4.75 (d, J=12.0 Hz, 1H, PhCH$_2$—), 4.66 (d, J=11.5 Hz, 1H, PhCH$_2$—), 4.64 (d, J=12.0 Hz, 1H, PhCH$_2$—), 4.22 (dd, J=7.0, 5.0 Hz, 1H), 4.06 (dd, J=5.0, 0.5 Hz, 1H), 3.96 (dd, J=11.5, 5.5 Hz, 1H), 3.87 (m, 1H), 3.72 (t, J=9.0 Hz, 1H), 3.64 (dd, J=10.0, 7.5 Hz, 1H), 3.53 (m, 1H), 3.24 (d, J=10.0 Hz, 1H), 3.21 (t, J=9.5 Hz, 2H), 3.18 (d, J=9.0 Hz, 1H), 1.51 (s, 3H), 1.36 (s, 3H), 1.26 (d, J=6.0 Hz, 3H), 1.18-1.05 (m, 21H, Si-i-Pr$_3$); $^{13}$C NMR (125 MHz, CDCl$_3$) δ 170.8, 138.7, 128.4, 128.2, 127.8, 109.2, 99.2, 97.9, 80.9, 78.6, 76.7, 76.4, 74.2, 73.1, 72.7, 70.0, 65.5, 28.2, 26.6, 21.0, 18.05, 18.00, 17.9, 16.5, 12.5; FTIR (neat film) 3483 (br), 3031, 2942, 2867, 1497, 1455, 1383, 1242, 1221, 1085, 1018, 883, 809, 735, 697 cm$^{-1}$; HRMS (ESI) m/z: Calcd for C$_{37}$H$_{56}$O$_9$Si (M+Na$^+$) 695.3591. found 695.3594.

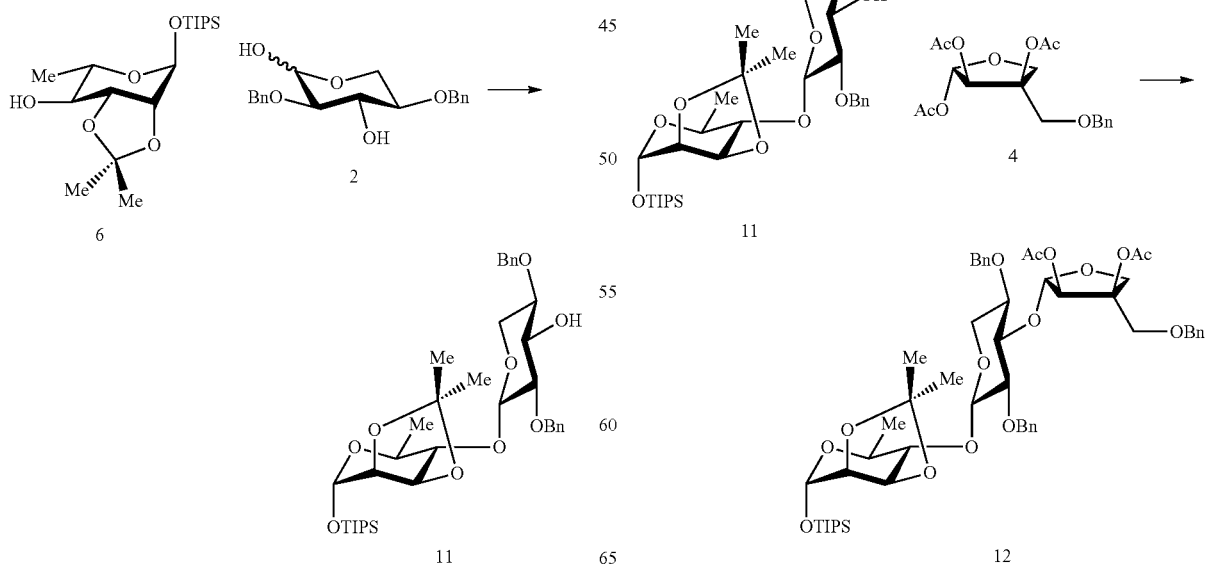

O-Triisopropylsilyl {[2,3-di-O-acetyl-5-O-benzyl-β-D-apiofuranosyl-(1→3)-2,4-di-O-benzyl-β-D-xylopyranosyl-(1→4)]}-2,3-di-O-isopropylidene-α-L-rhamnopyranoside (12)

To a solution of 1,2,3-tri-O-acetyl-5-O-benzyl-β-D-apiofuranoside (4) (466 mg, 1.27 mmol, 1.89 equiv) and 11 (452 mg, 0.672 mmol, 1.00 equiv) in dichloromethane (19 mL) at 0° C. was added t-butyldimethylsilyl trifluoromethanesulfonate (7.7 µL, 0.034 mmol, 0.050 equiv). After 25 min triethylamine (0.1 mL) was added. The reaction mixture was concentrated, and the residue was purified by silica gel chromatography (hexanes/ethyl acetate 4:1 to 3:2) to afford 12 (567 mg, 0.579 mmol, 86% yield) as a colorless oil. $R_f$=0.58 (hexanes/ethyl acetate 2:1); $^1$H NMR (CDCl$_3$, 500 MHz) δ 7.37-7.23 (m, 15H), 5.47 (s, 1H), 5.45 (s, 1H), 5.36 (s, 1H), 4.89 (d, J=1.5 Hz, 1H), 4.86 (d, J=2.0 Hz, 1H), 4.63 (d, J=11.0 Hz, 1H), 4.56 (d, J=12.0 Hz, 1H, PhC$\underline{H}_2$—), 4.50 (d, J=11.5 Hz, 1H, PhC$\underline{H}_2$—), 4.42 (d, J=12.0 Hz, 1H, PhC$\underline{H}_2$—), 4.39 (d, J=11.5 Hz, 1H, PhC$\underline{H}_2$—), 4.21 (d, J=10.5 Hz, 1H, PhC$\underline{H}_2$—), 4.18 (dd, J=7.0, 5.5 Hz, 1H), 4.10 (d, J=10.5 Hz, 1H, PhC$\underline{H}_2$—), 4.07 (d, J=10.5 Hz, 1H), 4.03 (d, J=5.5 Hz, 1H), 3.90-3.82 (m, 3H), 3.76 (t, J=9.0 Hz, 1H), 3.62 (dd, J=10.0, 7.5 Hz, 1H), 3.30 (m, 1H), 3.24 (dd, J=9.5, 8.0 Hz, 1H), 3.14 (dd, J=12.0, 10.0 Hz, 1H), 2.04 (s, 3H), 1.97 (s, 3H), 1.49 (s, 3H), 1.34 (s, 3H), 1.26 (d, J=6.5 Hz, 3H), 1.20-1.04 (m, 21H, Si-i-Pr$_3$); $^{13}$C NMR (125 MHz, CDCl$_3$) 170.3, 169.4, 138.7, 138.3, 138.1, 128.7, 128.6, 128.4, 128.2, 128.09, 128.04, 127.99, 109.6, 106.7, 101.8, 91.8, 85.9, 82.1, 78.9, 78.4, 78.3, 78.1, 77.5, 76.91, 76.85, 74.5, 73.6, 73.5, 73.2, 69.7, 64.3, 64.0, 28.1, 26.8, 21.6, 20.8, 18.03, 17.97, 17.94, 12.2; FTIR (neat film) 2943, 2868, 1747, 1455, 1370, 1247, 1084, 883, 809 cm$^{-1}$; HRMS (ESI) m/z: Calcd for $C_{53}H_{74}O_{15}Si$ (M+Na$^+$) 1001.4695. found 1001.4730.

O-Triisopropylsilyl {[5-O-benzyl-2,3-di-O-benzylidene-β-D-apiofuranosyl-(1→3)]-2,4-di-O-benzyl-β-D-xylopyranosyl-(1→4)]})-2,3-di-O-isopropylidene-α-L-rhamnopyranoside (S7)

Potassium carbonate (221 mg, 1.60 mmol, 6.99 equiv) was added to a solution of trisaccharide 12 (224 mg, 0.229 mmol, 1.00 equiv) in methanol (10 mL) and water (1 mL). The reaction was stirred at 23° C. for 1 h. The reaction was diluted with saturated aqueous NH$_4$Cl solution (100 mL) and extracted with dichloromethane (3×100 mL). The combined organic phase were dried (Na$_2$SO$_4$) and concentrated in vacuo.

The residue was treated with α,α-dimethoxytoluene (25 mL) and p-toluenesulfonic acid monohydrate (22 mg, 0.11 mmol, 0.51 equiv) and stirred at 23° C. for 2 h. The reaction mixture was then diluted with dichloromethane (150 mL), and washed with saturated aqueous NaHCO$_3$ (100 mL) and water (100 mL). The organic phase was dried (Na$_2$SO$_4$), filtered and concentrated in vacuo with heating to remove the excess α,α-dimethoxytoluene. The residue was purified by silica gel chromatography (hexanes/ethyl acetate 82:18) to give trisaccharide S7 (211 mg, 0.215 mmol, 94% yield over two steps). $^1$H NMR (CDCl$_3$, 400 MHz) δ 7.53-7.23 (m, 20H), 5.98 (s, 1H), 5.74 (s, 1H), 5.36 (s, 1H), 4.90 (d, J=7.6 Hz, 1H), 4.84 (d, J=11.0 Hz, 1H, PhC$\underline{H}_2$—), 4.69 (d, J=11.0 Hz, 1H, PhC$\underline{H}_2$—), 4.60 (d, J=1.4 Hz, 2H), 4.53 (d, J=11.6 Hz, 1H, PhC$\underline{H}_2$—), 4.52 (s, 1H), 4.46 (d, J=11.7 Hz, 1H, PhC$\underline{H}_2$—), 4.19 (dd, J=5.4, 1.7 Hz, 1H), 4.04 (dd, J=5.6, 0.7 Hz, 1H), 3.90-3.79 (m, 3H), 3.65 (s, 3H), 3.61 (dd, J=7.3, 2.7 Hz, 1H), 3.27 (dd, J=7.8, 1.4 Hz, 1H), 3.16 (dd, J=10.1, 1.4 Hz, 1H), 1.48 (s, 3H), 1.33 (s, 3H), 1.25 (d, J=6.5 Hz, 3H), 1.20-1.02 (m, 21H, Si-i-Pr$_3$); $^{13}$C NMR (100 MHz, CDCl$_3$) δ 138.34, 138.28, 138.20, 137.0, 129.9, 128.9, 128.7, 128.6, 128.54, 128.52, 128.04, 127.96, 127.90, 127.7, 127.4, 109.6, 107.5, 106.6, 101.8, 91.9, 87.3, 81.7, 78.4, 78.3, 78.1, 77.8, 76.8, 74.5, 73.8, 73.5, 73.2, 71.3, 64.3, 64.0, 28.1, 26.8, 18.04, 18.01, 17.95, 12.2; FTIR (neat film) 3090, 3066, 3033, 2943, 2895, 2867, 1497, 1455, 1383, 1370, 1241, 1221, 1086, 1055, 1019, 993, 883, 856, 808, 752, 735, 697 cm$^{-1}$; HRMS (ESI) m/z: Calcd for $C_{56}H_{74}O_{13}Si$ (M+Na$^+$) 1005.4796. found 1005.4838.

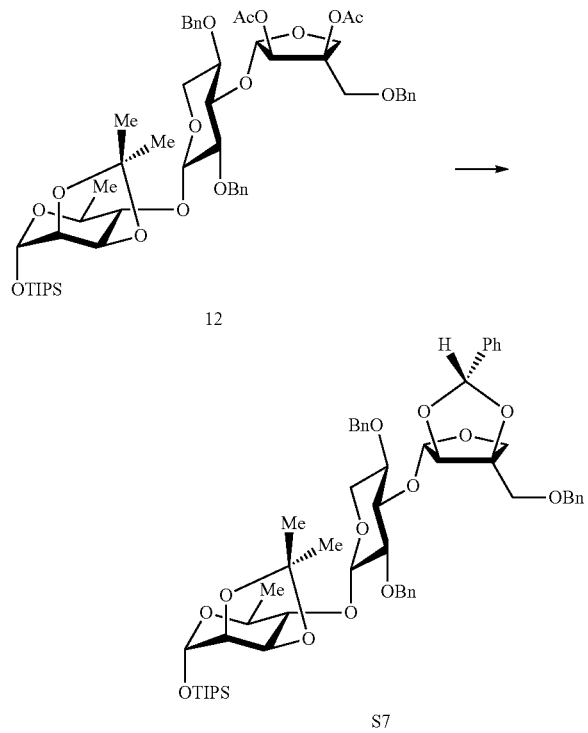

12

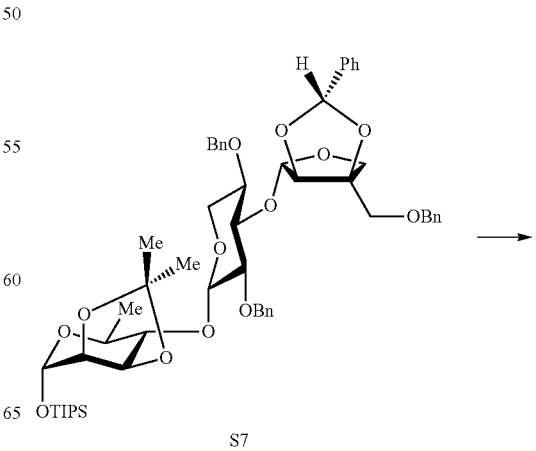

S7

145

-continued

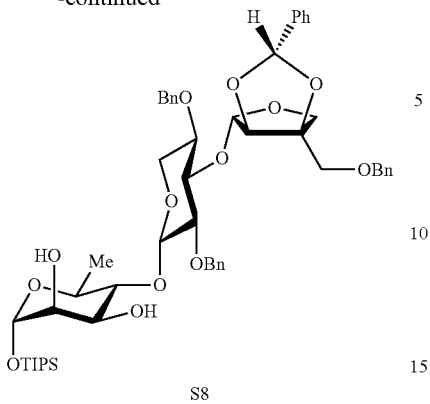

S8

O-Triisopropylsilyl {[5-O-benzyl-2,3-di-O-benzylidene-β-D-apiofuranosyl-(1→3)]-2,4-di-O-benzyl-β-D-xylopyranosyl-(1→4)]}-α-L-rhamnopyranoside (S8)

To a solution of trisaccharide S7 (133 mg, 0.135 mmol, 1.00 equiv) in a mixture of methanol (2.0 mL) and water (6 drops) was added p-toluenesulfonic acid monohydrate (13 mg, 0.068 mmol, 0.51 equiv). The reaction was stirred at 23° C. for 5 d and was then directly purified by silica gel chromatography (hexanes/ethyl acetate 1:4 to 1:1) to afford S8 (90 mg, 0.095 mmol 71% yield) and starting material S7 (10 mg, 0.010 mmol, 7.5% recovered). $^1$H NMR (CDCl$_3$, 500 MHz) δ 7.52-7.50 (m, 2H), 7.40-7.33 (m, 9H), 7.32-7.24 (m, 9H), 5.99 (s, 1H), 5.70 (s, 1H), 5.12 (s, 1H), 4.83 (d, J=10.5 Hz, 1H, PhCH$_2$—), 4.78 (d, J=10.5 Hz, 1H, PhCH$_2$—), 4.61 (d, 1H, J=2.0 Hz), 4.63 (d, J=12.5 Hz, 1H, PhCH$_2$—), 4.59 (d, J=12.5 Hz, 1H, PhCH$_2$—), 4.56-4.54 (m, 2H), 4.54 (d, J=11.5 Hz, 1H, PhCH$_2$—), 4.46 (d, J=11.5 Hz, 1H, PhCH$_2$—), 3.99 (s, 2H), 3.90-3.78 (m, 5H), 3.67 (m, 2H), 3.46 (t, J=9.0 Hz, 1H), 3.40-3.33 (m, 2H), 3.14 (dd, J=11.5, 10.5 Hz, 1H), 2.26 (d, J=3.0 Hz, 1H), 1.27 (d, J=6.5 Hz, 3H), 1.16-1.04 (m, 21H, Si-i-Pr$_3$); $^{13}$C NMR (125 MHz, CDCl$_3$) δ 138.2, 138.1, 137.0, 136.9, 129.9, 128.95, 128.86, 128.7, 128.62, 128.55, 128.2, 128.1, 128.0, 127.7, 127.4, 107.6, 106.7, 104.7, 93.9, 91.8, 87.3, 83.5, 82.8, 78.6, 76.6, 76.1, 73.8, 73.5, 73.4, 72.9, 71.6, 71.0, 66.1, 64.4, 17.97, 17.89, 17.7, 12.1; FTIR (neat film) 3468 (br), 3066, 3033, 2943, 2867, 1455, 1386, 1093, 1053, 986, 882, 861, 734, 696 cm$^{-1}$; HRMS (ESI) m/z: Calcd for C$_{33}$H$_{70}$O$_{13}$Si (M+Na$^+$) 965.4483. found 965.4470.

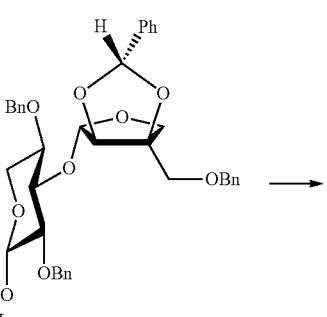

S8 →

146

-continued

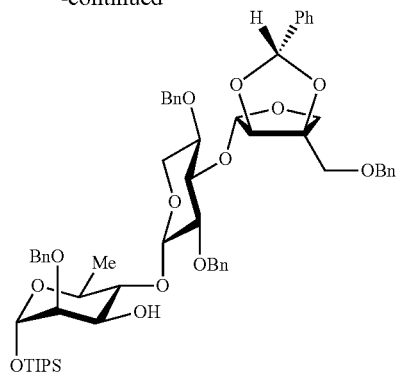

S9

O-Triisopropylsilyl 2-O-benzyl-{[5-O-benzyl-2,3-di-O-benzylidene-β-D-apiofuranosyl-(1→3)]-2,4-di-O-benzyl-β-D-xylnosynosyl-(1→4)]}-α-L-rhamnopyranoside (S9)

To a mixture of trisaccharide S8 (87 mg, 0.092 mmol, 1.0 equiv), dichloromethane (2.0 mL) and 20% aqueous NaOH (1.0 mL) was added n-Bu$_4$NBr (6 mg, 0.02 mmol, 0.2 equiv) and benzyl bromide (0.11 mL, 0.92 mmol, 10 equiv). After 20 h at 23° C., the reaction mixture was concentrated and the resulting residue was purified by silica gel chromatography (hexane/ethyl acetate 78:22) to afford S9 (80 mg, 84% yield). $^1$H NMR (CDCl$_3$, 500 MHz) δ 7.52-7.50 (m, 2H), 7.40-7.24 (m, 23H), 6.00 (s, 1H), 5.71 (s, 1H), 5.10 (s, 1H), 4.85 (d, J=11.0 Hz, 1H, PhCH$_2$—), 4.77 (d, J=11.0 Hz, 1H, PhCH$_2$—), 4.71 (d, J=12.0 Hz, 1H, PhCH$_2$—), 4.70 (d, J=8.0 Hz, 1H), 4.66 (d, J=12.0 Hz, 1H, PhCH$_2$—), 4.63 (d, J=12.5 Hz, 1H, PhCH$_2$—), 4.60 (d, J=12.5 Hz, 1H, PhCH$_2$—), 4.54 (d, J=12.0 Hz, 1H, PhCH$_2$—), 4.53 (s, 1H), 4.46 (d, J=12.0 Hz, 1H, PhCH$_2$—), 4.01-3.95 (m, 3H), 3.87-3.78 (m, 3H), 3.66 (s, 2H), 3.63 (dd, J=3.0, 1.5 Hz, 1H), 3.57 (t, J=9.0 Hz, 1H), 3.38 (m, 1H), 3.28 (dd, J=9.5, 8.0 Hz, 1H), 3.16 (t, J=11.5 Hz, 1H), 2.95 (d, J=6.5 Hz, 1H), 1.28 (d, J=6.0 Hz, 3H), 1.08-0.97 (m, 21H, Si-i-Pr$_3$); $^{13}$C NMR (125 MHz, CDCl$_3$) δ 138.2, 138.1, 138.0, 137.2, 136.8, 129.7, 128.8, 128.51, 128.45, 128.43, 128.3, 128.06, 128.04, 127.85, 127.82, 127.75, 127.5, 127.2, 107.4, 106.5, 104.1, 92.3, 91.6, 87.1, 82.2, 82.1, 79.4, 78.1, 76.5, 75.2, 73.6, 73.24, 73.17, 73.0, 71.6, 71.0, 66.4, 64.0, 17.76, 17.74, 17.69, 11.9; FTIR (neat film) 3477 (br), 3068, 3033, 2943, 1465 cm$^{-1}$; HRMS (ESI) m/z: Calcd for C$_{60}$H$_{76}$O$_{13}$Si (M+Na$^+$) 1055.4953. found 1055.5006.

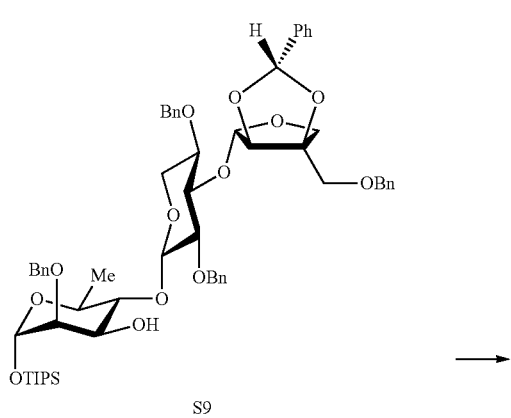

S9

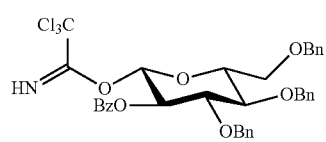

3

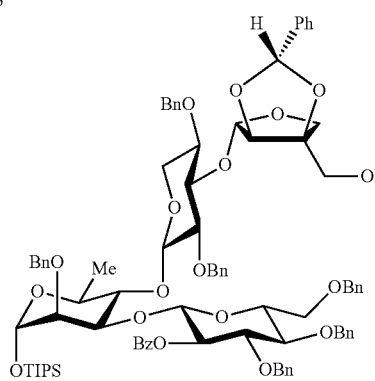

13

O-Triisopropylsilyl [2-O-benzoyl-3,4,6-tri-O-benzyl-β-D-glucopyranosyl-(1→3)]-2-O-benzyl-{[5-O-benzyl-2,3-di-O-benzylidene-β-D-apiofuranosyl-(1→3)]-2,4-di-O-benzyl-β-D-xylopyranosyl-(1→4)]}-α-L-rhamnopyranoside (13)

To a solution of trisaccharide S9 (88 mg, 0.085 mmol, 1.0 equiv) and glucosyl imidate 3 (131 mg, 0.187 mmol, 2.20 equiv) in diethyl ether (5.0 mL) at −45° C. was added a solution of trimethylsilyl trifluoromethanesulphonate (2.3 μL, 0.013 mmol, 0.15 equiv) in dichloromethane (115 μL). After 30 min at this temperature, triethylamine (0.15 mL) was added to the reaction mixture, which was concentrated and purified by silica gel chromatography (benzene/ethyl acetate 19:1) to afford 13 (115 mg, 0.0733 mmol, 86% yield). $^1$H NMR (500 MHz, CDCl$_3$) δ 8.18 (d, J=7.5 Hz, 2H), 7.64-7.14 (m, 43H), 6.06 (s, 1H), 5.91 (s, 1H), 5.34 (dd, J=9.5, 8.0 Hz, 1H), 4.98-4.92 (m, 3H), 4.86-4.81 (m, 2H), 4.79 (s, 1H), 4.77 (d, J=11.0 Hz, 1H, PhCH$_2$—), 4.75 (d, J=12.0 Hz, 1H, PhCH$_2$—), 4.70-4.58 (m, 6H), 4.47 (d, J=8.0 Hz, 1H), 4.42 (d, J=11.5 Hz, 1H, PhCH$_2$—), 4.37 (d, J=11.5 Hz, 1H, PhCH$_2$—), 4.32 (d, J=11.5 Hz, 1H), 4.20 (dd, J=9.0, 3.0 Hz, 1H), 4.15 (d, J=10.5 Hz, 1H, PhCH$_2$—), 4.13 (d, J=10.5 Hz, 1H, PhCH$_2$—), 3.88-3.70 (m, 7H), 3.66 (dd, J=11.5, 2.5 Hz, 1H), 3.59-3.53 (m, 2H), 3.44 (d, J=10.0 Hz, 1H), 3.29-3.23 (m, 1H), 3.20 (dd, J=9.0, 8.0 Hz, 1H), 2.32 (m, 1H), 2.05 (t, J=11.0 Hz, 1H), 1.28 (d, J=6.0 Hz, 3H), 1.10-0.90 (m, 21H, Si-i-Pr$_3$); $^{13}$C NMR (125 MHz, CDCl$_3$) δ 165.4, 139.2, 139.1, 138.71, 138.66, 138.64, 138.2, 138.1, 136.9, 133.5, 130.2, 130.1, 129.9, 129.4, 128.94, 128.85, 128.7, 128.60, 128.59, 128.57, 128.55, 128.45, 128.42, 128.1, 128.0, 127.95, 127.93, 127.8, 127.7, 127.6, 127.54, 127.50, 127.4, 107.4, 106.6, 102.7, 100.9, 94.0, 91.9, 87.4, 83.3, 81.8, 79.0, 78.3, 78.0, 77.5, 76.7, 75.3, 74.9, 74.67, 74.64, 74.5, 73.89, 73.87, 73.84, 73.57, 72.8, 71.4, 70.0, 67.3, 63.0, 18.10, 18.04, 18.02, 12.1; FTIR (neat film) 3030, 2938, 2862, 1734, 1452, 1264 cm$^{-1}$; HRMS (ESI) m/z: Calcd for C$_{94}$H$_{108}$O$_{19}$Si (M+Na$^+$) 1569.7332. found 1569.7397.

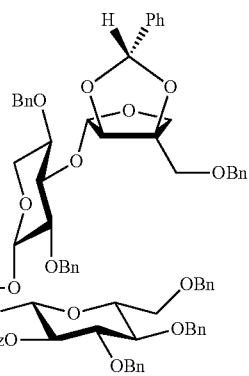

13

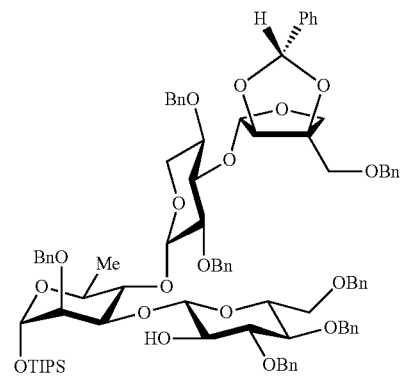

S10

O-Triisopropylsilyl 2-O-benzyl-[3,4,6-tri-O-benzyl-β-D-glucopyranosyl-(1→3)]-{[5-O-benzyl-2,3-di-O-benzylidene-β-D-apiofuranosyl-(1→3)]-2,4-di-O-benzyl-β-D-xylopyranosyl-(1→4)]}-α-L-rhamnopyranoside (S10)

To a solution of tetrasaccharide 13 (110 mg, 0.0701 mmol, 1.00 equiv) in dichloromethane (15 mL) at −78° C. was added diisobutylaluminium hydride solution (1.0 M in hexane, 0.14 mL, 0.14 mmol, 2.0 equiv). After 0.5 h, additional diisobutylaluminium hydride solution (1.0 M in hexane, 0.20 mL, 0.20 mmol, 2.9 equiv) was added, and 0.5 h later, the reaction was quenched with methanol at −78° C. The reaction mixture was concentrated, and the residue was purified by silica gel chromatography (hexanes/ethyl acetate 4:1) to afford S10 (95 mg, 0.065 mmol, 92% yield). $^1$H NMR (500 MHz, CDCl$_3$) δ 7.50-7.42 (m, 2H), 7.46-7.14 (m, 38H), 6.02 (s, 1H), 5.86 (s, 1H), 5.06 (d, J=8.0 Hz, 1H), 4.97-4.92 (m, 2H), 4.88-4.80 (m, 4H), 4.72 (d, J=11.0 Hz, 1H), 4.68-4.60 (m, 4H), 4.59-4.48 (m, 4H), 4.38 (d, J=12.0 Hz, 1H), 4.06-3.82 (m, 9H), 3.70 (s, 4H), 3.62 (dd, J=11.0, 4.0 Hz, 1H), 3.54-3.40 (m, 4H), 3.36-3.26 (m, 2H), 3.22 (d, J=7.5 Hz, 1H), 2.76 (m, 2H), 1.34 (d, J=6.0 Hz, 3H), 1.10-0.90 (m, 21H, Si-i-Pr$_3$); $^{13}$C NMR (125 MHz, CDCl$_3$) δ 139.3, 139.0, 138.48, 138.45, 138.2, 137.4, 136.8, 129.8, 129.4, 129.1, 128.9, 128.71, 128.66, 128.59, 128.56, 128.48, 128.44, 128.37, 128.05, 127.99, 127.7, 127.59, 127.57, 127.4, 107.8, 106.8, 105.0, 103.1, 93.7, 91.9, 87.5, 85.1, 83.1, 82.8, 79.5, 78.2, 77.4, 77.2, 77.1, 76.1, 75.9, 75.1, 74.7, 74.5, 73.9, 73.7, 73.6, 73.2, 71.3, 69.3, 67.2, 64.2, 18.2, 18.00, 17.97, 12.1; FTIR (neat film) 3436 (br), 3059, 3032, 2930, 2863, 1497, 1455, 1362, 1094, 883 cm$^{-1}$; HRMS (ESI) m/z: Calcd for C$_{87}$H$_{104}$O$_{18}$Si (M+NH$_4$$^+$) 1482.7336. found 1482.7333.

(96 mg, 0.061 mmol, 99%/yield). $^1$H NMR (500 MHz, CDCl$_3$) δ 7.50-7.44 (m, 2H), 7.38-7.02 (m, 38H), 5.96 (s, 1H), 5.89 (s, 1H), 5.03 (d, J=8.0 Hz, 1H), 4.95 (d, J=11.5 Hz, 1H, PhCH$_2$—), 4.89-4.82 (m, 3H), 4.80 (d, J=12.5 Hz, 1H, PhCH$_2$—), 4.75 (d, J=11.1 Hz, 1H, PhCH$_2$—), 4.71 (d, J=11.2 Hz, 1H, PhCH$_2$—), 4.64 (d, J=7.5 Hz, 1H), 4.63-4.48 (m, 7H), 4.46 (d, J=11.3 Hz, PhCH$_2$—, 1H), 4.39 (d, J=12.5 Hz, 1H, PhCH$_2$—), 4.20 (dd, 2H, 1H, J=9.0, 3.5 Hz), 4.01 (t, J=9.5 Hz, 1H), 3.98-3.78 (m, 5H), 3.65-3.54 (m, 4H), 3.50-3.38 (m, 3H), 3.36-3.24 (m, 3H), 3.22 (dd, J=9.5, 8.0 Hz, 1H), 2.11 (d, J=9.5 Hz, 1H), 1.31 (d, J=6.0 Hz, 3H), 1.06-0.89 (m, 29H), 0.72 (m, 6H), 0.56 (m, 1H); $^{13}$C NMR (125 MHz, CDCl$_3$) 139.4, 139.3, 139.0, 138.8, 138.3, 138.2, 137.0, 129.8, 128.9, 128.7, 128.6, 128.50, 128.45, 128.43, 128.4, 128.3, 128.2, 127.93, 127.90, 127.8, 127.74, 127.70, 127.66, 127.6, 127.5, 127.3, 127.2, 107.5, 106.7, 102.7, 102.1, 93.7, 91.9, 87.4, 85.0, 82.9, 79.3, 78.2, 77.5, 77.35, 77.32, 76.1, 75.7, 75.2, 74.6, 74.5, 74.0, 73.80, 73.78, 73.4, 73.0, 71.3, 69.0, 66.9, 64.1, 18.1, 18.0, 12.1, 7.5, 6.9, 6.1, 5.8; FTIR (neat film) 3065, 3032, 2943, 2871, 1497, 1455, 1364, 1178, 1148, 1094, 1028, 884, 735, 697 cm$^{-1}$; HRMS (ESI) m/z: Calcd for C$_{93}$H$_{118}$O$_{18}$Si$_2$ (M+Na$^+$) 1601.7754. found 1601.7816.

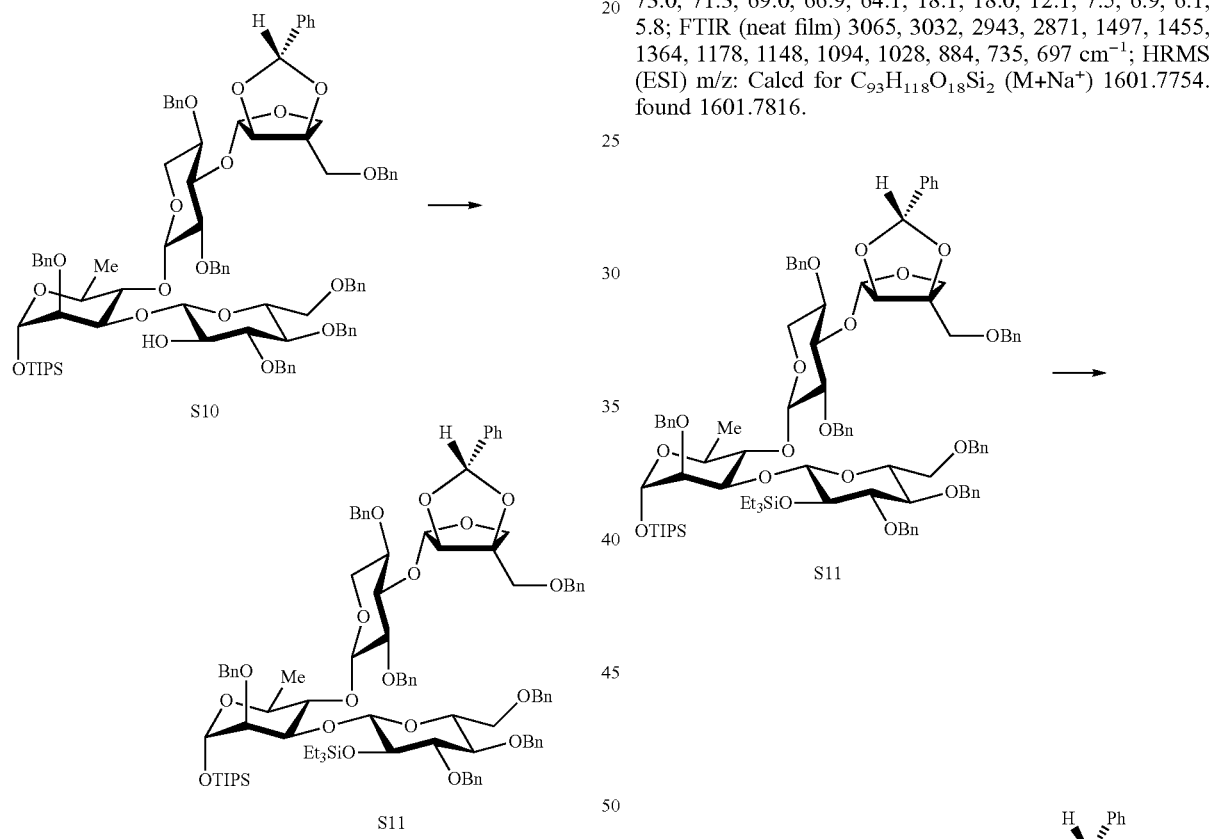

S10

S11

O-Triisopropylsilyl 2-O-benzyl-[3,4,6-tri-O-benzyl-2-O-triisopropylsilyl-β-D-glucopyranosyl-(1-3)]-{[5-O-benzyl-2,3-di-O-benzylidene-β-D-apiofuranosyl-(1→3)]-2,4-di-O-benzyl-β-D-xylopyranosyl-(1→4)]}-α-L-rhamnopyranoside (S11)

To a solution of tetrasaccharide S10 (90 mg, 0.061 mmol, 1.0 equiv) in dichloromethane (10 mL) at 0° C. was added 2,6-lutidine (0.21 mL, 1.8 mmol, 26 equiv) and triethylsilyl trifluoromethanesulfonate (0.21 mL, 0.92 mmol, 15 equiv). The reaction mixture was stirred at this temperature for 30 min and at 23° C. for 8 h. The reaction mixture was concentrated, and the residue was purified by silica gel chromatography (hexanes/ethyl acetate 23:2) to afford S11

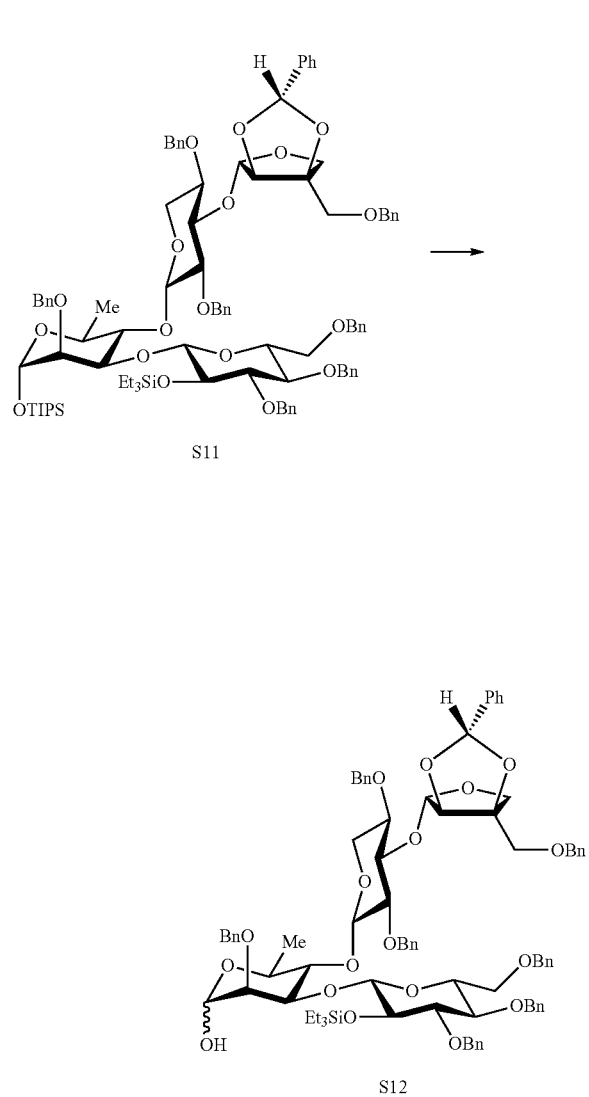

S12

2-O-benzyl-[3,4,6-tri-O-benzyl-2-O-triisopropylsilyl-β-D-glucopyranosyl-(1→3)]-{[5-O-benzyl-2,3-di-O-benzylidene-β-D-apiofuranosyl-(1→3)]-2,4-di-O-benzyl-β-D-xylopyranosyl-(1→4))]}-L-rhamnopyranose (S12)

To a solution of tetrasaccharide S11 (96 mg, 0.061 mmol, 1.0 equiv) in tetrahydrofuran (6 mL) at 0° C. was added tetrabutylammonium fluoride solution (1.0 M in tetrahydrofuran, 63 μL, 0.063 mmol, 1.0 equiv). After 3 min, silica gel (120 mg) was added to the reaction mixture, which was concentrated and purified by silica gel chromatography (hexanes/ethyl acetate 11:9) to afford hemiacetal S12 (88 mg, quantitative yield). $^1$H NMR (500 MHz, CDCl$_3$) δ 7.49-7.45 (m, 2H), 7.36-7.09 (m, 38H), 5.94 (s, 1H), 5.80 (s, 1H), 5.01 (dd, J=3.0, 2.8 Hz, 1H), 4.98-4.90 (m, 2H), 4.88-4.76 (m, 3H), 4.76-4.70 (m, 2H), 4.68-4.60 (m, 2H), 4.60-4.53 (m, 2H), 4.53-4.44 (m, 6H), 4.22 (dd, J=8.5, 3.5 Hz, 1H), 4.00-3.76 (m, 7H), 3.74 (dd, J=3.0, 2.0 Hz, 1H), 3.64-3.56 (m, 2H), 3.54-3.20 (m, 9H), 2.68 (m, 1H), 2.37 (d, J=3.5 Hz, 1H), 1.32 (d, J=6.5 Hz, 3H), 0.98 (m, 9H), 0.68-0.52 (m, 6H); $^{13}$C NMR (125 MHz, CDCl$_3$) δ 139.3, 138.9, 138.8, 138.7, 138.1, 137.4, 137.0, 128.8, 128.6, 128.54, 128.50, 128.45, 128.43, 128.40, 128.37, 128.3, 128.2, 127.9, 127.8, 127.71, 127.68, 127.64, 127.60, 127.57, 127.54, 127.4, 127.35, 127.30, 127.2, 107.4, 106.6, 102.0, 91.80, 91.78, 87.3, 82.4, 78.7, 78.4, 76.5, 75.9, 75.6, 74.9, 74.8, 74.6, 73.7, 73.5, 73.4, 72.9, 71.3, 69.1, 67.4, 18.2, 18.1, 17.9, 13.1, 12.5, 7.4, 5.7, 5.6; FTIR (neat film) 3401 (br), 3032, 2938, 2874, 1454, 1364, 1095, 1066, 734, 696 cm$^{-1}$; HRMS (ESI) m/z: Calcd for $C_{84}H_{98}O_{18}Si$ (M+Na$^+$) 1445.6420. found 1445.6449.

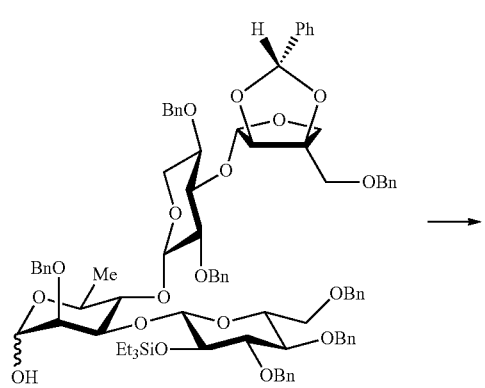

S12

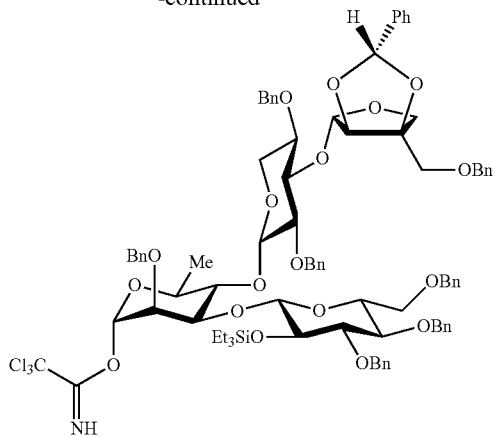

14

O-Trichloroacetimidoyl 2-O-benzyl-[3,4,6-tri-O-benzyl-2-O-triisopropylsilyl-β-D-glucopyranosyl-(1→3)]-{[5-O-benzyl-2,3-di-O-benzylidene-β-D-apiofuranosyl-(1→3)]-2,4-di-O-benzyl-β-D-xylopyranosyl-(1→4)]}-α-L-rhamnopyranoside (14)

To a solution of hemiacetal S12 (64 mg, 0.045 mmol, 1.0 equiv) in dichloromethane (10 mL) at 0° C. was added trichloroacetonitrile (0.9 mL, 0.9 mmol, 200 equiv) and 1,8-diazabicyclo[5.4.0]undec-7-ene (62 μL, 0.045 mmol, 10 equiv). After 3 h at 0° C., triethylamine (100 μL) was added. The reaction mixture was concentrated, and the residue was purified by silica gel chromatography (hexanes/ethyl acetate 7:3) to afford 14 (65 mg, 92% yield). $^1$H NMR (500 MHz, CDCl$_3$) δ 8.52 (s, 1H), 7.53-7.49 (m, 2H), 7.41-7.09 (m, 38H), 6.17 (d, J=2.0 Hz, 1H), 6.00 (s, 1H), 5.90 (s, 1H), 5.04 (d, J=7.8 Hz, 1H), 4.97 (d, J=11.8 Hz, 1H, PhC$\underline{H}_2$—), 4.89 (d, J=11.8 Hz, 1H, PhC$\underline{H}_2$—), 4.85 (d, J=12.2 Hz, 1H, PhC$\underline{H}_2$—), 4.84 (d, J=11.1 Hz, 1H, PhC$\underline{H}_2$—), 4.78 (d, J=11.1 Hz, 1H, PhC$\underline{H}_2$—), 4.74 (d, J=11.3 Hz, 1H, PhC$\underline{H}_2$—), 4.71 (d, J=11.3 Hz, 1H, PhC$\underline{H}_2$—), 4.65-4.45 (m, 9H), 4.39 (d, J=12.4 Hz, 1H, PhC$\underline{H}_2$—), 4.05-3.87 (m, 6H), 3.67 (d, J=10.5 Hz, 1H, PhC$\underline{H}_2$—), 3.64 (d, J=10.5 Hz, 1H, PhC$\underline{H}_2$—), 3.57 (t, J=9.4 Hz, 1H), 3.50-3.40 (m, 3H), 3.40-3.22 (m, 4H), 2.20 (d, J=9.3 Hz, 1H), 1.41 (d, J=6.2 Hz, 3H), 1.00-0.92 (m, 9H), 0.80-0.68 (m, 6H); $^{13}$C NMR (125 MHz, CDCl$_3$) 160.1, 139.1, 138.9, 138.5, 138.35, 138.30, 138.0, 137.9, 136.8, 129.6, 128.7, 128.4, 128.3, 128.24, 128.23, 128.13, 128.09, 128.0, 127.8, 127.75, 127.71, 127.6, 127.50, 127.48, 127.46, 127.34, 127.32, 127.29, 127.2, 127.1, 127.0, 107.3, 106.4, 102.4, 101.7, 96.4, 91.7, 91.4, 87.2, 84.8, 82.6, 78.0, 77.0, 76.9, 76.5, 76.1, 75.6, 75.4, 75.0, 74.31, 74.26, 73.6, 73.49, 73.46, 73.2, 72.8, 71.1, 70.1, 68.5, 18.0, 7.2, 5.5; FTIR (neat film) 3335, 3063, 3030, 2935, 2876, 1673, 1454, 1363, 1176, 1149, 1095, 1063, 1028, 796, 734, 697 cm$^{-1}$.

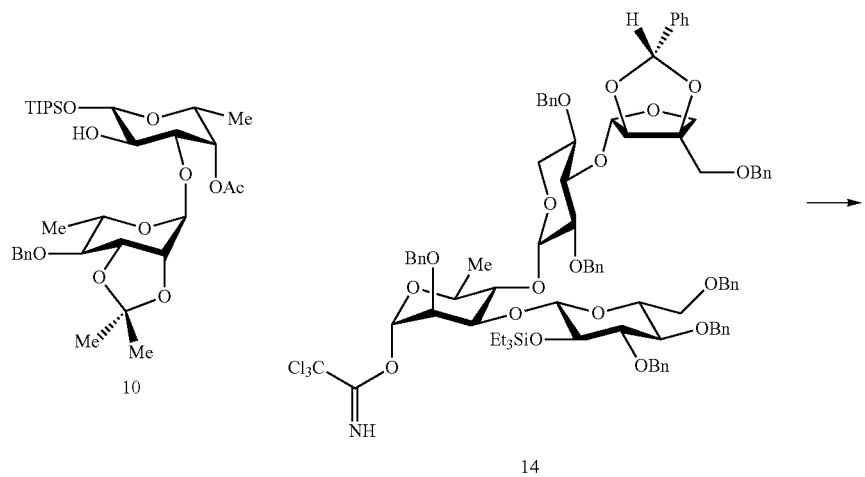
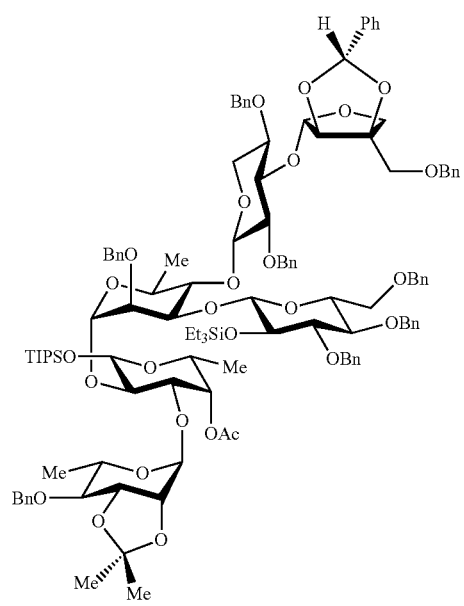

O-Triisopropylsilyl (2-O-benzyl-[3,4,6-tri-O-benzyl-2-O-triisopropylsilyl-β-D-glucopyranosyl-(1→3)]-{[5-O-benzyl-2,3-di-O-benzylidene-β-D-apiofuranosyl-(1→3)]-2,4-di-O-benzyl-β-D-xylopyranosyl-(1→4)]}-α-L-rhamnopyranoside-[1→2])-4-O-acetyl-[4-O-benzyl-2,3-di-O-isopropylidene-α-L-rhamnopyranose-(1→3)]-β-D-fucopyranoside (15)

Dichloromethane (1.5 mL) was added to disaccharide 10 (18 mg, 0.028 mmol, 2.8 equiv), imidate 14 (16 mg, 0.010 mmol, 1.0 equiv), and 4 Å molecular sieves (40 mg), and the resulting mixture was stirred for 30 min at 23° C. and was then cooled to −15° C. A solution of trimethylsilyl trifluoromethanesulphonate (0.145 μL, 0.000799 mmol, 0.0783 equiv) in dichloromethane (20 μL) was added. After 40 min triethylamine (60 μL) was added, and the reaction mixture was filtered, concentrated, and purified by silica gel chromatography (benzene/ethyl acetate 97:3) to afford 15 (13 mg, 62% yield). $^1$H NMR (500 MHz, CDCl$_3$) δ 7.46-7.42 (m, 2H), 7.37-7.07 (m, 43H), 5.90 (s, 1H), 5.72 (s, 1H), 5.26 (d, J=2.0 Hz, 1H), 5.09 (s, 1H), 4.92-4.76 (m, 5H), 4.71 (d, J=11.5 Hz, 1H, PhC$\underline{H}_2$—), 4.65 (d, J=12.0 Hz, 1H, PhC$\underline{H}_2$—), 4.62-4.36 (m, 11H), 4.18 (m, 1H), 4.08 (m, 2H), 3.96-3.82 (m, 5H), 3.73 (m, 1H), 3.67 (dd, J=10.0, 6.5 Hz, 1H), 3.64-3.48 (m, 5H), 3.42-3.34 (m, 2H), 3.34-3.26 (m, 3H), 3.24-3.16 (m, 2H), 3.12 (dd, J=9.5, 7.0 Hz, 1H), 2.11 (s, 3H), 1.34-1.24 (m, 9H), 1.18-1.02 (m, 21H), 0.84-0.74 (m, 9H), 0.64-0.54 (m, 6H); $^{13}$C NMR (125 MHz, CDCl$_3$) δ 171.0, 139.2, 138.7, 138.2, 136.9, 129.8, 129.4, 128.8, 128.65, 128.55, 128.43, 128.38, 128.2, 128.04, 128.00, 127.84, 127.78, 127.75, 127.66, 127.61, 127.4, 127.3, 127.1, 109.3, 107.3, 106.4, 97.0, 91.7, 87.2, 80.4, 79.0, 78.7, 78.5, 77.1, 76.8, 76.4, 75.56, 75.4, 74.6, 74.0, 73.7, 73.4, 73.0, 72.8, 71.3, 65.7, 63.9, 41.6, 29.9, 28.0, 26.2, 21.1, 18.8, 18.4, 18.3, 17.8, 16.5, 12.87, 7.3, 5.5; FTIR (neat film) 2930, 2868, 1744, 1068 cm$^{-1}$; LRMS (MALDI) m/z: Calcd for C$_{117}$H$_{150}$O$_{27}$Si$_2$ (M+Na) 2065.98. found 2066.60.

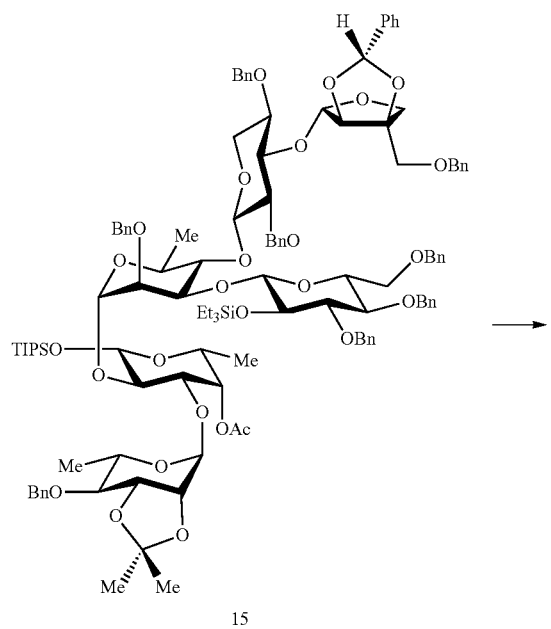

15

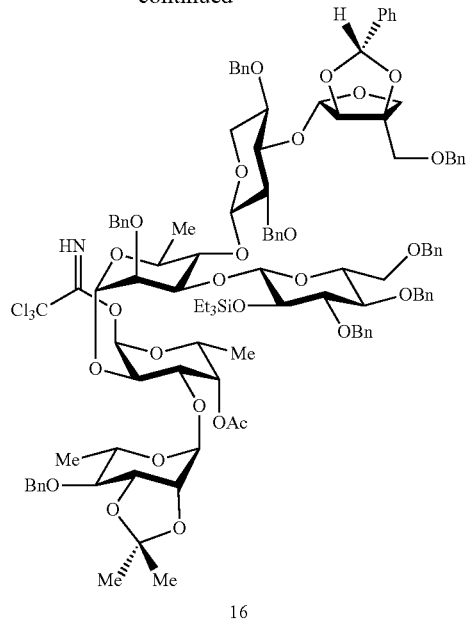

16

O-Trichloroacetimidoyl (2-O-benzyl-[3,4,6-tri-O-benzyl-2-O-triisopropylsilyl-β-D-glucopyranosyl-(1→3)-{[5-O-benzyl-2,3-di-O-benzylidene-β-D-apiofuranosyl-(1→3)]-2,4-di-O-benzyl-β-D-xylopyranosyl-(1→4)]}-α-rhamnopyranoside-[1→2])-4-O-acetyl-[4-O-benzyl-2,3-di-O-isopropylidene-α-L-rhamnopyranose-(1→3)]-α-D-fucopyranoside 17

To a solution of 15 (10.0 mg, 0.00489 mmol, 1.00 equiv) in tetrahydrofuran (1.50 mL) at 0° C. was added tetrabutylammonium fluoride solution (0.0245 M in tetrahydrofuran, 0.20 mL, 0.0049 mmol, 1.0 equiv). After 50 min, the solvent was removed in vacuo at 0° C. to give a pale yellow oil that was immediately subjected to further reaction. $R_f$=0.42 (benzene/ethyl acetate 9:1). The hemiacetal residue was dried by azeotropic removal of water with toluene (3×1 mL) and was then dissolved in dichloromethane (4.0 mL) and cooled to 0° C. Trichloroacetonitrile (74 μL, 0.74 mmol, 150 equiv) and 1,8-diazabicyclo[5.4.0]undec-7-ene (2.7 μL, 0.020 mmol, 4.0 equiv) were added, and the solution was stirred at 0° C. for 13.5 h and 23° C. for 2 h. The solution was then concentrated and purified by silica gel chromatography (benzene/ethyl acetate 99:1 to 9:1) to afford 16 (8.3 mg, 0.0041 mmol, 84% yield). $R_f$=0.53 (benzene/ethyl acetate 9:1); $^1$H NMR (500 MHz, CDCl$_3$) δ 8.54 (s, 1H, C=N$\underline{H}$), 7.49-6.95 (m, 45H), 6.41 (d, J=3.5 Hz, 1H), 5.90 (s, 1H), 5.68 (s, 1H), 5.28-5.20 (m, 2H), 5.04 (d, J=11.9 Hz, 1H), 4.92 (d, J=11.9 Hz, 1H), 4.87-4.64 (m, 3H), 4.84 (d, J=11.7 Hz, 1H), 4.83 (d, J=11.7 Hz, 1H), 4.68 (d, J=10.9 Hz, 1H), 4.64-4.39 (m, 11H), 4.32 (s, 1H), 4.28-4.19 (m, 3H), 4.19-4.08 (m, 3H), 3.91-3.78 (m, 4H), 3.78-3.61 (m, 3H), 3.57-3.33 (m, 6H), 3.30 (m, 1H), 3.23-3.09 (m, 3H), 2.16 (s, 3H, —C(O)C$\underline{H}_3$), 1.34 (s, 3H), 1.32-1.23 (m, 10H), 1.14 (d, J=6.5 Hz, 3H), 1.12 (s, 3H), 0.85 (t, J=7.8 Hz, 9H), 0.66-0.56 (m, 6H); FTIR (neat film) 2932, 2875, 1746, 1673, 1497, 1454, 1367, 1229, 1098, 1072, 990, 735, 698 cm$^{-1}$; LRMS (MALDI) m/z: Calcd for C$_{110}$H$_{130}$Cl$_3$NO$_{27}$NCl$_3$SiNa (M+Na) 2055.64. found 2055.73.

Final Assembly of Synthetic QS-7-Api

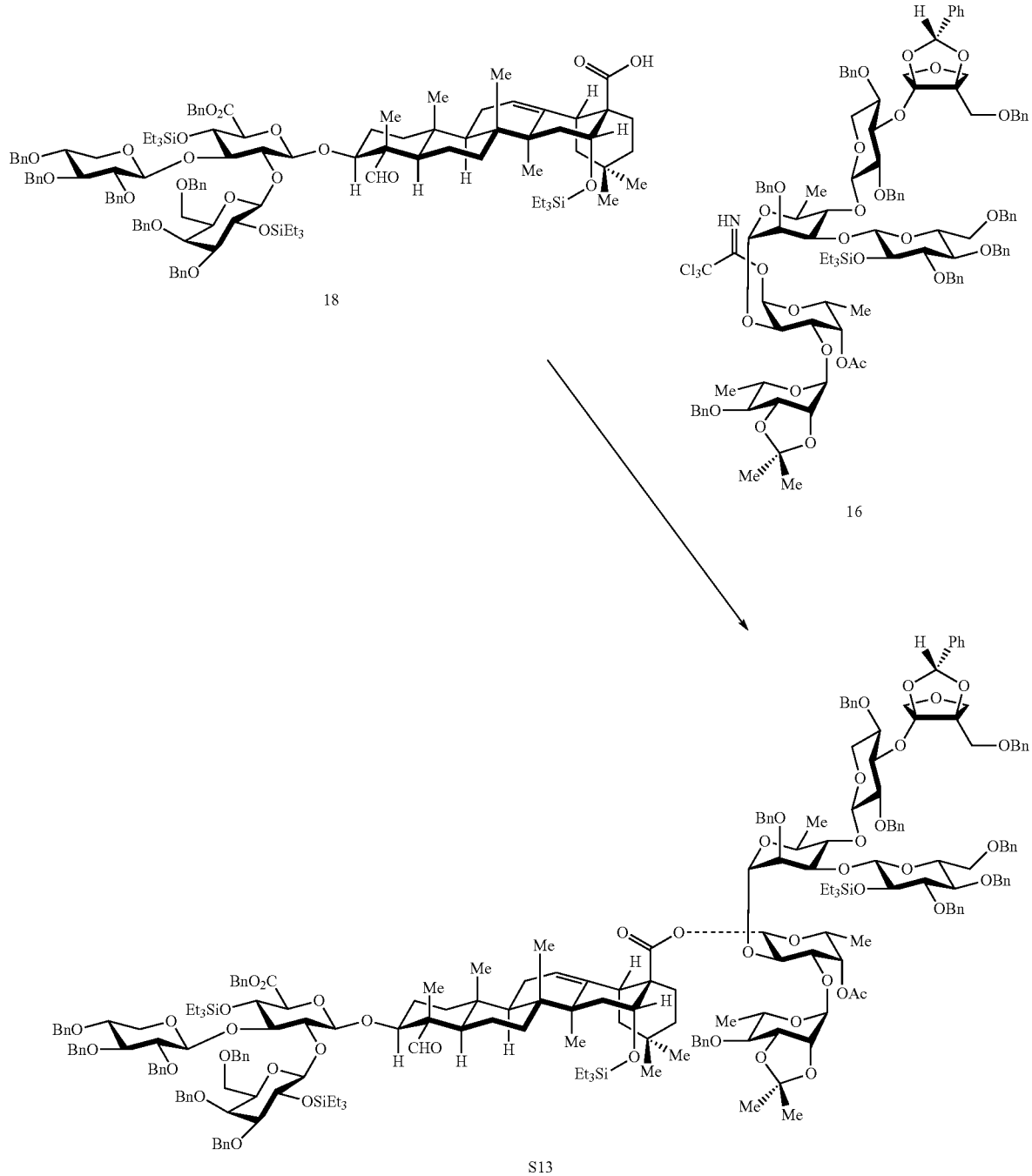

Fully-Protected Synthetic QS-7-Api (S13).

A solution of boron trifluoride diethyl etherate (0.40 μL, 0.0032 mmol, 1.0 equiv) in dichloromethane (20 μL) was injected to a solution of the imidate 16 (6.4 mg, 0.0031 mmol, 1.0 equiv), 18 (9.1 mg, 0.0047 mmol, 1.5 equiv) and 4 Å molecular sieves (20 mg) in dichloromethane (2.0 mL) at −78° C. The reaction temperature was allowed to warm to 23° C. slowly, and triethylamine (20 μL) was added after 16.5 h. The reaction was concentrated and purified by silica gel chromatography (hexanes/ethyl acetate 4:1) to afford S13 (8.5 mg, 0.0022 mmol, 71% yield) and starting material 18 (3.0 mg, 0.0016 mmol, 33% recovered). $R_f$=0.67 (benzene/ethyl acetate 7:3); characteristic resonances from $^1$H NMR (500 MHz, CDCl$_3$) δ 9.41 (s, 1H, —C$\underline{H}$O), 5.94 (s, 1H), 5.83 (s, 1H), 5.30 (d, J=7.3 Hz, 1H), 5.23 (m, 1H), 5.23 (d, J=12.4 Hz, 1H), 5.13 (d, J=12.4 Hz, 1H), 5.08 (s, 1H), 5.01 (m, 1H), 4.31 (t, J=6.6 Hz, 1H), 4.22 (m, 1H), 4.17 (d, J=7.1 Hz, 1H), 4.12 (q, J=7.1 Hz, 1H), 2.96 (m, 1H), 2.83 (m, 1H), 2.72 (m, 1H), 2.50 (m, 1H), 2.09 (s, 3H, —C(O)C$\underline{H}_3$), 1.39 (s, 3H, Me), 1.30 (s, 3H, Me), 1.12 (s, 3H, Me); see proton NMR below; MS (MALDI) m/z: Calcd for C$_{222}$H$_{284}$O$_{46}$Si$_4$Na (M+Na) 3821 (±2). found 3820 (±2).

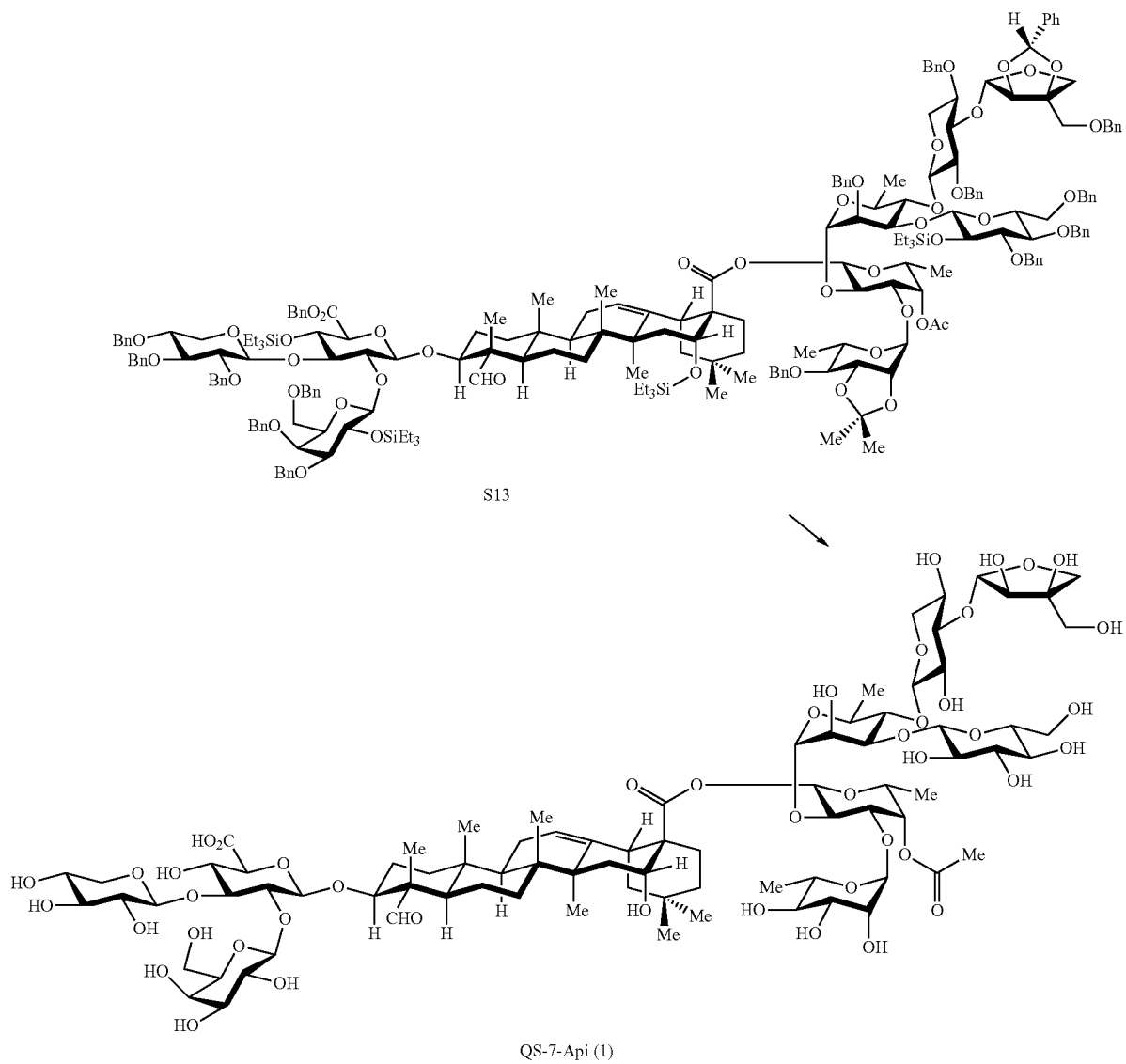

Synthetic QS-7-Api (1).

Two solutions of fully-protected QS-7-Api S13 (1.3 mg, 0.00034 mmol, 1.0 equiv) in dichloromethane (0.20 mL) were each transferred to a 10-mL round bottom flask and cooled to 0° C. A pre-cooled (0° C.) solution of trifluoroacetic acid (1.0 mL, TFA/water 4:1) was added to each flask. After vigorous stirring for 60 min, the reaction mixtures were concentrated in vacuo for 140 min at 0° C. to give a white solid residue. To both flasks were added tetrahydrofuran (1.0 mL), ethanol (2.0 mL), and 10% (dry basis) palladium on carbon, wet, Degussa type E101 NE/W (2.0 mg, 0.00094 mmol, 2.8 equiv). The two runs were stirred under hydrogen pressure (50 psi) for 44 h, and then the suspensions were combined and filtered through a 0.45 μm polyvinylidene fluoride filter disk, which was then washed with methanol (5 mL). The filtrate and rinsing were concentrated and purified by RP-HPLC on an XBridge Prep BEH300 C18 column (5 μm, 10×250 mm) using a linear gradient of 32→37% acetonitrile (0.05% TFA) in water (0.05% TFA) over 30 min at a flow rate of 5 mL/min. The fraction containing the major peak ($t_R$=14.85 min) was collected and lyophilized to dryness to afford synthetic QS-7-Api (1) (0.9 mg 0.0005 mmol, 70% yield) as a white solid. $^1$H NMR (500 MHz, 7:3 $D_2O$:$CD_3CN$) δ 9.36 (s, 1H, —CHO), 5.39 (d, J=8.0 Hz, 1H), 5.34 (m, 1H, $R_2C$=CHR), 5.22 (d, J=3.1 Hz, 1H), 5.12 (d, J=2.9 Hz, 1H), 5.03 (s, 1H), 4.86 (s, 1H), 4.67 (d, J=7.7 Hz, 1H), 4.63 (d, J=7.8 Hz, 1H), 4.55 (d, J=7.7 Hz, 1H), 4.50 (d, J=7.7 Hz, 1H), 4.33 (m, 1H), 4.05 (d, J=10.1 Hz, 1H), 4.02 (m, 1H), 3.99-3.94 (m, 2H), 3.92-3.57 (m, 22H), 3.55-3.45 (m, 7H), 4.33 (m, 1H), 3.42-3.15 (m, 12H), 2.86 (dd, J=14.5, 3.6 Hz, 1H), 2.14 (s, 3H, —C(O)CH$_3$), 1.89-1.30 (m, 14H), 1.28 (s, 3H, Me), 1.22 (d, J=6.2 Hz, 3H, Me), 1.15 (d, J=6.1 Hz, 3H, Me), 1.08 (s, 3H, Me), 1.05 (m, 1H), 1.02 (m, 1H), 0.99 (d, J=6.3 Hz, 3H, Me), 0.93 (s, 3H, Me), 0.89 (s, 3H, Me), 0.84 (s, 3H, Me), 0.71 (s, 3H, Me).

Natural QS-7-Api (1).

Brenntag Quil-A (205 mg, batch L77-244) was fractionated by RP-HPLC on an XBridge Prep C18 OBD column (5 μm, 19×150 mm) using a linear gradient of 30-40% acetonitrile (0.05% TFA) in water (0.05% TFA) over 30 min at a flow rate of 15 mL/min. Crude natural QS-7-Api (1) ($t_R$=15.25 min) was collected and further purified on an XBridge Prep BEH300 C18 column (5 μm, 10×250 mm) using a linear gradient of 32→37% acetonitrile (0.05% TFA) in water (0.05% TFA) over 30 min at a flow rate of 5 mL/min. The fraction containing QS-7-Api (1) ($t_R$=14.85 min) was collected and lyophilized to dryness to afford natural QS-7-Api (1) (2.0 mg) as a white solid (~70% pure by $^1$H NMR).

Preparation of the Semisynthetic Triterpene-Trisaccharide

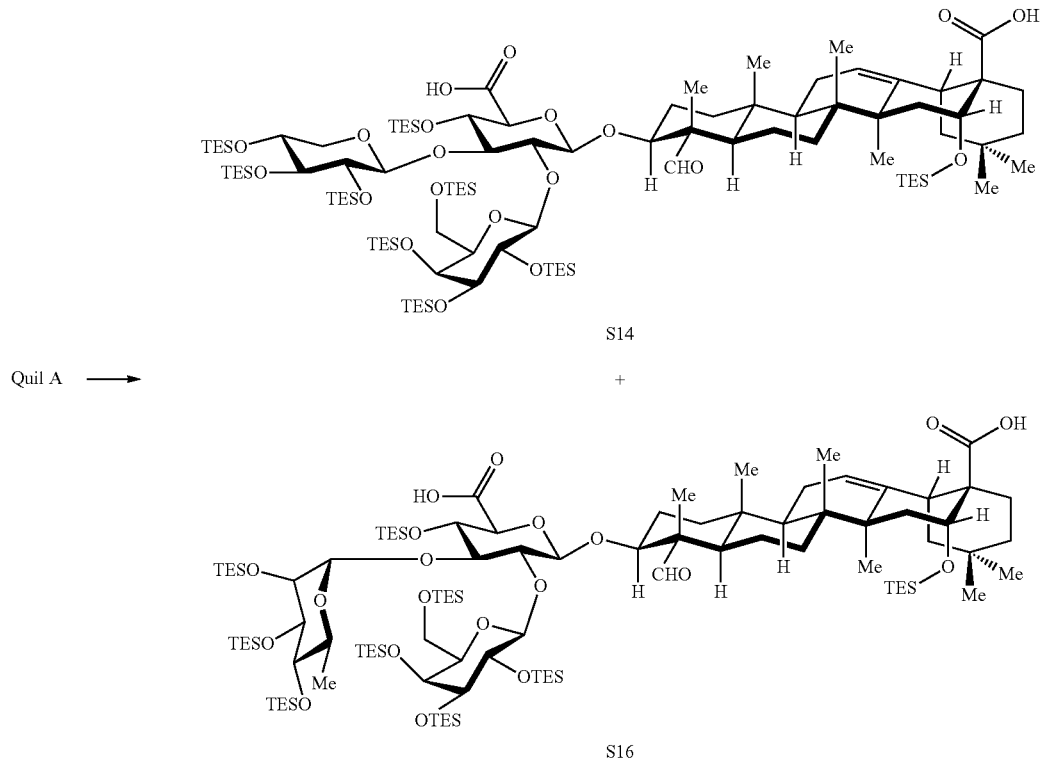

O-(16-O-triethylsilyl-quillaic Acid) 4-O-triethylsilyl-[(2,3,4-tri-O-triethylsilyl-β-D-xylopyranosyl)-(1→3)]-[(2,3,4,6-tetra-O-triethylsilyl-β-D-galactopyranosyl-(1→2)]-β-D-glucuronoside (S14) and
O-(16-O-triethylsilyl-quillaic Acid) 4-O-triethylsilyl-[(2,3,4-tri-O-triethylsilyl-α-L-rhamnopyranosyl)-(1→3)]-[(2,3,4,6-tetra-O-triethylsilyl-β-D-galactopyranosyl-(1→2)]-β-D-glucuronoside (S16)

A mixture of Brenntag Quil A (1.15 g. batch L77-244) and potassium hydroxide (0.97 g) in ethanol (25 mL) and water (25 mL) was heated at 80° C. for 7.25 h, then cooled to 0° C. and neutralized with 1 N aqueous NaOH. The reaction mixture was concentrated to one-half volume and purified by silica gel chromatography (chloroform/methanol/water/acetic acid 15:9:2:1). The major product spot by TLC was isolated, concentrated, and dried by azeotropic removal of solvents with toluene (2×20 mL) and lyophilization from water (4×30 mL) to afford a mixture of prosapogenins as a light tan foam (0.576 g). $R_f$=0.44 (chloroform/methanol/water/acetic acid 15:9:2:1); characteristic resonances from $^1$H NMR: (500 MHz, CD$_3$OD) δ 9.44 (s, 1H, —CHO), 5.33 (m, 1H, R$_2$C=CHR), 4.80 (d, J=7.4 Hz, 1H), 4.63 (d, J=7.7 Hz, 1H), 4.43 (s, 1H), 4.37 (d, J=6.9 Hz, 1H); $^1$H NMR (500 MHz, 7:3 D$_2$O:CD$_3$CN) δ 9.36 (s, 1H, —CHO), 5.29 (m, 1H, R$_2$C=CHR), 4.68 (d, J=7.7 Hz, 1H), 4.59 (d, J=8.2 Hz, 1H).

Pyridine (8 mL) was added to the prosapogenin (0.560 g), and the suspension was concentrated. Additional pyridine (8.6 mL) was added, followed by triethylsilyl trifluoromethanesulfonate (1.98 mL, 8.76 mmol). Further triethylsilyl trifluoromethanesulfonate was added to the reaction after 66 h (0.33 mL, 1.5 mmol), 89 h (66 μL, 0.29 mmol), and 112 h (0.13 mL, 0.54 mmol). After 5 d, the reaction mixture was concentrated and passed through a plug of silica gel (hexane/ethyl acetate 4:1 to 7:3) to give a light yellow oil that was then dissolved in methanol (10 mL) and tetrahydrofuran (10 mL). The solution was stirred for 3.5 d, and then it was concentrated and purified by silica gel chromatography (hexane/ethyl acetate 4:1 to 7:3) to afford diacid S14 (0.257 g) and diacid S16 (0.095 g) as white solids.

S14 R$_f$=0.39 (benzene/ethyl acetate 4:1); $^1$H NMR (500 MHz, CDCl$_3$) δ 9.63 (s, 1H, —CHO), 5.33 (m, 1H, R$_2$C=CHR), 4.54 (m, 1H), 4.50 (d, J=7.3 Hz, 1H), 4.44 (d, J=5.9 Hz, 1H), 4.39 (d, J=7.4 Hz, 1H), 3.95-3.87 (m, 4H), 3.83-3.78 (m, 2H), 3.74 (t, J=9.0 Hz, 1H), 3.65-3.58 (m, 3H), 3.48 (m, 1H), 3.43-3.31 (m, 3H), 3.25 (t, J=7.9 Hz, 1H), 3.12 (t, J=10.8 Hz, 1H), 2.95 (dd, J=13.9, 3.7 Hz, 1H), 2.20 (t, J=13.3 Hz, 1H), 1.91-1.04 (m, 23H), 1.34 (s, 3H, Me), 1.23 (s, 3H, Me), 1.04-0.91 (m, 86H), 0.89 (s, 3H, Me), 0.80-0.54 (m, 56H); $^{13}$C NMR (125.77 MHz, CDCl$_3$) δ 212.12, 183.57, 174.57, 143.28, 122.32, 103.27, 101.72, 101.27, 86.07, 78.98, 78.88, 76.68, 76.45, 76.04, 75.99, 75.28, 74.99, 65.56, 60.44, 54.06, 49.52, 49.02, 46.47, 46.33, 41.56, 40.36, 39.76, 38.02, 36.29, 35.31, 34.85, 32.78, 32.43, 31.66, 30.61, 26.67, 25.14, 24.42, 23.42, 20.41, 17.05, 15.93, 12.15, 7.66, 7.55, 7.36, 7.25, 7.07, 6.98, 6.91, 6.04, 5.81, 5.59, 5.50, 5.42, 5.40, 5.15, 4.58; FTIR (neat film) 2953, 2912, 2877, 1722, 1460, 1414, 1378, 1239, 1163, 1103, 1007, 973, 825, 801, 738 cm$^{-1}$; LRMS (ESI) m/z: Calcd for C$_{101}$H$_{198}$O$_{20}$Si$_9$Na (M+Na$^+$) 2006.2. found 2006.5.

S16 $R_f$=0.74 (benzene/ethyl acetate 4:1); characteristic resonances from $^1$H NMR (500 MHz, CDCl$_3$) δ 9.39 (s, 1H), 5.33 (s, 1H), 5.02 (d, J=2.2, 1H), 4.60 (s, 1H), 4.51 (s, 1H), 4.46 (m, 1H), 4.25 (d, J=7.3, 1H), 4.15 (d, J=6.7, 1H), 3.92 (s, 1H), 3.83 (d, J=5.6, 1H), 3.77 (s, 1H), 3.55 (m, 1H), 3.37 (d, J=8.7, 1H), 3.28 (m, 1H), 2.93 (dd, J=14.0, 3.7, 1H), 2.20 (m, 1H), 1.36 (s, 3H), 1.17 (d, J=6.2, 3H), 1.14 (s, 3H), 0.89 (s, 3H); $^{13}$C NMR (126 MHz, CDCl$_3$) δ 143.35, 122.24, 102.81, 99.43, 97.18, 82.71, 77.86, 76.28, 75.83, 74.84, 74.05, 73.68, 73.09, 71.62, 70.85, 70.49, 60.71, 54.47, 48.98, 48.43, 46.53, 41.54, 40.85, 39.83, 38.06, 36.82, 36.10, 35.31, 34.81, 32.83, 32.32, 31.34, 30.66, 26.64, 24.45, 23.60, 20.50, 18.42, 16.92, 16.12, 10.88, 7.42, 7.38, 7.30, 7.23, 7.20, 7.17, 7.11, 7.04, 6.95, 5.62, 5.57, 5.47, 5.45, 5.40, 5.23, 5.15, 5.11, 4.62; FTIR (neat film) 2953, 2913, 2876, 1724, 1459, 1414, 1379, 1240, 1108, 1006, 974, 909, 885, 856, 821, 779, 738 cm$^{-1}$; LRMS (ESI) min: Calcd for $C_{102}H_{200}O_{20}Si_9Na$ (M+Na$^+$) 2020.3. found 2020.3.

(3.0 μL, 0.021 mmol, 0.51 equiv) was added to the reaction. After stirring for 20 h, the reaction was concentrated and purified by silica gel chromatography (benzene/ethyl acetate 1:0 to 24:1) to afford 21 (58.0 mg, 0.00279 mmol, 68% yield) as a white solid. $R_f$=0.69 (benzene/ethyl acetate 9:1); (500 MHz, CDCl$_3$) δ 9.70 (s, 1H, —C$\underline{H}$O), 7.40-7.27 (m, 5H, aromatic), 5.34 (m, 1H, R$_2$C=C$\underline{H}$R), 5.28 (d, J=12.5 Hz, 1H, PhC$\underline{H}_2$—), 5.09 (d, J=12.3 Hz, 1H, PhC$\underline{H}_2$—), 4.55 (d, J=7.6 Hz, 1H), 4.53 (m, 1H), 4.42 (d, J=7.3 Hz, 1H), 4.12 (d, J=7.6 Hz, 1H), 3.97-3.71 (m, 8H), 3.64-3.53 (m, 3H), 3.48 (m, 1H), 3.39 (dd, J=9.3, 2.5 Hz, 1H), 3.37-3.31 (m, 2H), 3.25 (t, J=8.0 Hz, 1H), 3.12 (t, J=10.9 Hz, 1H), 2.94 (dd, J=14.0, 3.7 Hz, 1H), 2.21 (t, J=13.7 Hz, 1H), 1.93-1.04 (m 20H), 1.35 (s, 3H, Me), 1.30 (s, 3H, Me), 1.04-0.84 (m, 90H), 0.84-0.53 (m, 56H), see proton NMR below; $^{13}$C NMR (125.77 MHz, CDCl$_3$) δ 212.59, 182.49, 168.53, 143.44, 135.45, 128.62, 128.43, 128.29, 122.31, 103.63, 101.55, 101.01, 86.22, 79.02, 78.90, 76.61, 76.25, 76.02,

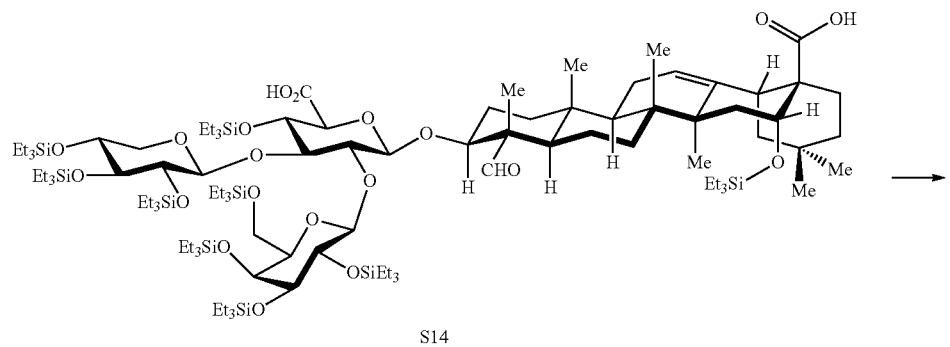

S14

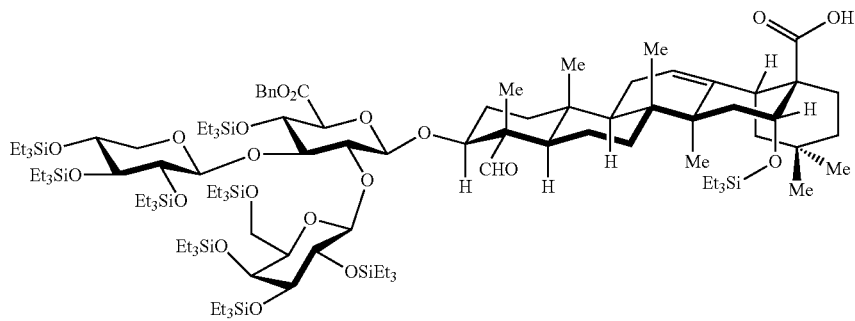

21

O-(16-O-triethylsilyl-quillaic Acid) 4-O-triethylsilyl-[(2,3,4-tri-O-triethylsilyl-β-D-xylopyranosyl)-(1→3)]-[(2,3,4,6-tetra-O-triethylsilyl-β-D-galactopyranosyl-(1→2)]-β-D-glucuronoside Benzyl Ester (21)

To a solution of S14 (81.3 mg, 0.0409 mmol, 1.00 equiv), tri-1-butylpyridine (102 mg, 0.412 mmol, 10.1 equiv) and pyridine (30 μL, 0.37 mmol, 9.1 equiv) in dichloromethane (0.68 mL) was added benzyl chloroformate (15 μL, 0.11 mmol, 2.6 equiv). After 6 h, additional benzyl chloroformate 75.27, 75.12, 72.79, 72.67, 71.59, 71.22, 66.98, 65.51, 60.47, 54.05, 49.58, 48.90, 46.52, 46.31, 41.61, 40.35, 39.76, 38.07, 36.28, 35.31, 34.78, 32.81, 32.49, 31.68, 30.63, 26.68, 25.47, 24.45, 23.43, 20.40, 16.97, 15.86, 12.29, 7.69, 7.59, 7.38, 7.27, 7.12, 6.99, 6.92, 6.07, 5.81, 5.61, 5.53, 5.51, 5.43, 5.40, 5.16, 4.58; FTIR (neat film) 2954, 2914, 2877, 1754, 1723, 1705, 1459, 1414, 1379, 1240, 1170, 1103, 1073, 1007, 972, 825, 801, 739 cm$^{-1}$; LRMS (ESI) m/z: Calcd for $C_{108}H_{204}O_{20}Si_9Na$ (M+Na$^+$) 2096.3. found 2096.7.

Final Assembly of Semisynthetic QS-7-Api

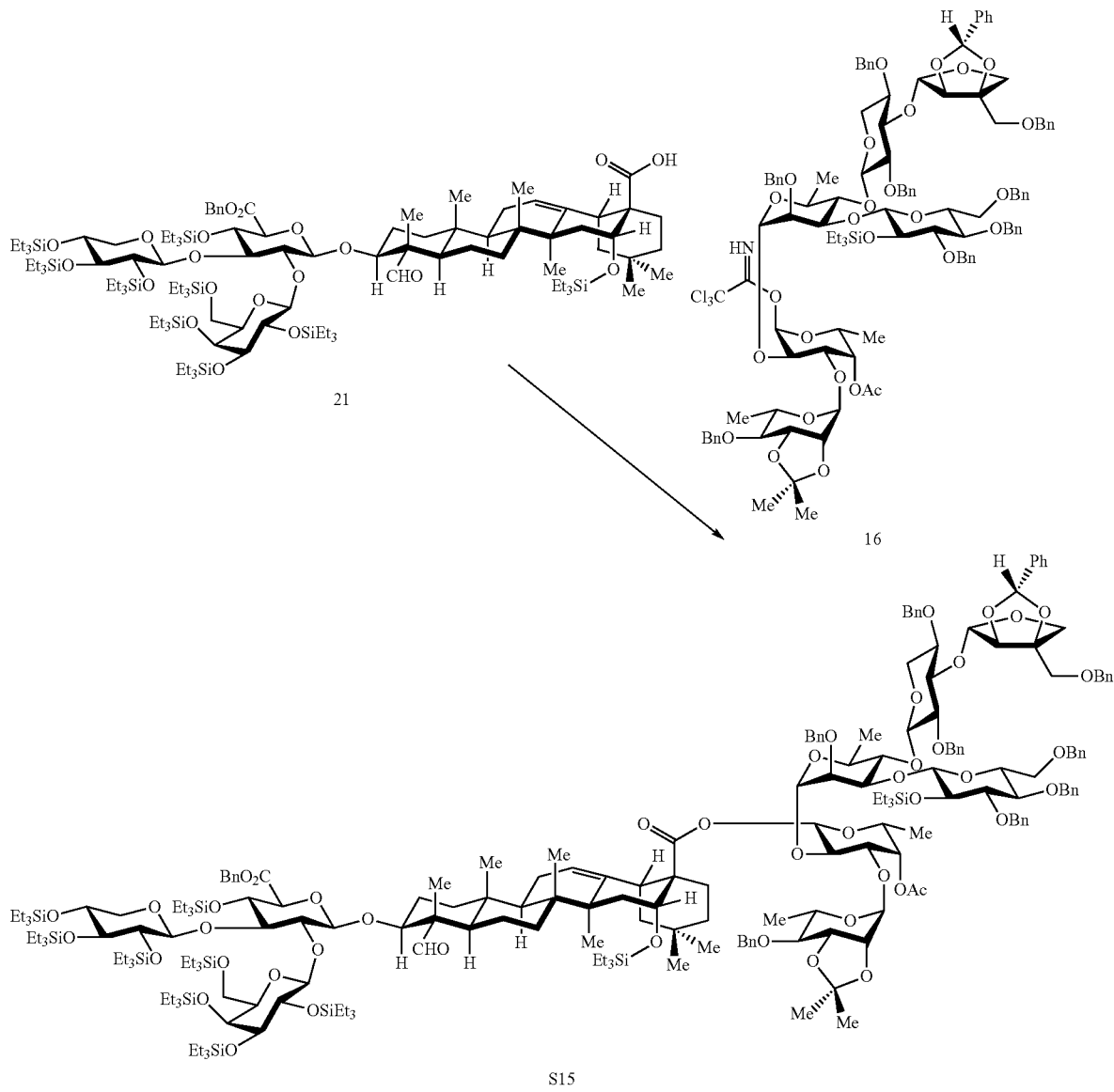

Fully-Protected Semisynthetic QS-7-Api (S15).

A solution of boron trifluoride diethyl etherate (0.50 μL, 0.0040 mmol, 1.0 equiv) in dichloromethane (20 μL) was added to a solution of the imidate 16 (8.3 mg, 0.0041 mmol, 0.98 equiv) and 21 (12.7 mg, 0.00612 mmol, 1.50 equiv) in dichloromethane (0.50 mL) with 4 Å molecular sieves (86 mg) at −78° C. The reaction temperature was allowed to warm to 23° C. slowly, and triethylamine (2.8 μL) was added after 14.5 h. The reaction was concentrated and purified by silica gel chromatography (silica pretreated with 0.1% triethylamine in benzene, then benzene/ethyl acetate 99:1 to 24:1) to afford S15 (8.5 mg, 0.0033 mmol, 80% yield). $R_f$=0.52 (benzene/ethyl acetate 19:1); characteristic resonances from $^1$H NMR: (500 MHz, CDCl$_3$) δ 9.69 (s, 1H, —CHO), 7.49-7.04 (m, 50H, aromatic), 5.94 (s, 1H), 5.83 (s, 1H), 5.31 (d, J=7.2 Hz, 1H), 5.29-5.23 (m, 2H), 5.12-5.06 (m, 2H), 5.01 (s, 1H), 4.93 (d, J=11.9 Hz, 1H), 4.91-4.44 (m, 19H), 4.42 (d, J=7.3 Hz, 1H), 4.37 (d, J=4.7 Hz, 1H), 4.35 (d, J=3.9 Hz, 1H), 4.23 (dd, J=2.5, 8.7 Hz, 1H), 4.19 (d, J=7.3 Hz, 1H), 4.10-4.07 (m, 2H), 3.98-3.43 (m, 2H), 3.43-3.29 (m, 7H), 3.29-3.08 (m, 6H), 2.97 (dd, J=13.8, 3.5 Hz, 1H), 2.83 (bs, 1H), 2.73 (bs, 1H), 2.10 (s, 3H, —C(O)CH$_3$), 1.54 (s, 3H, Me), 1.40 (s, 3H, Me), 1.30 (s, 3H, Me), 1.12 (s, 31H, Me); see proton NMR below; $^{13}$C NMR (125.77 MHz, CDCl$_3$) δ 212.57, 176.57, 170.56, 168.54, 142.90, 139.36, 139.17, 138.90, 138.61, 138.14, 138.02, 136.90, 135.46, 128.82, 128.61, 128.54, 128.43, 128.36, 128.32, 128.27, 128.21, 128.07, 127.91, 127.80, 127.69, 127.62, 127.56, 127.43, 127.39, 127.24, 127.04, 109.06, 107.31, 106.46, 103.64, 101.91, 101.75, 101.56, 101.00, 99.70, 99.54, 93.81, 91.69, 87.28, 86.19, 84.99, 82.50, 80.58, 79.16, 79.02, 78.90, 78.51, 76.61, 76.35, 76.24, 76.00, 75.72, 75.44, 75.28, 74.82, 74.67, 74.41, 73.69, 73.34, 73.07, 72.96, 72.86, 72.79, 72.66, 72.52, 71.57, 71.23, 70.26, 68.92, 68.48, 66.96, 65.61, 63.99, 60.45, 54.05, 49.58, 48.92, 46.67, 46.26, 41.56, 40.14, 38.19, 36.20, 34.50, 33.07, 32.68, 30.79, 29.85, 28.23, 26.68, 26.50, 25.51, 24.74, 23.61, 22.85, 20.95, 20.44, 18.53, 17.83, 17.68, 16.67, 16.06, 14.27, 12.36, 7.76, 7.60, 7.39, 7.30, 7.27, 7.11, 6.99, 6.92, 6.07, 5.80, 5.60, 5.52, 5.43, 5.40, 5.17, 4.58; FTIR (neat film) 2953, 2935, 2914, 2877, 1747, 1456, 1377, 1239, 1239, 1172, 1100, 1008, 824, 735, 697 cm$^{-1}$.

The reaction flask was cooled to 0° C. and charged with a pre-cooled (0° C.) solution of trifluoroacetic acid (1.0 mL, TFA/water 1:1). After stirring for 95 min, the reaction mixture was concentrated in vacuo at 0° C. The resulting white solid residue was purified by RP-HPLC on an XBridge Prep BEH300 C18 column (5 µm, 10×250 mm) using a linear gradient of 32→37% acetonitrile (0.05% TFA)

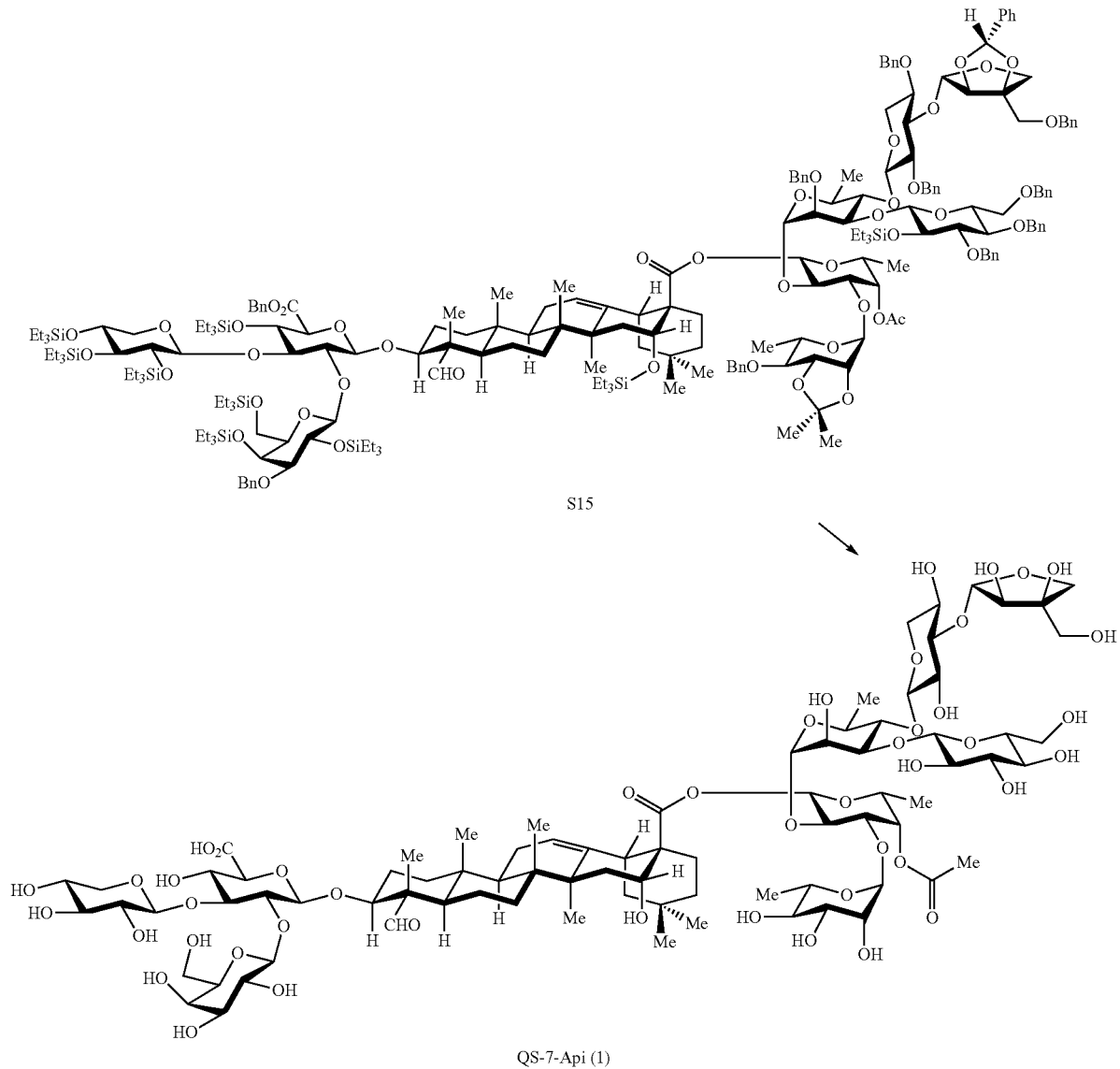

Semisynthetic QS-7-Api (1).

A solution of fully-protected semisynthetic QS-7-Api S15 (1.1 mg, 0.00028 mmol, 1.0 equiv) in tetrahydrofuran (1.0 mL) and ethanol (1.0 mL) in a 10-mL round-bottom flask was charged with 10% (dry basis) palladium on carbon, wet, Degussa type E101 NE/W (2.2 mg, 0.00094 mmol, 3.7 equiv). The reaction suspension was stirred under hydrogen pressure (50 psi) for 15 h and then was filtered through a 0.45 Lm polyvinylidene fluoride filter disk. The filter was washed with methanol (4 mL), and the filtrate and rinsing were concentrated in a 25-mL round bottom flask to give a clear residue.

in water (0.05% TFA) over 30 min at a flow rate of 5 mL/min. The fraction containing the major peak ($t_R$=14.85 min) was collected and lyophilized to dryness. A total of three deprotection runs were performed on S15 (3.3 mg, 0.00084 mmol) to afford semisynthetic QS-7-Api (1) (1.2 mg, 0.00064 mmol, 77% yield) as a white solid. $^1$H NMR (500 MHz, 7:3 D$_2$O:CD$_3$CN) δ 9.36 (s, 1H, —CHO), 5.39 (d, J=8.0 Hz, 1H), 5.34 (m, 1H, R$_2$C=CHR), 5.22 (d, J=3.1 Hz, 1H), 5.12 (d, J=2.9 Hz, 1H), 5.03 (s, 1H), 4.86 (s, 1H), 4.67 (d, J=7.7 Hz, 1H), 4.63 (d, J=7.8 Hz, 1H), 4.55 (d, J=7.7 Hz, 1H), 4.50 (d, J=7.7 Hz, 1H), 4.33 (m, 1H), 4.05 (d, J=10.1 Hz, 1H), 4.02 (m, 1H), 3.99-3.94 (m, 2H), 3.92-3.57 (m, 22H), 3.55-3.45 (m, 7H), 4.33 (m, 1H), 3.42-3.15 (m, 12H), 2.86 (dd, J=14.5, 3.6 Hz, 1H), 2.14 (s, 3H, —C(O)CH₃), 1.89-1.30 (m, 14H), 1.28 (s, 3H, Me), 1.22 (d, J=6.2 Hz, 3H, Me), 1.15 (d, J=6.1 Hz, 3H, Me), 1.08 (s, 3H, Me), 1.05 (m, 1H), 1.02 (m, 1H), 0.99 (d, J=6.3 Hz, 3H, Me), 0.93 (s, 3H, Me), 0.89 (s, 3H, Me), 0.84 (s, 3H, Me), 0.71 (s, 3H, Me).

Example 2

This Example demonstrates that certain methods described above for Example 1 are applicable to substrates that differ in chemical structure.

Final Assembly of Semisynthetic QS-21-Api zene/ethyl acetate 99:1 to 47:3) to afford 140 (13.8 mg, 0.0033 mmol, 420% yield) as a clear film. R$_f$=0.42 (benzene/ethyl acetate 19:1); characteristic resonances from $^1$H NMR (500 MHz, CDCl₃) δ 9.68 (s, 1H), 5.96 (s, 1H), 5.71 (s, 1H), 5.28 (d, J=12.4, 1H), 5.09 (d, J=12.4, 1H), 4.19 (d, J=7.2, 2H), 2.92 (dd, J=13.6, 3.7, 1H), 2.23 (t, J=13.5, 1H), 1.42 (s, 3H), 1.34 (s, 3H), 1.29 (s, 3H), 1.26 (s, 3H), 1.22 (s, 3H); $^{13}$C NMR (126 MHz, CDCl₃) δ 171.03, 170.73, 168.51, 138.25, 138.12, 137.41, 136.92, 135.43, 129.75, 128.65, 128.62, 128.57, 128.54, 128.43, 128.40, 128.29, 128.26, 127.97, 127.93, 127.85, 127.81, 127.62, 127.32, 107.37, 106.52, 91.72, 87.23, 85.97, 84.24, 81.34, 79.22, 79.03, 78.38, 76.62, 76.20, 75.97, 75.28, 74.13, 73.72, 73.41, 73.10,

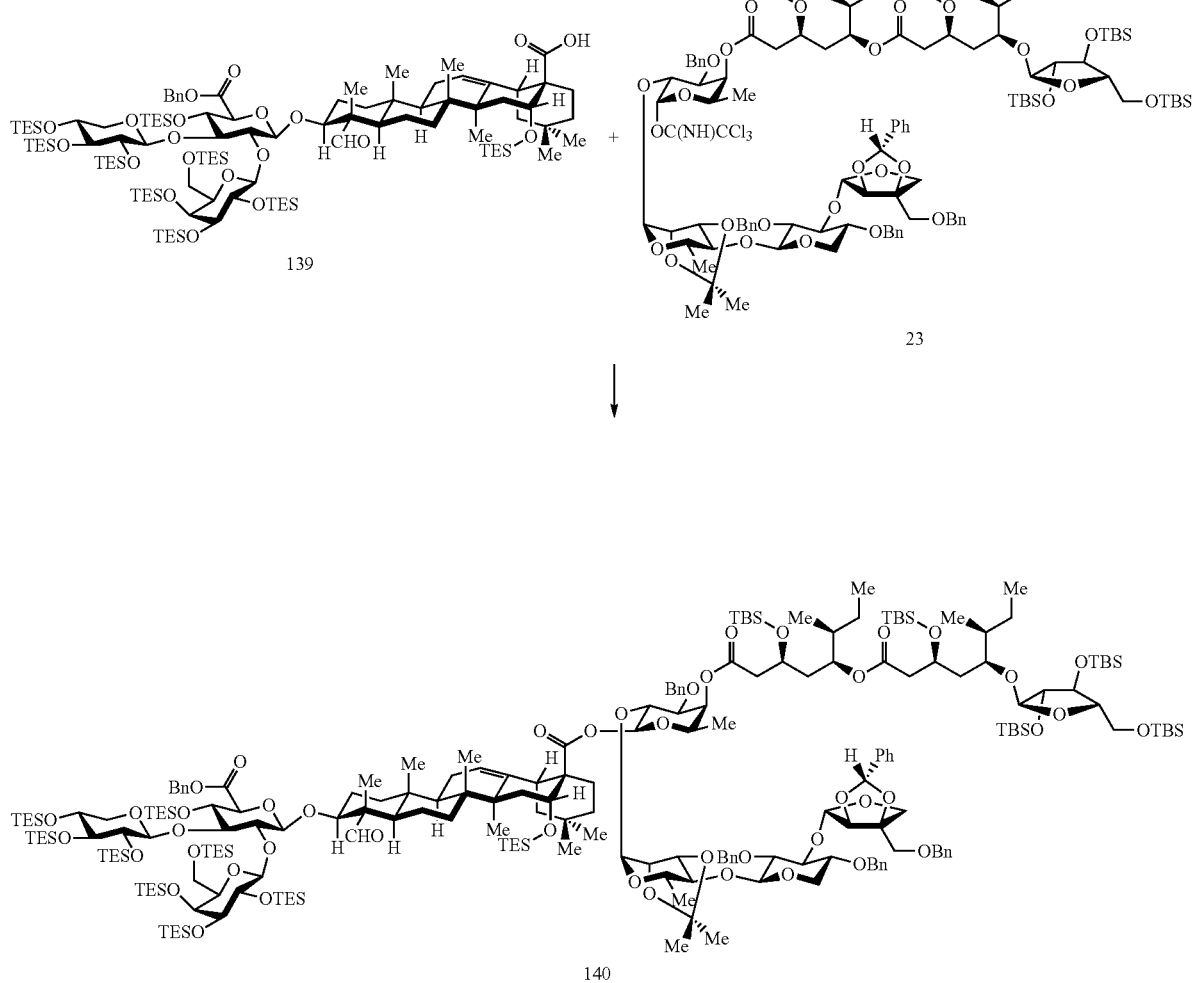

Fully protected QS-21-Api (140).

A solution of boron trifluoride diethyl etherate (0.49 µL, 0.0039 mmol, 0.50 equiv) in dichloromethane (10 µL) was added to a solution of imidate 23 (17.6 mg, 0.00780 mmol, 1.00 equiv) and carboxylic acid 139 (24.3 mg, 0.0117 mmol, 1.50 equiv) in dichloromethane (0.260 mL) with 4 Å molecular sieves (50 mg) at −78° C. The reaction temperature was allowed to warm to 23° C. slowly, and triethylamine (20 µL) was added after 16 h. The reaction was concentrated and purified by silica gel chromatography (silica pretreated with 0.2% triethylamine in benzene, then ben- 72.75, 71.92, 71.59, 71.20, 67.00, 63.87, 63.27, 60.43, 54.11, 49.01, 43.58, 41.68, 40.86, 40.04, 39.56, 36.98, 36.30, 32.96, 30.66, 29.88, 27.56, 26.55, 26.12, 26.06, 25.94, 25.90, 25.09, 24.59, 24.23, 18.53, 18.10, 18.04, 18.02, 17.87, 17.74, 17.28, 16.45, 14.66, 14.59, 12.35, 12.12, 7.70, 7.60, 7.53, 7.39, 7.32, 7.30, 7.27, 7.12, 7.04, 6.99, 6.93, 6.07, 5.80, 5.61, 5.53, 5.49, 5.42, 5.40, 5.18, 5.05, 4.58, −4.09, −4.29, −4.36, −4.38, −4.45, −4.57, −4.77, −5.07, −5.17; FTIR (neat film) 2954, 2935, 2877, 1735, 1458, 1380, 1250, 1163, 1096, 1005, 836, 777, 737, 698 cm$^{-1}$; LRMS (ESI) m/z: Calcd for $C_{221}H_{382}O_{46}Si_{14}Na_2$ (M+2Na$^{++}$) 2105.2. found 2106.2.

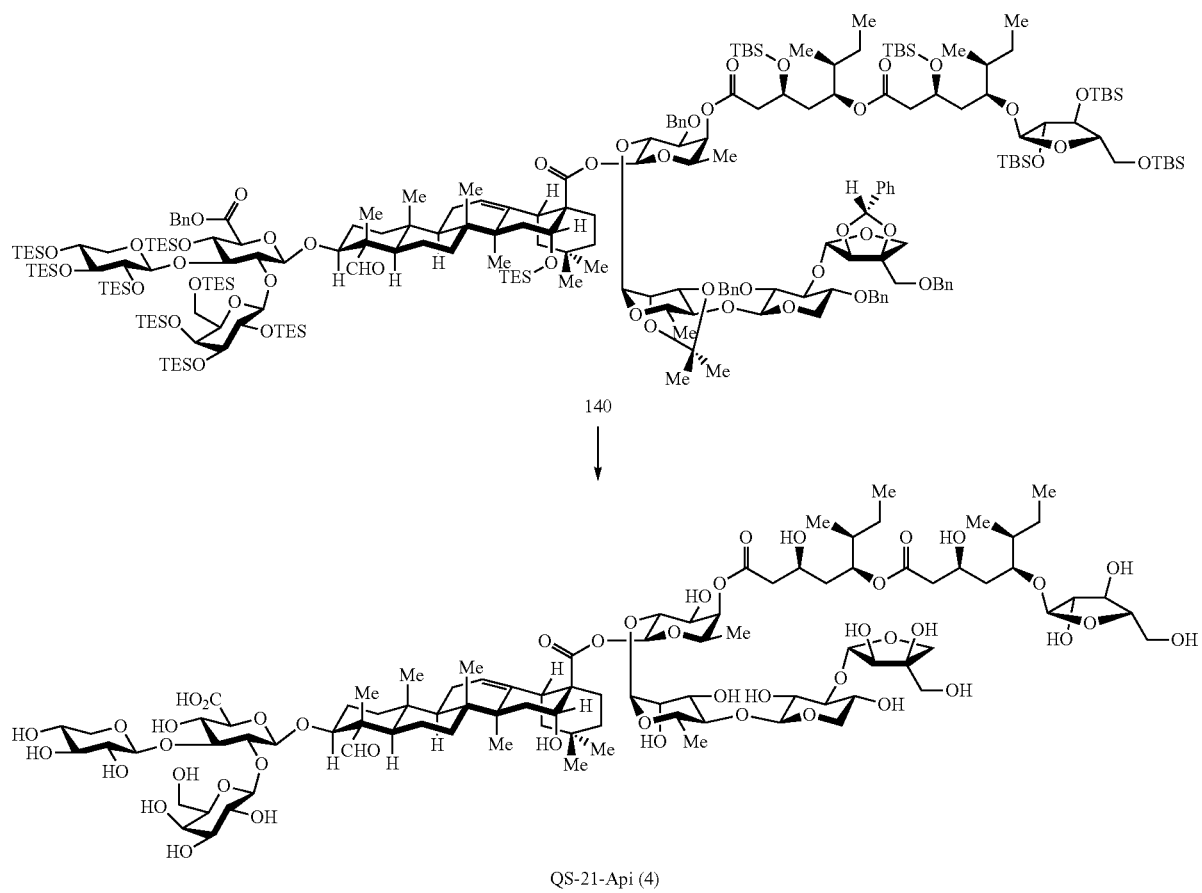

140

↓

QS-21-Api (4)

QS-21-Api (4).

Three solutions of fully protected second-generation QS-2-Api 140 (3×2.0 mg, 0.0014 mmol, 1.0 equiv) in tetrahydrofuran (3×1.0 mL) and ethanol (3×1.0 mL) in three 10-mL round-bottom flasks were charged with 10% (dry basis) palladium on carbon, wet, Degussa type E101 NE/W (3×3.8 mg, 0.0054 mmol, 3.7 equiv). The reaction suspensions were stirred under hydrogen pressure (50 psi) for 23 h and then filtered through three 0.45 μm polyvinylidene fluoride filter disks. The filters were washed with methanol, and the filtrate and rinsing were concentrated in three 25-mL round bottom flasks to give the partially protected product as a clear residue.

The reaction flasks were cooled to 0° C. and charged with a pre-cooled (0° C.) solution of trifluoroacetic acid (3×1.0 mL, TFA/water 3:1). After stirring for 75 min, the reaction mixtures were concentrated in vacuo at 0° C. The resulting white solid residue was purified by RP-HPLC on an XBridge Prep BEH300 C18 column (5 μm, 10×250 mm) using a linear gradient of 35→45% acetonitrile (0.05% TFA) in water (0.05% TFA) over 30 min at a flow rate of 5 mL/min. The fractions containing the major peak ($t_R$=27.6 min) were collected and lyophilized to afford synthetic QS-21-Api (4) (1.4 mg, 0.00070 mmol, 49% yield) as a white solid. LRMS (ESI) m/z: Calcd for $C_{92}H_{147}O_{46}$ (M-H$^+$) 1987.92. found 1988.33. The $^1$H NMR spectrum of QS-21-Api (4) was found to be in agreement with the previously reported characterization.

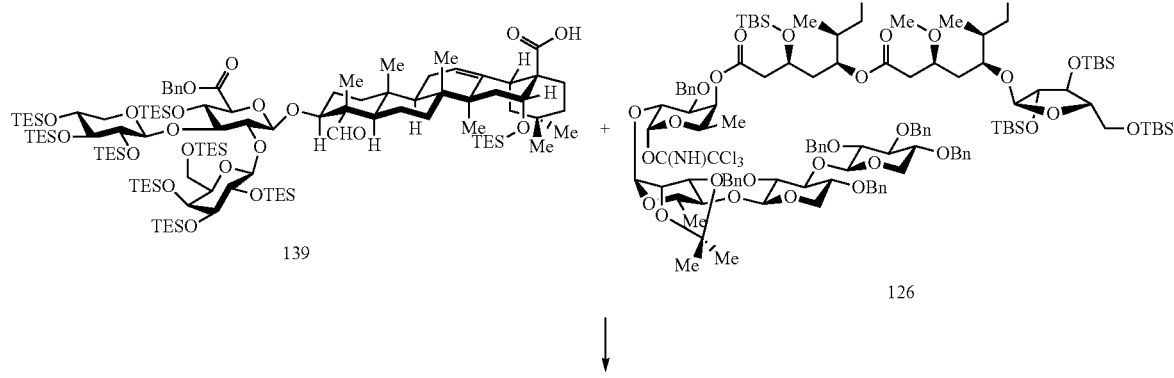

139 + 126

↓

-continued

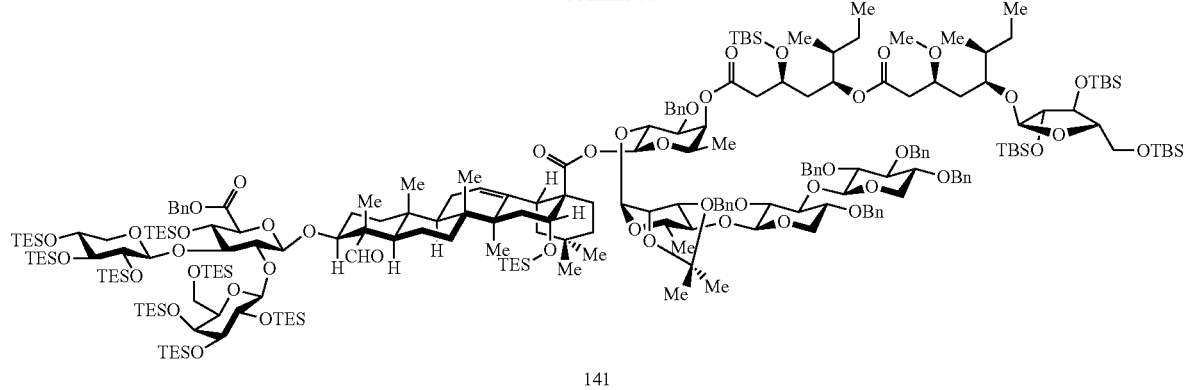

141

Fully Protected QS-21-Xyl (141).

A solution of boron trifluoride diethyl etherate (0.33 µL, 0.0026 mmol, 0.50 equiv) in dichloromethane (10 ILL) was added to a solution of imidate 126 (12.4 mg, 0.00529 mmol, 1.00 equiv) and carboxylic acid 139 (15.8 mg, 0.00761 mmol, 1.44 equiv) in dichloromethane (0.176 mL) with 4 Å molecular sieves (62 mg) at −78° C. The reaction temperature was allowed to warm to 23° C. slowly, and triethylamine (20 µL) was added after 21 h. The reaction was concentrated and purified by silica gel chromatography (silica pretreated with 0.5% triethylamine in benzene, then benzene/ethyl acetate 99:1 to 97:3:3) to afford 141 in about 77% purity (14.2 mg, 0.0026 mmol, 49% yield) as a clear film. $R_f$=0.49 (benzene/ethyl acetate 19:1); characteristic resonances from $^1$H NMR (500 MHz, CDCl$_3$) δ 9.68 (s, 1H), 5.28 (d, J=12.4, 1H), 5.20 (d, J=1.6, 1H), 5.09 (d, J=12.3, 1H), 4.97 (m, 1H), 4.94 (d, J=11.5, 1H), 4.92 (d, J=7.8, 1H), 4.47 (d, J=10.1, 1H), 4.42 (d, J=7.2, 1H), 4.37 (d, J=10.7, 1H), 4.18 (d, J=7.1, 2H), 3.13 (t, J=10.8, 1H), 3.04 (t, J=10.9, 1H), 2.92 (dd, J=14.6, 3.9, 1H), 2.22 (t, J=13.8, 1H), 1.43 (s, 3H), 1.34 (s, 3H), 1.28 (s, 3H), 1.26 (s, 3H), 1.22 (s, 3H); $^{13}$C NMR (126 MHz, CDCl$_3$) δ 175.39, 171.03, 170.72, 168.51, 143.57, 138.90, 138.87, 138.67, 138.47, 138.38, 137.42, 135.43, 128.62, 128.60, 128.51, 128.48, 128.44, 128.42, 128.34, 128.29, 128.15, 128.12, 128.11, 127.97, 127.78, 127.73, 127.60, 109.74, 107.38, 103.71, 103.28, 102.41, 101.56, 100.99, 93.65, 86.02, 84.20, 84.00, 82.82, 82.79, 79.87, 79.20, 79.03, 78.92, 78.52, 78.35, 76.66, 76.20, 76.00, 75.79, 75.73, 75.26, 75.15, 74.58, 74.45, 73.48, 73.26, 72.81, 72.66, 72.01, 71.58, 71.25, 67.14, 66.96, 66.32, 65.54, 64.03, 63.81, 63.28, 60.40, 54.10, 49.60, 48.99, 46.35, 43.65, 42.79, 41.69, 40.91, 40.02, 39.52, 38.67, 37.00, 36.29, 32.90, 32.71, 30.65, 29.89, 27.58, 26.61, 26.12, 26.06, 25.94, 25.90, 25.72, 25.03, 24.52, 24.23, 18.55, 18.10, 18.07, 18.04, 18.02, 17.62, 17.25, 16.40, 16.05, 14.65, 14.60, 12.35, 12.23, 12.08, 7.70, 7.60, 7.39, 7.32, 7.29, 7.27, 7.12, 6.99, 6.93, 6.07, 5.81, 5.61, 5.53, 5.48, 5.42, 5.18, 5.03, 4.58, −4.08, −4.11, −4.30, −4.36, −4.38, −4.44, −4.57, −4.74, −5.07, −5.17; FTIR (neat film) 2955, 2877, 1735, 1458, 1380, 1250, 1165, 1091, 1006, 837, 777, 735, 698 cm$^{-1}$; LRMS (ESI) m/z: Calcd for $C_{228}H_{390}O_{46}Si_{14}Na_2$ (M+2Na$^{++}$) 2151.2. found 2151.6.

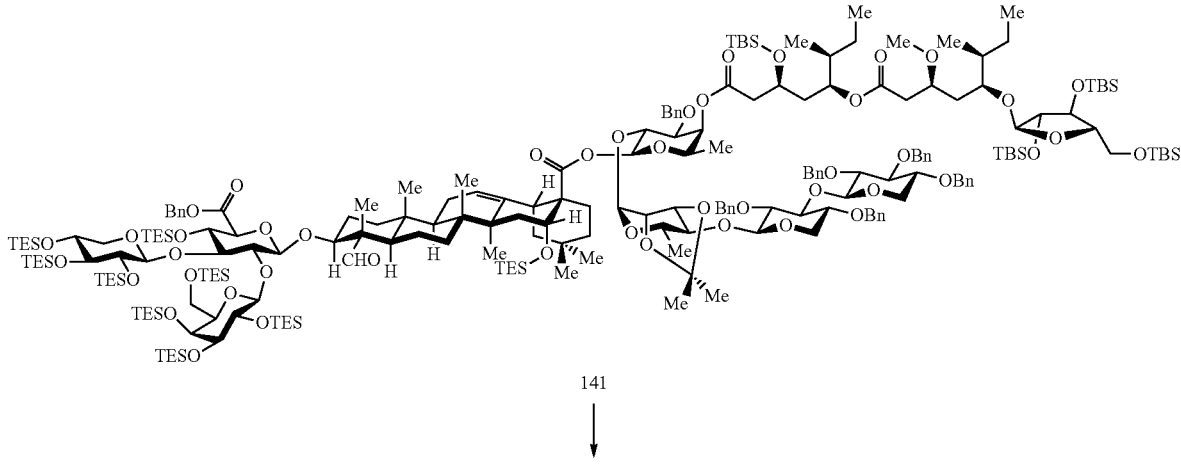

141

↓

-continued

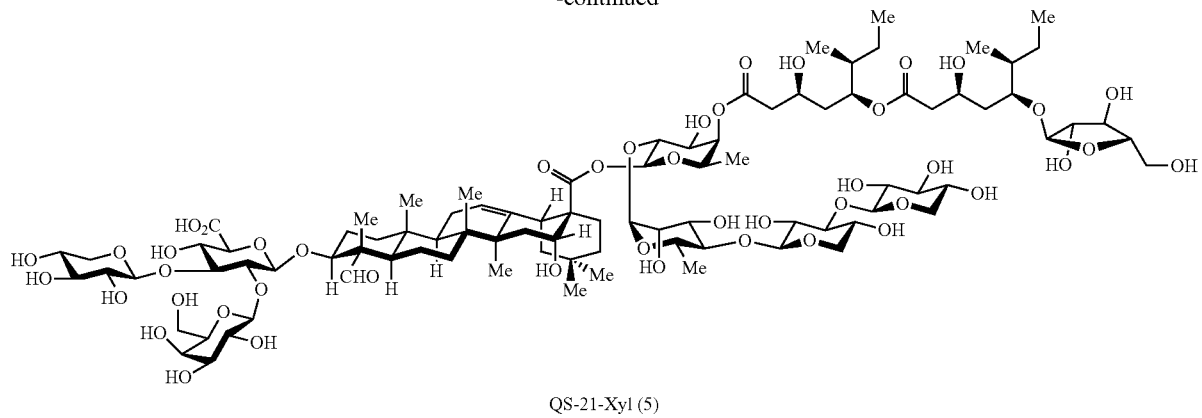

QS-21-Xyl (5)

QS-21-Xyl (5).

Three solutions of fully protected second-generation QS-2-Xyl 141 (3×2.0 mg, 0.0014 mmol, 1.0 equiv) in tetrahydrofuran (3×1.0 mL) and ethanol (3×1.0 mL) in three 10-mL round-bottom flasks were charged with 10% (dry basis) palladium on carbon, wet, Degussa type E101 NE/W (3×3.8 mg, 0.0054 mmol, 3.7 equiv). The reaction suspensions were stirred under hydrogen pressure (50 psi) for 23 h and then filtered through three 0.45 μm polyvinylidene fluoride filter disks. The filters were washed with methanol, and the filtrate and rinsing were concentrated in three 25-mL round bottom flasks to give the partially protected product as a clear residue.

The reaction flasks were cooled to 0° C. and charged with a pre-cooled (0° C.) solution of trifluoroacetic acid (3×1.0 mL, TFA/water 3:1). After stirring for 75 min, the reaction mixtures were concentrated in vacuo at 0° C. The resulting white solid residue was purified by RP-HPLC on an XBridge Prep BEH300 C18 column (5 μm, 10×250 mm) using a linear gradient of 35→45% acetonitrile (0.05% TFA) in water (0.05% TFA) over 30 min at a flow rate of 5 mL/min. The fractions containing the major peak ($t_R$=27.7 min) were collected and lyophilized to afford synthetic QS-21-Xyl (5) (1.4 mg, 0.00070 mmol, 50% yield) as a white solid. LRMS (ESI) m/z: Calcd for $C_{92}H_{147}O_{46}$ (M-H$^+$) 1987.92. found 1987.94. The $^1$H NMR spectrum of QS-21-Xyl (5) was found to be in agreement with the previously reported characterization.

Example 3

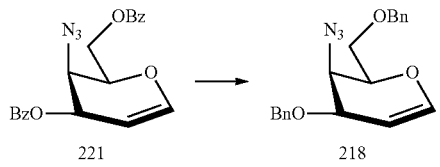

3,6-Di-O-benzyl-4-azido-4-deoxy-D-galactal (218)

Sodium hydroxide (0.115 g, 2.89 mmol, 0.357 equiv) was added to a solution of glycal 221 (2.930 g, 8.063 mmol, 1.000 equiv) in methanol (40 mL) at 0° C., and the reaction was stirred at 23° C. After 14 h, the reaction was concentrated to a sticky tan solid, and trace solvent was removed by co-evaporation with toluene (7 mL).

1 Dimethylformamide (40 mL) was added to the residue, and the resulting brown suspension was cooled to 0° C. Sodium hydride (60% dispersion in oil, 0.977 g, 24.4 mmol, 3.03 equiv) was added to the reaction, followed by benzyl bromide (4.80 mL, 40.3 mmol, 5.01 equiv). After 3 h, the orange suspension was stirred at 23° C. for 16 h. The reaction was quenched with methanol (20 mL), diluted with dichloromethane (100 mL), and washed with water (100 mL). The aqueous layer was extracted with dichloromethane (80 mL), and the combined organic layers were washed with water (100 mL), dried with magnesium sulfate, and purified by silica gel chromatography (hexane/ethyl acetate 9:1 to 4:1) to afford 218 (2.199 g, 6.258 mmol, 78% yield) as a yellow oil. $R_f$=0.61 (hexane/ethyl acetate 3:1); $^1$H NMR (400 MHz, CDCl$_3$) δ 7.41-7.26 (m, 10H), 6.37 (dd, J=6.3, 1.9, 1H), 4.83 (dt, J=6.4, 1.8, 1H), 4.70 (d, J=12.0, 1H), 4.63 (d, J=11.9, 1H), 4.61 (d, J=11.8, 1H), 4.55 (d, J=11.8, 1H), 4.41 (m, 1H), 4.08 (t, J=6.6, 1H), 3.97 (m, 1H), 3.70 (dd, J=6.6, 1.7, 2H); $^{13}$C NMR (126 MHz, CDCl$_3$) δ 144.69, 137.76, 137.69, 128.68, 128.67, 128.14, 128.09, 128.04, 127.76, 101.00, 74.66, 73.84, 71.57, 70.92, 68.84, 55.39; FTIR (neat film) 3031.5, 2868.5, 2109.9, 1650.9, 1496.5, 1454.2, 1333.0, 1277.3, 1230.7, 1097.1, 1052.8, 1028.2, 735.9, 697.6, 668.1 cm$^{-1}$; HRMS (ESI) m/z: Calcd for $C_{20}H_{21}N_3O_3Na$ (M+Na$^+$) 374.1481. found 374.1479.

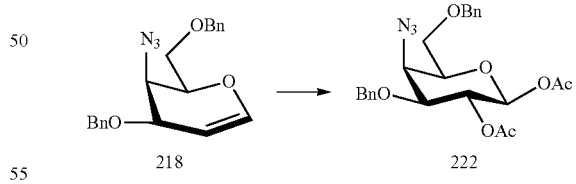

O-Acetyl 2-O-acetyl-4-azido-4-deoxy-3,6-di-O-benzyl-β-D-galactopyranoside (222)

Boron trifluoride diethyl etherate (74.0 μL, 0.636 mmol, 0.219 equiv) was added to a solution of glycal 218 (1.020 g, 2.904 mmol, 1.000 equiv) and iodobenzene diacetate (1.119 g, 3.474 mmol, 1.196 equiv) in dichloromethane (36 mL) in a cold bath at −50° C. After 25 min, the yellow solution was transferred to a cold bath at −25° C. and stirred for an additional 30 min. Triethyl amine (2.0 mL) was added, and the resulting suspension was diluted with dichloromethane (20 mL) and washed with saturated aqueous sodium bicarbonate solution (30 mL). The aqueous layer was extracted with dichloromethane (30 mL), and the combined organic layers were dried with magnesium sulfate and purified by silica gel chromatography (hexane/ethyl acetate 4:1 to 3:1) to afford 222 (1.163 g, 2.477 mmol, 85% yield) as a yellow solid. $R_f$=0.25 (hexane/ethyl acetate 3:1); $^1$H NMR (400 MHz, CDCl$_3$) δ 7.41-7.28 (m, 10H), 5.51 (d, J=8.3, 1H), 5.30 (dd, 0.1=9.8, 8.4, 1H), 4.74 (d, J=12.2, 1H), 4.56 (d, J=12.3, 1H), 4.54 (s, 2H), 4.08 (dd, J=3.6, 1.1, 1H), 3.74 (td, J=6.7, 1.3, 1H), 3.69 (dd, J=9.8, 3.6, 1H), 3.63 (d, J=6.8, 2H), 2.06 (s, 3H), 2.00 (s, 3H); $^{13}$C NMR (126 MHz, CDCl$_3$) δ 169.50, 169.38, 137.51, 137.25, 128.73, 128.69, 128.32, 128.23, 128.20, 127.92, 92.47, 78.73, 73.86, 72.60, 72.23, 69.78, 67.82, 59.10, 20.96, 20.88; FTIR (neat film) 2920.8, 2107.7, 1755.9, 1454.8, 1368.4, 1232.5, 1214.6, 1059.1, 739.3, 698.4 cm$^{-1}$; HRMS (ESI) m/z: Calcd for $C_{24}H_{27}N_3O_7Na$ (M+Na$^+$) 492.1747. found 492.1755.

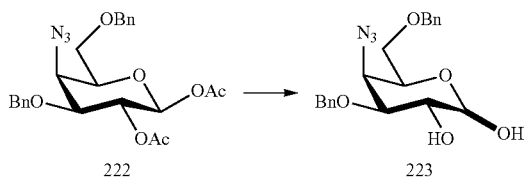

4-azido-4-deoxy-3,6-di-O-benzyl-D-galactopyranose (223)

Potassium carbonate (0.600 g, 4.34 mmol, 3.99 equiv) was added to a solution of diacetate 222 (0.511 g, 1.09 mmol, 1.00 equiv) in methanol (50 mL) and water (5 mL). After 1.5 h, the yellow solution was decanted from the undissolved potassium carbonate and concentrated to about 4 mL and then diluted with dichloromethane (50 mL) and washed with saturated aqueous sodium bicarbonate solution (10 mL). The aqueous layer was extracted with dichloromethane (2×10 mL) and the combined organic layers were dried with magnesium sulfate and purified by silica gel chromatography (ethyl acetate) to afford 223 (0.353 g, 0.917 mmol, 84% yield) as a yellow oil (1:1 α:β). $R_f$=0.17, 014 (hexane/ethyl acetate 1:1); $^1$H NMR (400 MHz, CDCl$_3$) δ 7.43-7.27 (m, 20H), 5.28 (d, J=3.8, 1H), 4.78 (d, J=11.5, 1H), 4.78 (d, J=11.5, 1H), 4.67 (d, J=11.5, 1H), 4.68 (d, J=11.5, 1H), 4.58 (d, J=11.9, 1H), 4.56 (d, J=11.9, 1H), 4.52 (d, J=11.9, 1H), 4.51 (d, J=11.9, 1H), 4.51 (d, J=7.7, 1H), 4.21 (td, J=6.5, 1.1, 1H), 4.02 (dd, J=3.4, 1.3, 1H), 3.99 (dd, J=9.9, 3.8, 2H), 3.85 (dd, J=9.7, 3.5, 1H), 3.73 (dd, J=9.5, 7.7, 1H), 3.69-3.51 (m, 6H); $^{13}$C NMR (126 MHz, CDCl$_3$) 137.62, 137.50, 137.48, 128.67, 128.59, 128.16, 128.13, 128.10, 128.09, 128.07, 128.02, 128.00, 97.08, 92.50, 80.85, 78.06, 73.64, 73.61, 72.63, 72.51, 72.14, 71.82, 69.25, 68.76, 68.68, 67.38, 60.27, 59.49; FTIR (neat film) 3401.3, 3032.4, 2921.6, 2105.6, 1454.4, 1367.2, 1279.3, 1095.8, 1028.3, 738.1, 698.0 cm$^{-1}$; HRMS (ESI) m/z: Calcd for $C_{20}H_{23}N_3O_5Na$ (M+Na$^+$) 408.1535. found 408.1535.

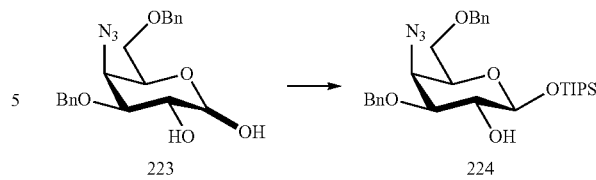

O-triisopropylsilyl 4-azido-4-deoxy-3,6-di-O-benzyl-β-D-galactopyranoside (222)

Triisopropylsilyl chloride (0.63 mL, 3.0 mmol, 1.2 equiv) was added to a solution of hemiacetal 223 (0.959 g, 2.49 mmol, 1.00 equiv), imidazole (0.409 g, 6.01 mmol, 2.41 equiv), and 4-dimethylaminopyridine (29 mg, 0.24 mmol, 0.096 equiv) in dimethylformamide (2.5 mL). After 19 h, the yellow solution was concentrated and purified by silica gel chromatography (hexane/ethyl acetate 19:1 to 9:1) to afford 224 (0.800 g, 1.48 mmol, 59% yield) as a colorless oil. $R_f$=0.49 (hexane/ethyl acetate 4:1); $^1$H NMR (500 MHz, CDCl$_3$) δ 7.43-7.24 (m, 10H), 4.78 (d, J=11.8, 1H), 4.75 (d, J=11.8, 1H), 4.55 (d, J=11.6, 1H), 4.52 (d, J=12.0, 1H), 4.51 (d, J=7.3, 1H), 3.98 (d, J=3.6, 1H), 3.72 (ddd, J=9.5, 7.3, 2.1, 1H), 3.69-3.58 (m, 3H), 3.56 (dd, J=9.6, 3.7, 1H), 2.26 (d, J=2.2, 1H), 1.19-0.99 (m, 21H); $^{13}$C NMR (126 MHz, CDCl$_3$) δ 137.86, 137.84, 128.70, 128.63, 128.08, 128.05, 127.97, 127.93, 98.09, 80.69, 73.81, 73.78, 72.80, 72.01, 68.83, 59.83, 17.96, 17.90, 12.33; FTIR (neat film) 3463.8, 2943.4, 2866.2, 2108.6, 1455.3, 1366.1, 1280.0, 1185.4, 1099.0, 1028.7, 1014.6, 997.6, 883.5, 805.4, 736.3, 695.5, 669.0 cm$^{-1}$; HRMS (ESI) m/z: Calcd for $C_{29}H_{43}N_3O_5SiNa$ (M+Na$^+$) 564.2870. found 564.2870.

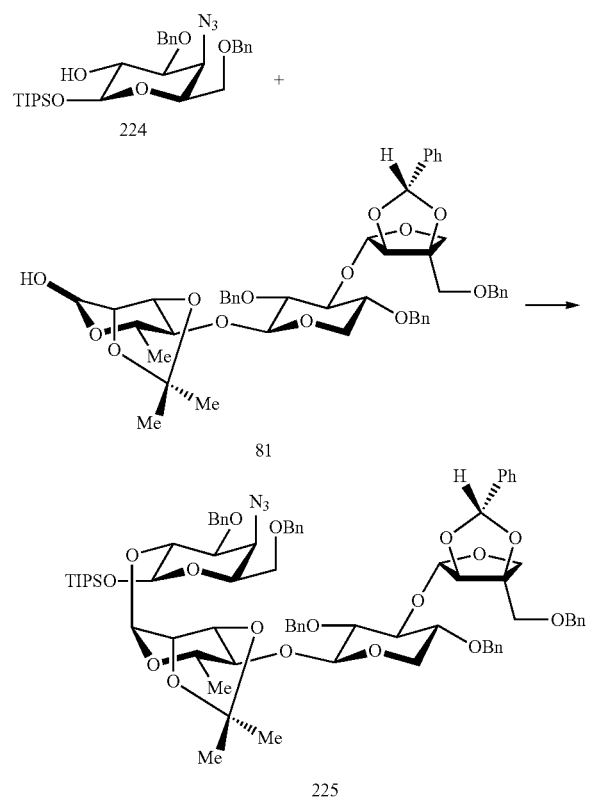

Azido Tetrasaccharide 225.

Trifluoromethanesulfonic anhydride (70 μL, 0.42 mmol, 2.0 equiv) was added to a solution of trisaccharide 81 (0.168 mg, 0.203 mmol, 1.00 equiv), phenyl sulfoxide (173 mg, 0.855 mmol, 4.20 equiv) and 2,4,6-tri-tert-butylpyridine (262 mg, 1.06 mmol, 5.21 equiv) in dichloromethane (20 mL) at −78° C. The reaction stirred in a cold bath at −78° C. for 8 min and then was transferred to a bath between −55 and −50° C. for 70 min. A solution of pyranoside 224 (137 mg, 0.253 mmol, 1.24 equiv) in dichloromethane (3.0 mL) at −78° C. was added via cannula, and the reaction was warmed slowly from −50° C. to 0° C. over 4 h and then stirred at 23° C. for 45 min. Triethylamine (1.0 mL) was added to the reaction mixture, which was concentrated and purified by silica gel chromatography (benzene/ethyl acetate 49:1 to 9:1) to afford tetrasaccharide 225 (185 mg, 0.137 mmol, 67% yield) as a clear film. $R_f$=0.59 (benzene/ethyl acetate 9:1), $^1$H NMR (500 MHz, CDCl$_3$) δ 7.53-7.18 (m, 30H), 5.95 (s, 1H), 5.67 (s, 2H), 4.89 (d, J=7.6, 1H), 4.86 (d, J=11.1, 1H), 4.72 (d, J=11.6, 1H), 4.63-4.47 (m, 8H), 4.44 (d, J=11.8, 1H), 4.41 (s, 1H), 4.13 (dd, J=7.5, 5.7, 1H); 4.04 (d, J=5.6, 1H), 4.01 (dd, J=3.4, 0.8, 1H), 3.97-3.83 (m, 3H), 3.93 (s, 2H), 3.79 (t, J=9.0, 1H), 3.69-3.53 (m, 7H), 3.36 (td, J=9.6, 5.3, 1H), 3.24 (dd, J=9.1, 7.6, 1H), 3.14 (dd, J=11.6, 10.0, 1H), 1.48 (s, 3H), 1.34 (s, 3H), 1.23 (d, J=6.2, 3H), 1.10-0.95 (m, 21H); $^{13}$C NMR (126 MHz, CDCl$_3$) δ 138.22, 138.12, 137.76, 137.01, 136.95, 129.72, 128.89, 128.79, 128.74, 128.63, 128.56, 128.52, 128.41, 128.38, 128.32, 128.32, 128.09, 128.01, 127.92, 127.83, 127.75, 127.59, 127.32, 109.15, 107.30, 106.46, 102.56, 97.27, 97.13, 91.65, 87.15, 82.33, 81.20, 78.43, 78.28, 78.49, 76.74, 76.26, 74.06, 73.99, 73.81, 73.66, 73.33, 72.97, 71.74, 71.67, 71.15, 68.68, 64.51, 63.78, 58.89, 27.95, 26.60, 18.07, 17.99, 17.93, 12.43; FTIR (neat film) 2927.8, 2866.8, 2108.8, 1455.1, 1367.0, 1184.5, 1092.1, 990.3, 735.7, 697.8 cm$^{-1}$; HRMS (ESI) m/z: Calcd for C$_{76}$H$_{95}$N$_3$O$_{17}$SiNa (M+Na$^+$) 1372.6328. found 1382.6343.

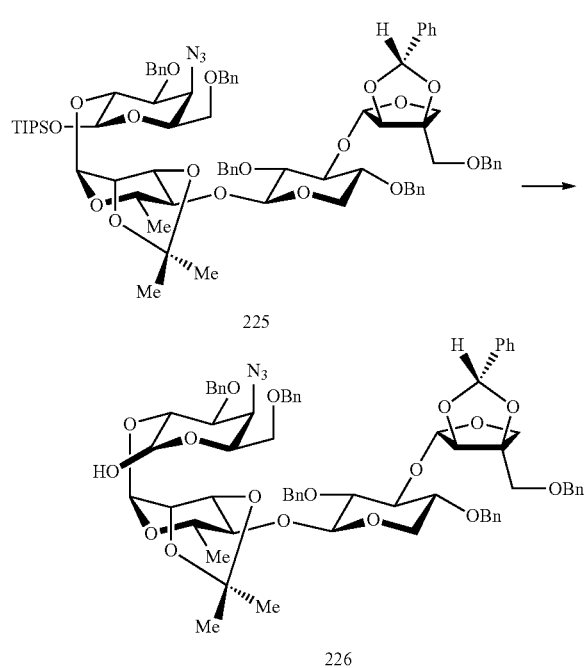

225

226

Azido Tetrasaccharide Hemiacetal 226.

Tetrabutylammonium fluoride solution (1.0 M in tetrahydrofuran, 14 μL, 0.014 mmol, 1.0 equiv) was added to a solution of triisopropylsilyl acetal 225 (18.5 mg, 0.0137 mmol, 1.00 equiv) in tetrahydrofuran (1.8 mL) at 0° C. After 17 min, methanol (1.0 mL) was added, and the solvent was removed in vacuo at 0° C. to give a pale yellow oil that was purified by silica gel chromatography (benzene/ethyl acetate 19:1 to 9:1) to afford 226 (15.2 mg, 0.0127 mmol, 93% yield). $R_f$=0.61 (benzene/ethyl acetate 4:1); characteristic resonances from $^1$H NMR (500 MHz, CDCl$_3$) δ 7.54-7.20 (m, 30H), 5.96 (s, 1H), 5.69 (s, 1H), 4.87 (dd, J=12.2, 7.5, 1H), 4.83 (d, J=11.4, 1H), 4.72 (d, J=11.7, 1H), 3.38 (m, 1H), 3.26 (m, 1H), 3.16 (m, 1H); FTIR (neat film) 3426.0, 2933.1, 2107.1, 1454.6, 1370.7, 1220.2, 1092.6, 1027.0, 992.4, 735.5, 698.3 cm$^{-1}$; HRMS (ESI) m/z: Calcd for C$_{67}$H$_{75}$N$_3$O$_{17}$Na (M+Na$^+$) 1216.4994. found 1216.4939.

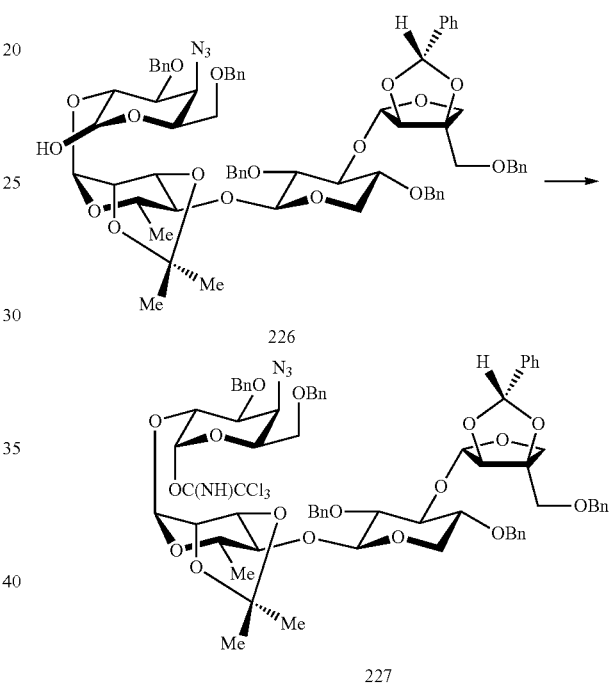

226

227

Azido Tetrasaccharide Trichloroacetimidate 227.

Trichloroacetonitrile (191 μL, 1.91 mmol, 150 equiv) and 1,8-diazabicyclo[5.4.0]undec-7-ene (7.6 μL, 0.051 mmol, 4.0 equiv) were added to a solution of hemiacetal 226 (15.2 mg, 0.0127 mmol, 1.00 equiv) at 0° C. After 14 h at 0° C. and 45 min at 23° C., the solution was concentrated and purified by silica gel chromatography (benzene/ethyl acetate 19:1 to 4:1) to afford 227 (16.2 mg, 0.0121 mmol, 95% yield) as a clear film. $R_f$=0.50 (benzene/ethyl acetate 9:1); characteristic peaks from $^1$H NMR (500 MHz, CDCl$_3$) δ 8.52 (s, 1H), 7.59-7.14 (m, 30H), 5.95 (s, 1H), 5.67 (s, 1H), 5.23 (s, 1H), 4.88 (d, J=7.5, 1H), 4.79 (d, J=10.8, 1H), 4.77 (d, J=11.2, 1H), 4.67 (d, J=11.7, 1H), 4.20 (dd, J=10.0, 3.5, 1H), 3.83 (dd, J=11.5, 5.5, 2H), 3.78 (t, J=9.0, 1H), 3.33 (m, 1H), 3.21 (dd, J=8.9, 7.8, 1H), 3.13 (dd, J=11.7, 9.9, 1H), 1.21 (d, J=6.0, 3H); $^{13}$C NMR (126 MHz, CDCl$_3$) δ 161.14, 138.18, 138.09, 138.01, 137.63, 137.48, 136.89, 129.76, 128.70, 128.64, 128.56, 128.52, 128.46, 128.39, 128.21, 128.14, 128.11, 128.09, 127.95, 127.92, 127.84, 127.60, 127.31, 110.02, 109.41, 107.24, 106.55, 106.48, 101.83, 99.71, 95.88, 95.45, 91.73, 91.67, 91.19, 87.17, 80.69, 78.23, 77.26, 76.67, 76.60, 76.02, 74.68, 73.83, 73.81, 73.69, 73.36, 73.04, 72.68, 71.13, 69.97, 68.26, 64.96, 63.77, 60.35, 27.88, 26.55, 17.84, 17.60, 12.42; FTIR (neat film) 3031.0, 2932.9, 2110.8, 1671.8, 1454.8, 1368.6, 1280.7, 1242.2, 1220.8, 1095.6, 1020.0, 991.5, 912.4, 860.5, 795.0, 735.0, 698.1, 677.1 cm$^{-1}$; HRMS (ESI) m/z: Calcd for $C_{69}H_{75}Cl_3N_4O_{17}Na$ (M+Na$^+$) 1359.4091. found 1359.4127.

(d, J=11.1, 1H), 4.18 (d, J=7.3, 1H), 4.11 (dd, J=6.4, 2.7, 1H), 3.24 (m, 2H), 3.13 (m, 2H), 2.88 (dd, J=14.1, 3.7, 1H), 2.20 (t, J=13.5, 1H), 1.40 (s, 3H), 1.32 (s, 3H), 1.29 (s, 3H), 1.22 (s, 3H), 1.15 (d, J=6.2, 3H), 0.85 (s, 3H); $^{13}$C NMR (126 MHz, CDCl$_3$) δ 212.45, 175.31, 168.49, 143.39, 138.22, 138.13, 138.09, 137.64, 137.11, 136.89, 135.42, 129.73, 128.70, 128.63, 128.60, 128.57, 128.55, 128.53,

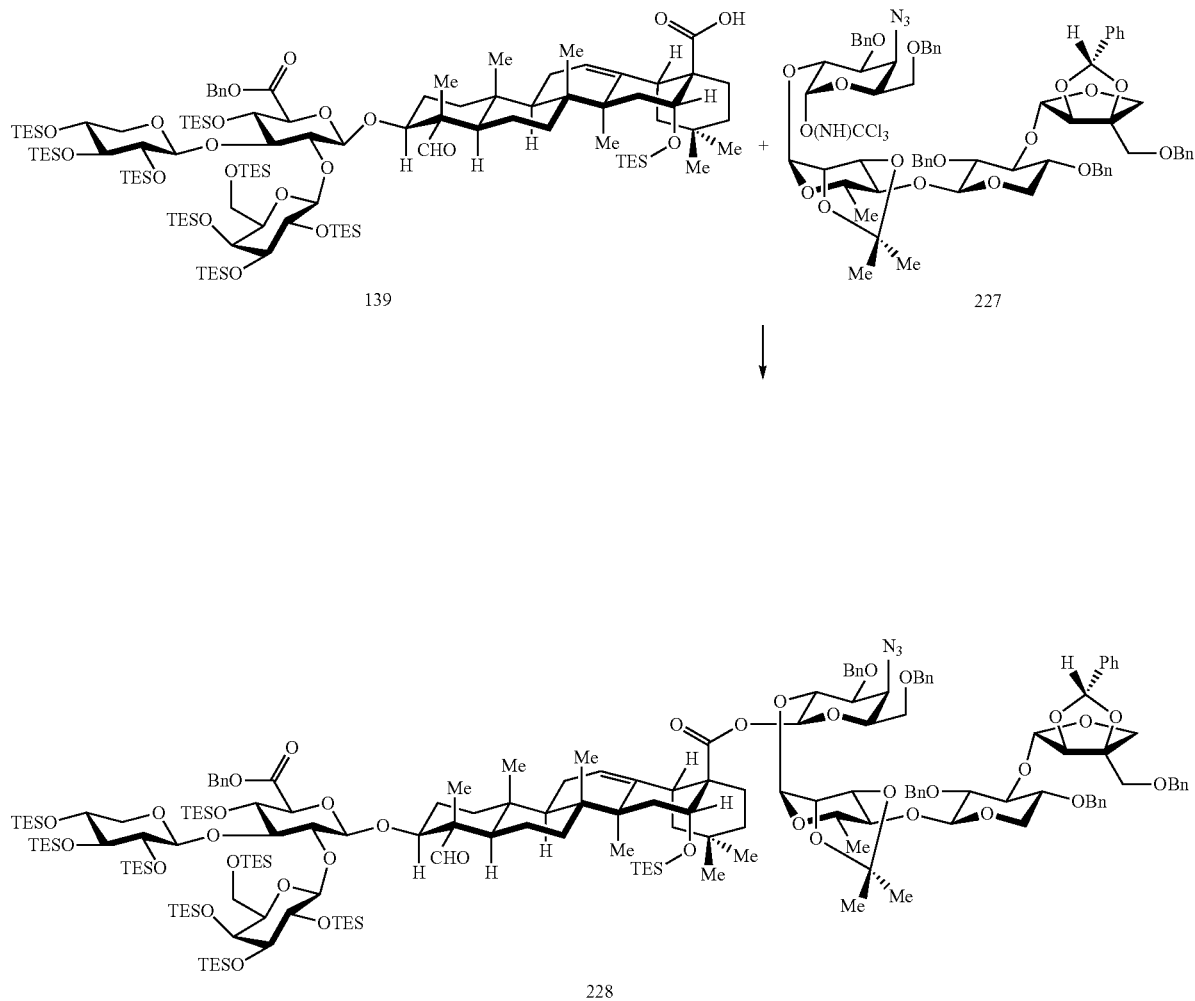

Azido Saponin 228.

Boron trifluoride diethyl etherate (2.0 µL, 0.016 mmol, 0.51 equiv) was added to a solution of imidate 227 (41.7 mg, 0.0311 mmol, 1.00 equiv) and carboxylic acid 139 (88.6 mg, 0.0427 mmol, 1.37 equiv) with 4 Å molecular sieves (147 mg) in dichloromethane (1.04 mL) at −78° C. After 3 min, the reaction flask was transferred to a −43° C. cold bath (11:10 ethanol:water/CO$_2$), and the reaction temperature was allowed to warm slowly to 23° C. Triethylamine (0.20 mL) was added after 14.5 h, and the reaction was concentrated and purified by silica gel chromatography (silica pretreated with 0.2% triethylamine in benzene, then benzene/ethyl acetate 49:1 to 9:1) to afford 228 (83.5 mg, 0.0257 mmol, 82% yield) as a white solid. R$_f$=0.58 (benzene/ethyl acetate 9:1); characteristic resonances from $^1$H NMR (500 MHz, CDCl$_3$) δ 9.68 (s, 1H), 5.95 (s, 1H), 5.70 (s, 1H), 5.17 (d, J=2.4, 1H), 5.08 (d, J=12.4, 1H), 4.83 (d, J=11.2, 1H), 4.79 (d, J=7.6, 1H), 4.71 (d, J=11.1, 1H), 4.61 128.43, 128.40, 128.38, 128.27, 128.12, 128.04, 127.98, 127.96, 127.91, 127.83, 127.78, 127.60, 127.30, 121.97, 109.70, 107.32, 106.50, 103.64, 102.30, 101.56, 100.99, 97.96, 93.89, 91.70, 87.20, 86.20, 81.33, 80.93, 78.97, 78.88, 78.77, 78.28, 76.77, 76.58, 75.99, 75.25, 74.12, 73.73, 73.70, 73.37, 73.08, 72.77, 72.68, 72.02, 71.57, 71.20, 71.15, 67.67, 67.60, 66.96, 65.49, 63.81, 60.42, 59.03, 54.06, 49.52, 49.04, 46.75, 46.29, 41.60, 40.83, 39.91, 38.12, 36.23, 35.32, 34.89, 32.87, 32.60, 30.88, 30.57, 29.87, 27.53, 26.50, 25.78, 25.48, 24.44, 23.44, 20.37, 17.73, 17.29, 15.97, 12.30, 7.68, 7.58, 7.47, 7.37, 7.31, 7.27, 7.25, 7.10, 6.97, 6.91, 6.05, 5.79, 5.59, 5.51, 5.48, 5.41, 5.38, 5.14, 5.03, 4.57; FTIR (neat film) 2952.9, 2912.2, 2876.4, 2106.7, 1752.4, 1497.1, 1456.5, 1379.5, 1240.2, 1165.7, 1098.7, 1006.1, 913.3, 863.1, 824.5, 736.4, 697.5 cm$^{-1}$; LRMS (ESI) m/z: Calcd for $C_{176}H_{279}N_3O_{35}Si_9Na_2$ (M+2Na$^{++}$) 1646.39. found 1648.64.

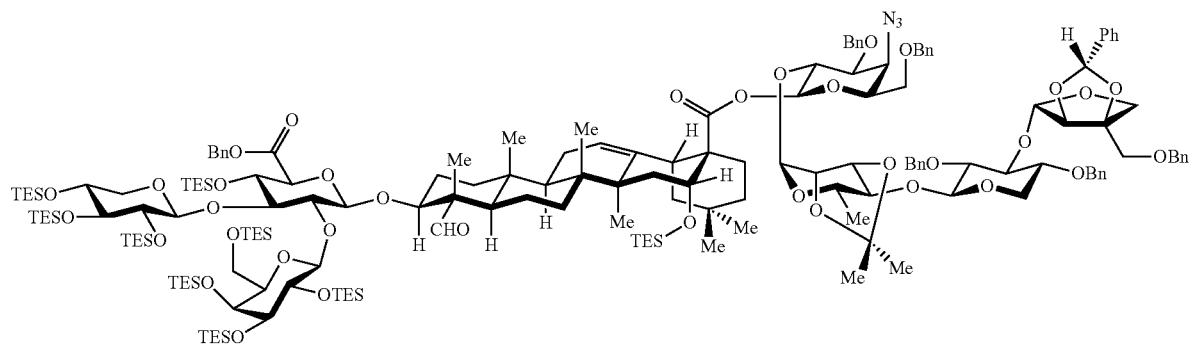

228

↓

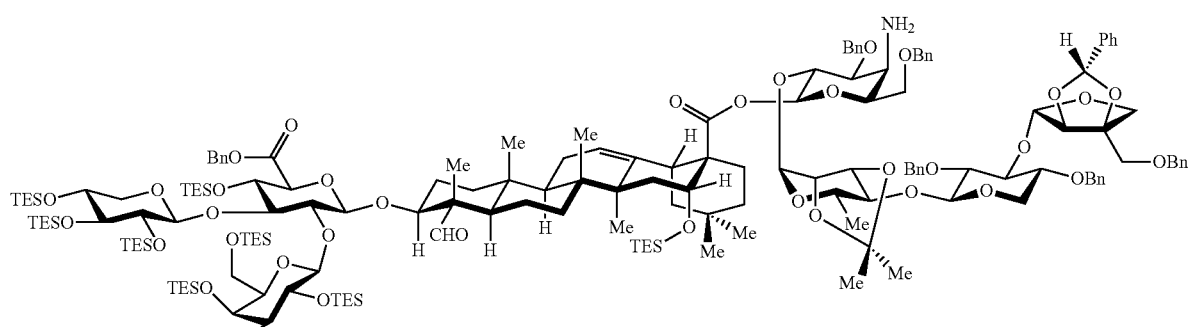

229

Amino Saponin 229.

A yellow solution of diphenyldiselenide (45.8 mg, 0.147 mmol, 1.00 equiv) and hypophosphorous acid, 50% in water (0.16 mL, 1.6 mmol, 11 equiv) in tetrahydrofuran (2.0 mL) was heated at 40° C. for 40 min until it turned colorless. The solution was then removed from the heat, diluted with benzene (2.0 mL) and deionized water (2.0 mL). The lower phase of the resulting biphasic suspension was removed by syringe (2.4 mL), and the remaining organic layer was dried with sodium sulphate.

This freshly prepared solution of phenylselenol (1.7 mL, ~0.14 mmol, 30 equiv) was added to a solution of azido saponin 228 (15.0 mg, 0.00461 mmol, 1.00 equiv) in triethylamine (5.0 mL) and was heated at 30° C. for 15 h.

A second solution of phenylselenol was prepared by heating diphenyldiselenide (53.7 mg, 0.172 mmol, 1.00 equiv) and hypophosphorous acid, 50% in water (0.19 mL, 1.8 mmol, 11 equiv) in tetrahydrofuran (2.0 mL) was heated at 40° C. for 30 min until it turned colorless. This solution of phenylselenol was then removed from the heat, diluted with benzene (2.0 mL) and deionized water (2.0 mL). The lower phase of the resulting biphasic suspension was removed by syringe (2.4 mL), and the remaining organic layer was dried with sodium sulphate.

The second solution of phenylselenol (1.5 mL, ~0.14 mmol, 30 equiv) was added to the reaction flask containing azido saponin 228, which was heated at 40° C. for 8 h. Additional phenylselenol solution (0.6 mL, ~0.06 mmol, 12 equiv) was added, and the reaction was stirred at 40° C. for an additional 2 h. The reaction mixture was concentrated and purified by silica gel chromatography (benzene to 3:2 benzene/ethyl acetate) to afford 228 (13.6 mg, 0.00422 mmol, 91% yield) as a white solid film. $R_f$=0.24 (benzene/ethyl acetate 9:1); characteristic resonances from $^1$H NMR (500 MHz, CDCl$_3$) δ 9.69 (s, 1H), 5.96 (s, 1H), 5.71 (s, 1H), 5.37 (d, J=7.8, 1H), 5.31 (m, 1H), 5.28 (d, J=12.4, 1H), 5.19 (d, J=1.7, 1H), 5.09 (d, J=12.4, 1H), 4.83 (d, J=11.1, 1H), 4.82 (d, J=7.5, 1H), 4.64 (t, J=10.9, 2H), 4.59 (d, J=1.8, 2H), 4.18 (d, J=7.3, 1H), 3.25 (t, J=8.4, 2H), 3.14 (m, 2H), 2.89 (dd, J=14.5, 4.0, 1H), 1.42 (s, 3H), 1.33 (s, 3H), 1.29 (s, 3H), 1.24 (s, 3H), 1.16 (d, J=6.2, 3H); FTIR (neat film) 2952.7, 2912.3, 2876.2, 1753.9, 1453.9, 1097.9, 1006.5, 862.44, 824.6, 737.1, 697.1, 668.4 cm$^{-1}$.

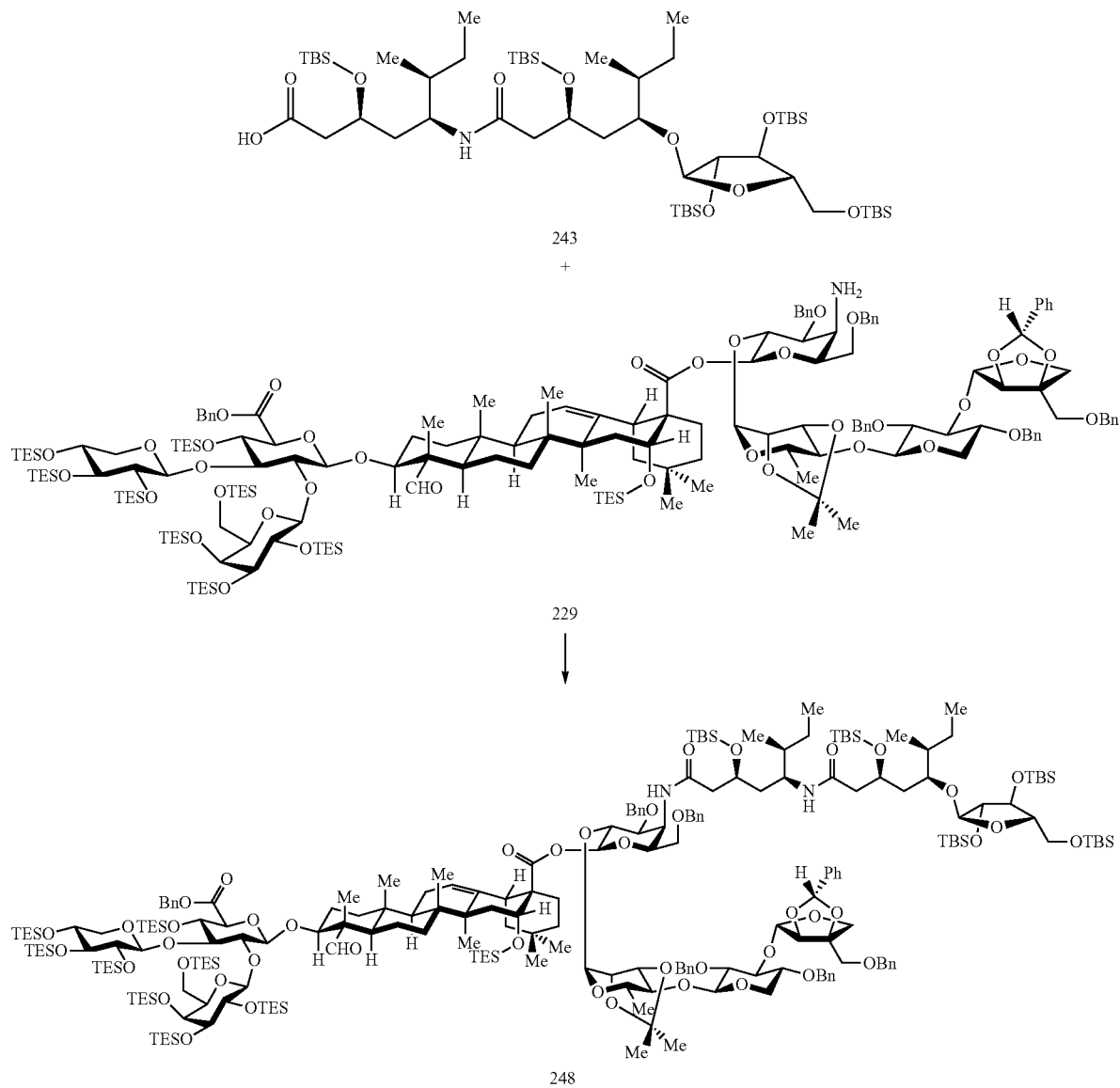

Fully Protected Compound I-9 (248).

A solution of ethyl chloroformate (0.45 μL, 0.0047 mmol, 1.2 equiv) in tetrahydrofuran (10 μL) was added to a solution of carboxylic acid 243 (5.0 mg, 0.0047 mmol, 1.2 equiv) and triethylamine (0.82 μL, 0.0059 mmol, 1.5 equiv) in tetrahydrofuran (1.0 mL) at 0° C. After 2.5 h, amino saponin 229 (12.7 mg, 0.00394 mmol, 1.00 equiv) was added in a solution of tetrahydrofuran (3.0 mL). The reaction was warmed slowly to 10° C. over 12 h and stirred at 10° C. for an additional 2 h. The reaction was concentrated and purified by silica gel chromatography (hexane/ethyl acetate 4:1) to afford 248 (15.6 mg, 0.00365 mmol, 93% yield) as a clear film. $R_f$=0.30 (hexane/ethyl acetate 4:1); characteristic resonances from $^1$H NMR (500 MHz, CDCl$_3$) δ 9.69 (s, 1H), 6.31 (d, J=9.0, 1H), 6.25 (d, J=9.9, 1H), 5.96 (s, 1H), 5.72 (s, 1H), 5.37 (d, J=7.3, 1H), 5.34 (m, 1H), 5.28 (d, J=12.4, 1H), 5.18 (s, 1H), 5.09 (m, 1H), 4.85 (d, J=11.1, 1H), 4.82 (d, J=10.6, 1H), 4.78 (d, J=7.6, 1H), 4.37 (d, J=10.4, 1H), 4.23 (m, 1H), 4.18 (d, J=7.2, 1H), 3.25 (m, 2H), 3.13 (td, J=11.2, 3.8, 2H), 2.90 (dd, J=14.3, 2.8, 1H), 2.22 (t, J=13.3, 1H), 1.44 (s, 3H), 1.34 (s, 3H), 1.29 (s, 3H), 1.20 (s, 3H), 1.11 (d, J=6.1, 3H); $^{13}$C NMR (126 MHz, CDCl$_3$) δ 170.74, 170.67, 168.50, 138.25, 138.12, 138.10, 138.01, 137.76, 136.91, 135.44, 129.75, 128.65, 128.62, 128.57, 128.54, 128.48, 128.46, 128.43, 128.40, 128.29, 127.97, 127.92, 127.84, 127.66, 127.62, 127.31, 109.73, 107.38, 107.02, 106.52, 91.72, 87.22, 86.49, 86.21, 84.14, 81.41, 79.17, 76.02, 74.21, 73.72, 73.54, 73.39, 73.12, 71.22, 71.17, 67.74, 66.98, 63.90, 63.85, 63.41, 54.07, 50.12, 48.85, 41.61, 39.88, 38.68, 36.80, 36.26, 32.85, 30.57, 29.85, 27.52, 26.57, 25.67, 25.38, 24.40, 18.56, 18.21, 18.13, 18.06, 18.02, 17.69, 17.14, 15.98, 15.04, 14.35, 12.30, 12.07, 7.70, 7.60, 7.39, 7.33, 7.31, 7.27, 7.11, 6.99, 6.93, 6.07, 5.81, 5.60, 5.53, 5.49, 5.42, 5.40, 5.04, 4.59, −3.85, −3.99, −4.37, −4.42, −4.45, −4.57, −4.68, −5.10, −5.17; FTIR (neat film) 2954.1, 2933.4, 2877.0, 2858.3, 1752.3, 1675.5, 1458.6, 1379.5, 1251.0, 1099.8, 836.6, 777.8, 737.0, 697.0, 668.5 cm$^{-1}$; LRMS (ESI) m/z: Calcd for $C_{228}H_{390}N_2O_{45}Si_{14}Na_2$ (M+2Na$^{++}$) 2157.24. found 2157.27.

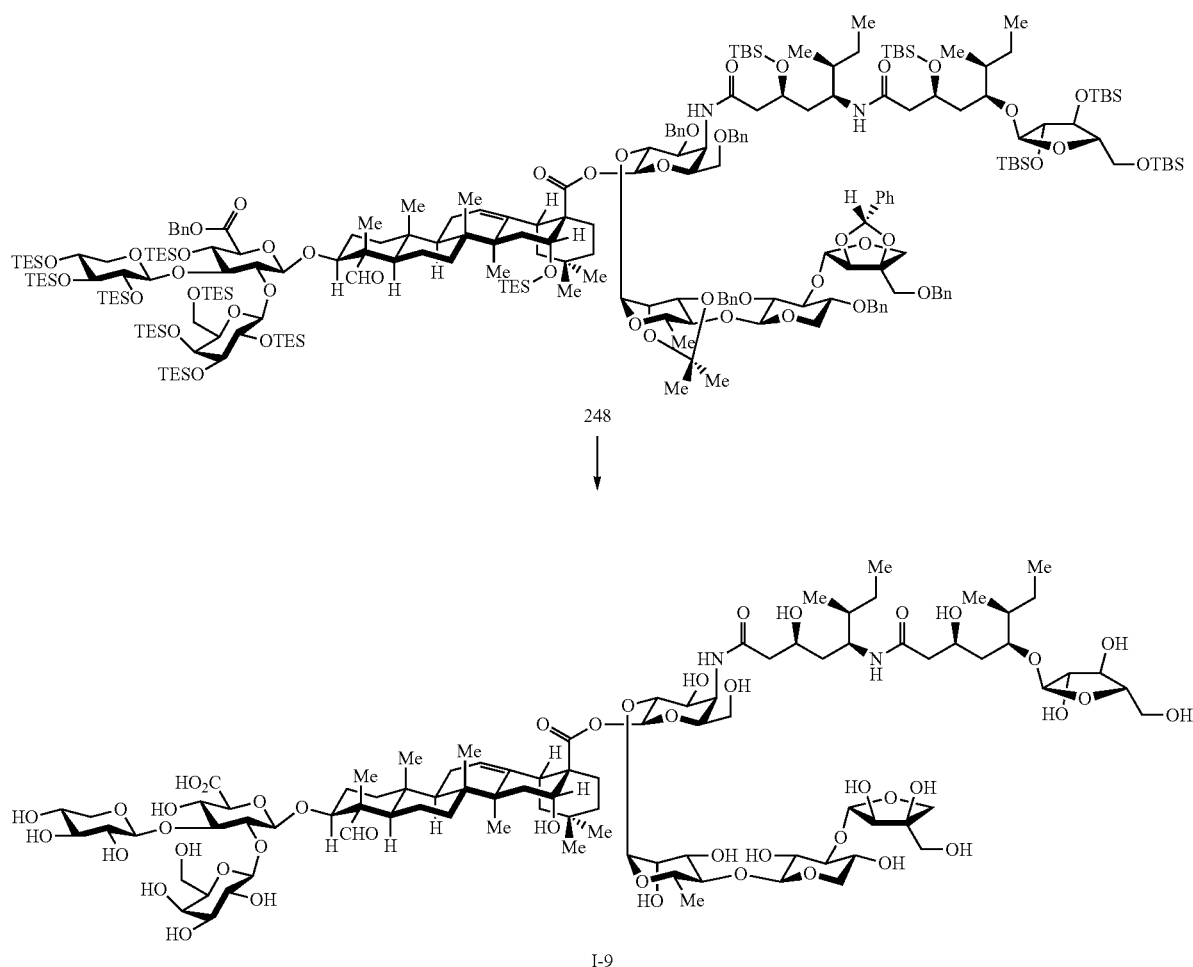

248

↓

I-9

Compound I-9.

Three solutions of fully protected I-9 248 (3×2.0 mg, 0.0014 mmol, 1.0 equiv) in tetrahydrofuran (3×1.0 mL) and ethanol (3×1.0 mL) in three 10-mL round bottom flasks were charged with 10% (dry basis) palladium on carbon, wet, Degussa type E101 NE/W (3×3.8 mg, 0.0054 mmol, 3.8 equiv). The three parallel reactions were stirred under hydrogen pressure (50 psi) for 24 h, and then the suspensions were each filtered through a 0.45 μm polyvinylidene fluoride filter disk, washed with methanol (5 mL), and concentrated in a 25-mL round bottom flask.

A pre-cooled (0° C.) solution of trifluoroacetic acid (1.0 mL, TFA/water 3:1) was added to each flask. After vigorous stirring for 75 min, the three parallel reactions were concentrated in vacuo for 1 h at 0° C. to give white solid residue. This crude product was purified by RP-HPLC on an XBridge Prep BEH300 C18 column (5 μm, 10×250 mm) using a linear gradient of 30-50% acetonitrile (0.05% TFA) in water (0.05% TFA) over 30 min at a flow rate of 5 mL/min. The fraction containing the major peak ($t_R$=12.15 min) was collected and lyophilized to dryness to afford compound I-9 (2.4 mg, 85% yield) as a white solid. Characteristic resonances from $^1$H NMR (500 MHz, 7:3 D$_2$O: CD$_3$CN) δ 9.36 (s, 1H), 5.34 (m, 1H), 5.31 (d, J 7.9, 1H), 5.19 (d, J=3.1, 1H), 5.17 (d, J=1.5, 1H), 4.98 (d, J=2.1, 1H), 4.67 (d, J=7.8, 1H), 4.56 (d, J=7.8, 1H), 4.51 (d, J=7.7, 1H), 4.28 (d, J=4.6, 1H), 4.06 (d, J=10.1, 1H), 2.87 (dd, J=14.6, 3.3, 1H), 2.43 (d, J=6.6, 1H), 2.39 (dd, J=7.5, 13.8, 1H), 2.33 (dd, J=14.0, 5.3, 1H), 1.29 (s, 3H), 1.24 (d, J=6.0, 3H), 1.08 (s, 3H), 0.94 (s, 3H), 0.90 (s, 3H), 0.68 (s, 3H); LRMS (ESI) m/z: Calcd for C$_{92}$H$_{149}$N$_2$O$_{45}$ (M-H$^+$) 2001.94. found 2002.12.

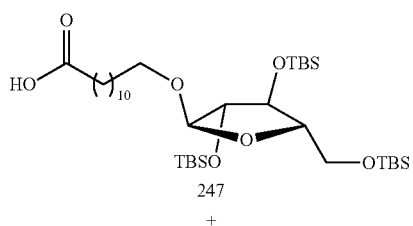

247

+

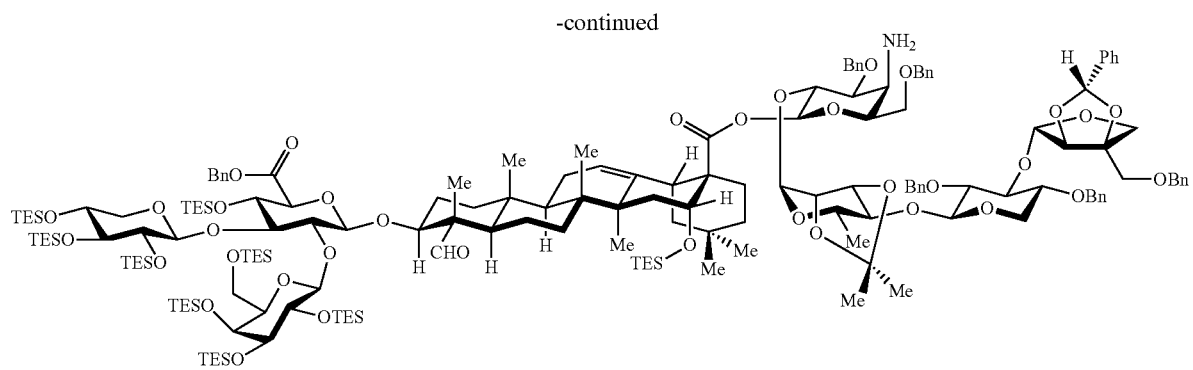

229

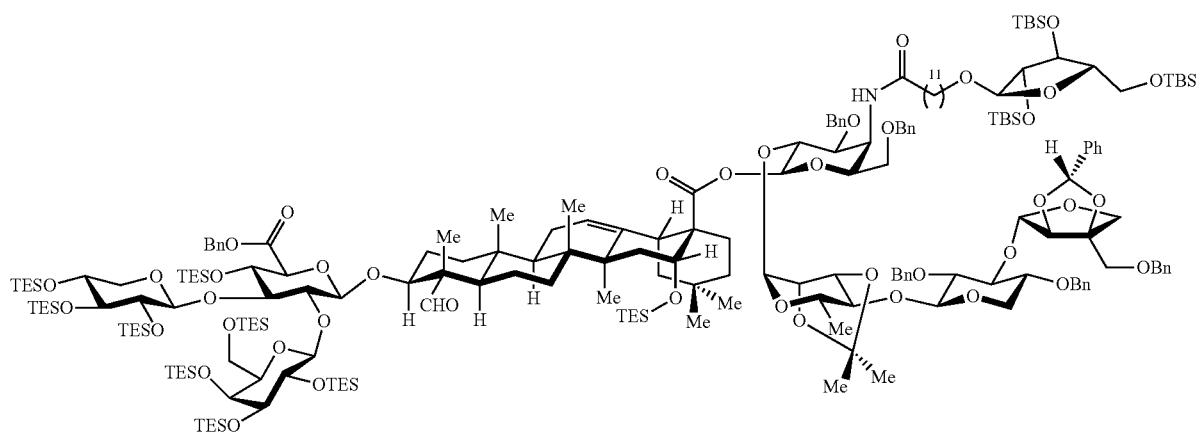

249

Fully Protected Compound I-10 (249).

A solution of ethyl chloroformate (0.30 μL, 0.0031 mmol, 2.0 equiv) in tetrahydrofuran (10 μL) was added to a solution of carboxylic acid 247 (2.1 mg, 0.0030 mmol, 2.0 equiv) and triethylamine (0.45 μL, 0.0033 mmol, 2.1 equiv) in tetrahydrofuran (1.0 mL) at 0° C. After 1.5 h, amino saponin 229 (5.0 mg, 0.0016 mmol, 1.0 equiv) was added in a solution of tetrahydrofuran (3.0 mL). The reaction was warmed slowly to 12° C. over 14 h, concentrated, and purified by silica gel chromatography (benzene to benzene/ethyl acetate 47:3) to afford 249 (5.4 mg, 89% yield) as a clear film. Rf=0.64 (benzene/ethyl acetate 9:1); characteristic resonances from $^1$H NMR (500 MHz, CDCl$_3$) δ 9.69 (s, 1H), 5.96 (s, 1H), 5.71 (s, 1H), 5.62 (m, 1H), 5.39 (d, J=6.6, 1H), 5.28 (d, J=12.4, 1H), 5.19 (s, 1H), 5.09 (d, J=12.4, 1H), 4.85 (d, J=11.2, 1H), 4.82 (d, J=7.6, 1H), 4.79 (d, J=10.6, 1H), 4.75 (d, J=1.6, 1H), 4.64 (d, J=11.2, 1H), 4.59 (d, J=1.7, 2H), 4.18 (d, J=7.3, 1H), 3.25 (m, 2H), 3.14 (dd, J=19.6, 10.2, 2H), 2.88 (dd, J=14.1, 3.5, 1H), 2.21 (t, J=13.4, 1H), 2.14 (t, J=7.4, 1H), 1.43 (s, 3H), 1.34 (s, 3H), 1.30 (s, 3H), 1.23 (s, 3H), 1.12 (d, J=6.1, 3H); $^{13}$C NMR (126 MHz, CDCl$_3$) δ 138.24, 138.11, 137.64, 136.91, 135.44, 129.77, 128.64, 128.62, 128.57, 128.55, 128.51, 128.49, 128.45, 128.41, 128.29, 127.98, 127.93, 127.85, 127.62, 127.32, 109.64, 108.54, 107.38, 106.53, 91.72, 87.23, 84.34, 84.25, 81.46, 79.00, 78.89, 78.74, 78.67, 78.24, 74.25, 73.73, 73.65, 73.40, 73.11, 71.84, 71.57, 71.20, 67.87, 66.99, 63.87, 63.11, 54.03, 46.21, 41.71, 39.94, 37.06, 36.23, 32.86, 32.08, 30.60, 29.93, 29.88, 29.86, 29.81, 29.72, 29.67, 29.59, 29.46, 27.62, 26.53, 26.39, 26.08, 25.96, 25.90, 24.47, 22.86, 20.40, 18.53, 18.04, 18.00, 17.72, 17.32, 16.04, 14.27, 12.33, 7.70, 7.60, 7.39, 7.32, 7.29, 7.27, 7.12, 6.99, 6.93, 6.08, 5.81, 5.61, 5.53, 5.50, 5.42, 5.40, 5.08, 4.58, 1.19, −4.18, −4.38, −4.54, −4.64, −5.03, −5.16; FTIR (neat film) 2952.9, 2929.0, 2876.6, 2856.9, 1750.9, 1734.2, 1457.5, 1241.6, 1219.9, 1099.2, 1006.0, 836.7, 737.2, 697.5 cm$^{-1}$; LRMS (ESI) m/z: Calcd for C$_{210}$H$_{351}$NO$_{42}$Si$_{12}$Na$_2$ (M+2Na$^{++}$) 1970.62. found 1971.83.

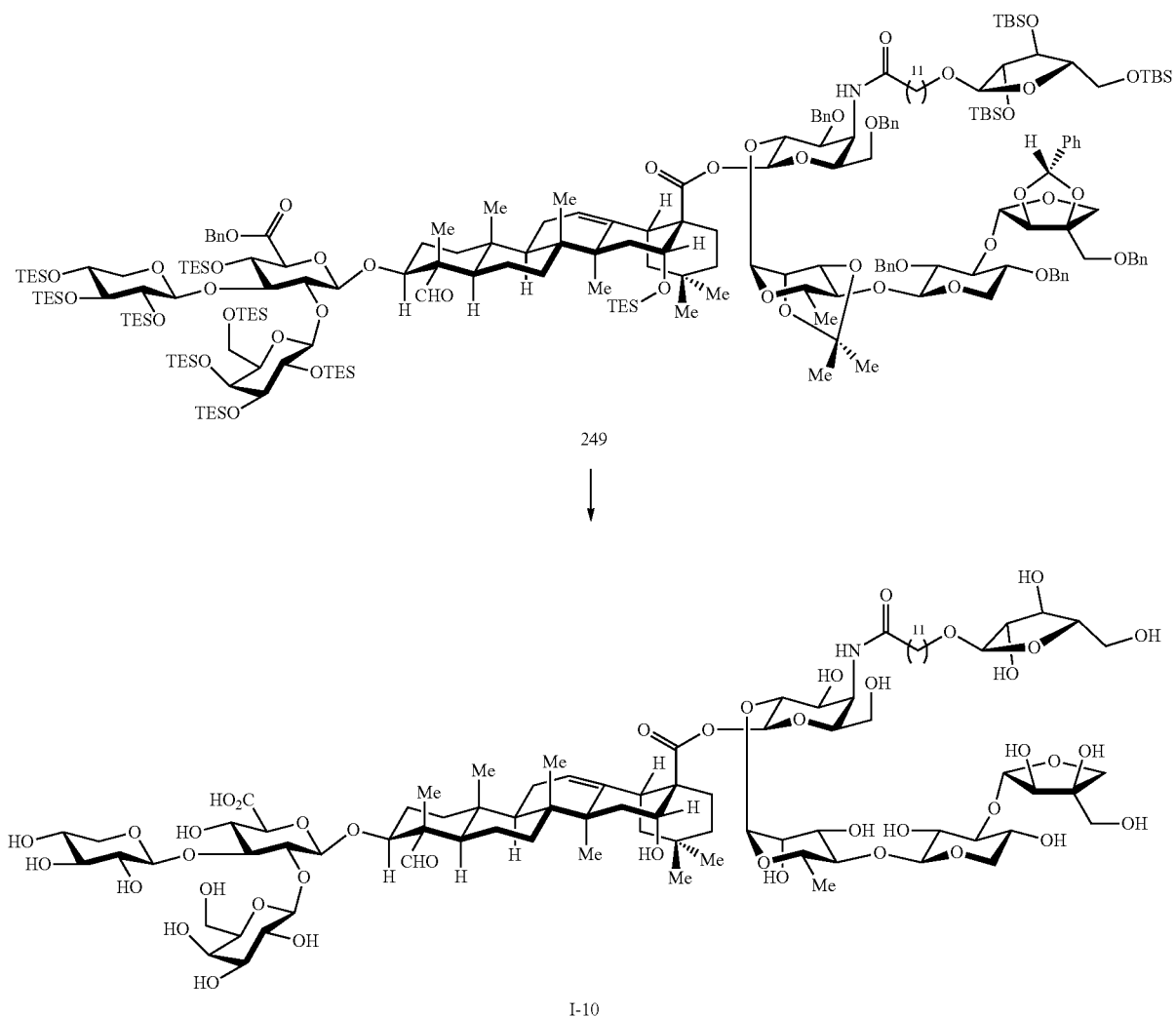

249

↓

I-10

Compound I-10.

Fully protected I-10 (249) (5.4 mg, 0.0014 mmol, 1.0 equiv) was equally divided into three 10-mL round bottom flasks and dissolved in tetrahydrofuran (3×1.0 mL) and ethanol (3×1.0 mL). The three parallel reactions were charged with 10% (dry basis) palladium on carbon, wet, Degussa type E101 NE/W (3×3.2 mg, 0.0045 mmol, 3.3 equiv) and stirred under hydrogen pressure (50 psi) for 24.5 h. The three suspensions were combined and filtered through two 0.45 μm polyvinylidene fluoride filter disks, washed with methanol (5 mL), and concentrated in two 25-mL round bottom flasks.

A pre-cooled (0° C.) solution of trifluoroacetic acid (1.0 mL, TFA/water 3:1) was added to both flasks. After vigorous stirring for 60 min, the two parallel reactions were concentrated in vacuo for 2 h at 0° C. to afford white solid residue.

This crude product was purified by RP-HPLC on an XBridge Prep BEH300 C18 column (5 μm, 10×250 mm) using a linear gradient of 30-40% acetonitrile (0.05% TFA) in water (0.05% TFA) over 17 min at a flow rate of 5 mL/min. The fraction containing the major peak ($t_R$=15.5 min) was collected and lyophilized to dryness to afford compound I-10 (2.0 mg, 78% yield) as an amorphous white solid. Characteristic resonances from $^1$H NMR (500 MHz, 7:3 $D_2O$:$CD_3CN$) δ 9.36 (s, 4H), 5.34 (m, 1H), 5.32 (d, J=7.9, 1H), 5.19 (d, J=3.1, 1H), 5.17 (d, J=1.4, 1H), 4.87 (d, J=1.8, 1H), 4.67 (d, J=7.7, 1H), 4.56 (d, J=7.8, 1H), 4.52 (d, J=7.9, 1H), 4.24 (d, J=4.2, 1H), 4.06 (d, J=10.1, 1H), 3.96 (d, J=3.1, 1H), 2.89 (dd, J=14.3, 3.5, 1H), 1.08 (s, 3H), 0.94 (s, 3H), 0.92 (s, 3H), 0.85 (s, 3H), 0.68 (s, 3H); LRMS (ESI) m/z: Calcd for $C_{86}H_{138}NO_{42}$ (M-H$^+$) 1856.87. found 1857.03.

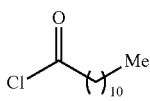

250

+

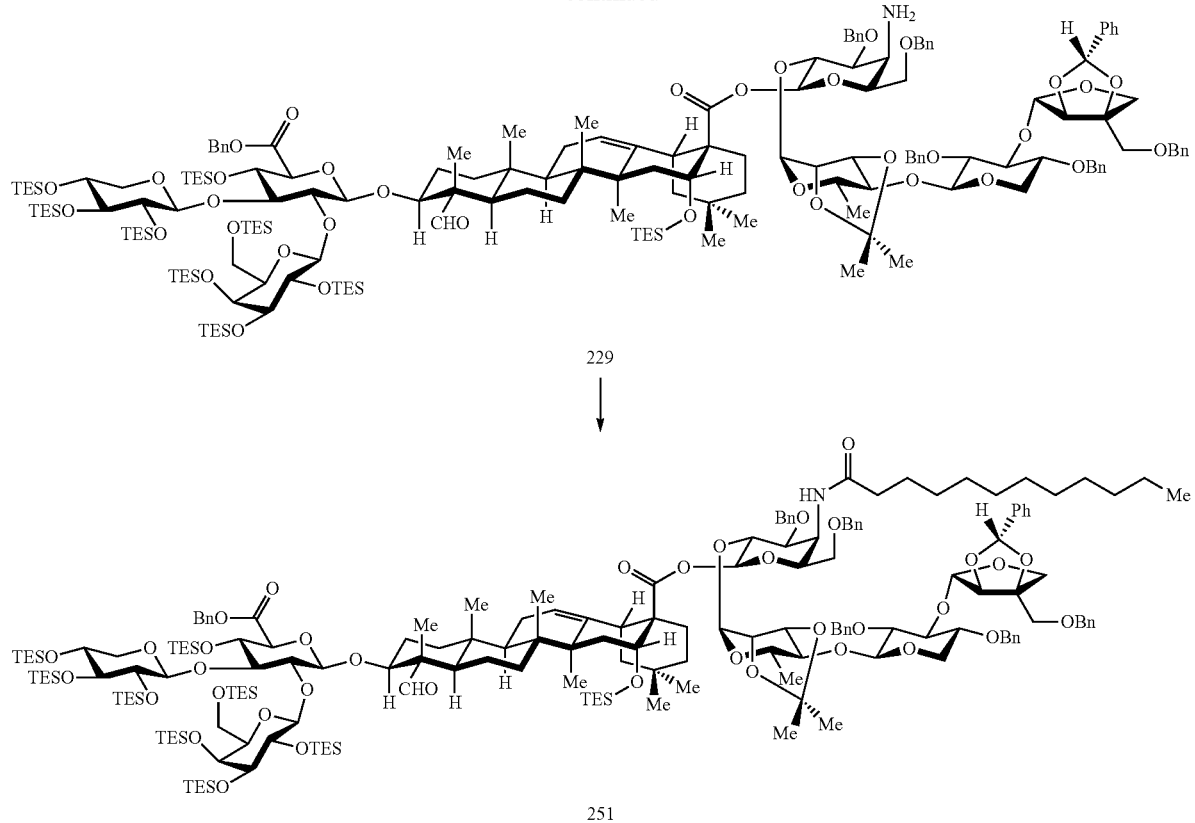

Fully Protected Compound I-8 (251).

Lauroyl chloride (6.6 µL, 0.029 mmol, 12 equiv) was added to a solution of amine 229 (7.7 mg, 0.0024 mmol, 1.0 equiv) and tri-tert-butylpyridine (52.5 mg, 0.212 mmol, 89 equiv) in dichloromethane (10 mL). After 16 h, the reaction was concentrated and purified by silica gel chromatography (benzene to benzene/ethyl acetate 4:1) to afford 251 (8.0 mg, 0.0023 mmol, 98% yield) as a clear film. $R_f$=0.58 (benzene/ethyl acetate 9:1); characteristic resonances from $^1$H NMR (500 MHz, CDCl$_3$) δ 9.70 (s, 1H), 5.96 (s, 1H), 5.71 (s, 1H), 5.62 (m, 1H), 5.38 (d, J=6.9, 1H), 5.30 (m, 1H), 5.28 (d, J=12.4, 1H), 5.20 (d, J=1.6, 1H), 5.09 (d, J=12.4, 1H), 4.64 (d, J=11.2, 1H), 4.59 (d, J=1.8, 2H), 4.18 (d, J=7.3, 1H), 3.25 (m, 2H), 3.14 (m, 2H), 2.88 (dd, J=13.5, 3.0, 1H), 2.21 (t, 0.1=13.8, 1H), 2.15 (t, J=7.1, 1H), 1.44 (s, 3H), 1.12 (d, J=6.1, 3H); $^{13}$C NMR (126 MHz, CDCl$_3$) δ 138.25, 128.64, 128.61, 128.57, 128.55, 128.52, 128.48, 128.45, 128.41, 128.29, 127.98, 127.92, 127.85, 127.83, 127.62, 127.32, 112.24, 91.72, 74.25, 73.73, 73.64, 73.10, 63.86, 54.03, 46.16, 39.96, 36.22, 32.85, 32.08, 32.05, 31.02, 30.60, 30.43, 29.84, 29.76, 29.74, 29.61, 29.59, 29.53, 29.47, 29.39, 29.22, 27.61, 25.93, 25.51, 24.46, 22.84, 19.68, 17.73, 14.28, 7.69, 7.60, 7.39, 7.31, 7.27, 7.11, 6.99, 6.92, 6.07, 5.80, 5.60, 5.53, 5.49, 5.42, 5.39, 5.08, 4.58; FTIR (neat film) 2952.9, 2934.8, 2876.3, 1749.9, 1698.43, 1457.2, 1375.7, 1239.9, 1098.5, 1006.4, 697.5, 669.4 cm$^{-1}$; LRMS (ESI) m/z: Calcd for $C_{187}H_{301}NO_{37}Si_9Na_2$ (M+2Na$^{++}$) 1725.47. found 1723.82.

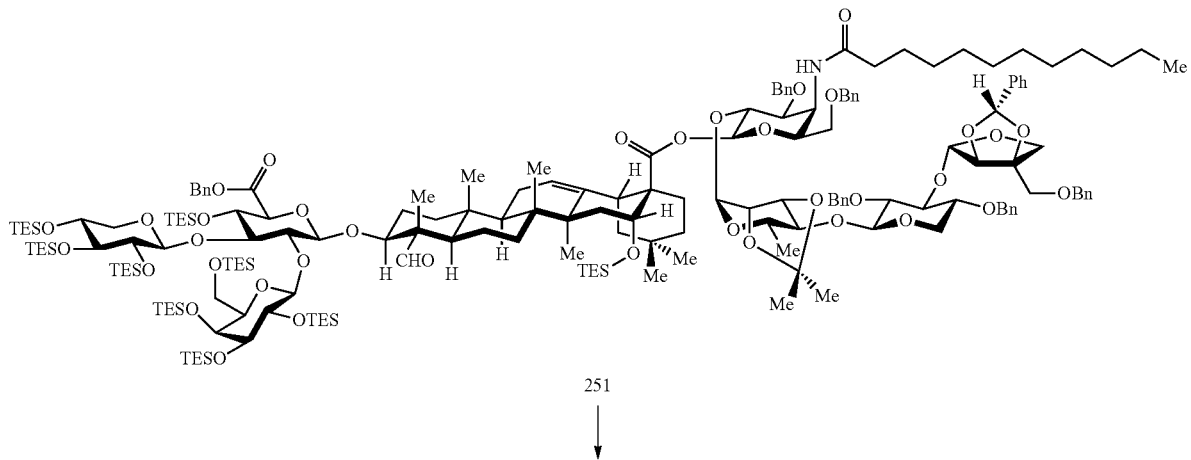

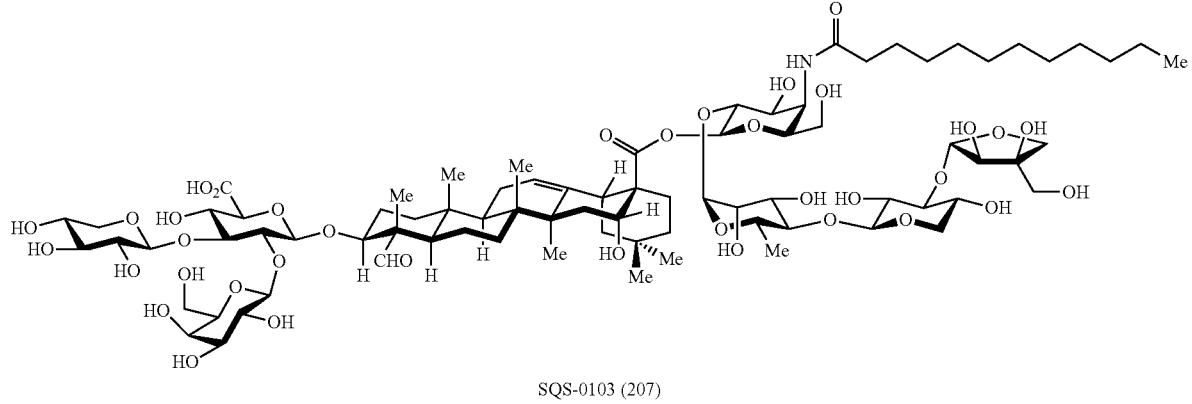

SQS-0103 (207)

Compound I-8.

Three parallel solutions of fully protected I-8 (251) (3×1.25 mg, 0.0011 mmol, 1.0 equiv) in tetrahydrofuran (3×1.0 mL) and ethanol (3×1.0 mL) in 10-mL round bottom flasks were charged with 10% (dry basis) palladium on carbon, wet, Degussa type E101 NE/W (3×2.3 mg, 0.0054 mmol, 2.9 equiv). The three parallel reactions were stirred under hydrogen pressure (50 psi) for 26 h, and then the suspensions were combined and filtered through two 0.45 μm polyvinylidene fluoride filter disks, washed with methanol (5 mL), and concentrated in two 25-mL round bottom flasks.

A pre-cooled (0° C.) solution of trifluoroacetic acid (1.0 mL, TFA/water 1:1) was added to both parallel reactions. After vigorous stirring for 35 min, the reactions were concentrated in vacuo at 0° C. to give white solid residue. This crude product was purified by RP-HPLC on an XBridge Prep BEH300 C18 column (5 μm, 10×250 mm) using a linear gradient of 50-65% acetonitrile (0.05% TFA) in water (0.05% TFA) over 30 min at a flow rate of 5 mL/min. The product eluted as a broad peak ($t_R$=12.78 min), and this fraction was collected and lyophilized to dryness to afford compound I-8 (1.3 mg, 0.00076 mmol, 69% yield) as an amorphous solid. Characteristic resonances from $^1$H NMR (500 MHz, 1:1 $D_2O:CD_3CN$) δ 9.36 (s, 3H), 5.31 (m, 1H), 5.28 (d, J=7.7, 1H), 5.19 (s, 1H), 5.17 (d, J=3.1, 1H), 4.66 (d, J=7.8, 1H), 4.53 (d, J=7.8, 1H), 4.48 (d, J=7.9, 1H), 4.40 (d, J=7.7, 1H), 4.05 (d, J=10.1, 2H), 3.95 (d, J=3.1, 1H), 2.87 (m, 2H), 1.08 (s, 3H), 0.93 (s, 3H), 0.90 (s, 3H), 0.67 (s, 3H); LRMS (ESI) m/z: Calcd for $C_{81}H_{130}NO_{37}$ (M-H$^+$) 1708.83. found 1709.37.

Example 4

Preclinical Evaluation of Synthetic QS-21 with GD3-KLH Conjugate Vaccine.

This example demonstrates the in vivo immunogenicity of certain compounds of the present invention. Using similar protocols, the immuno-potentiating properties of the synthetic adjuvants SQS-21-Api and SQS-21-Xyl were evaluated in mice (C57BL/6J, female, six weeks of age). Although our previous synthetic chemistry efforts had unambiguously verified the chemical structure of SQS-21-Api (Kim, Y.-J.; Wang, P.; Navarro-Villalobos, M.; Rohde, B. D.; Derryberry, J.; Gin, D. Y. *J. Am. Chem. Soc.* 2006, 128, 11906-11915) and SQS-21-Xyl (Deng, K.; Adams, M. M.; Damani, P.; Livingston, P. O.; Ragupathi, G.; Gin, D. Y. *Angew. Chem., Int. Ed.* 2008, 47, 6395-6398) as being identical to that of the principal constituents within NQS-21 (Wang, P.; Kim, Y.-J.; Navarro-Villalobos, M.; Rohde, B. D.; Gin, D. Y. *J. Am. Chem. Soc.* 2005, 127, 3256-3257; Jacobsen, N. E.; Fairbrother, W. J.; Kensil, C. R.; Lim, A.; Wheeler, D. A.; Powell, M. F. *Carbohydr. Res.* 1996, 280, 1-14), this experiment was undertaken to evaluate the synthetic saponins to verify their biological activity given the variable heterogeneity in composition within naturally derived NQS-21 (Note: NQS-21=naturally derived QS-21; SQS-21-Mix=synthetic QS-21; SQS-21-Api=synthetic QS-21-Api; SQS-21-Xyl=synthetic QS-21-Xyl; SQS-7=synthetic QS-7). NQS-21 is isolated as a 65:35 mixture of its Apiose and Xylose isomeric forms, yet it is extremely difficult to separate these constituents from trace natural saponin impurities from the tree bark. As a result, it was necessary to explore whether there were any naturally derived trace saponin impurities that may function as the immuno-active constituent.

Groups of five mice were immunized with the melanoma antigen GD3 ganglioside conjugated to KLH (GD3-KLH) at a 10 μg antigen dose per vaccination. As the negative control, mice were vaccinated with the GD3-KLH antigen only. As a positive control, vaccinations were performed with naturally derived NQS-21 (derived by fractionating a mixture of saponins from *Quillaja saponaria*) at a dose of 20 μg, an amount known to induce measurable antibody responses with acceptable toxic effects in mice. Evaluation of the adjuvant activity of synthetic SQS-21 adjuvants at the same dose (20 μg) included a reconstituted mixture of SQS-21-Api and SQS-21-Xyl in a 65:35 mixture (SQS-21-Mix) to mimic typical isomeric ratios found within NQS-21. Similar evaluations were performed on each of the separate saponin isomers, SQS-21-Api and SQS-21-Xyl at 20 μg doses. Mice were immunized weekly for three weeks with the stated doses of specified adjuvants, and were bled 10 days after the third vaccination. Immunopotentiation was assessed by testing for the presence of antibody against GD3 and KLH by ELISA, and against a tumor cell-line SK-MEL-28, expressing GD3 antigen, by FACS.

Antibody Response (ELISA).

Figures 2A, 2B, 2C:
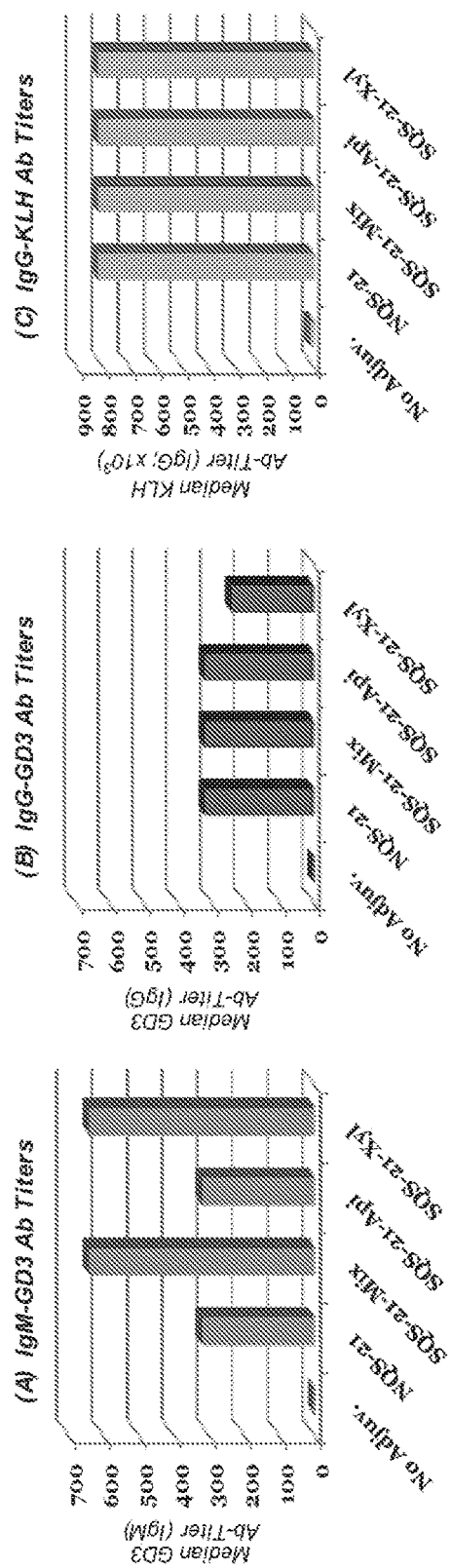
FIGS. 2a-c show Anti-GD3 and Anti-KLH antibody titers after vaccination with GD3-KLH conjugate (10 μg) with adjuvants NQS-21, SQS-21-Mix, SQS-21-Api, or SQS-21-Xyl each at 20 μg doses.

The antibody response after vaccination with GD3-KLH conjugate with or without adjuvant was determined with an ELISA assay using either GD3 ganglioside or KLH protein as target. Comparison of the different adjuvants at the same doses (10 and 20 μg) of SQS-21, SQS-21-Api and SQS-21-Xyl were all equally effective at inducing and IgM antibody response against GD3 after 3 weekly vaccinations with antibody titers in each case significantly higher than the group with GD3-KLH alone. After the third vaccination, no IgG antibodies against GD3 were detected; however, after the fourth immunization IgM and IgG antibody titers were induced in most mice. Again, there were no significant differences between the various groups. The IgG antibody response against KLH was also strikingly elevated in all groups with no group demonstrating significantly higher or lower titers than the others. All were at least 20 fold higher than the GD3-KLH alone group. A graphical representation (FIG. 2) of the antibody titers at 20 μg QS-adjuvant dose clearly illustrates that the SQS-21 adjuvants possess comparable adjuvant activity to that of NQS-21. FIGS. 2a-c show Anti-GD3 and Anti-KLH antibody titers after vaccination with GD3-KLH conjugate (10 μg) with adjuvants NQS-21, SQS-21-Mix, SQS-21-Api, or SQS-21-Xyl each at 20 μg doses. Each value represents median value of five mice (sera tested 7 days after $3^{rd}$ and $4^{th}$ vaccination). NQS-21=naturally derived QS-21; SQS-21-Mix=synthetic QS-21.

Cell Surface Reactivity by Flow Cytometry (FACS).

Figure 3:
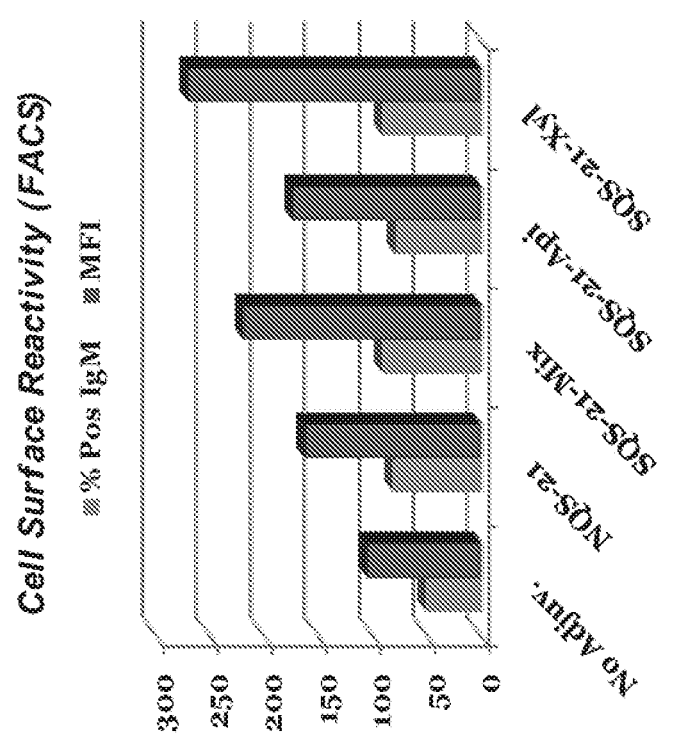
FIG. 3 shows a comparison of cell surface reactivity against cell line SK-Mel-28 between vaccinations with various SQS-adjuvants at 20 μg doses.

Immunopotentiation was also assessed by testing for the presence of antibody against a tumor cell-line SK-MEL-28) expressing GD3 antigen by FACS. Sera drawn 7 days after the $4^{th}$ vaccination was tested for cell surface reactivity by flow cytometry using the SK-Mel-28 (GD3 positive) cell line. The median FACS results are represented graphically at 20 μg QS-adjuvant dose for direct comparison (FIG. 3). Presera obtained from mice before immunization showed less than 10% positive cells and sera from mice vaccinated with all three synthetic adjuvants showed significant positive reactivity with SK-Mel-28. These data reinforce the comparable adjuvant activity of synthetic SQS-21 relative to that of NQS-21.

Toxicity.

Figure 4:
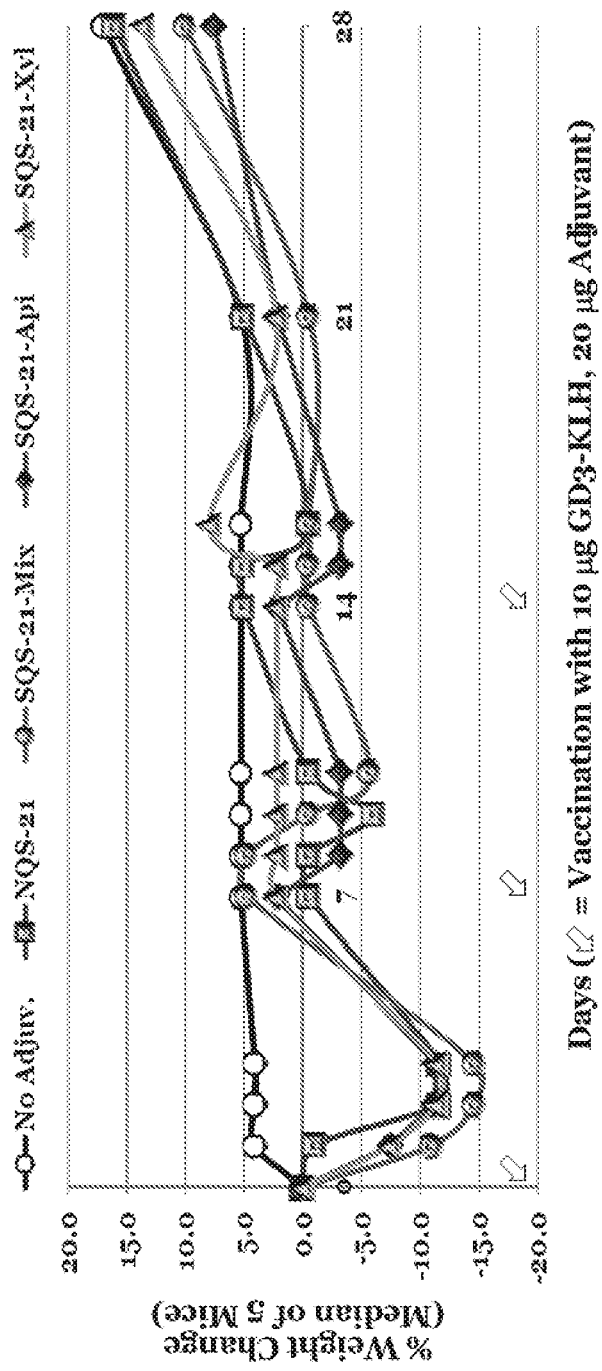
FIG. 4 depicts a toxicity study in C57BL/6J Female Mice injected with GD3-KLH (10 μg) plus SQS-21-Mix, SQS-21-Api, or SQS-21-Xyl (20 μg each), compared to that with no adjuvant or natural NQS-21 (20 μg).

As a measure of toxicity, loss of weight was monitored at 0 h, 24 h, 48 h and 72 h after each injection. The median weight loss for groups of five mice receiving SQS-21-Mix, SQS-21-Api or SQS-21-Xyl at the three different doses is demonstrated in FIG. 4. As the negative control, vaccinations employing GD3-KLH only (no adjuvant) led to no appreciable weight loss after each injection. As the positive control, the presence of NQS-21 (20 μg) elicited notable and expected weight loss after each injection. This pattern of weight loss over the 4-week duration is very similar to that of the other groups of mice vaccinated with SQS-21 synthetic adjuvants (mix, and separate isomers), again signaling a comparable biological profile of SQS-21 compared to that of NQS-21.

Example 5

Preclinical Evaluation of Selected Compounds of Formula II with GD3-KLH Conjugate Vaccine.

Synthetic efforts have resulted in the preparation of compounds of formula II, including compounds I-8, I-9, and I-10. In these compounds, structural variations within the hydrolytically labile acyl chain of natural QS compounds take the form of significantly more stable amide-linked constructs, along with dramatically simplified linear alkyl chain variants.

Figure 5:
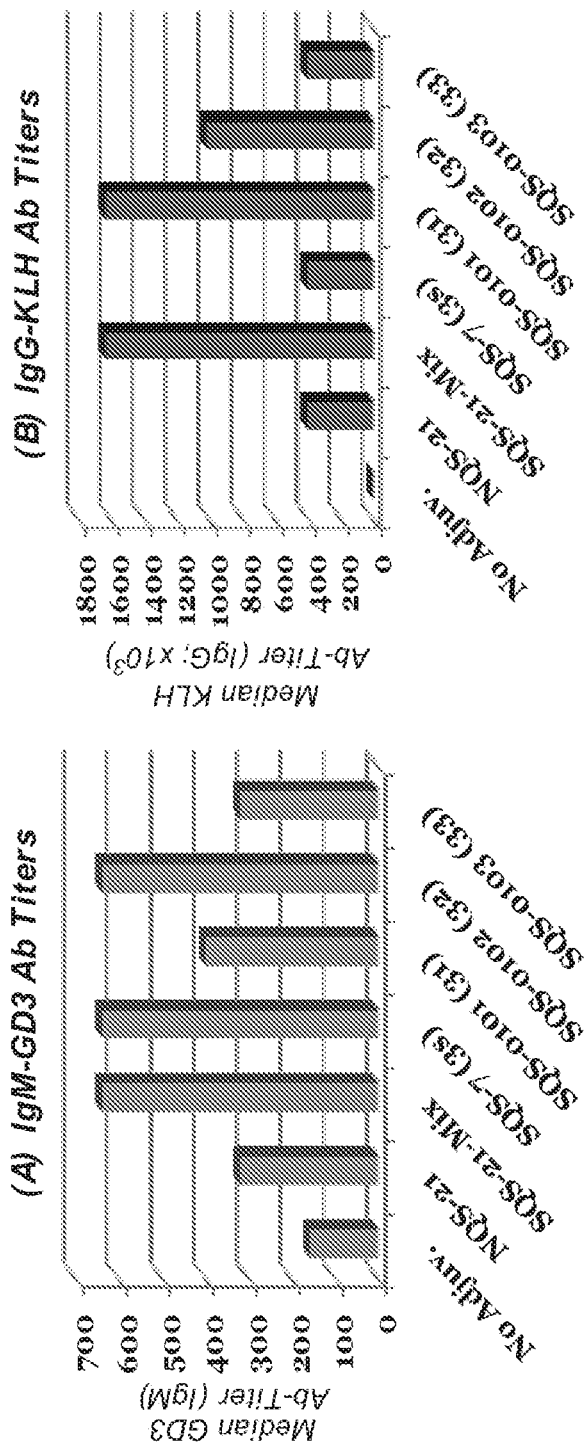
FIG. 5 shows the results on adjuvant activity of synthetic SQS-analogues employing GD3-KLH antigen. Antibody-titers are median values of groups of five mice, wherein adjuvant dose is 10 μg. SQS-7=synthetic QS-7-Api. SQS-0101=compound I-9; SQS-0102=compound I-10; SQS-0103=compound I-8.
Figure 6:
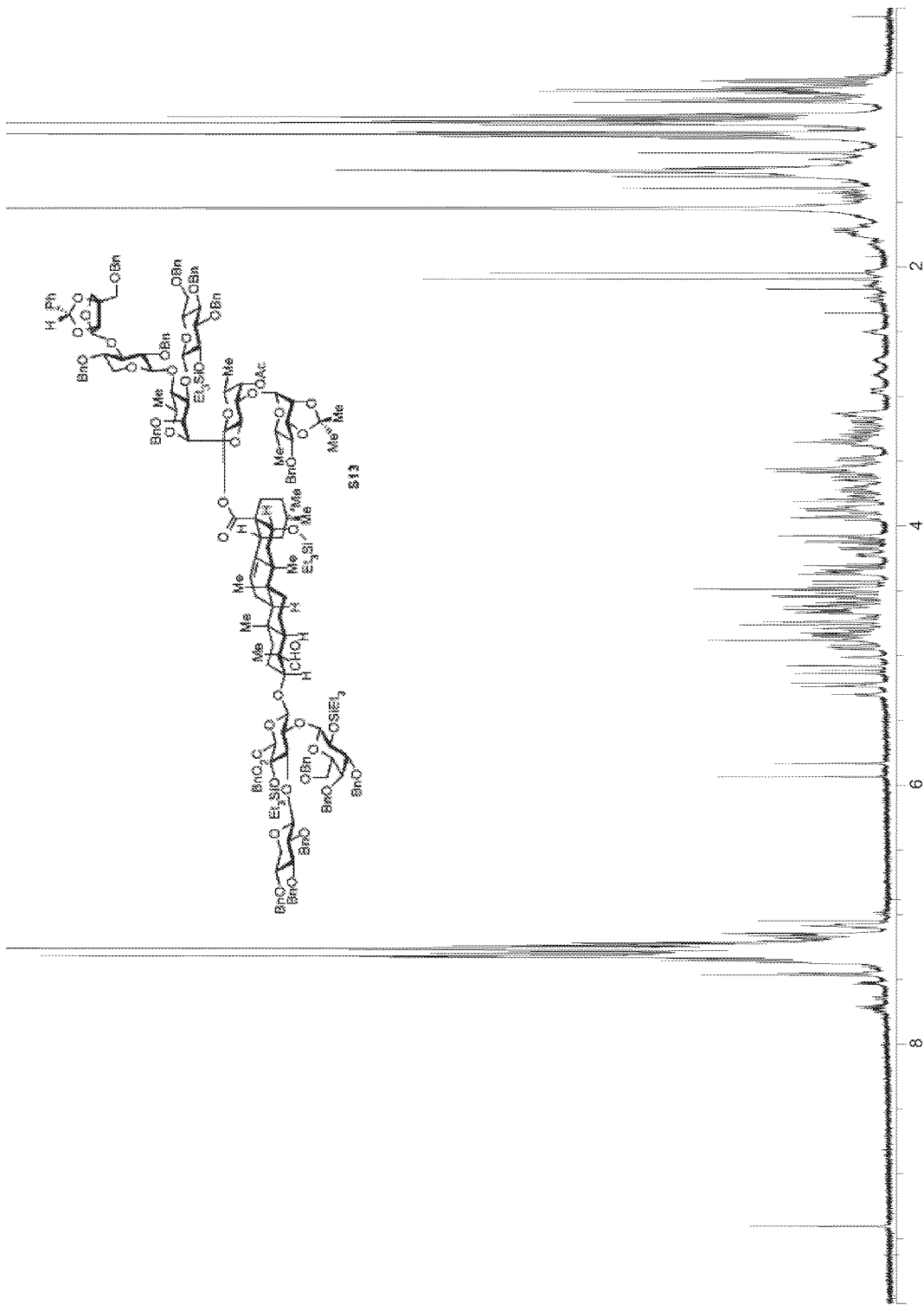
FIGS. 6-14 show $^1$H-NMR spectra of compounds described herein.
Figure 7:
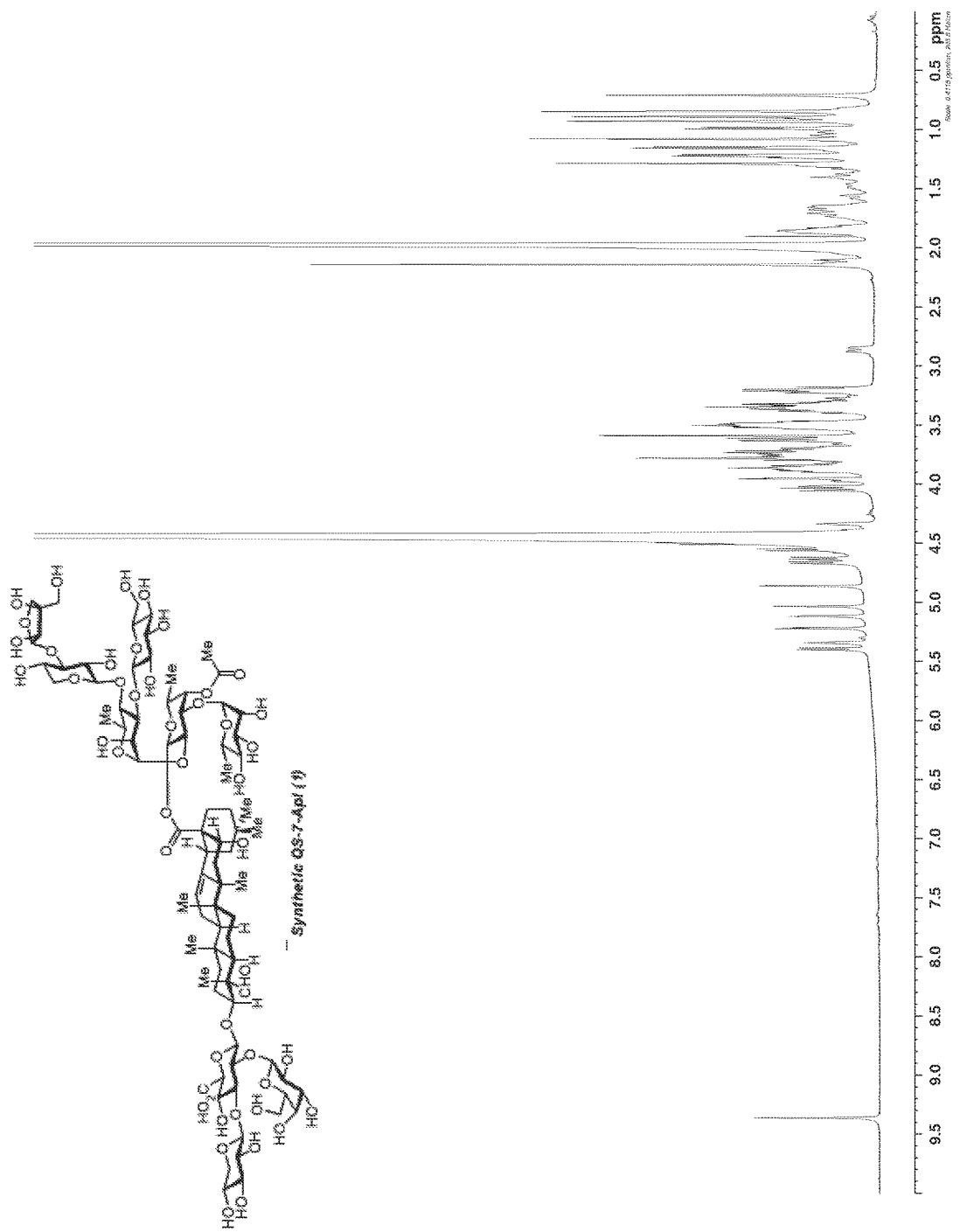
Figure 8:
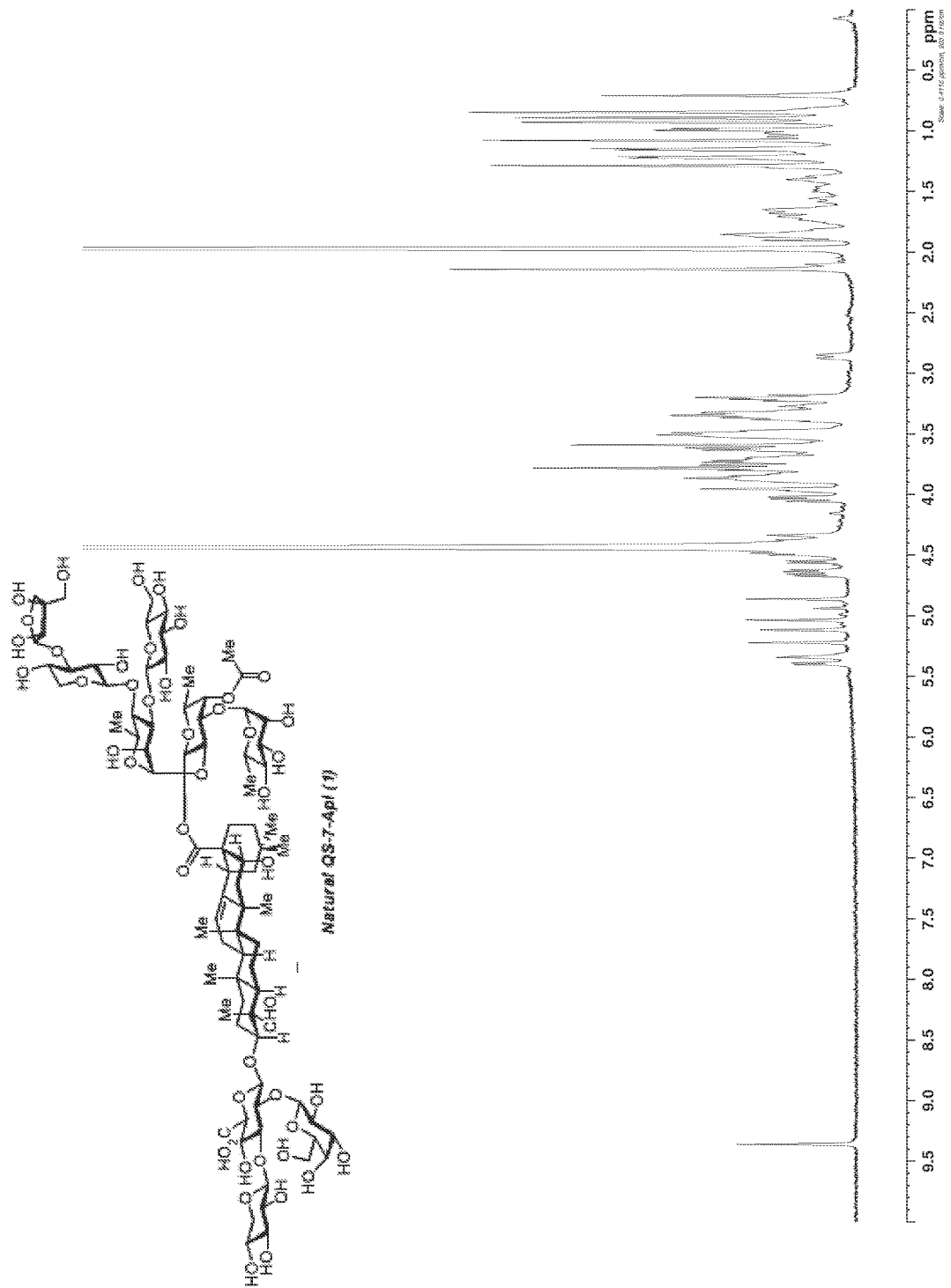
Figure 9:
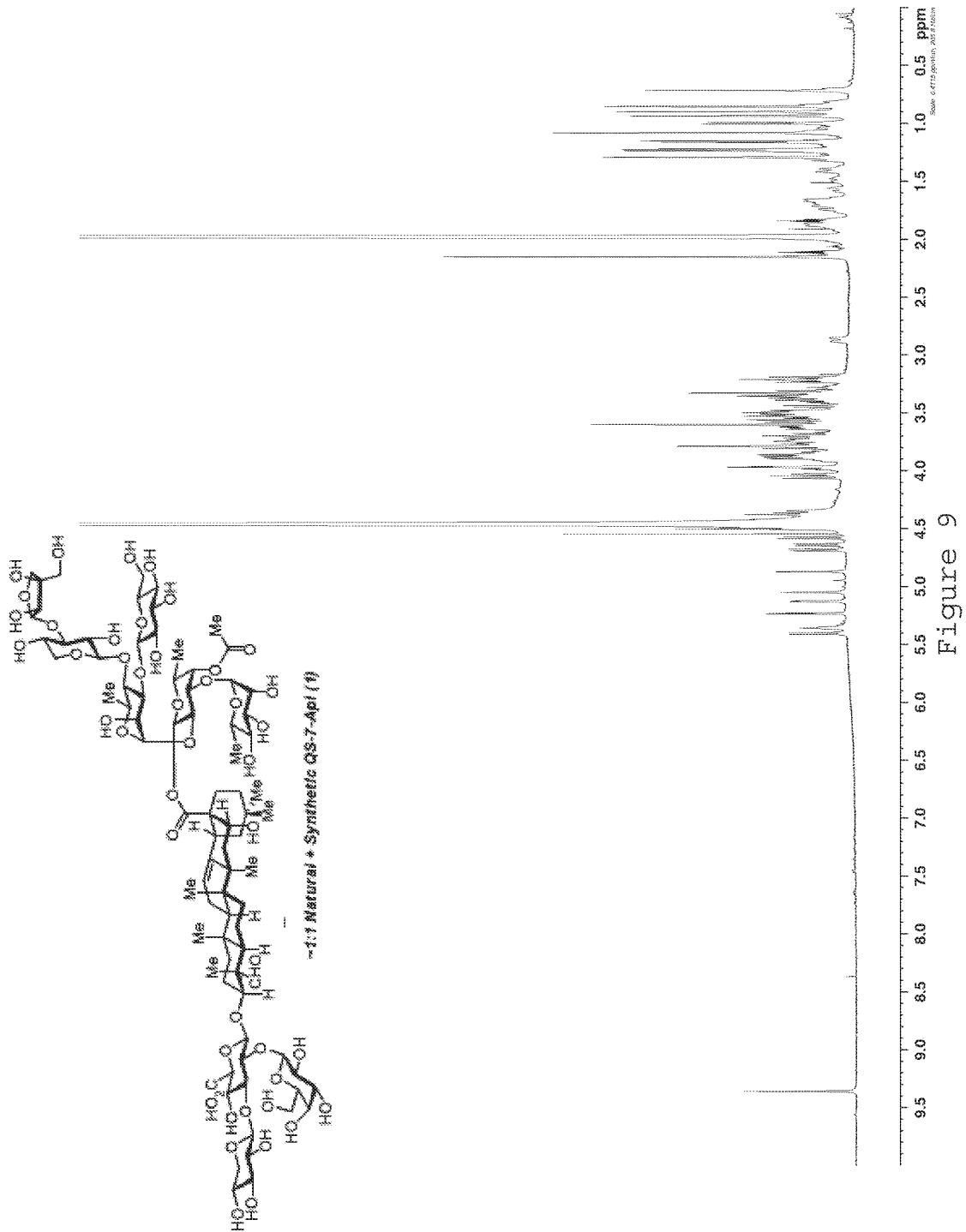
Figure 10:
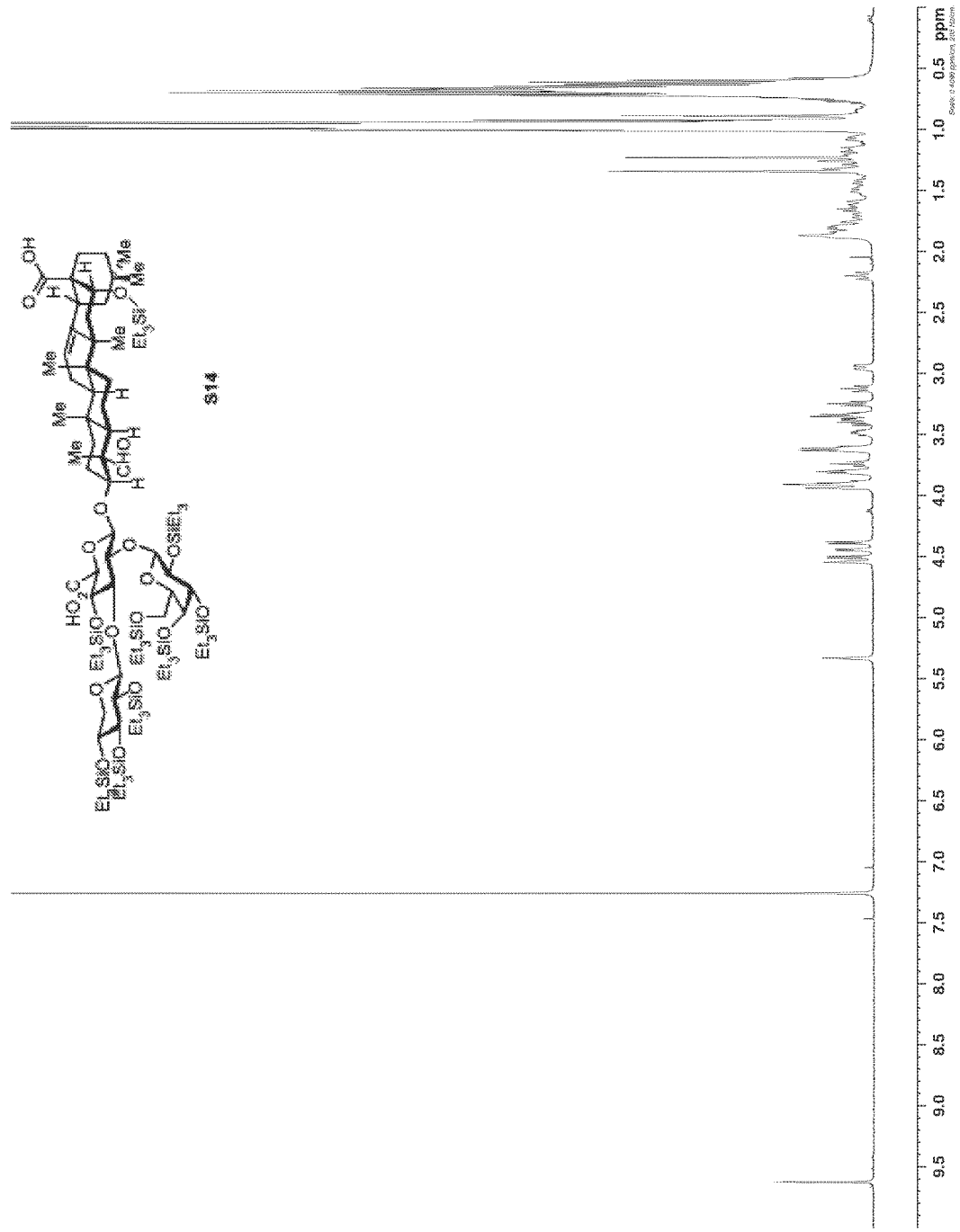
Figure 11:
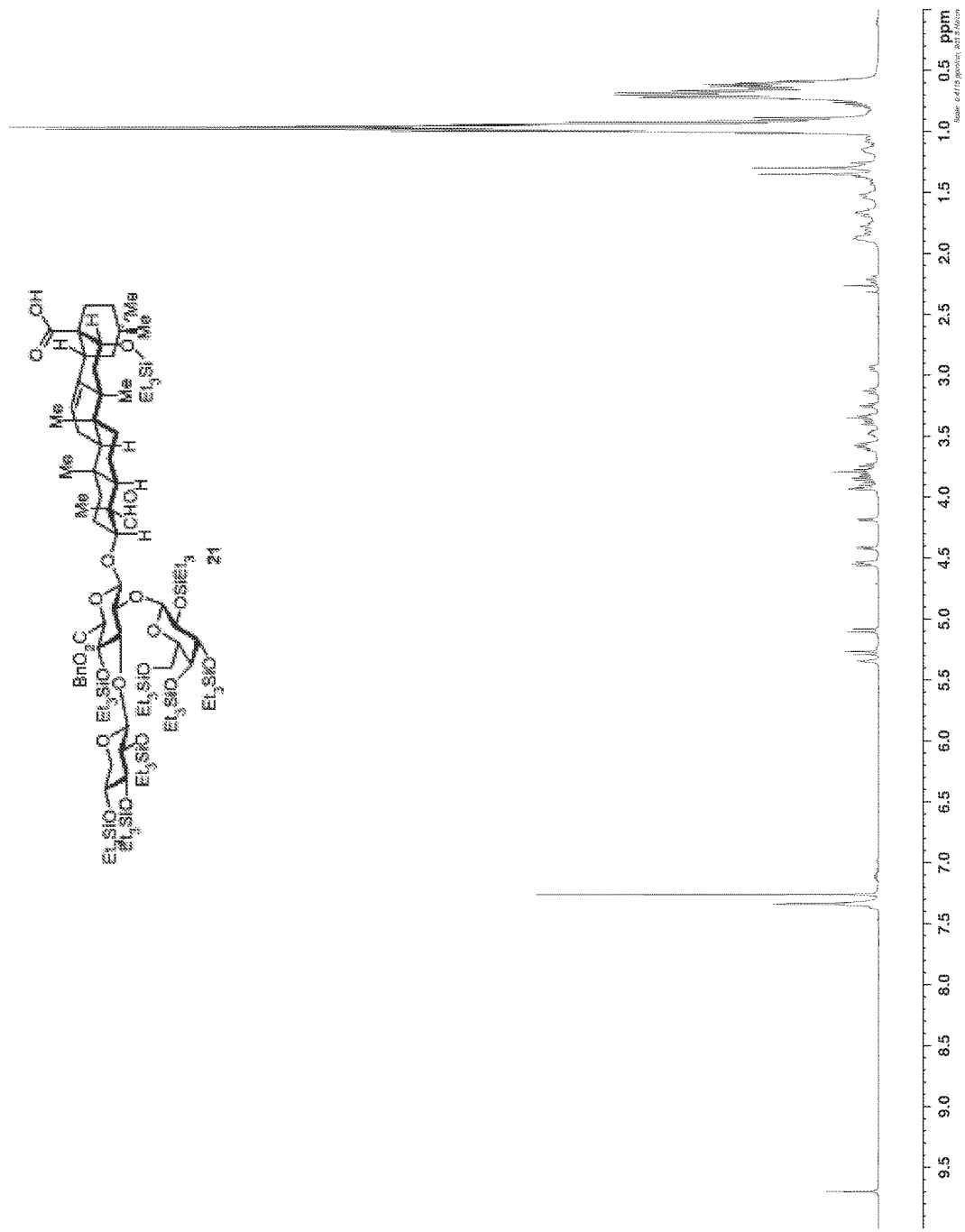
Figure 12:
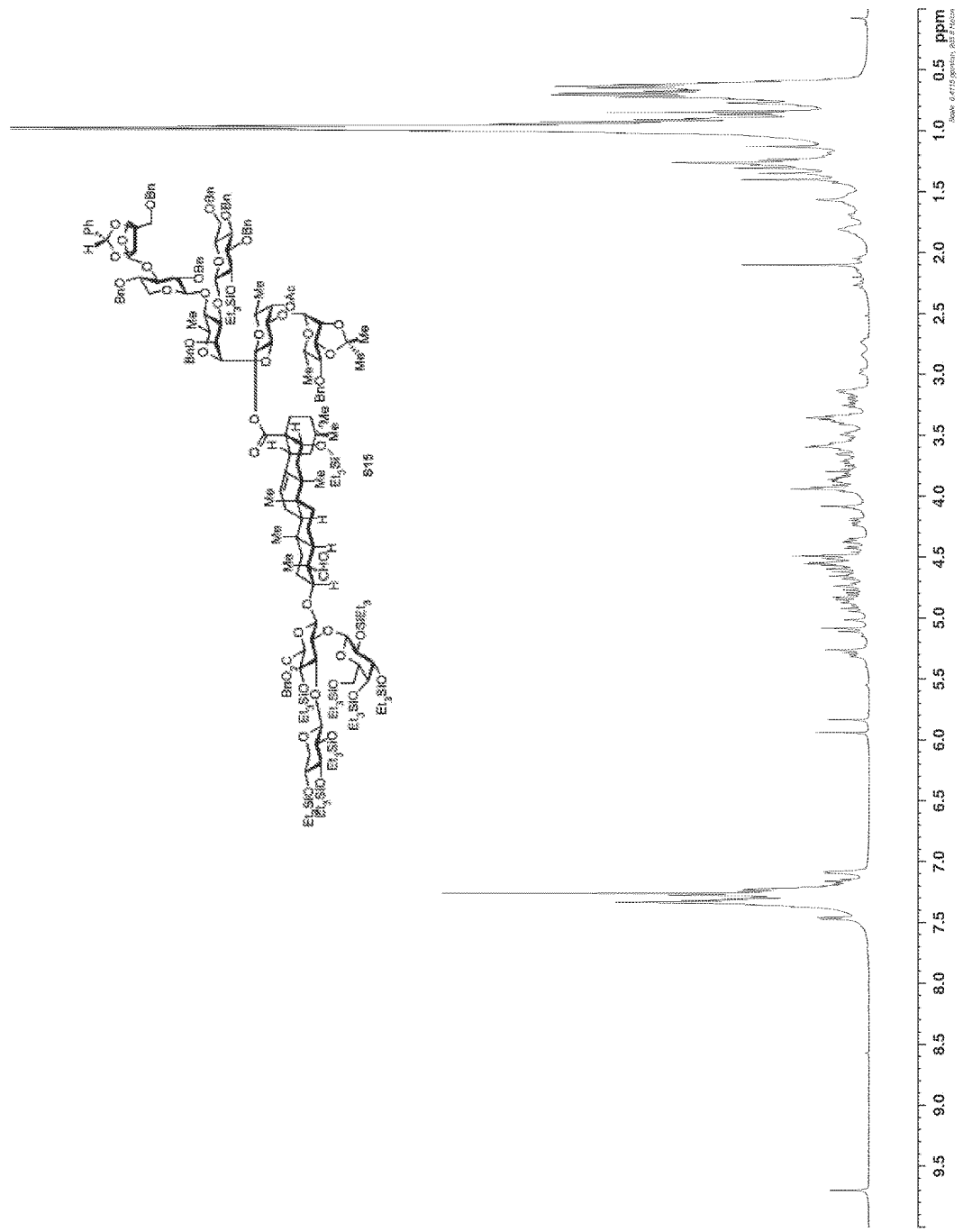
Figure 13:
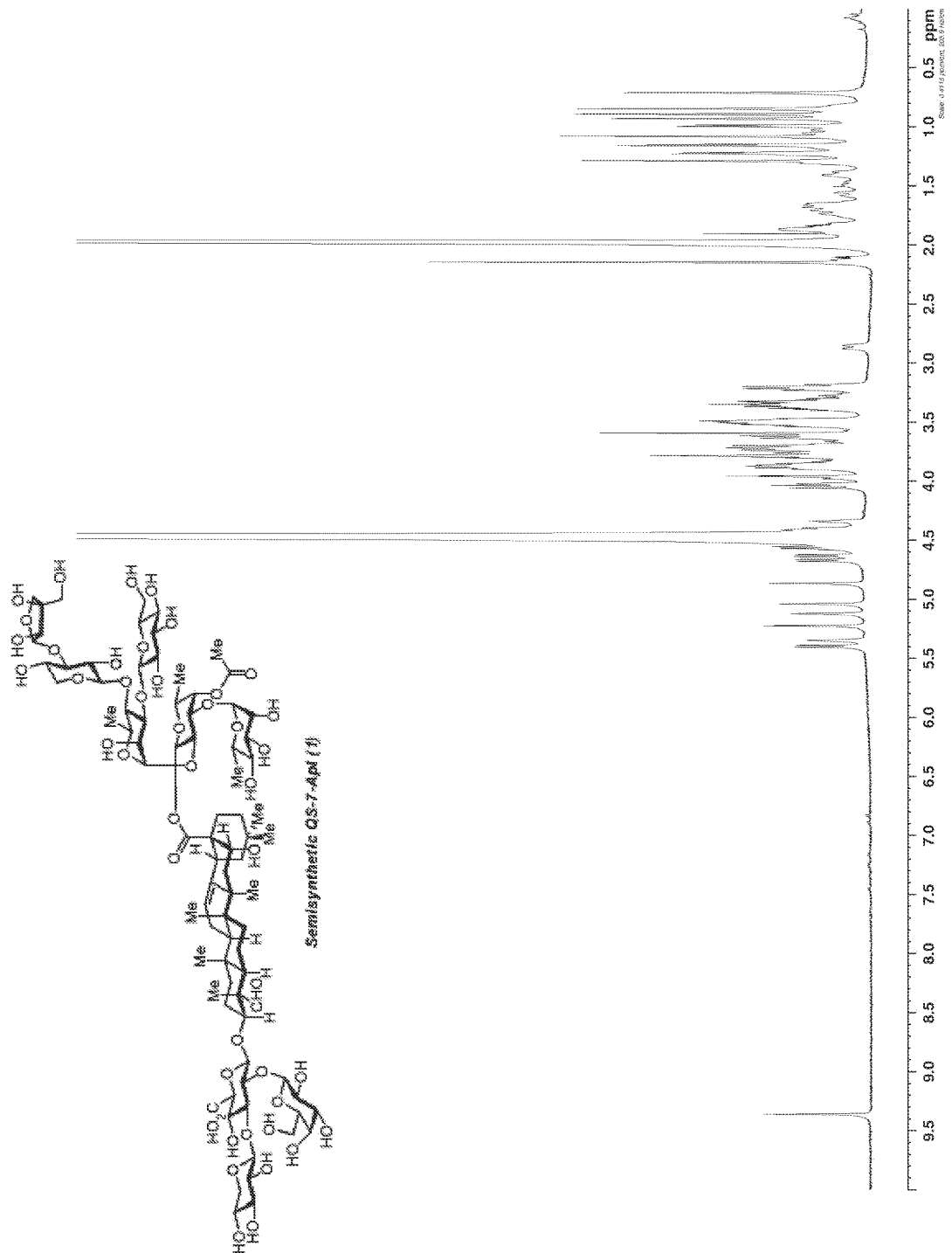
Figure 14:
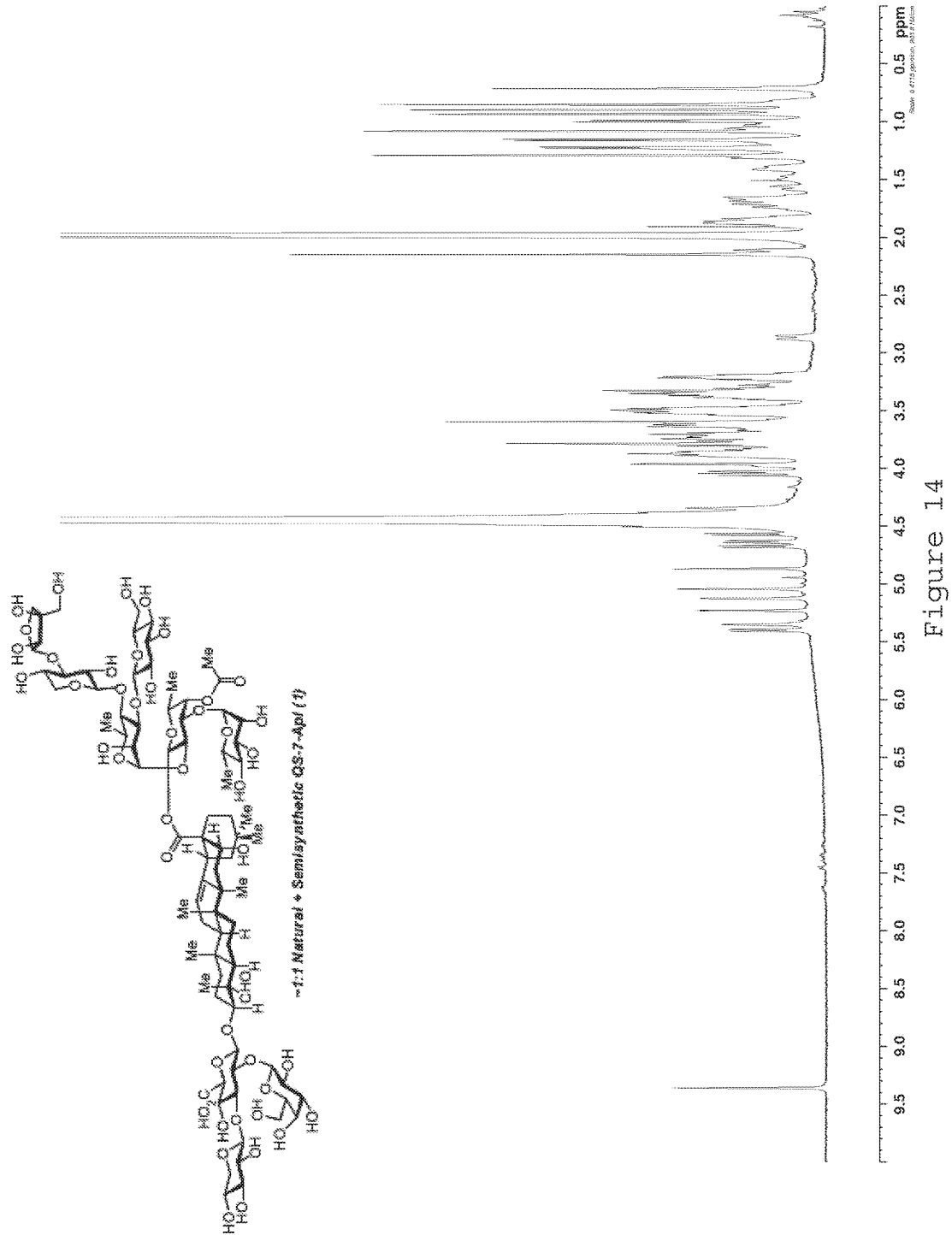

Groups of five mice were vaccinated (3×@ 1-wk intervals, booster @ wk 7) with GD3-KLH antigen (10 μg) along with the adjuvant of interest (10 μg). As a negative control, one group was vaccinated with the antigen only, devoid of adjuvant. As positive controls, two groups were vaccinated with either natural NQS-21 or synthetic SQS-21-Mix, both of which were established to be potent immunoadjuvants in this assay (see FIG. 2). Three compounds of formula II, as well as our recently synthesized QS-7-Api adjuvant, were evaluated in parallel for comparison (FIG. 5).

Antibodies to GD3 in the blood samples were measured by ELISA (FIG. 5A). These preliminary data reveal that these synthetic compounds are at least as active as NQS-21 in terms of immunopotentiating ability. These activities are reinforced by the strikingly high Ab titers (0.8-1.6×$10^6$, FIG. 5B) against the protein antigen KLH. Detailed toxicity assessment of these novel adjuvants is currently underway.

This important collection of preliminary data (FIG. 5) establishes the concepts that: (1) hydrolytically stable compounds of formula II are active immunopotentiators; and (2) that the present invention provides novel and potent adjuvant compounds with potencies that rival and exceed that of natural NQS-21.

The invention claimed is:

1. A compound selected from the group consisting of:

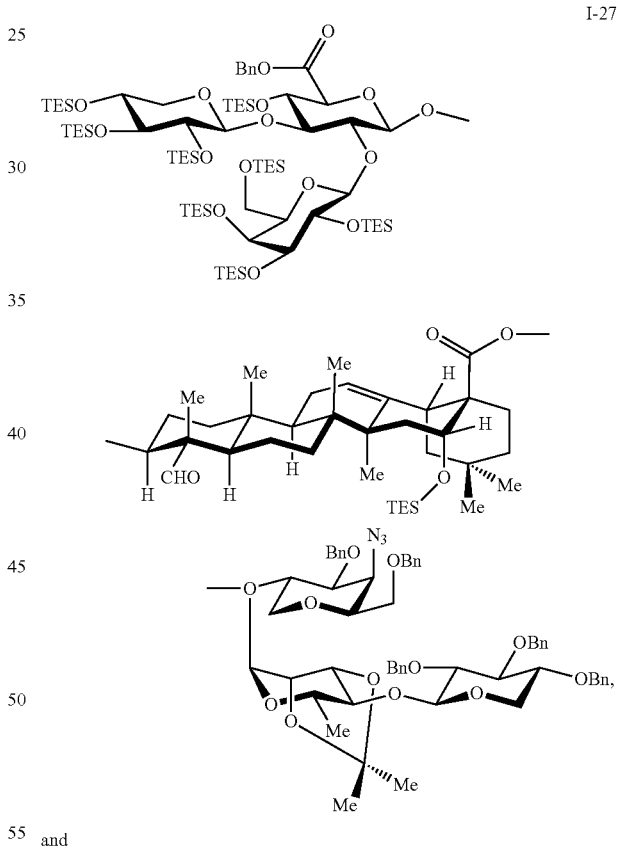

and

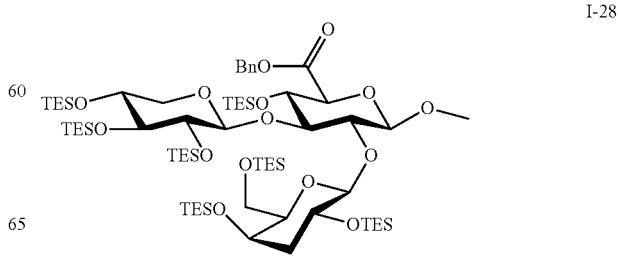

-continued
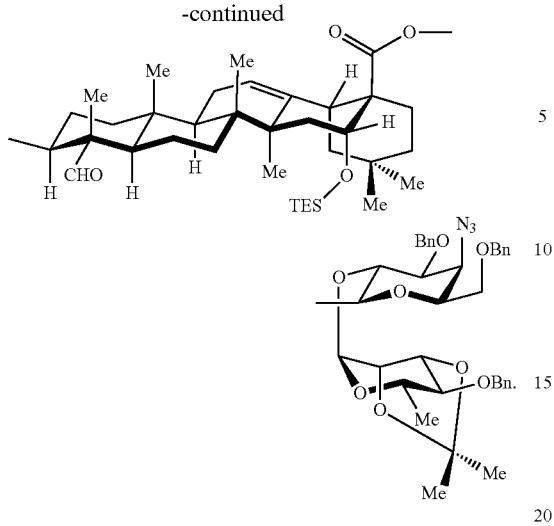
* * * * *